US007729863B2

(12) United States Patent
Ostrander et al.

(10) Patent No.: US 7,729,863 B2
(45) Date of Patent: Jun. 1, 2010

(54) METHODS AND MATERIALS FOR CANINE BREED IDENTIFICATION

(75) Inventors: Elaine Ostrander, Seattle, WA (US); Leonid Kruglyak, Seattle, WA (US); Heidi G Parker, Seattle, WA (US); Lisa V Kim, Sammamish, WA (US); Matthew Stephens, Seattle, WA (US); Tiffany B Malek, Seattle, WA (US); Nathan B Sutter, Seattle, WA (US); Scott Carlson, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 648 days.

(21) Appl. No.: 10/536,369

(22) PCT Filed: Dec. 15, 2004

(86) PCT No.: PCT/US2004/042267

§ 371 (c)(1),
(2), (4) Date: Feb. 1, 2006

(87) PCT Pub. No.: WO2005/059110

PCT Pub. Date: Jun. 30, 2005

(65) Prior Publication Data

US 2006/0235625 A1 Oct. 19, 2006

Related U.S. Application Data

(60) Provisional application No. 60/530,464, filed on Dec. 17, 2003.

(51) Int. Cl.
*G06F 7/00* (2006.01)
(52) U.S. Cl. .................. 702/19; 702/20; 703/13; 707/102; 435/6
(58) Field of Classification Search .................. None
See application file for complete search history.

(56) References Cited

U.S. PATENT DOCUMENTS

| | | | |
|---|---|---|---|
| 5,804,388 A | 9/1998 | Aguirre et al. | |
| 5,874,217 A | 2/1999 | Halverson et al. | |
| 6,210,897 B1 | 4/2001 | Andersson et al. | |
| 6,274,319 B1 | 8/2001 | Messier et al. | |
| 6,287,254 B1* | 9/2001 | Dodds | 600/300 |
| 6,331,441 B1 | 12/2001 | Balch et al. | |
| 6,524,609 B1 | 2/2003 | Myers | |
| 6,537,213 B2 | 3/2003 | Dodds | |
| 6,576,280 B2 | 6/2003 | Bebiak | |
| 6,730,023 B1 | 5/2004 | Dodds | |
| 2002/0022772 A1 | 2/2002 | Dodds | |
| 2002/0081356 A1 | 6/2002 | Bebiak et al. | |
| 2003/0135096 A1 | 7/2003 | Dodds | |
| 2003/0139655 A1 | 7/2003 | Dodds | |
| 2004/0146915 A1 | 7/2004 | Ferrie et al. | |
| 2005/0090718 A1 | 4/2005 | Dodds | |
| 2006/0008815 A1* | 1/2006 | Rosenfeld et al. | 435/6 |
| 2006/0147962 A1 | 7/2006 | Jones | |

FOREIGN PATENT DOCUMENTS

| | | |
|---|---|---|
| EP | 1 454 915 A1 | 9/2004 |
| WO | WO 97/13876 A1 | 4/1997 |
| WO | WO 97/31011 A1 | 8/1997 |
| WO | 98/54360 A1 | 12/1998 |
| WO | WO 00/56922 A2 | 9/2000 |
| WO | 01/08720 A2 | 2/2001 |
| WO | WO 01/11026 A1 | 2/2001 |
| WO | 01/28415 A1 | 4/2001 |
| WO | 01/84950 A1 | 11/2001 |
| WO | WO 02/061659 A2 | 8/2002 |
| WO | WO 02/102172 A1 | 12/2002 |
| WO | 03/029912 A2 | 4/2003 |
| WO | WO 2004/061124 A2 | 7/2004 |
| WO | WO 2004/063390 A2 | 7/2004 |
| WO | WO 2005/040350 A3 | 5/2005 |

OTHER PUBLICATIONS

Francisco, L.V., et al., "A Class of Highly Polymorphic Tetranucleotide Repeats for Canine Genetic Mapping," *Mammalian Genome* 7:359-362, 1996.
Guyon, R., et al , "A 1-Mb Resolution Radiation Hybrid Map of the Canine Genome," *Proc. Natl. Acad. Sci. USA* 100 (9):5296-5301, 2003.
"Affymetrix—DNA Analysis Products: The HG-U133 Plus Array is Here," Affymetrix.com, © 2001, <http://www.affymetrix.com/products/application/dna_analysis_products.affx> [retrieved Nov. 13, 2003].
"Allele Frequency Analysis," © 2003 SEQUENOM, Inc., <http://www.sequenom.com/Files/applications/allele_frequency_analysis.html> [retrieved Nov. 13, 2003].
Brouillette, J.A., and P.J. Venta, "Within-Breed Heterozygosity of Canine Single Nucleotide Polymorphisms Identified by Across-Breed Comparison," *International Society for Animal Genetics, Animal Genetics* 33(6):464-467, Dec. 2002.
"Canine Parentage Verification and Identification," © 2004 MetaMorphix, Inc., <http://www.metamorphixinc.com/about6a.html> [retrieved Nov. 10, 2004].
Corander, J., et al., "Bayesian Analysis of Genetic Differentiation Between Populations," *Genetics* 163:367-374, Jan. 2003.

(Continued)

*Primary Examiner*—Mary K Zeman
(74) *Attorney, Agent, or Firm*—Christensen O'Connor Johnson Kindness PLLC

(57) ABSTRACT

In one aspect, the invention provides methods for determining the contributions of canid populations to a canid genome. The methods comprise the steps of: (a) obtaining the identity of one or both alleles in a test canid genome for each of a set of markers; and (b) determining the contributions of canid populations to the test canid genome by comparing the alleles in the test canid genome to a database comprising canid population profiles, wherein each canid population profile comprises genotype information for the set of markers in the canid populations.

44 Claims, 2 Drawing Sheets

OTHER PUBLICATIONS

Cornuet, J.-M., et al., "New Methods Employing Multilocus Genotypes to Select or Exclude Populations as Origins of Individuals," *Genetics* 153:1989-2000, Dec. 1999.

Das, M., et al., "A Set of Canine Interrepeat Sequence PCR Markers for High-Throughput Genotyping," *Physiol. Genomics* 4:13-24, 2000.

Davies, N., et al., "Bioinvasions of the Medfly *Ceratitis Capitata*: Source Estimation Using DNA Sequences at Multiple Intron Loci," *Genetics* 153:351-360, Sep. 1999.

DeNise, S., et al., "Power of Exclusion for Parentage Verification and Probability of Match for Identity in American Kennel Club Breeds Using 17 Canine Microsatellite Markers," *International Society for Animal Genetics, Animal Genetics* 35:14-17, Feb. 2004.

Falush, D., et al., "Inference of Population Structure using Multilocus Genotye Data: Linked Lock and Correlated Allele Frequencies," *Genetics* 164:1567-1587, Aug. 2005.

*Fast-Track Genotyping Services: Powerful Full-Service Center to Accelerate Your Discovery*, Illumina, Inc., San Diego, Cal., © 2003, 8-page brochure.

Fisher, M.C., et al., "Disease Surveillance in Recombining Pathogens: Multilocus Genotypes Identify Sources of Human *Coccidioides* Infections," *PNAS* 99(13):9067-9071, Jun. 25, 2002.

Gordon, K., "Trait Leaders: California-based MMI Genomics Inc. Is Developing the Genetic Selection Tools of the Future," *ANGUSJournal*:80-81, Apr. 2003.

"High Performance Genotyping," © 2003 SEQUENOM, Inc., <http://www.sequenom.com/Files/applications/high_performance_genotyping.html> [retrieved Nov. 13, 2003].

Ichikawa, Y., et al., "Canine Parentage Testing Based on Microsatellite Polymorphisms," *J. Vet. Med. Sci.* 63(11):1209-1213, Nov. 2001.

Irion, D.N., et al., "Analysis of Genetic Variation in 28 Dog Breed Populations With 100 Microsatellite Markers," *Journal of Heredity* 94(1):81-87, 2003.

Jianbing, F., et al., "High-Density Fiber Optic Array Technology and Its Applications in Functional Genomic Studies," *Chinese Science Bulletin* 48(18):1903-1905, Sep. 2003.

Kennedy, G.C., et al., "Large-Scale Genotyping of Complex DNA," *Nat Biotechnol.* 21(10):1233-1237, Oct. 2003.

Koskinen, M.T., "Individual Assignment Using Microsatellite DNA Reveals Unambiguous Breed Identification in the Domestic Dog," *Animal Genetics* 34:297-301, 2003.

Koskinen, M.T., et al., "Assessment of the Population Structure of Five Finnish Dog Breeds with Microsatellites," *Animal Genetics* 31:310-317, 2000.

"MassARRAY Homogenous MassEXTEND™ (hME) Assay," © 2003 SEQUENOM, Inc., <http://www.sequenom.com/Files/applications/hme_assay.html> [retrieved Nov. 13, 2003].

*New MassARRAY™ Homogenous MassEXTEND™ (hME) Assay*, Sequenom Inc., San Diego, Cal., Bulletin 1021, n.d.

Pascual, M., et al., "Microsatellite Variation in Colonizing and Palearctic Populations of *Drosophila subobscura*," *Mol. Biol. Evol.* 18(5):731-740, 2001.

Rannala, B., and J.L. Mountain, Detecting Immigration by Using Multilocus Genotypes, *Proc. Natl. Acad. Sci. USA* 94:9197-9201, Aug. 1997.

Rosenberg, N.A., et al., "Empirical Evaluation of Genetic Clustering Methods Using Multilocus Genotypes from 20 Chicken Breeds," *Genetics* 159:699-713, Oct. 2001.

Tiret, L., et al., "Assignation of Highly Polymorphic Markers on a Canine Purebred Pedigree," *Mammalian Genome* 11:703-705, 2000.

Villablanca, D.N., and G.K. Roderick, "Determining the Source of Individuals: Multilocus Genotyping in Nonequilibium Population Genetic," <http://www.ncbi.nlm.gov/entrez/query/fcgi?cmd=Retrieve &db=PubMed&list_uids=10234242 &dopt=Abstract> (abstract), *Trends in Ecology and Evolution* (1):17-21, Jan. 1999.

Wilson, G.A., and B. Rannala, "Bayesian Inference of Recent Migration Rates Using Multilocus Genotypes," *Genetics* 163:1177-1191, Mar, 2003.

Zajc, I., and J. Sampson, "Utility of Canine Microsatellites in Revealing the Relationships of Pure Bred Dogs," *The Journal of Heredity* 90(1):104-107, Jan. 1999.

Brooks, M.B., et al., "von Willebrand Disease Phenotype and von Willebrand Factor Marker Genotype in Doberman Pinschers," *American Journal of Veterinary Research* 62(3):364-369, Mar. 2001.

Brouillette, J.A., et al., "Estimate of Nucleotide Diversity in Dogs With a Pool-and-Sequence Method," *Mammalian Genome* 11:1079-1086, 2000.

Caughey, G.H., et al., "Cloning and Expression of the Dog Mast Cell α-Chymase Gene," *Journal of Immunology* 159:4367-4375, 1997.

Coronado, V.A., et al., "New Haplotypes in the Bedlington Terrier Indicate Complexity in Copper Toxicosis," *Mammalian Genome* 14:483-491, 2003.

Kennedy, L.J., et al., "Extensive Interbreed, but Minimal Intrabreed, Variation of DLA Class II Alleles and Haplotypes in Dogs," *Tissue Antigens* 59:194-204, 2002.

Kijas, J.M.H., et al., "Detection of the Causal Mutation for Canine Leukocyte Adhesion Deficiency (CLAD) Using Pyrosequencing," *Animal Genetics* 31:326-328, 2000.

LaFond, E., et al., "Breed Susceptibility for Developmental Orthopedic Diseases in Dogs," *Journal of the American Animal Hospital Association* 38:467-477, Sep./Oct. 2002.

Masuda, K., et al., "Breed Differences in Genotype and Allele Frequency of Catechol O-Methyltransferase Gene Polymorphic Regions in Dogs," *Journal of Veterinary Medical Science* 66(2):183-187, 2004.

Newton, J.M., et al., "Melanocortin 1 Receptor Variation in the Domestic Dog," *Mammalian Genome* 11:24-30, 2000.

Niimi, Y., et al., "Breed Differences in Allele Frequency of the Dopamine Receptor D4 Gene in Dogs," *Journal of Heredity* 92(5):433-436, 2001.

Ordovas, J.M., "Gene-Diet Interaction and Plasma Lipid Responses to Dietary Intervention," *Biochemical Society Transactions* 30(2):68-73, 2002.

Parker, H.G., et al., "Genetic Structure of the Purebred Domestic Dog," *Science* 304:1160-1164, May 21, 2004.

Pearce-Kelling, S.E., et al., "Test Matings Confirm Allelism of prcd Across Many Dog Breeds," Abstract No. 3673, *Proceedings of the Association for Research in Vision and Ophthalmology Annual Meeting*, Fort Lauderdale, Florida, May 5-10, 2002.

Pellegrini, B., et al., "Cloning and Characterization of Opticin cDNA: Evaluation as a Candidate for Canine Oculo-Skeletal Dysplasia," *Gene* 282:121-131, 2002.

Reference SNP(refSNP) Cluster Report, refSNP ID: rs8499601, National Center for Biotechnology Information (NCBI) Single Nucleotide Polymorphism, Sep. 14, 2003, <http://ncbi.nlm.nih.gov/SNP/snp_ref.cgi?rs=8499601> [retrieved May 5, 2006], 2 pages.

Riehl, J., et al., "Inheritance of von Willebrand's Disease in a Colony of Doberman Pinschers," *American Journal of Veterinary Research* 61(2):115-120, Feb. 2000.

Salavaggione, O.E., et al., "Canine Red Blood Cell Thiopurine S-Methyl-transferase: Companion Animal Pharmacogenetics," *Pharmacogenetics* 12(9):713-724, 2002.

Salavaggione, O.E., et al., "Cat Red Blood Cell Thiopurine S-Methyl-transferase: Companion Animal Pharmacogenetics," *The Journal of Pharmacology and Experimental Therapeutics* 308(2):617-626, 2004.

Sunde, R.A., "Research Needs for Human Nutrition in the Post-Genome-Sequencing Era," *Journal of Nutrition* 131:3319-3323, 2001.

Swanson, K.S., et al., "Nutritional Genomics: Implications for Companion Animals," *Journal of Nutrition* 133(10):3033-3040, Oct. 2003, <http://jn.nutrition.org/cgi/content/full/133/10/3033> [retrieved May 12, 2006].

Takahasi, S., et al., "Lineage Classification of Canine Inheritable Disorders Using Mitochondrial DNA Haplotypes," *Journal of Veterinary Medical Science* 64(3):255-259, 2002.

Williams, C.M., "British Nutrition Foundation Annual Lecture: Chips With Everything? Nutritional Genomics and the Application of Diet in Disease Prevention," *British Nutrition Foundation Nutrition Bulletin* 28:139-146, 2003.

Sutter, N B., et al., "Megabase Linkage Disequilibrium in *Canis familiaris*," American Journal of Human Genetics 73 (5):438, 2003.

Davies, N., et al., "Determining the Source of Individuals: Multilocus Genotyping in Nonequilibrium Population Genetics," Trends in Ecology and Evolution 14(1):17-21, Jan. 1999 [Abstract]. (Previously cited in IDS of May 2006 under incorrect author.).

Girman, D.J., et al., "Molecular Genetic and Morphological Analyses of the African Wild Dog (*Lycaon pictus*)," Journal of Heredity 84(6):450-459, Nov.-Dec. 1993.

Kennedy, L.J., et al., "Interbreed Variation of DLA-DRB1, DQA1 Alleles and Haplotypes in the Dog," Veterinary Immunology and Immunopathology 69(2-4):101-111, Aug. 1999.

MacHugh, D.E., et al., "Genetic Structure of Seven European Cattle Breeds Assessed Using 20 Microsatellite Markers," Animal Genetics 29(5):333-340, Oct. 1998.

Ostrander, E.A., et al., "Identification and Characterization of Dinucleotide Repeat (CA)n. Markers for Genetic Mapping in Dog," Genomics 16(1):207-213, Apr. 1993.

Ostrander, E.A., "The Canine Genome," Presentation at The Genome of *Homo sapiens*, vol. LXVIII, Cold Spring Harbor Symposia, Cold Spring Harbor Laboratory, New York, May 2003, 24 pages.

Parker, H.G., et al., "The Phylogeny of the Domestic Dog: Finding Historical Links Through Genetic Analysis," Poster presented at The Genome of *Homo sapiens*, vol. LXVIII, Cold Spring Harbor Symposia, Cold Spring Harbor Laboratory, New York, May 2003, 24 pages.

Pearson, H., "Mutt Origins Exposed," Nature Science Update, Jun. 3, 2003, <http://www.nature.com/nature-events/conference-news/hsgs2003/030602-4.html> [retrieved Dec. 9, 2003], 2 pages.

Pennisi, E., "Genome Resources to Boost Canines' Role in Gene Hunts," Science 304(5674):1093-1095, May 2004.

Rosenberg, N.A., et al., "Empirical Evaluation of Genetic Clustering Methods Using Multilocus Genotypes from 20 Chicken Breeds," Genetics 159(2):699-713, Oct. 2001.

Vilà, C., et al., "Multiple and Ancient Origins of the Domestic Dog," Science 276(5319):1687-1689, Jun. 1997.

Vilà, C., et al., "Phylogenetic Relationships, Evolution, and Genetic Diversity of the Domestic Dog," Journal of Heredity 90(1):71-77, Jan.-Feb. 1999.

Wayne, R.K., and E.A. Ostrander, "Origin, Genetic Diversity, and Genome Structure of the Domestic Dog," BioEssays 21(3):247-257, Mar. 1999.

Zajc, I., et al., "Variability of Canine Microsatellites Within and Between Different Dog Breeds," Mammalian Genome 8(3):182-185, Mar. 1997.

Kell, D.B., "Genotype-Phenotype Mapping: Genes as Computer Programs," TRENDS in Genetics 18(11):555-559, Nov. 2002.

Office Action dated Oct. 7, 2008, from U.S. Appl. No. 11/303,853, filed Dec. 16, 2005.

Office Action dated Feb. 3, 2010, issued in corresponding Canadian Application No. 2,550,219, filed Dec. 15, 2004.

* cited by examiner

PHYDO CERTIFICATE of PARENTAGE

It is hereby certified that ___Fido___ owned by ___Ms. Smith___
has the following parentage:

Border Collie 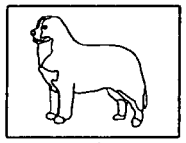  Bullmastiff 

95% CONFIDENCE     99% CONFIDENCE

Fido 

Please note that many dog breeds are predisposed to diseases and congenital conditions.

The following predispositions have been identified for Border Collies and Bullmastiffs:

Border Collie

Central progressive retinal atrophy
Ceroid liposuscinosis
Corneal dystrophy
Cryptorchidism
Dearness
Osteochondritis dissecans
Patent ductus arteriosus

Bullmastiff

Abnormal dentition
Bloat
Brachury
Cervical vertebrae malformation
Cleft palate
Contact dermatitis, alopeccia and eczema
Entropion
Eversion of the cartilage of the third eyelid
Folliculitis and furunculosis, bacterial
Glaucoma
Hip and elbow dysplasia
Progressive retinal atrophy
Vaginal hyperplasia Approved _____

For additional information regarding disease predisposition and congenital conditions and diagnostic tests please contact your local veterinary clinic.

*Fig.1.*

METHODS AND MATERIALS FOR CANINE BREED IDENTIFICATION

CROSS-REFERENCE TO RELATED APPLICATION

This application claims the benefit of U.S. Provisional Application No. 60/530,464, filed Dec. 17, 2003.

STATEMENT OF GOVERNMENT LICENSE RIGHTS

This invention was made with government support under HG300035 awarded by National Institutes of Health. The government has certain rights in the invention.

FIELD OF THE INVENTION

The invention relates to determining the contribution of one or more canid populations to the genome of a canid using polymorphic markers.

BACKGROUND OF THE INVENTION

Canis familiaris, the domestic dog, is a single species divided into more than 400 phenotypically divergent genetic isolates termed breeds, 152 of which are recognized by the American Kennel Club in the United States (American Kennel Club (1998) The Complete Dog Book, eds. Crowley & Adelman, Howell Book Hues, New York, N.Y.). Distinct breeds of dog are characterized by unique constellations of morphology, behavior, and disease susceptibility (Ostrander et al. (2000) Trends in Genetics 16:117-23). A variety of dog morphologies have existed for millennia, and reproductive isolation between them was formalized with the advent of breed clubs and breed standards in the mid 19th century. Since that time, the promulgation of the "breed barrier" rule—no dog may become a registered member of a breed unless both its dam and sire are registered members—has ensured a relatively closed genetic pool among dogs of each breed.

Over 350 inherited disorders segregate in the purebred dog population (Patterson et al. (1988) J. Am. Vet. Med. Assoc. 193:1131.) Many of these mimic common human disorders and are restricted to particular breeds or groups of breeds as a result of aggressive inbreeding programs used to generate specific morphologies.

There are many potential uses for objectively determining the breed of an individual dog, such as the certification of dogs as belonging to a particular breed. Because historical records vary in reliability from breed to breed, a genetic analysis that does not rely on prior population information is the most direct and accurate method for determining population structure. Over the past decade, molecular methods have been used to enhance our understanding of wild canid species and to determine their relationships to the domestic dog. Mitochondrial DNA sequence analyses describe the relationship between the domestic dog and the wolf, elucidating the multiple domestication events that occurred 40,000-100,000 years ago (Vila et al. (1997) Science 276:1687-9; Savolainen et al. (2002) Science 298:1610-3, Leonard et al. (2002) Science 298:1613-6). However, the evolution of mitochondrial DNA is too slow to allow inference of relationships among modern dog breeds, most of which have existed for fewer than 400 years. In addition, phylogenetic distances measures and tree building programs are not equipped to deal with reticulate evolution as is commonly observed in dog populations (Zajc et al. (1997) Mamm. Genome 8(3):182-5; Koskinen & Bredbacka (2000) Animal Genetics 31:310-17; Irion et al. (2003) J. Hered. 94(1):81-7). One previous study showed that nuclear microsatellite loci could be used to assign dogs from five breeds to their breed of origin, demonstrating large genetic distances among these breeds (Koskinen (2003) Anim. Genet. 34:297). Another study used microsatellites to detect relatedness of two breed pairs in a collection of 28 breeds but could not establish broader phylogenetic relationships among the breeds (Irion et al. (2003) J. Hered 94:81-7). The failure to find such relationships could reflect the properties of microsatellite loci (Irion et al. (2003) J. Hered. 94:81-7), the limited number of breeds examined, or the analytical methods used in the study. Alternatively, it may reflect the complex structure in purebred dog populations, due to the recent origin of most breeds and the mixing of ancestral types in their creation.

There is a need for methods for defining related groups of breeds and for unambiguously identifying breed contributions to the genome of an individual dog. The present invention addresses this and other needs.

SUMMARY OF THE INVENTION

In one aspect, the invention provides methods for determining the contributions of canid populations to a canid genome. The methods comprise the steps of: (a) obtaining the identity of one or both alleles in a test canid genome for each of a set of markers; and (b) determining the contributions of canid populations to the test canid genome by comparing the alleles in the test canid genome to a database comprising canid population profiles, wherein each canid population profile comprises genotype information for the set of markers in the canid population. The set of markers may comprise at least about five markers, for example, at least about five markers set forth on the map of the canine genome. Exemplary markers suitable for use in the methods of the invention include, for example, microsatellite markers, single nucleotide polymorphisms (SNPs), mitochondrial markers, and restriction fragment length polymorphisms. For example, the set of markers may comprise at least 5 of the SNP markers set forth in Table 2, and/or at least 5 microsatellite markers set forth in Table 1. The set of markers may comprise one or more population-specific markers, such as one or more population-specific SNP markers or one ore more population-specific microsatellite markers. For example, one or more SNP markers may be selected from the group consisting of 372c5t-82, 372e13t-57, 372m6t-88, 372m23t-76, 373a15t-112, 373e1t-50, 373e1t-130, 373g19t-246, 373i8s-224, 373k8s-181, 372c5s-168, 372C15S-196, 372e15s-71, and 373a21t-93.

The identity of one or both alleles in a test canid genome for each of the set of markers may be obtained using methods standard in the art, such as hybridization, Polymerase Chain Reaction, size fractionation, DNA sequencing, etc. For example, step (a) of the methods may comprise amplifying genomic DNA of the test canid using primers specific for each of the set markers and determining the size of the amplification product. Step (a) may also comprise amplifying genomic DNA of the test canid using primers specific for each of the set of markers and determining the nucleotide sequence of the amplification product. In some embodiments, the primers are selected from the group consisting of SEQ ID NOs:1-200. In some embodiments, the primers are selected from the group consisting of SEQ ID NOs:1-244-327.

The genotype information in a canid population profile may comprise information such as the identity of one or both alleles of most or all the markers in the set of markers in one or more canids that are members of that canid population, and/or estimated allele frequencies for at least one allele of most or all of the markers in the set of markers in that canid population. Each estimated allele frequency in a canid population profile is typically based on the identities of one or both alleles in at least two genomes of canids that are members of the canid population. The database of canid population profiles may comprise between about five and several hundreds of canid population profiles, such as at least about 100 canid population profiles. In some embodiments, the canid population profiles comprise profiles of registered breeds, such as breeds registered by the American Kennel Club.

In some embodiments, the set of markers comprises fewer than about 1500 SNP markers and wherein the method determines the contributions of at least 87 canid populations to the test canid genome. In some embodiments, the set of markers comprises fewer than about 200 SNP markers (such as about 100 SNP markers, or about 50 SNP markers) and wherein the method determines the contributions of at least 87 canid populations to the test canid genome.

In step (b) of the method, the likelihood that one or more canid populations contributed to the test canid genome may be determined using any suitable algorithm, such as Bayesian model-based clustering algorithms or assignment algorithms. In some embodiments, step (b) comprises determining the probability that a specific canid population contributed to the genome of the test canid by determining the conditional probability that the alleles in the test canid genome would occur in the specific canid population divided by the sum of conditional probabilities that the alleles in the test canid genome would occur in each canid population in the database. In some embodiments, step (b) comprises discriminating between the contributions of two or more genetically related canid populations to the test canid genome by comparing the alleles in the test canid genome to a database comprising profiles of the two or more genetically related canid populations. Exemplary genetically related canid populations include, but are not limited to, Belgian Sheep Dog and Belgian Tervuren; Collie and Shetland Sheep Dog; Whippet and Greyhound; Siberian Husky and Alaskan Malamute; Mastiff and Bullmastiff; Greater Swiss Mountain Dog and Bernese Mountain Dog; West Highland White Terrier and Cairn Terrier; and Lhasa Apso, Shih Tzu, and Pekinese.

In some embodiments, the methods of the invention further comprise the step of providing a document displaying the contributions of one or more canid populations to the genome of the test canid genome. The document may provide information regarding the one or more canid populations that contributed to the genome of the test canid or the test canid, such as health-related information (e.g., disease predispositions), insurance information, or any other kind of information. The document may also provide a certification of the contributions of one or more canid populations to the genome of the test canid genome. In some embodiments, the document provides a representation (e.g., a photograph, drawing, or other depiction) of the one or more canid populations that contributed to the genome of the test canid.

In some embodiments, the invention provides methods for defining one or more canid populations, comprising: (a) for each of a set of canid genomes, obtaining the identity of one or both alleles for each of a set of markers; and (b) defining one or more canid populations by determining the likelihood that one or more members of the set of canid genomes define distinct canid populations characterized by a set of allele frequencies for each marker using statistical modeling.

In another aspect, the invention provides substrates comprising nucleic acid sequences for obtaining the identity of one or both alleles in a canid genome for each of a set of markers.

In a further aspect, the invention provides a computer-readable medium comprising a data structure stored thereon for use in distinguishing canid populations, the data structure comprising: (a) a marker field, which is capable of storing the name of a marker or of an allele of the marker; and (b) a genotype information field, which is capable of storing genotype information for the marker in a canid population, wherein a record comprises an instantiation of the marker field and an instantiation of the genotype information field and a set of records represents a canid population profile. For example, the genotype information field may be capable of storing an estimate of the frequency of the allele of a marker (e.g., an SNP marker) in a canid population. The genotype information field may also be capable of storing the identity of one or both alleles of each of a set of markers in one or more canids that are members of that canid population. In some embodiments, the computer readable medium comprises a substrate having stored thereon: computer-readable information comprising (a) a data structure for use in distinguishing canid populations, the data structure comprising: (i) a marker field, which is capable of storing the name of a marker or of an allele of the marker; and (ii) a genotype information field, which is capable of storing genotype information for the marker in a canid population, wherein a record comprises an instantiation of the marker field and an instantiation of the genotype information field and a set of records represents a canid population profile; and, (b) computer-executable instructions for implementing a method for determining the contributions of canid populations to a canid genome, comprising: (i) obtaining the identity of one or both alleles in a test canid genome for each of a set of markers; and (ii) determining the contributions of canid populations to the test canid genome by comparing the alleles in the test canid genome to a database comprising canid population profiles, wherein each canid population profile comprises genotype information for the set of markers in the canid population.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows an exemplary document displaying the contributions of two canid populations (Border Collie and Bullmastiff) to the genome of a test canid (Fido), along with information about disease predispositions for the two canid populations.

DETAILED DESCRIPTION OF THE PREFERRED EMBODIMENT

Figure 2:
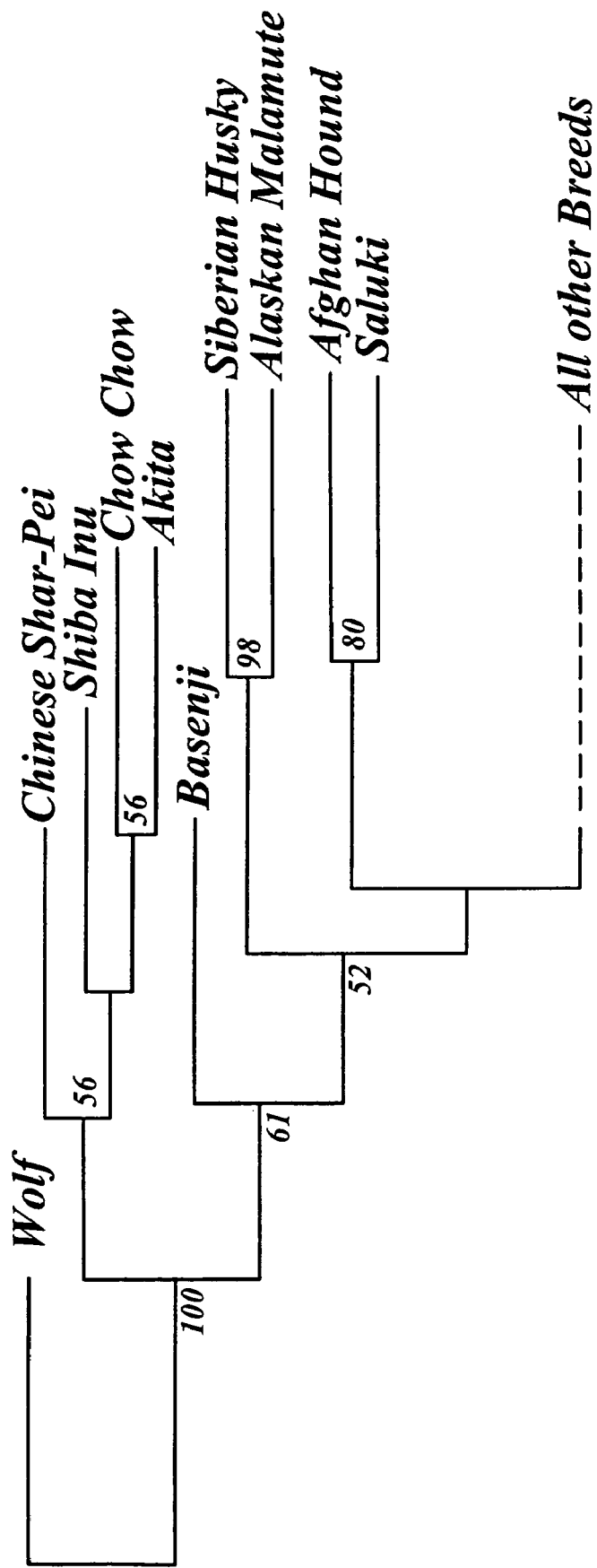
FIG. 2 shows a consensus neighbor-joining tree of 85 dog breeds and the gray wolf, as described in EXAMPLE 4. Nine breeds that form branches with statistical support are shown. The remaining 76 breeds show little phylogenetic structure and have been combined into one branch labeled "All Other Breeds" for simplification. The trees that formed the consensus are based on the chord distance measure. 500 bootstrap replicates of the data were carried out, and the fraction of bootstraps supporting each branch is indicated at the corresponding node as a percentage for those branches supported in over 50% of the replicates. The wolf population at the root of the tree consists of 8 individuals, one from each of the following countries: China, Oman, Iran, Sweden, Italy, Mexico, Canada and the United States. Branch lengths are proportional to bootstrap values.

The specification hereby incorporates by reference in their entirety the files contained on the two compact discs filed herewith. The first compact disc includes Tables 3 and 4, the second compact disc includes a sequence listing.

Unless specifically defined herein, all terms used herein have the same meaning as they would to one skilled in the art of the present invention.

In a first aspect, the invention provides methods for determining the contributions of canid populations to a canid genome, comprising: (a) obtaining the identity of one or both alleles in a test canid genome for each of a set of markers; and (b) determining the contributions of canid populations to the test canid genome by comparing the alleles in the test canid genome to a database comprising canid population profiles, wherein each canid population profile comprises genotype information for the set of markers in the canid population.

As used here, the term "determining the contributions of canid populations" refers to estimating or inferring using statistical methods the contributions of canid populations to draw conclusions regarding whether one or more canid populations contributed to the genome of a test canid.

The term "canid" as used herein refers to an animal that is a member of the family Canidae, which includes wolves, jackals, foxes, coyote, and the domestic dog. For example, a canid may be a domestic dog, a wolf, or an animal that has some genetic contributions from more than one species of the family Canidae. The term "canid population" refers to a group of canids related by descent, such as a domestic dog breed. The term "breed" refers to an intraspecies group of animals with relatively uniform phenotypic traits that have been selected for under controlled conditions by man. For example, the American Kennel Club (AKC) recognizes 152 breeds distributed in seven breed groups (Herding, Hound, Nonsporting, Sporting, Terrier, Toy, and Working) (American Kennel Club (1998) *The Complete Dog Book*, eds. Crowley & Adelman, Howell Book Hues, New York, N.Y.). The methods of the invention may be used to estimate the genetic contributions of any dog breed, including, but not limited to Afghan Hound, Airedale Terrier, Akita, Alaskan Malamute, American Eskimo Dog, American Foxhound, American Hairless Rat Terrier, American Staffordshire Terrier, American Water Spaniel, Australian Cattle Dog, Australian Shepherd, Australian Terrier, Basenji, Basset Hound, Beagle, Bearded Collie, Bedlington Terrier, Belgian Laekenois, Belgian Malinois, Belgian Sheepdog, Belgian Tervuren, Bernese Mountain Dog, Bichon Frise, Bloodhound, Border Collie, Border Terrier, Borzoi, Boston Terrier, Bouvier des Flandres, Boykin Spaniel, Boxer, Briard, Brittany, Bulldog, Brussels Griffon, Bullmastiff, Bull Terrier, Cairn Terrier, Cardigan Welsh Corgi, Cavalier King Charles Spaniel, Chesapeake Bay Retriever, Chihuahua, Chinese Crested, Chinese Shar-Pei, Chow Chow, Clumber Spaniel, Cocker Spaniel, Collie, Curly-Coated Retriever, Dachshund, Dalmatian, Dandie Dinmont Terrier, Doberman Pinscher, Dogo Canario, English Cocker Spaniel, English Foxhound, English Setter, English Springer Spaniel, Entlebucher Mountain Dog, Field Spaniel, Flat-Coated Retriever, French Bulldog, German Longhaired Pointer, German Shepherd Dog, German Shorthaired Pointer, German Wirehaired Pointer, Giant Schnauzer, Golden Retriever, Gordon Setter, Great Dane, Great Pyrenees, Greater Swiss Mountain Dog, Greyhound, Harrier, Havanese, Ibizan Hound, Irish Setter, Irish Terrier, Irish Water Spaniel, Irish Wolfhound, Italian Greyhound, Jack Russell Terrier, Keeshond, Kerry Blue Terrier, Komondor, Kuvasz, Labrador Retriever, Leonberger, Lhasa Apso, Lowchen, Maltese, Manchester Terrier—Standard, Manchester Terrier—Toy, Mastiff, Miniature Bull Terrier, Miniature Pinscher, Miniature Poodle, Miniature Schnauzer, Munsterlander, Neapolitan Mastiff, Newfoundland, New Guinea Singing Dog, Norwegian Elkhound, Norwich Terrier, Old English Sheepdog, Papillon, Pekingese, Pembroke Welsh Corgi, Petit Basset Griffon Vendeen, Pharaoh Hound, Pointer, Polish Lowland Sheepdog, Pomeranian, Portuguese Water Dog, Presa Canario, Pug, Puli, Pumi, Rhodesian Ridgeback, Rottweiler, Saint Bernard, Saluki, Samoyed, Schipperke, Scottish Deerhound, Scottish Terrier, Silky Terrier, Shetland Sheepdog, Shiba Inu, Shih Tzu, Siberian Husky, Smooth Fox Terrier, Soft Coated Wheaten Terrier, Spinone Italiano, Staffordshire Bull Terrier, Standard Poodle, Standard Schnauzer, Sussex Spaniel, Tibetan Spaniel, Tibetan Terrier, Toy Fox Terrier, Toy Poodle, Vizsla, Weimaraner, Welsh Springer Spaniel, Welsh Terrier, West Highland White Terrier, Wirehaired Pointing Griffon, Whippet, Yorkshire Terrier.

The methods of the invention may also be used to determine genetic contributions from canid populations that are subsets of recognized breeds, for example, a group of Dalmatians originating from a particular breeder, or a group of canids that are not, or not yet, recognized as a breed. Similarly, the methods of the invention may be used to determine genetic contributions from canid populations that are not domestic dogs.

The first step in the methods of the invention comprises obtaining the identity of one or both alleles in a test canid genome for each of a set of markers. The term "marker" refers to any polymorphic genomic locus that is sufficiently informative across the canid populations used in the methods of the invention to be useful for estimating the genetic contribution of these canid populations to the genome of a test canid. A genomic locus is polymorphic if it has at least two alleles. The term "allele" refers to a particular form of a genomic locus that may be distinguished from other forms of the genomic locus by its nucleic acid sequence. Thus, different alleles of a genomic locus represent alternative nucleic acid sequences at that locus. In any individual canid genome, there are two alleles for each marker. If both alleles are the same, the genome is homozygous for that marker. Conversely, if the two alleles differ, the genome is heterozygous for that marker.

Population-specific alleles are alleles that are present at some frequency in one canid population but have not been observed in the sampled canids from comparison canid populations (although they may be present at a significantly lower frequency). Population-specific alleles may be used to assign an individual to a particular population. Accordingly, the difference in allele frequencies between populations can be used for determining genetic contributions.

A "set of markers" refers to a minimum number of markers that are sufficient for determining the genetic contribution of the canid populations used in the methods of the invention to the genome of a test canid. The minimum number of markers required depends on the informativeness of the markers for the particular canid populations that are being used, as further described below. The set of markers may comprise at least about 5 markers, at least about 10 markers, at least about 50 markers, or more than about 100 markers.

Representative markers that may be used according to the invention include microsatellite markers, mitochondrial markers, restriction fragment length polymorphisms, and single nucleotide polymorphisms (SNPs). Useful canine microsatellite markers include, but are not limited to, dinucleotide repeats, such as $(CA)_n$, trinucleotide repeats, and tetranucleotide repeats, such as $(GAAA)_n$ (Francisco et al. (1996) *Mamm. Genome* 7:359-62; Ostrander et al. (1993) *Genomics* 16:207-13). Exemplary markers for use in the methods of the invention include the microsatellite markers set forth in Table 1, the SNP markers set forth in Table 2, and the markers described in Guyon et al. (2003) *Proc. Natl. Acad. Sci U.S.A.* 100(9):5296-5301. The set of markers used in the methods of the invention may comprise at least about 5 markers from the microsatellite markers in Table 1 and/or at least about 5 markers from the SNP markers in Table 2. In some embodiments, the set of markers are selected from the group consisting of 372c5t-82, 372e13t-57, 372m6t-88, 372m23t-76, 373a15t-112, 373e1t-50, 373e1t-130, 373g19t-246, 373i8s-224, 373k8s-181, 372c5s-168, 372C15S-196, 372e15s-71, and 373a21t-93. In some embodiments, a set of markers comprising fewer than about 1500 SNP markers is used to determine the contributions of at least 87 canid populations to the test canid genome. In some embodiments, a set of markers comprising fewer than about 200 SNP markers is used to determine the contributions of at least 87 canid populations to the test canid genome.

According to the methods of the invention, the identities of one or both alleles of each marker may be obtained. In some embodiments, the identities of one or both alleles of a marker in a test canid may be determined experimentally using methods that are standard in the art. For example, the identities of one or both alleles of a genomic marker may be determined using any genotyping method known in the art. Exemplary genotyping methods include, but are not limited to, the use of hybridization, Polymerase Chain Reaction (PCR), size fractionation, DNA sequencing, DNA microarrays, high density fiber-optic arrays of beads (see, e.g., Jianbing et al. (2003) *Chin. Sci. Bull.* 48(18):1903-5), primer extension, mass spectrometry (see, e.g., Jurinke et al. (2002) *Meth. Mol. Biol.* 187:179-92), and whole-genome sampling analysis (see, e.g., Kennedy et al. (2003) *Nat. Biotechnol.* 21(10):1233-7). The identities of alleles of markers in a test canid may also have been previously determined and be available from sources such as published literature.

In some embodiments, the genomic DNA of the test canid may be amplified using primers specific for the markers, followed by size analysis or sequencing of the amplification product. Exemplary methods for obtaining the identities of one or both alleles of markers in canid genomes are described in EXAMPLE 1. In some embodiments, the primers used for amplifying genomic DNA containing microsatellite markers are selected from the group consisting of SEQ ID NOs:1-200, although other primers and other microsatellite markers may be used. In some embodiments, the primers used for amplifying genomic DNA containing SNP markers are selected from the group consisting of SEQ ID NOs:244 to 327, although other primers and other SNP markers may be used. The identities of alleles of 68-100 microsatellite markers in 422 canids, including 414 dogs representing 85 breeds, and 8 wolves are set forth in Table 3 (filed herewith on a compact disc). The identities of alleles of 100 SNP markers in 189 canids, including 186 dogs representing 67 breeds, two wolves, and a coyote are set forth in Table 4 (filed herewith on a compact disc).

The minimum number of markers included in the set of markers used in the first step of the methods of the invention depends on the informativeness of the markers for the particular canid populations that are being used. The informativeness of a marker is a function of the number of different alleles within and between the canid populations used in the methods of the invention, the frequency of these alleles, and the rate of mutation rate at the locus. The degree of polymorphism of a genomic locus may be evaluated by an estimation of the polymorphic information content (PIC), which is a function of the number of alleles and their frequency distribution. Exemplary PIC values for microsatellite markers suitable for use in the methods of the invention are set forth in Table 1. Suitable markers for use in the methods of the invention may have an average PIC value of about 0.65%, as shown in EXAMPLE 1.

Methods of determining the number of alleles of markers in different canid populations and their frequencies within and between canid populations are described in EXAMPLE 1. For example, the mean number of alleles per maker, the expected heterozygosity (based on Hardy-Weinberg Equilibrium assumptions), the observed heterozygosity, and the estimated inbreeding coefficients across 95 microsatellite markers in 94 canids, including 90 dogs representing 18 breeds, and 4 wolves, are described in EXAMPLE 1.

The existence of breed barriers would predict that dogs from the same breed should be more similar genetically than dogs from different breeds. To test this prediction, the proportion of genetic variation between individual dogs that could be attributed to breed membership was estimated. Analysis of molecular variance for microsatellite data including 96 markers in 328 dogs representing 68 breeds showed that variation between breeds accounts for more than 27% of total genetic variation, as described in EXAMPLE 1. Similarly, the genetic distance between breeds calculated from SNP marker data including 75 SNPs in 120 dogs representing 60 breeds was $F_{ST}$=0.36, as described in EXAMPLE 1. These observations are consistent with previous reports that analyzed fewer dog breeds (Koskinen (2003) *Anim. Genet.* 34:297; Irion et al. (2003) *J. Hered.* 94:81), confirming the prediction that breed barriers have led to strong genetic isolation among breeds, and are in striking contrast to the much lower genetic differentiation (typically in the range of 5-10%) found between human populations (Rosenberg et al. (2002) *Science* 298:2381-5; Cavelli-Sforza et al. (1994) *The History and Geography of Human Genes*, Princeton University Press, Princeton). Variation among breeds in dogs is on the high end of the range reported for livestock populations (MacHugh et al. (1998) *Anim. Genet.* 29:333; Laval et al. (2000) *Gen. Sel. Evol.* 32:187). Strong genetic differentiation among dog breeds indicates that breed membership may be determined from genotype information for individual canids.

The influence of the number of distinct alleles of a marker in a dataset on the informativeness of the marker is shown in EXAMPLE 2. For example, in an analysis of 19 canid populations and 95 microsatellite markers, 86% of canids were correctly assigned to their breed using 5 markers that each had more than 10 distinct alleles, and 95% of canids were correctly assigned using 10 or more markers that each had more than 10 distinct alleles. For markers with 1-3 distinct alleles, 46% of canids were correctly assigned to their breed using 5 markers, and 62% of canids were correctly assigned using 10 or more markers.

The influence of the number of markers used on the ability to discriminate between 19 canid populations using genotype information for 95 markers for 4 or 5 canids per canid population is shown in EXAMPLE 2. For example, the minimum number of markers required to successfully assign 100% of individuals to the correct canid population ranged between 2 (Pekingese) and 52 (American Hairless Terrier) depending on the canid population. The minimum number of microsatellite markers required to successfully assign at least 90% of all 94 tested individuals across the 19 canid populations, with the chosen canid population having 100% accuracy, ranged between 8 (for Pekingese) to 95 (for Preso Canario, Chihuahua, and American Hairless Terrier).

The second step of the methods of the first aspect of the invention comprises determining the contributions of canid populations to the test canid genome by comparing the alleles in the test canid genome to a database comprising canid population profiles, wherein each canid population profile comprises genotype information for alleles of the markers in the set of markers in the canid population. A "canid population profile" as used herein refers to the collection of genotype information for the set of markers in a canid population. Thus, a canid population profile may comprise genotype information for most or all alleles of most or all markers in the set of markers in the canid population. For example, a canid population profile may comprise genotype information for each allele of each marker in the set of markers in the canid population. The genotype information in a canid population profile may comprise information such as the identity of one or both alleles of most or all of the markers in the set of markers in one or more canids that are members of that canid population, and/or estimated allele frequencies for at least one allele of most or all of the markers in the set of markers in that canid population. An "allele frequency" refers to the rate of occurrence of an allele in a population. Allele frequencies are typically estimated by direct counting. Generally, allele frequencies in a canid population are estimated by obtaining the identity of one or both alleles for each of the set of markers in at least about five members of that canid population. A "database of canid population profiles" refers to the collection of canid population profiles for all of the canid populations used in an exemplary method of the invention. In some embodiments, the database of canid population profiles comprises between about five and about 500 canid population profiles, such as about 20 canid population profiles, about 50 canid population profiles, or about 100 canid population profiles.

Determining the contributions of canid populations to the test canid genome encompasses both assigning a canid genome to a particular canid population and determining the fraction of the canid genome that was derived from one or more canid populations. In some embodiments of the method, a Bayesian model-based clustering approach is used. There are two broad classes of clustering methods that are used to assign individuals to populations (Pritchard et al. (2000) *Genetics* 155:945-59). Distance-based methods calculate a pairwise distance matrix to provide the distance between every pair of individuals. Model-based methods proceed by assuming that observations from each cluster are random draws from some parametric model; inference for the parameters corresponding to each cluster is then done jointly with inference for the cluster membership of each individual, using standard statistical methods. Any standard statistical method may be used in the methods of the invention, including maximum likelihood, bootstrapping methodologies, Bayesian methods and any other statistical methodology that can be used to analyze genotype data. These statistical methods are well-known in the art. Many software programs for population genetics studies have been developed and may be used in the methods of the invention, including, but not limited to TFPGA, Arlequin, GDA, GENEPOP, GeneStrut, POPGENE (Labate (2000) *Crop. Sci.* 40:1521-1528), and structure (Pritchard et al. (2000) *Genetics* 155:945-59).

An exemplary Bayesian model-based clustering approach is provided by the genotype clustering program structure (Pritchard et al. (2000) *Genetics* 155:945-59), which has proven useful for defining populations within a species (Rosenburg et al. (2001) *Genetics* 159:699-713; Rosenburg et al. (2002) *Science* 298:2381-5; Falush et al. (2003) *Genetics* 164(4):1567-87). The clustering method used by structure requires no prior information about either phenotype or genetic origin to accurately place an individual or set of related individuals in a population.

Any algorithms useful for multi-locus genotype analysis may be used in the methods of the invention, for example, classic assignment algorithms. Suitable algorithms include those described in Rannala & Mountain (1997) *Proc. Natl. Acad. Sci. U.S.A.* 94:9197-9201 and Cornuet et al. (1999) *Genetics* 153:1989-2000 and variations thereof. Exemplary programs available for multi-locus genotype analysis include Doh (available at www2.biology.ualberta.ca/jbrzusto/Doh.php) and GeneClass (available at www.montpellier.inra.fr/URLB/geneclass/genecass.htm).

In some embodiments, the methods of the invention comprise determining the probability that a specific canid population contributed to the genome of the test canid by determining the conditional probability that the alleles in the test canid genome would occur in the specific canid population divided by the sum of conditional probabilities that the alleles in the test canid genome would occur in each canid population in the database.

Some embodiments of the methods of the invention comprise discriminating between the contributions of two or more genetically related canid populations to the test canid genome by comparing the alleles in the test canid genome to a database comprising profiles of the two or more genetically related canid populations. The two or more genetically related canid populations may comprise Belgian Sheep Dog and Belgian Tervuren; Collie and Shetland Sheep Dog; Whippet and Greyhound; Siberian Husky and Alaskan Malamute; Mastiff and Bullmastiff; Greater Swiss Mountain Dog and Bernese Mountain Dog; West Highland White Terrier and Cairn Terrier; or Lhasa Apso, Shih Tzu, and Pekinese.

Using an assignment algorithm on genotype information for 95 microsatellite markers from 94 canids, including 90 canids representing 18 breeds and 4 wolves, the methods of the invention have been used to assign each individual canid to its breed with 99% accuracy, as described in EXAMPLE 2. A clustering algorithm used on the same genotype information predicted 20 canid populations and assigned each canid to one population with 99% accuracy, as described in EXAMPLE 3.

Using an assignment algorithm on genotype information for 68 microsatellite markers from 341 canids representing 72 breeds, the methods of the invention have been used to assign 96% of the canids to the correct breed, as described in EXAMPLE 2. Using an assignment algorithm on genotype information for 96 microsatellite markers from 414 canids representing 85 breeds, the methods of the invention have been used to assign 99% of the canids to the correct breed, as described in EXAMPLE 4. Similar results were obtained using a clustering algorithm. Using an assignment algorithm on genotype information for 100 SNP markers from 189 canids representing 67 breeds, the methods of the invention have been used to assign 80% of canids to the correct breed with a probability of 99% of greater, as described in EXAMPLE 6.

The methods of the invention are also useful for determining the contributions of canid populations to mixed-breed canids. Admixed individuals represent approximately 50% of the canine population. Models that detect an individual's admixed state can be considered to group into two classes: models that require a combinatoric set of unique alleles for each of the possible mixtures of ancestral populations (Nason & Ellstrand (1993) *J. Hered.* 84: 1-12; Epifanio & Philipp (1997) *J. Hered.* 88:62-5), and Bayesian methods where ancestral populations are not required to contain a combination describing unique alleles, but instead assign individuals to admixed states probabilistically based on differences in allele frequencies between populations (Corander et al. (2003) *Genetics* 163(1): 367-74; Anderson & Thompson (2002) *Genetics* 160:1217-29, Pritchard et al. (2000) *Genetics* 155:945-59, Rannala & Mountain (1997) *Proc. Natl. Acad. Sci. U.S.A.* 94:9197-9201. The latter set of models are more informative for most populations and data sets as they allow for a Bayesian posterior probabilistic assignment vector for each population/generation combination, thereby allowing for uncertainty analysis to be incorporated into the assignment vector; but existing models for the exact, recent admixture assignments of individuals from multiple ancestral populations are limited in their scope as they have been developed thus far only for two generation prediction and allow for only a few ancestral populations. For example, the methods of Anderson & Thompson (2002) are developed for a two generation, two population model with unlinked microsatellite data. A naïve Bayesian classification model that incorporates linked and unlinked microsatellite loci information, higher-dimensioned ancestral populations, and higher-ordered generation pedigrees for the probabilistic assignment of individuals to mixtures of ancestral subpopulations is described in EXAMPLE 7. This model simultaneously addresses the generation, subpopulation, and linkage limitations of previous models, and 2- and 3-generational models have been implemented for exact admixture detection and assignment, as described in EXAMPLE 7.

Using a clustering algorithm on in silico mixes of genotype information for 95 markers from 85 canids, consisting of 81 canids representing 18 breeds and 4 wolves, the methods of the invention have been used to identify in silico mixing at the parent level with 100% accuracy, as described in EXAMPLE 5. The methods of the invention were also highly accurate at detecting in silico mixing at the grandparent level, and fairly accurate at detecting in silico mixing at the great-grandparent level, as shown in EXAMPLE 5. Thus, the methods of the invention may be used to discriminate mixes at the parent and grandparent level from pure-bred dogs (as well as ½ wolf and ¼ wolf mixes from dogs) and identify breed contributions in the genome of a mixed-breed dog.

Using a Bayesian classification model on in silico mixes of genotype information for 96 markers from 429 canids representing 88 breeds, the methods of the invention have been used to correctly assign more than 98% of F1 mixes and more than 94% of F2 mixes, as described in EXAMPLE 7. Using this model on genotype information for 72 markers from 160 known mixed-breed canids, the methods of the invention have been used to correctly assign more than 96% of F1 mixes and more than 91% of F2 mixes, as described in EXAMPLE 7.

The methods of the invention may further comprise the step of providing a document displaying the contributions of one or more canid populations to the genome of the test canid genome. The term "document" refers to a chart, certificate, card, or any other kind of documentation. The document may display the contributions of one or more canid populations to the test canid genome in a numeric format or in a graphic format. For example, the document may include photographs or other depictions, drawings, or representations of the one or more canid populations. The document may also provide confidence values for the determined contributions (such as 80%, 85%, 90% 95%, or 99% confidence). In some embodiments, the document provides a certification of the contributions of one or more canid populations to the genome of the test canid genome.

In some embodiments, the document additionally provides information regarding the one or more canid populations that contributed to the genome of the test canid or the test canid. The information regarding canid populations that contributed to the genome of the test canid may include information related to the characteristics and origin of the canid population or any other kind of information that would be useful to the owner of the test canid. In some embodiment, the information includes health-related information. Many canid populations have predispositions to particular diseases or conditions. For example, Afghan hounds are predisposed to glaucoma, hepatitis, and hypothyroidism; Basenji are predisposed to coliform enteritis and pyruvate kinase deficiency; Beagles are predisposed to bladder cancer and deafness; Bernese Mountain dogs are predisposed to cerebellar degeneration; Border Terriers are predisposed to oligodendroglioma; and Labrador Retrievers are predisposed to food allergies (see, e.g., Dr. Bob's All Creatures Site, Breed Predisposition to Disease and Congenital Conditions; Patterson et al. (1988) *J. Am. Vet. Med. Assoc.* 193:1131). Of the genetic diseases discovered in dogs, 46% are believed to occur predominantly or exclusively in one or a few breeds (Patterson et al. (1988) *J. Am. Vet. Med. Assoc.* 193:1131.) Therefore, information regarding the contributions of one or more canid populations to the genome of the test canid genome is particularly valuable to mixed-breed canid owners or caretakers (both professional and non-professional) for the purpose of proactively considering health risks for individual tested animals. For example, a mixed breed dog that is found to be a mixture of Newfoundland and Bernese Mountain Dog should be actively monitored for genetic diseases that occur with rare frequency in the general population of dogs, but occur with significant frequency in these specific breeds; thus, a mixed-breed individual of this type would benefit from screens for malignant histiocytosis (disease heritability of 0.298 in Bernese Mountain dogs, Padgett et al. 1995 *J. Small Anim. Pract.* 36(3):93-8) in addition to Type I cystinuria genetic screens (nonsense mutation isolated in Newfoundlands at exon 2 of SLC3A1 gene, Henthorn et al. (2000) *Hum. Genet.* 107(4):295-303).

Health-related information may also include potential treatments, special diets or products, diagnostic information, and insurance information. An exemplary document displaying the contributions of one or more canid populations to the genome of a test canid is shown in FIG. 1.

In some embodiments, the invention provides methods for defining one or more canid populations, comprising: (a) for each of a set of canid genomes, obtaining the identity of one or both alleles for each of a set of markers; and (b) defining one or more canid populations by determining the likelihood that one or more members of the set of canid genomes define distinct canid populations characterized by a set of allele frequencies for each marker. Exemplary methods of the invention for defining one or more canid populations are described in EXAMPLES 3 and 4.

In another aspect, the invention provides substrates comprising nucleic acid sequences for determining the identity of one or both alleles in a canid genome for each of a set of markers. The substrates may be in any form suitable for determining the identity of alleles of markers. For example, the substrate may be in the form of a microarray or a collection of beads.

In a further aspect, the invention provides a computer-readable medium comprising a data structure stored thereon for use in distinguishing canid populations, the data structure comprising: a marker field, which is capable of storing the name of a marker (for example, an SNP marker) or the name of an allele of a marker; and a genotype information field, which is capable of storing genotype information for the marker (for example, the identity of one or both alleles of the marker in a canid genome or an estimate of the frequency of an allele of the marker in a canid population), wherein a record comprises an instantiation of the marker field and an instantiation of the genotype information field and a set of records represents a canid population profile.

A "computer-readable medium" refers to any available medium that can be accessed by computer and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information, such as computer-readable instructions, data structures, program modules, or other data. Computer storage media include, but are not limited to, RAM, ROM, EEPROM, flash memory or other memory technology, CD-ROM, digital versatile disks (DVD) or other optical disk storage, magnetic cassettes, magnetic tapes, magnetic disk storage or other magnetic storage devices, or any other computer storage media. Communication media typically embody computer-readable instructions, data structures, program modules or other data in a modulated data signal, such as a carrier wave or other transport mechanism that includes any information delivery media. The term "modulated data signal" means a signal that has one or more of its characteristics set or changed in such a manner as to encode information in the signal. By way of example, and not limitation, communication media include wired media, such as a wired network or direct-wired connection, and wireless media, such as acoustic, RF infrared, and other wireless media. A combination of any of the above should also be included within the scope of computer-readable media.

A "data structure" refers to a conceptual arrangement of data and is typically characterized by rows and columns, with data occupying or potentially occupying each cell formed by a row-column intersection. The data structure in the computer-readable medium of the invention comprises a marker field and a genotype information field, as described above. The instantiation of the marker field and the genotype information field provides a record, and a set of record provides a canid population profile. Thus, the data structure may be used to create a database of canid population profiles.

In some embodiments, the computer readable medium comprises a substrate having stored thereon: (a) a data structure for use in distinguishing canid populations, the data structure comprising: (i) a marker field, which is capable of storing the name of a marker or of an allele of a marker; and (ii) a genotype information field, which is capable of storing genotype information for the marker, wherein a record comprises an instantiation of the marker field and an instantiation of the frequency field and a set of records represents a canid population profile; and (b) computer-executable instructions for implementing a method for determining the contributions of canid populations to a canid genome, comprising: (i) obtaining the identity of one or both alleles in a test canid genome for each of a set of markers; and (ii) determining the contributions of canid populations to the test canid genome by comparing the alleles in the test canid genome to a database comprising canid population profiles, wherein each canid population profile comprises genotype information for the set of markers in the canid population.

The following examples merely illustrate the best mode now contemplated for practicing the invention, but should not be construed to limit the invention.

Example 1

This example describes a representative method of the invention for obtaining the identity of one or both alleles for a set of markers and selecting markers suitable for determining the contribution of canid populations to the genome of a canid.

A. Methods

1. Sample Collection and DNA Extraction

Canid DNA samples from 513 American Kennel Club-registered dogs representing 103 breeds and 8 gray wolves from eight countries (China, Oman, Italy, Iran, U.S.A. (Alaska), Canada (Quebec), Sweden, Mexico) were obtained by collecting buccal (cheek) swabs and/or blood samples from volunteers at dog shows and dog club specialty events, as well as by mail-in donations. American Kennel Club registration number and detailed pedigree information was requested for all dogs, as participation was limited to unrelated dogs that did not share grandparents. Pedigree information was also collected for 84% of sampled individuals. In many cases, five-generation pedigrees were obtained, and while dogs sometimes appear redundantly at the great-grandparent level or higher, inspection of the complete lineage indicates a high degree of unrelatedness among dogs of the same breed. For those individuals where a pedigree was not available, unrelatedness was verified by breed club representatives. Each individual canid was given a canid identification number. Abbreviations used for breeds and other canid populations are shown in Table 5. In addition DNA samples from 160 mixed-breed canids comprising admixture components from 20 AKC breeds were obtained by collecting buccal swabs.

Buccal swabs were collected in a manner similar to that suggested by the American Kennel Club (AKC) website using cytology brushes (Medical Packaging Corp., Camarillo, Calif.). DNA was extracted from buccal swabs using QiaAmp blood kits following manufacturers' protocol (Qiagen, Valencia, Calif.). DNA extraction from blood was done as described previously (Comstock et al. (2002) *Mol. Ecol.* 11:2489-98).

2. Analysis of Microsatellite Markers

One hundred dinucleotide microsatellite markers were chosen from the 1596 microsatellites currently localized on the 3300 marker map of the dog (Guyon et al. (2003) *Proc. Natl. Acad. Sci U.S.A.* 100(9):5296-5301) (Table 1). Markers were selected based on informativeness, calculated as a PIC, value, and distribution across all 38 autosomes. Selected markers had an average PIC value of 0.65% (range 36%-86%) and an average spacing of 29.5 Mb (range 21.5-50.9 Mb). Dinucleotide, rather than tetranucleotide microsatellites were chosen to reduce the number of spurious mutations observed that could hamper breed identification.

DNA samples were arrayed on five 96-well plates. A positive control was included on each plate to ensure consistent allele binning. PCR was performed in 10 microliter reactions containing 1 ng of genomic DNA and final concentrations of the following reagents: 16 mM ammonium sulfate, 67 mM Tris-HCl pH 8.8, 2.0 mM $MgCl_2$, 0.1 mM dNTPs, 300 nM forward primers (SEQ ID NOs:1-100), reverse primers (SEQ ID NOs:101-200), and dye-labeled M13 Primers (PE Applied Biosystems, Foster City, Calif. USA). Forward primers were redesigned to include a 19 base M13 forward (−29) sequence, 5'-CACGACGTTGTAAAACGAC-3' (SEQ ID NO:201), on the 5 prime end. Samples were labeled by the addition of 0.25 pmol of an M13 primer (SEQ ID NO:201) tagged with either 6FAM™, VIC™, NED™ or PET™ (ABI, Foster City, Calif.) dyes to each reaction. PCR incubation was carried out according to standard protocols (see, e.g., Lowe et al. (2003) *Genomics* 82: 86-95). Annealing temperatures used are provided in Table 1. Four samples labeled with different dyes were multiplexed following completion of PCR by combining 3 microliters of each reaction mix into a single 96 well plate. Samples were denatured in 2 volumes Hi-Di™ formamide with 16 pmol of GeneScan™-500LIZ™ size standard (ABI, Foster City, Calif.) according to manufacturers' protocols. All samples were loaded on an ABI 3730 DNA Analyzer™ (PE applied Biosystems) capillary electrophoresis instrument for allele separation. Genotypes were called using GeneMapper™ v3.0 software (ABI, Foster City, Calif.). All calls were checked manually and each subsequent run was scanned for the appearance of new alleles outside existing bins. Four markers failed to amplify consistently and were discarded.

3. SNP Discovery and Genotyping

Fifty canine bacterial artificial chromosomes (BACs) were chosen at random from the canine radiation hybrid map (Guyon et al. (2003) *Proc. Natl. Acad. Sci U.S.A.* 100(9): 5296-5301). The Primer3 program described in Krawetz S, Misener S (eds) *Bioinformatics Methods and Protocols: Methods in Molecular Biology*. Humana Press, Totowa, N.J., pp 365-386 was used to design primers from each BAC end sequence. The resulting amplicons averaged 334 base pairs. Primers were used to amplify 19867 base pairs of non-continuous genomic sequence in 189 dogs representing 67 domestic dog breeds, coyote, and the gray wolf. The resulting PCR products were sequenced using standard methods on an ABI 3700 capillary sequencer with standard ABI dye terminator chemistry (ABI, Foster City, Calif.) and resequence. All sequence reads were aligned and viewed using Phred, Phrap and Consed (Ewing & Green (1998)*Genome Res.* 8:186-94; Ewing et al. (1998) *Genome Res.* 8:175-85; available at www.genome.washington.edu). The computer program Polyphred was used to identify regions of polymorphism, both SNP and insertion/deletion, within and between sequence reads (Nickerson et al. (1997) *Nucl. Acids Res.* 25:2745-51, available at droog.mbt.washington.edu). All allele calls were confirmed manually and confirmed through visual inspection of the traces.

4. Statistical Analysis

An analysis of molecular variance (AMOVA) was performed with GDA (Lewis & Zaykin (2001) Genetic Data Analysis: Computer Program for the Analysis of Allelic Data, Version 1.0 (d16c) under assumption of Hardy-Weinberg equilibrium. Similar results were obtained for the fraction of genetic variation among breeds when inbreeding was allowed for in the analysis.

Expected heterozygosity for each breed was calculated from allele frequencies using Tajima's unbiased estimator (Tajima (1989) *Genetics* 123:585-95).

B. Results

1. Informativeness of Dinucleotide Microsatellites

The identities of alleles (length of the amplified region) of 68-100 microsatellite markers in 422 canids, including 414 dogs representing 85 breeds, and 8 wolves, are set forth in Table 3 (filed herewith on a compact disc). 148 alleles were found to be unique to a specific canid population: 1 each to ACKR, AUST, BORD, BOX, BULD, DACH, GOLD, GSHP, GSMD, IBIZ, KEES, NELK, PEKE, POM, ROTT, SFXT, TERV, and WHIP, 2 each to BEAG, CAIR, HUSK, IRSE, MAST, OES, SCHP, SCWT, SPOO, and SSHP, 3 each to AMAL, BMD, KOMO, NEWF, STBD, and WSSP, 4 each to KUVZ, PNTR, and PRES, 5 each to BSJI and SHAR, 6 to AKIT, and 64 to WOLF.

Six different datasets were used for subsequent analyses, as further described in EXAMPLES 2-5 and 7. The first dataset included genotype information for 95 microsatellite markers (microsatellite markers 1-14, 16, 18-21, 23-36, 39-100, see Table 1) in 94 canids, including 90 canids representing 18 breeds and 4 wolves (dataset 1, Table 6). The second dataset included genotype information for 68 microsatellite markers (microsatellite markers 2-8, 11, 12, 14-16, 18-21, 23, 24, 26-32, 34-36, 38, 41, 42, 44-46, 50, 51, 53, 54, 56, 60-64, 67, 68, 70-74, 78, 79, 81-83, 85, 87-91, 93-98, see Table 1) in 341 canids representing 72 breeds (dataset 2, Table 7). The third dataset included genotype information for 96 microsatellite markers (microsatellite markers 1-9, 11-38, 40-42, 44-75, 77-100, see Table 1) in 414 canids representing 85 breeds (dataset 3, Table 8). The fourth dataset included genotype information for 96 microsatellite markers (microsatellite markers 1-9, 11-38, 40-42, 44-75, 77-100, see Table 1) in 85 canids, including 81 dogs representing 18 breeds, and 4 wolves (dataset 4, Table 9). The fifth dataset included genotype information for 96 microsatellite markers (microsatellite markers 1-9, 11-38, 40-42, 44-75, 77-100, see Table 1) in 429 canids representing 88 breeds. The sixth dataset included genotype information for 72 of the microsatellite markers in Table 1 in 160 mixed-breed canids, as set forth in Table 3 (filed herewith on a compact disc).

The proportion of polymorphic markers, the mean number of alleles per maker, the mean number of alleles per polymorphic maker, the expected heterozygosity (based on Hardy-Weinberg Equilibrium assumptions), the observed heterozygosity, and the estimated inbreeding coefficients across 95 microsatellite markers in dataset 1 are shown in Table 10. The expected heterozygosity of 85 canid populations averaged over 96 microsatellites (dataset 3) using Tajima's unbiased estimator is shown in Table 11.

The existence of breed barriers would predict that dogs from the same breed should be more similar genetically than dogs from different breeds. To test this prediction, the proportion of genetic variation between individual dogs that could be attributed to breed membership was estimated. Analysis of molecular variance in the microsatellite data for 96 microsatellites in 414 dogs representing 85 breeds (dataset 3, Table 8) showed that variation between breeds accounts for more than 27% of total genetic variation.

2. Informativeness of SNP Markers

Using 189 canids representing 67 domestic breeds, coyote and wolf, 100 polymorphic sites in approximately 20 Kb of non-continuous canine genomic sequence were identified, as shown in Table 2. These include 92 single base substitutions and 11 insertion or deletion mutations ranging from one to eight nucleotides in length. The identities of alleles for 100 SNP markers in 189 canids, including 186 dogs representing 67 breeds, two wolves, and a coyote are set forth in Table 4 (filed herewith on a compact disc). Minor allele frequencies in 75 SNPs from 120 dogs representing 60 breeds ranged from 0.4% to 48%, as shown in Table 2. Fourteen of these SNPs were breed-specific: 372c5t-82 (English Shepherd), 372e13t-57 (Cocker Spaniel), 372m6t-88 (English Shepherd), 372m23t-76 (Alaskan Malamute), 373a15t-112 (Chesapeake Bay Retriever), 373e1t-50 (Spinoni Italiano), 373e1t-130 (Scottish Deerhound), 373g19t-246 (Borzoi), 373i8s-224 (Chesapeake Bay Retriever), 373k8s-181 (Tibetan Terrier), 372c5s-168 (Akita), 372C15S-196 (Labrador Retriever), 372e15s-71 (Field Spaniel), 373a21t-93 (Italian Greyhound).

When all dogs were considered as a single population, the observed heterozygosity (Tajima & Nei (1984) *Mol. Biol. Evol.* 1:269-85) was $8 \times 10^{-4}$, essentially the same as that seen in the human population (Sachidanandam et al. (2001) *Nature* 409:928-33; Venter et al. (2001) *Science* 291:3104-51). However, when the breeds are separated, there is a 4-fold range in heterozygosity between the least outbred (Scottish Deerhound, $2.5 \times 10^{-4}$) to most outbred (English Shepherd, $1.0 \times 10^{-3}$). The genetic distance between breeds calculated from the SNP data for 75 SNPs in 120 dogs representing 60 breeds was $F_{ST}$=0.36.

The expected heterozygosity of 60 canid populations based on allele frequencies at 75 SNP loci (dataset 3) using Tajima's unbiased estimator is shown in Table 12. Each breed is represented by 2 dogs.

Example 2

This example describes a representative method of the invention for estimating the contributions of canid populations to a canid genome using an assignment test calculator on genotype information for 95 microsatellite markers from 94 canids, and on genotype information for 68 microsatellite markers from 341 canids.

A. Methods

1. Datasets

Dataset 1 included genotype information for 95 microsatellite markers from 94 canids, including 90 dogs representing 18 breeds, and 4 wolves (AHRT, AKIT, BEAG, BMD, BOX, BULD, BULM, CHIH, DACH, GOLD, IBIZ, MAST, NEWF, PEKE, POM, PRES, PUG, ROTT, WOLF, see Table 5 for abbreviations of canid populations). The 95 microsatellite markers were microsatellite markers 1-14, 16, 18-21, 23-36, 39-100 (Table 1). The dataset contained genotype information from 5 canids for each breed and 4 wolves (Table 6). The genotype information for the canids in dataset 1 is set forth in Table 3 (filed herewith on a compact disc).

Dataset 2 included genotype information for 68 markers from 341 canids representing 72 breeds (ACKR, AFGH, AHRT, AIRT, AKIT, AMAL, AMWS, AUSS, AUST, BASS, BEAG, BEDT, BELS, BLDH, BMD, BORD, BORZ, BOX, BSJI, BULD, BULM, CAIR, CHBR, CHIH, CKCS, CLSP, COLL, DACH, DANE, DNDT, DOBP, ECKR, FCR, GOLD, GREY, GSD, GSHP, GSMD, HUSK, IBIZ, IRSE, IRTR, IWOF, KEES, KOMO, KUVZ, LAB, MAST, MBLT, MNTY, NELK, NEWF, OES, PEKE, PNTR, POM, PRES, PTWD, PUG, RHOD, ROTT, SCHP, SCWT, SFXT, SHAR, SPOO, SSHP, STBD, TERV, WHIP, WHWT, WSSP, see Table 5 for abbreviations of canid populations). The 68 microsatellite markers were microsatellite markers 2-8, 11, 12, 14-16, 18-21, 23, 24, 26-32, 34-36, 38, 41, 42, 44-46, 50, 51, 53, 54, 56, 60-64, 67, 68, 70-74, 78, 79, 81-83, 85, 87-91, 93-98 (Table 1). The dataset contained genotype information from 5 canids for each breed, except for SFXT (2 canids), ACKR, AFGH, DNDT, OES (3 canids each), AIRT, BASS, BEDT, IRTR, MNTY, SCHP, SCWT, and TERV (4 canids each) (Table 7). The genotype information for the canids in dataset 2 is set forth in Table 3 (filed herewith on a compact disc).

2. Doh Analysis

The assignment test calculator Doh was used as described in Paetkau D. et al., Molecular Ecology 4: 347-354 (1995) for an analysis of the two datasets of genotype information. All individual canids were designated with their known population except for the canid to be tested, which was then assigned by the program to the canid population with the highest probability of generating the test canid's genotype. The program repeats this procedure with each canid as test canid.

B. Results

1. Doh Analyses Using Dataset 1

Using Doh on the genotype information in dataset 1, including genotype information for 95 microsatellite markers in 94 canids (90 dogs representing 18 breeds, and 4 wolves), 99% of the canids were assigned to the correct canid population. 100% canids were correctly assigned for the following breeds: AHRT, AKIT, BEAG, BMD, BOX, BULD, CHIH, DACH, GOLD, IBIZ, MAST, NEWF, PEKE, POM, PUG, ROTT, WOLF. The only canid that was misassigned was one dog (out of 5 dogs) of the Presa Canario breed. The misassigned Presa Canario dog was assigned to Chihuahua.

It was found that the discrimination power of the allelic patterns depended on the number of independent microsatellite loci, the allelic diversity at each locus, and the number of individuals sampled from each breed. To evaluate the effect of the number of alleles of a marker and the number of markers on informativeness of that marker, a Doh assignment analysis for the first 19 breeds was performed with 5, 10, 15, and 20 markers, binning markers with 1-3 distinct alleles found in the dataset, 4-6 distinct alleles, 7-10 distinct alleles, and more than 10 distinct alleles. For the bins that did not contain 20 markers, the maximum number of markers was used. For markers with more than 10 distinct alleles, 86% of canids were correctly assigned to their breed using five markers, and 95% of canids were correctly assigned using 10, 15, or 20 markers. For markers with 7-10 distinct alleles, 84% of canids were correctly assigned to their breed using 5 markers, and 91% of canids were correctly assigned using 10 markers, and 94% of canids were correctly assigned using 15, or 20 markers. For markers with 4-6 distinct alleles, 62% of canids were correctly assigned to their breed using 5 markers, and 71% of canids were correctly assigned using 10, 15, or 20 markers. For markers with 1-3 distinct alleles, 46% of canids were correctly assigned to their breed using 5 markers, and 62% of canids were correctly assigned using 10, 15, or 20 markers.

The minimum number of microsatellite markers found in a 2-class (0-1) directed search of the allele frequency patterns within the 95 markers required to successfully assign 100% of the individuals to the correct canid populations (incorrect assignment is to any other breed) was 2 for PEKE, 3 for BOX, POM, and WOLF, 4 for AKIT, MAST, and PUG, 5 for NEWF and ROTT, 6 for BMD, 8 for BEAG, 11 for IBIZ, 12 for GOLD, 17 for DACH, 19 for BULD, 26 for BULM, 44 for PRES, 49 for CHIH, and 52 for AHRT. There is a positive correlation between the minimum number of microsatellite markers required for 100% (0-1) discrimination, and the mean number of alleles across the 95 microsatellite markers for the 94 canids tested in 19 canid populations (see Table 10).

The minimum number of microsatellite markers found in a multiclass (0, 1, 2, ... 18) directed search of the allele frequency patterns within the 95 markers required to successfully assign at least 90% of all 94 tested individuals across the 19 canid populations, with the chosen canid population having 100% accuracy, was 8 for PEKE, BOX, POM, WOLF, AKIT, MAST, PUG, NEWF, ROTT, and BMD, 11 for BEAG, 14 for IBIZ, 14 for GOLD, 23 for DACH, 24 for BULD, 28 for BULM, and 95 for PRES, CHIH, and AHRT.

As expected, the discrimination power reflects the level of inbreeding observed in each breed. For example, certain breeds have allelic variation 3-fold less than the average breed allelic variation and those breeds have both higher discrimination power and the characteristic population dynamics of long population bottlenecks and small effective population sizes 2. Doh Analysis Using Dataset 2

Using Doh on the genotype information in dataset 2, including genotype information for 68 markers from 341 canids representing 72 breeds, 96% of the dogs tested were assigned to the correct breed, as shown in Table 13. If both Belgian breeds (Belgian Sheepdog and Belgian Tervuren) were counted as one breed, 98% of the dogs tested were assigned to the correct breed.

Example 3

This example describes a representative method of the invention for estimating the contributions of canid populations to a canid genome using cluster analysis on genotype information for 95 microsatellite markers from 94 canids.

A. Methods

1. Dataset

Dataset 1 included genotype information for 95 microsatellite markers from 94 canids, including 90 dogs representing 18 breeds, and 4 wolves, as described in EXAMPLE 2.

2. Cluster Analysis

Cluster analysis was performed using the multilocus genotype clustering program structure (Pritchard et al. (2000) *Genetics* 155:945-59; Falush et al. (2003) *Science* 299:1582-5), which employs a Bayesian model-based clustering algorithm to identify genetically distinct subpopulations based on patterns of allele frequencies. Multiple runs were completed for each value of K (number of genetic clusters) with burn-in lengths of 10,000 steps and 100,000 iterations of the Gibbs sampler. The correlated allele frequency model was used with asymmetric admixture allowed. All values of K from 2 to 80 were tested and the clustering solutions that produced the highest likelihood were retained for further verification. To choose the overall best clustering solution for the data set, an all-pairs Wilcoxon two-sample test was performed for the 5 highest likelihood values of K.

3. Nested Set Clustering

Starting with the complete data set, all individuals were hierarchically divided into sub-clusters where each (K+1)th sub-cluster was created by splitting one of the previous K clusters based on the highest observed likelihood value across 10 runs. Employing a hierarchical method for deriving clusters of individuals may infer a reasonable methodology for ascertaining population phylogeny when genetic variability between sub-populations is reduced due to a modified amount of admixture.

B. Results

A maximum likelihood calculation using structure predicted 20 populations in dataset 1 (95 markers in 19 canid populations) and assigned each individual to one group with 99% accuracy, as shown in Table 14. The one individual that was not assigned to its breed group was a single Presa Canario, which was placed between the Bulldog and the Bullmastiff groups. The Presa Canario is a recreated breed that has been developed through admixture of various mastiff types. The misassigned dog, in particular, can trace its heritage to both a bulldog and a Bullmastiff within the last 12 generations.

The clustering assignment was not able to distinguish between the Bullmastiffs and the Mastiffs at this level of analysis but this was solved by nested analysis, as shown in Tables 15A-D. In the nested analysis, the same clustering algorithms were applied in a stepwise fashion. First, the entire set was divided into two populations. Based on maximum likelihood, one of these two populations was then divided into two to provide a total of three populations. This process was repeated until all populations were resolved. The divisions from five to nine groups clearly show the relationships between the mastiff type breeds. This relationship and the hierarchy predicted conforms perfectly to that expected from breed accounts.

Example 4

This example describes a representative method of the invention for estimating the contributions of canid populations to a canid genome using cluster analysis on genotype information for 96 microsatellite markers in 85 canid populations.

A. Methods

1. Dataset

Dataset 3 included genotype information for 96 markers from 414 canids representing 85 breeds (ACKR, AFGH, AHRT, AIRT, AKIT, AMAL, AMWS, AUSS, AUST, BASS, BEAG, BEDT, BELS, BICH, BLDH, BMD, BORD, BORZ, BOX, BSJI, BULD, BULM, CAIR, CHBR, CHIH, CHOW, CKCS, CLSP, COLL, DACH, DANE, DOBP, ECKR, FBLD, FCR, GOLD, GREY, GSD, GSHP, GSMD, GSNZ, HUSK, IBIZ, IRSE, IRTR, ITGR, IWOF, KEES, KERY, KOMO, KUVZ, LAB, LHSA, MAST, MBLT, MNTY, MSNZ, NELK, NEWF, OES, PEKE, PHAR, PNTR, POM, PRES, PTWD, PUG, RHOD, ROTT, SALU, SAMO, SCHP, SCWT, SHAR, SHIB, SHIH, SPOO, SSHP, SSNZ, STBD, TIBT, TERV, WHIP, WHWT, WSSP, see Table 5 for abbreviations of canid populations). The 96 microsatellite markers were microsatellite markers 1-9, 11-38, 40-42, 44-75, 77-100 (Table 1). The dataset contained genotype information for 5 canids for all breeds, except for AIRT, BASS, BEDT, BICH, FBLD, IRTR, MNTY, PHAR, SCHP, SCWT, TERV (4 canids each) (Table 8). The genotype information for the canids in this dataset is set forth in Table 3 (filed herewith on a compact disc).

2. Statistical Analyses

Structure was run for 100,000 iterations of the Gibbs sampler after a burn-in of 20,000 iterations. The correlated allele frequency model was used with asymmetric admixture allowed. The similarity coefficient across runs of structure was computed as described (Rosenberg et al. (2002) *Science* 298:2381-5). When the program was run on a partial data set of 68 breeds, it was noted that at values of K above 40 the program created clusters to which no individuals were assigned, and the clusters were unstable from run to run. This is most likely because the algorithm, which was initially designed to separate 2-3 populations, is unable to handle such large numbers of populations simultaneously. Because structure has previously been shown to reliably separate 20 populations (Rosenberg et al. (2001) *Genetics* 159:699-713), the data were divided set into 8 subsets of 10 to 11 breeds each, all possible pairs of these subsets were analyzed. Historically related or morphologically similar breeds were retained in the same subset.

Structure was then applied to the entire data set at K=2 to K=10, with fifteen runs at each K. As K is increased, structure first separates the most divergent groups into clusters, followed by separation of more closely related groups (Rosenberg et al. (2002) *Science* 298: 2381). In the analysis, the likelihood increased with increasing values of K, reflecting additional structure found at each K, but multiple different clustering solutions were found for K>4, and therefore K=2 to 4 were used to describe the global breed structure, with phylogenetic analysis and cluster analysis of subgroups used to define constellations of closely related breeds. Structure runs at K=2-5 were repeated under the no admixture model with similar results. In a separate analysis, eight wolves were added to the structure run at K=2. The wolves were sampled from eight countries: China, Oman, Iran, Italy, Sweden, Mexico, Canada (Ontario) and the United States (Alaska). All wolves clustered together with the first cluster of dog breeds shown in Table 16.

Each breed was assigned to one of the four groups based on breed average majority and structure was run on each group at K=2-4. No additional consistent patterns were observed within the individual groups apart from the reported breed pairs and trio. Outlier analysis was carried out using the software package fdist2. Eleven markers were identified as potential "outliers" with Fst values above the 95th percentile achieved by simulation under the infinite allele model with 85 populations assumed and an average of 10 haploid genotypes per population (Beaumont & Nichols (Dec. 22, 1996) *Proceedings: Biological Sciences* 263: 1619). Assignment and structure analysis performed with these markers removed did not result in significant changes.

For the phylogenetic tree analysis, individual dogs and wolves were assigned to one of 86 populations based on breed or species. Distances between the populations were computed using the program Microsat (E. Minch, A. Ruiz-Linares, D. Goldstein, M. Feldman, L. L. Cavalli-Sforza (1995, 1996)) with the chord distance measure. 500 bootstrap replicates were generated. Neighbor-joining trees were constructed for each replicate using the program Neighbor, and the program Consense was used to create a majority-rule consensus tree. Both of these programs are part of the Phylip package (Felsenstein (1989) *Cladistics* 5: 164). The wolf population was designated as the outgroup in order to root the tree. Wolves from eight different countries were combined into one population for simplicity on the tree shown in FIG. 2. When taken as individuals, all wolves split off from a single branch, which falls in the same place as the root. The splitting order in the phylogenetic analysis was not correlated with heterozygosity (Table 11), and the twelve breeds that split off first closely mirrored the first cluster identified by structure. These observations argue that the analysis identified a distinct subgroup of genetically related breeds, rather than splitting off idiosyncratic breeds that are unusually inbred or that recently mixed with wild canids.

The assignment test was carried out with the Doh assignment test calculator available from J. Brzustowski as described in Paetkau D. et al., Molecular Ecology 4: 347-354 (1995). All dogs were designated with their known breed except for the one dog to be tested, which was then assigned by the program to the breed with the highest probability of generating the test dog's genotype. The program repeats this procedure with each dog as the test dog. The Belgian Sheepdog and Belgian Tervuren breeds were combined into one designation for this analysis; when they are treated as separate breeds the individual dogs are assigned to one or the other essentially at random.

B. Results

When structure was applied to overlapping subsets of 20-22 breeds at a time, it was observed that most breeds formed distinct clusters consisting solely of all the dogs from that breed, as shown in Table 17. Dogs in only four breeds failed to consistently cluster with others of the same breed: Perro de Presa Canario, German Shorthaired Pointer, Australian Shepherd, and Chihuahua. In addition, six pairs of breeds clustered together in the majority of runs: Belgian Sheepdog and Belgian Tervuren, Collie and Shetland Sheepdog, Whippet and Greyhound, Siberian Husky and Alaskan Malamute, Mastiff and Bullmastiff, and Greater Swiss Mountain Dog and Bernese Mountain Dog. These pairings are expected based on known breed history.

To test whether these closely related breed pairs were nonetheless genetically distinct, structure was applied to each of these clusters. In all but one case the clusters separated into two populations corresponding to the individual breeds, as shown in Table 18. The single exception was the cluster containing Belgian Sheepdogs and Belgian Tervurens. The European and Japanese Kennel Clubs classify them as coat color and length varieties of a single breed (Yamazaki & Yamazaki (1995) *Legacy of the Dog: The Ultimate Illustrated Guide to Over 200 Breeds*, Chronicle Books, San Francisco, Calif.; Wilcox & Walkowicz (1995) *Atlas of Dog Breeds of the World*, T.F.H. Publications, Neptune City, N.J.), and while the American Kennel Club recognizes these as distinct breeds, the breed barrier is apparently too recent or insufficiently strict to have resulted in genetic differentiation. This example confirms that the algorithm only separates groups that have true genetic differences (Falush et al. (2003) *Science* 299:1582-5; Pritchard & Rosenberg (1999) *Am. J. Hum. Genet.* 65:200-8).

To test whether a dog could be assigned to its breed based on genotype data alone, the direct assignment method (Paetkau et al. (1995) *Mol. Ecol.* 4:347-54) with a leave-one-out analysis was used. 99% of individual dogs were correctly assigned to the correct breed. Only four dogs out of 414 were assigned incorrectly: one Beagle (assigned to Perro de Presa Canario), one Chihuahua (assigned to Cairn Terrier), and two German Shorthaired Pointers (assigned to Kuvasz and Standard Poodle, respectively). All four errors involved breeds that did not form single-breed clusters in the structure analysis.

Having demonstrated that modern dog breeds form distinct genetic units, it was attempted to define broader historical relationships among the breeds. First, standard neighbor-joining methods were used to build a majority-rule consensus tree of breeds (FIG. 2), with distances calculated using the chord distance measure (Cavalli-Sforza & Edwards (1967) *Evolution* 32:550), which does not assume a particular mutation model and is thought to perform well for closely related taxa (Goldstein et al. (1995) *Genetics* 139:463). The tree was rooted using wolf samples. The deepest split in the tree separated four Asian spitz-type breeds, and within this branch the Shar-Pei split first, followed by the Shiba Inu, with the Akita and Chow Chow grouping together. The second split separated the Basenji, an ancient African breed. The third split separated two Arctic spitz-type breeds, the Alaskan Malamute and Siberian Husky, and the fourth split separated two Middle Eastern sight hounds, the Afghan and Saluki, from the remaining breeds.

The first four splits exceeded the "majority rule" criterion, appearing in more than half of the bootstrap replicates. In contrast, the remaining breeds showed few consistent phylogenetic relationships, except for close groupings of five breed pairs that also clustered together in the structure analysis, one new pairing of the closely related West Highland White Terrier and Cairn Terrier, and the significant grouping of three Asian companion breeds of similar appearance, the Lhasa Apso, Shih Tzu, and Pekingese. A close relationship among these three breeds was also observed in the structure analysis, with at least two of the three clustering together in a majority of runs. The flat topology of the tree likely reflects a largely common founder stock and occurrence of extensive gene flow between phenotypically dissimilar dogs before the advent of breed clubs and breed barrier rules. In addition, it probably reflects the recreation of some historically older breeds that died out during the famines, depressions and wars of the 19th and 20th centuries, using stock from phenotypically similar or historically related dogs.

While the phylogenetic analysis showed separation of several breeds with ancient origins from a large group of breeds with presumed modern European origins, additional subgroups may be present within the latter group that are not detected by this approach for at least two reasons (Rosenberg et al. (2001) *Genetics* 159:699). First, the true evolutionary history of dog breeds is not well-represented by the bifurcating tree model assumed by the method, but rather involved mixing of existing breeds to create new breeds (a process that continues today). Second, methods based on genetic distance matrices lose information by collapsing all genotype data for pairs of breeds into a single number.

The clustering algorithm implemented in structure was explicitly designed to overcome these limitations (Pritchard et al. (2000) *Am. J. Hum. Genet.* 67:170-81; Falush et al. (2003) *Genetics* 164:1567; Rosenberg et al. (2001) *Genetics* 159:69-713) and has been applied to infer the genetic structure of several species (Rosenberg et al. (2002) *Science* 298:2181-5; Falush et al. (2003) *Science* 299:1582-5; Rosenberg et al. (2001) *Genetics* 159:699-713). Structure was run on the entire data set using increasing values of K (the number of subpopulations the program attempts to find) to identify ancestral source populations. In this analysis, a modern breed could closely mirror a single ancestral population or represent a mixture of two or more ancestral types.

At K=2, one cluster was anchored by the first seven breeds to split in the phylogenetic analysis, while the other cluster contained the large number of breeds with a flat phylogenetic topology (Table 19A). Five runs of the program produced nearly identical results, with a similarity coefficient (Rosenberg et al. (2002) *Science* 298:2381) of 0.99 across runs. Seven other breeds share a sizeable fraction of their ancestry with the first cluster. These fourteen breeds all date to antiquity and trace their ancestry to Asia or Africa. When a diverse set of wolves from eight different countries was included in the analysis, they fell entirely within this cluster (Table 20). The branch leading to the wolf outgroup also fell within this group of breeds in the phylogenetic analysis (FIG. 2).

At K=3, additional structure was detected that was not readily apparent from the phylogenetic tree (Table 19B). The new third cluster consisted primarily of breeds related in heritage and appearance to the Mastiff and is anchored by the Mastiff, Bulldog and Boxer, along with their close relatives the Bullmastiff, French Bulldog, Miniature Bull Terrier and Perro de Presa Canario. Also included in the cluster are the Rottweiler, Newfoundland and Bernese Mountain Dog, large breeds that are reported to have gained their size from ancient Mastiff-type ancestors. Less expected is the inclusion of the German Shepherd Dog. The exact origins of this breed are unknown, but the results suggest that the years spent as a military and police dog in the presence of working dog types, such as the Boxer, are responsible for shaping the genetic background of this popular breed. Three other breeds showed partial and inconsistent membership in this cluster across structure runs (Table 16), which lowered the similarity coefficient to 0.84.

At K=4, a fourth cluster was observed, which included several breeds used as herding dogs: Belgian Sheepdog, Belgian Tervuren, Collie and Shetland Sheepdog (Table 19C). The Irish Wolfhound, Greyhound, Borzoi and Saint Bernard were also frequently assigned to this cluster. While historical records do not suggest that these dogs were ever used to herd livestock, the results suggest that these breeds are either progenitors to, or descendants of, herding types. The breeds in the remaining cluster are primarily of relatively recent European origins, and are mainly different types of hunting dogs: scent hounds, terriers, spaniels, pointers and retrievers. Clustering at K=4 showed a similarity coefficient of 0.61, reflecting similar cluster membership assignments for most breeds but variable assignments for other breeds across runs (Table 16). At K=5 the similarity coefficient dropped to 0.26 and no additional consistent subpopulations were inferred, suggesting lack of additional high-level substructure in the sampled purebred dog population.

The results paint the following picture of the relationships among domestic dog breeds. Different breeds are genetically distinct, and individuals can be readily assigned to breeds based on their genotypes. This level of divergence is surprising given the short time since the origin of most breeds from mixed ancestral stocks and supports strong reproductive isolation within each breed as a result of the breed barrier rule. The results support at least four distinct breed groupings representing separate "adaptive radiations." A subset of breeds with ancient Asian and African origins splits off from the rest of the breeds and shows shared patterns of allele frequencies. At first glance, the inclusion of breeds from Central Africa (Basenji), the Middle East (Saluki and Afghan), as well as Tibet (Tibetan Terrier, Lhasa Apso), China (Chow Chow, Pekingese, Sharpei, Shi Tzu), Japan (Akita, Shiba Inu), and the Arctic (Alaskan Malamute, Siberian Husky, Samoyed) in a single genetic cluster is surprising. However, it is hypothesized that early pariah dogs originated in Asia and migrated with nomadic human groups both south to Africa and north to the Arctic, with subsequent migrations occurring throughout Asia (Savolainen et al. (2002) *Science* 298:1610; Leonard et al. (2002) *Science* 298:1613; Sablin & Khlopachev (2002) *Current Anthropology* 43:795). This cluster includes Nordic breeds that phenotypically resemble the wolf, such as the Alaskan Malamute and Siberian Husky, and shows the closest genetic relationship to the wolf, which is the direct ancestor of domestic dogs. Thus dogs from these breeds may be the best living representatives of the ancestral dog gene pool. It is notable that several breeds commonly believed to be of ancient origin are not included in this group, for example the Pharaoh Hound and Ibizan Hound. These are often thought to be the oldest of all dog breeds, descending directly from the ancient Egyptian dogs drawn on tomb walls more than 5000 years ago. The results indicate, however, that these two breeds have been recreated in more recent times from combinations of other breeds. Thus, while their appearance matches the ancient Egyptian sight hounds, their genomes do not. Similar conclusions apply to the Norwegian Elkhound, which clusters with modern European breeds rather than with the other Arctic dogs, despite reports of direct descent from Scandinavian origins over 5000 years ago (American Kennel Club (1998) *The Complete Dog Book*, eds. Crowley & Adelman, Howell Book House, New York, N.Y.; Wilcox & Walkowicz (1995) *Atlas of Dog Breeds of the World*, T.F.H. Publications, Neptune City, N.J.).

The large majority of breeds appears to represent a more recent radiation from shared European stock. While the individual breeds are genetically differentiated, they appear to have diverged at essentially the same time. This radiation probably reflects the proliferation of distinct breeds from less codified phenotypic varieties following the introduction of the breed concept and the creation of breed clubs in Europe in the 1800s. A more sensitive cluster analysis is able to discern additional genetic structure of three subpopulations within this group. One contains Mastiff-like breeds and appears to reflect shared morphology derived from a common ancestor. Another includes Shetland Sheep Dog, the two Belgian Sheepdogs, and Collie, and may reflect shared ancestral herding behavior. The remaining population is dominated by a proliferation of breeds dedicated to various aspects of the hunt. For these breeds, historical and breed club records suggest highly intertwined bloodlines, consistent with the results obtained.

Dog breeds have traditionally been grouped on the basis of their roles in human activities, physical phenotypes, and historical records. The results described above provide an independent classification based on patterns of genetic variation. This classification supports a subset of traditional groupings and also reveals previously unrecognized connections among breeds. An accurate understanding of the genetic relationships among breeds lays the foundation for studies aimed at uncovering the complex genetic basis of breed differences in morphology, behavior, and disease susceptibility.

Example 5

This example describes an in silico method for estimating the contribution of parent, grandparent and great-grandparent canids from different canid populations to the genomes of mixed progeny canids using microsatellite markers.

A. Methods

1. Dataset

Dataset 4 included genotype information for 95 markers from 85 canids, consisting of 81 dogs from 18 different dog breeds and 4 wolves (AHRT, AKIT, BEAG, BMD, BOX, BULD, BULM, CHIH, DACH, GOLD, IBIZ, MAST, NEWF, PEKE, POM, PRES, PUG, ROTT, WOLF, see Table 5 for abbreviations of canid populations). The 95 microsatellite markers were microsatellite markers 1-14, 16, 18-21, 23-36, 39-100 (Table 1). This dataset was chosen on the basis of the fact that greater than 90% of each of the 85 canids' genome was assigned to the correct breed. The four wolves were designated as one canid population. 12 breeds were represented by 5 dogs each, 3 breeds by 4 dogs, and 3 breeds by 3 dogs, as shown in Table 9. The genotypes for each of the microsatellite markers used in each canid are set forth in Table 3 (filed herewith on a compact disc).

2. Cluster Analyses

In silico canid mixes were created by randomly drawing one of the two alleles from each parent at each locus and designating them as the mix's alleles at that locus. An F1 mix was produced by an in silico mixing of alleles of two of the original 81 canids. An N2 mix was then produced by in silico mixing the F1 with one of its two parents, and an N3 mix was produced by in silico mixing the N2 with that same parent.

Three types of mixes were formed, test mixes, control mixes, and grandparent mixes. In the test mixes, the two parents were selected from two different breeds, chosen at random. 100 F1, N2, and N3 mixes were formed. Note that an F1 mix has two parents from different breeds, an N2 mix has three of four grandparents from one breed and one from another, and an N3 mix has seven of eight great-grandparents from one breed and one from another.

In the control mixes, the two parents were chosen from the same breed and 100 F1, N2, and N3 mixes were formed by the same procedure. Note that these all correspond to pure-bred dogs from the chosen breed.

Several grandparent mixes were also formed by choosing the four grandparents from 4 different breeds.

All the 300 test mixes were run together in a run of structure with the 85 chosen canids. The same analysis was performed for the control mixes, and for the 4 grandparent mixes. The program was run with the following parameter settings: #define NUMINDS 395; #define NUMLOCI 95; #define LABEL 1; #define POPDATA 1; #define POPFLAG 1; #define PHENOTYPE 0; #define MARKERNAMES 0; #define MAPDISTANCES 0; #define ONEROWPERIND 1; #define PHASEINFO 0; #define PHASED 0; #define EXTRACOLS 0; #define MISSING 0; #define PLOIDY 2; #define MAXPOPS 19; #define BURNIN 5000; #define NUMREPS 5000; #define USEPOPINFO 1; #define GENSBACK 0; #define MIGRPRIOR 0.0; #define NOADMIX 0; #define LINKAGE 0; #define INFERALPHA 1; #define ALPHA 1.0; #define POPALPHAS 0; #define UNIFPRIORALPHA 1; #define ALPHAMAX 10.0; #define ALPHAPROPSD 0.025; #define FREQSCORR 1; #define ONEFST 0; #define FPRIORMEAN 0.01; #define FPRIORSD 0.05; #define INFERLAMBDA 0; #define LAMBDA 1; #define COMPUTEPROB 1; #define PFROMPOPFLAGONLY 0; #define ANCESTDIST 1; #define NUMBOXES 1000; #define ANCESTPINT 0.95; #define STARTATPOPINFO 1; #define METROFREQ 10; #define UPDATEFREQ 1; #define PRINTQHAT 1.

Each of the 85 canids was designated as belonging to its appropriate breed, and the mixes were not assigned to any breed.

B. Results

For the control mixes, each mix was always assigned by the program to the correct breed, and the fraction of the genome assigned to that breed exceeded 95% in all 300 cases (the minimum was 95.75%), 98% in 297 cases, and 99% in 266 cases. Therefore, assignment of <95% of genome to a single breed provided unambiguous detection of mixing for the test mixes, and assignment of <98% provides strong evidence of mixing at the 0.99 confidence level.

For the F1 test mixes, all 100 mixes were correctly assigned genome contributions from the two parent breeds, with contributions of each breed ranging from 28% to 70%. In 82 of 100 cases each of the two parent breeds was assigned a contribution of >40% and <60%. This shows that mixes between two breeds can be reliably identified 100% of the time at the parent level.

For the N2 test mixes, 0.99 of 100 cases had <98% of the genome assigned to one breed, and 97 of 100 cases had <95% of the genome assigned to one breed, showing highly accurate ability to detect mixing at the grandparent level. In all but one case where mixing was detected, both breeds contributing to the mix were accurately identified (in one case the breed contributing one of the 4 grandparents was not detected as contributing significantly). In 80-85% of the cases, the N2 mixes could be reliably discriminated from F1 mixes (that is, it could be determined that the mixing occurred at the level of grandparents and not parents).

For the N3 test mixes, 85 of 100 cases had <98% of the genome assigned to one breed, and 77 of 100 cases had <95% of the genome assigned to one breed, showing fairly good ability to detect mixing at the great-grandparent level. In all cases where mixing was detected, both breeds contributing to the mix were accurately identified. In all cases, the N3 mixes could be reliably discriminated from F1 mixes (that is, it could be determined that the mixing occurred at the level of great-grandparents and not parents), but there was less ability to distinguish between mixes at the grandparent and great-grandparent levels.

Finally, for mixes with four different grandparents, all four grandparent breeds were reliably identified, with contributions of each breed to the genome of the mix estimated in the 20-30% range.

These results clearly demonstrate the ability of the method to discriminate mixes at the parent and grandparent level from pure-bred dogs (as well as ½ wolf and ¼ wolf mixes from dogs), with some ability to discriminate mixes at the great-grandparent level. The method also accurately identifies breed contributions in the genome of a mixed-breed dog. Larger databases containing more dogs from each breed, as well as additional markers and optimized sets of markers chosen according to criteria described elsewhere in this application, permits more accurate discrimination of mixing at the level of great-grandparents and, by straightforward extension, mixing that occurred in more distant ancestors.

Example 6

This example describes a representative method of the invention for estimating the contribution of canid populations to the genome of test canids using SNP markers.

A. Methods

1. Dataset

A dataset of single nucleotide polymorphisms (SNPs) in a variety of dog breeds was used to calculate the frequency of each allele in each breed. The database contained genotype information for 100 SNPs from 189 canids representing 67 breeds, with two to eleven purebred dogs per breed, as described in EXAMPLE 1. The identities of alleles in the dogs are set forth in Table 4 (filed herewith on a compact disc).

2. Doh Analysis

Using a leave-one-out procedure each dog was temporarily removed from the database and assigned to a breed based on comparison of the dog's genotypes to allele frequencies of each breed. Bayes' Theorem was used for the assignment: the probability that a dog comes from a given breed is the conditional probability that the observed genotype would occur in a dog of that breed divided by the sum of conditional probabilities that the observed genotype would occur for every breed in the database (essentially as described in Cornuet et al. (1999) *Genetics* 153:1989-2000). Software was developed to implement this algorithm. Breeds with only two individuals were included in the database but no attempt was made to classify their members because temporarily removing one of the two members did not leave enough information to calculate reliable allele frequencies.

B. Results

The output of this analysis was, for each dog, a list of the probabilities that the dog had come from each breed in the database, as shown in Table 21. Eighty percent of dogs were assigned to the correct breed with a probability of 99% or greater. For breeds in which genotypes were obtained for five or more individuals, 88% of the dogs were assigned to the correct breed with 99 percent probability. Fourteen dogs (sixteen percent of the total tested) were not assigned to the correct breed with better than 65% probability. Of these, thirteen were assigned incorrectly with a probability of fifty percent or better, nearly three-quarters with a probability of greater than ninety percent. The remaining dog was assigned 20-45% probabilities of coming from several breeds, one of which was correct.

These results demonstrate the feasibility of breed assignment based on SNP markers. Performance may be improved by generating SNP genotype profiles for a larger number of dogs (5 or more from each breed), using a larger set of SNPs, and selecting SNPs to be maximally informative. SNPs can be selected for inclusion in the panel both based on having a high heterozygosity across breeds (i.e., both alleles occur at high frequency) and based on large differences in frequency between breeds.

Example 7

This example describes a naive Bayesian classification model for estimating the contribution of parent and grandparent canids from different canid populations to the genomes of mixed progeny canids using microsatellite markers.

A. Methods

1. Dataset

Dataset 5 included genotype information for 96 markers from 429 canids representing 88 breeds (ACKR, AFGH, AHRT, AIRT, AKIT, AMAL, AMWS, ASBT, AUSS, AUST, BASS, BEAG, BEDT, BELS, BICH, BLDH, BMD, BORD, BORZ, BOX, BRIA, BSJI, BULD, BULM, CAIR, CHBR, CHIH, CHOW, CKCS, CLSP, COLL, DACH, DANE, DOBP, ECKR, FBLD, FCR, GOLD, GREY, GSD, GSHP, GSMD, GSNZ, HUSK, IBIZ, IRSE, IRTR, ITGR, IWOF, KEES, KERY, KOMO, KUVZ, LAB, LHSA, MAST, MBLT, MNTY, MSNZ, NELK, NEWF, OES, PEKE, PHAR, PNTR, POM, PRES, PTWD, PUG, RHOD, ROTT, SALU, SAMO, SCHP, SCWT, SHAR, SHIB, SHIH, SPOO, SSHP, SSNZ, STBD, TIBT, TERV, TPOO, WHIP, WHWT, WSSP, see Table 5 for abbreviations of canid populations). The 96 microsatellite markers were microsatellite markers 1-9, 11-38, 40-42, 44-75, 77-100 (Table 1). The genotype information for the canids in this dataset is set forth in Table 3 (filed herewith on a compact disc).

Dataset 6 included genotype information for 72 of the markers in Table 1 from 160 mixed-breed canids with known admixture composition. The genotype information for the mixed-breed canids in this dataset is set forth in Table 3 (filed herewith on a compact disc).

2. Analyses

A naïve Bayesian classification model was developed that incorporates linked and unlinked microsatellite loci information, higher-dimensioned ancestral populations, and higher-ordered generation pedigrees for the probabilistic assignment of individuals to mixtures of ancestral subpopulations. Two- and three-generational models were implemented for exact admixture detection and assignment, simultaneously addressing the generation, subpopulation and linkage limitations of previous models.

The 2-generational model closely follows the model outlined in Anderson & Thompson (2002) *Genetics* 160:1217-29, with extensions for greater than two classes of "pure" subpopulations. For the L unlinked loci, we have N subpopulations (deemed breeds), and $j_l$ alleles at the $l^{th}$ locus. For each individual at the L loci, we have a genotype: $(g_l^{(0)}, g_l^{(1)})$. Aggregating subpopulation allele information provides information about the frequency of any given allele, denoted as $f_{lj}^{(t)}$. Thus for individual, non-admixed subpopulation assignments we have:

$$P(g|\text{breed } i) = \prod_{l=1}^{L} f_{1g_l^{(0)}}^{(i)} f_{1g_l^{(1)}}^{(i)} \text{ and } P(\text{breed } i|g)$$

$$= \frac{P(g|\text{breed } i)P(\text{breed } i)}{\sum_{i=1}^{N} P(g|\text{breed } i)P(\text{breed } i)}.$$

For a parental mixture assignment we now have:

$$P(g|b1 \text{ paternal}, b2 \text{ maternal}) =$$

$$\prod_{l=1}^{L} \left\{ \left( f_{1g_l^{(0)}}^{(b_1)} f_{1g_l^{(1)}}^{(b_2)} + f_{1g_l^{(0)}}^{(b_2)} f_{1g_l^{(1)}}^{(b_1)} \right) I(g_l^{(0)} \neq g_l^{(1)}) + f_{1g_l}^{(b_1)} f_{1g_l}^{(b_2)} I(g_l^{(0)} = g_l^{(1)}) \right\}$$

where superscripts of (0) denote paternal relations and (1) denote maternal relations (with obvious interchangeability options).

The 3-generation model allows the extension of the model to consider 4-subpopulation, 2-generation representation across the N subpopulations:

$$P(g|(b1 \times b2) \times (b3 \times b4)) =$$

$$\prod_{l=1}^{L} \left\{ \left[ \left( .5 f_{1g_l^{(0)}}^{(b_1)} + .5 f_{1g_l^{(0)}}^{(b_2)} \right) \left( .5 f_{1g_l^{(1)}}^{(b_3)} + .5 f_{1g_l^{(1)}}^{(b_4)} \right) + \left( .5 f_{1g_l^{(0)}}^{(b_1)} + .5 f_{1g_l^{(0)}}^{(b_2)} \right) \right. \right.$$

-continued $$\left. \left( .5 f_{1g_l^{(1)}}^{(b_3)} + .5 f_{1g_l^{(1)}}^{(b_4)} \right) \right] I(g_l^{(0)} \neq g_l^{(1)}) +$$

$$\left. \left( .5 f_{1g_l}^{(b_1)} + .5 f_{1g_l}^{(b_2)} \right) \left( .5 f_{1g_l}^{(b_3)} + .5 f_{1g_l}^{(b_4)} \right) I(g_l^{(0)} = g_l^{(1)}) \right\}$$

Exhaustive searches for the mixtures with the highest posterior probability are possible for 2- and 3-generation models.

For the in silico individuals, model validation was performed via a leave-one-out cross validation, where sampled alleles used in creating the in silico mixed-breed individual are removed from the ancestral population and allele frequencies are updated prior to maximum likelihood mixture proportion assignment.

B. Results

Analysis on in-silico mixed-breed individuals across all 96 dinucleotide markers show that the model at 2- and 3-generations performs exceedingly well with 98.4% of F1 mixes and 94.3% of F2 mixes correctly assigned, with no obvious patterns for breed-specific deficits. Analysis on the 160 known mixed-breed individuals genotyped at 72 of the 96 dinucleotide markers show that the model at 2- and 3-generations performs nearly as accurately with 96.2% of F1 mixes and 91.8% of F2 mixes correctly assigned.

While the preferred embodiment of the invention has been illustrated and described, it will be appreciated that various changes can be made therein without departing from the spirit and scope of the invention.

TABLE 1

Microsatellite Markers

| | Marker Name | Forward Primer | Reverse Primer | Reference | Ann. Temp. (° C.) | PIC |
|---|---|---|---|---|---|---|
| 1 | REN285G14 | SEQ ID NO: 1 | SEQ ID NO: 101 | 1[a] | 55 | NA |
| 2 | C01.673 | SEQ ID NO: 2 | SEQ ID NO: 102 | 1 | 58 | 0.36 |
| 3 | REN112I02 | SEQ ID NO: 3 | SEQ ID NO: 103 | 1 | 58 | 0.76 |
| 4 | REN172C02 | SEQ ID NO: 4 | SEQ ID NO: 104 | 1 | 55 | 0.48 |
| 5 | FH2793 | SEQ ID NO: 5 | SEQ ID NO: 105 | 2[b] | 58 | 0.76 |
| 6 | REN143K19 | SEQ ID NO: 6 | SEQ ID NO: 106 | 1 | 55 | 0.5 |
| 7 | FH2890 | SEQ ID NO: 7 | SEQ ID NO: 107 | 2 | 55 | 0.59 |
| 8 | C02.466 | SEQ ID NO: 8 | SEQ ID NO: 108 | 1 | 58 | 0.55 |
| 9 | C02.894 | SEQ ID NO: 9 | SEQ ID NO: 109 | 1 | 58 | 0.72 |
| 10 | C02.342 | SEQ ID NO: 10 | SEQ ID NO: 110 | 1 | | 0.77 |
| 11 | FH2895 | SEQ ID NO: 11 | SEQ ID NO: 111 | 2 | 58 | 0.7 |
| 12 | REN157C08 | SEQ ID NO: 12 | SEQ ID NO: 112 | 1 | 55 | 0.72 |
| 13 | C03.445 | SEQ ID NO: 13 | SEQ ID NO: 113 | 1 | 58 | 0.6 |
| 14 | FH2732 | SEQ ID NO: 14 | SEQ ID NO: 114 | 2 | 58 | 0.84 |
| 15 | FH2776 | SEQ ID NO: 15 | SEQ ID NO: 115 | 2 | 58 | 0.49 |
| 16 | REN160J02 | SEQ ID NO: 16 | SEQ ID NO: 116 | 1 | 58 | 0.82 |
| 17 | REN262N08 | SEQ ID NO: 17 | SEQ ID NO: 117 | 1 | 55 | 0.72 |
| 18 | REN92G21 | SEQ ID NO: 18 | SEQ ID NO: 118 | 1 | 58 | 0.66 |
| 19 | REN285I23 | SEQ ID NO: 19 | SEQ ID NO: 119 | 1 | 55 | 0.58 |
| 20 | C05.414 | SEQ ID NO: 20 | SEQ ID NO: 120 | 1 | 58 | 0.47 |
| 21 | FH2752 | SEQ ID NO: 21 | SEQ ID NO: 121 | 2 | 58 | 0.38 |
| 22 | REN210I14 | SEQ ID NO: 22 | SEQ ID NO: 122 | 1 | 55 | 0.66 |
| 23 | REN37H09 | SEQ ID NO: 23 | SEQ ID NO: 123 | 3[c] | 58 | 0.67 |
| 24 | REN97M11 | SEQ ID NO: 24 | SEQ ID NO: 124 | 1 | 55 | NA |
| 25 | REN286L19 | SEQ ID NO: 25 | SEQ ID NO: 125 | 1 | 58 | 0.66 |
| 26 | FH2860 | SEQ ID NO: 26 | SEQ ID NO: 126 | 2 | 55 | 0.62 |
| 27 | REN204K13 | SEQ ID NO: 27 | SEQ ID NO: 127 | 1 | 55 | 0.48 |
| 28 | C08.373 | SEQ ID NO: 28 | SEQ ID NO: 128 | 1 | 58 | 0.68 |
| 29 | C08.618 | SEQ ID NO: 29 | SEQ ID NO: 129 | 1 | 55 | 0.82 |
| 30 | C09.173 | SEQ ID NO: 30 | SEQ ID NO: 130 | 1 | 58 | 0.78 |
| 31 | C09.474 | SEQ ID NO: 31 | SEQ ID NO: 131 | 1 | 55 | 0.78 |
| 32 | FH2885 | SEQ ID NO: 32 | SEQ ID NO: 132 | 2 | 55 | 0.74 |
| 33 | C10.781 | SEQ ID NO: 33 | SEQ ID NO: 133 | 1 | 55 | 0.62 |

TABLE 1-continued

Microsatellite Markers

| | Marker Name | Forward Primer | Reverse Primer | Reference | Ann. Temp. (° C.) | PIC |
|---|---|---|---|---|---|---|
| 34 | REN73F08 | SEQ ID NO: 34 | SEQ ID NO: 134 | 1 | 55 | 0.54 |
| 35 | REN154G10 | SEQ ID NO: 35 | SEQ ID NO: 135 | 1 | 55 | 0.71 |
| 36 | REN164B05 | SEQ ID NO: 36 | SEQ ID NO: 136 | 1 | 55 | 0.5 |
| 37 | FH2874 | SEQ ID NO: 37 | SEQ ID NO: 137 | 2 | 55 | NA |
| 38 | C11.873 | SEQ ID NO: 38 | SEQ ID NO: 138 | 1 | 58 | 0.81 |
| 39 | REN258L11 | SEQ ID NO: 39 | SEQ ID NO: 139 | 1 | | 0.72 |
| 40 | REN213F01 | SEQ ID NO: 40 | SEQ ID NO: 140 | 1 | 55 | 0.82 |
| 41 | REN208M20 | SEQ ID NO: 41 | SEQ ID NO: 141 | 1 | 58 | 0.64 |
| 42 | REN94K11 | SEQ ID NO: 42 | SEQ ID NO: 142 | 1 | 55 | 0.56 |
| 43 | REN120P21 | SEQ ID NO: 43 | SEQ ID NO: 143 | 1 | | 0.5 |
| 44 | REN286P03 | SEQ ID NO: 44 | SEQ ID NO: 144 | 1 | 58 | 0.78 |
| 45 | C13.758 | SEQ ID NO: 45 | SEQ ID NO: 145 | 1 | 55 | 0.75 |
| 46 | C14.866 | SEQ ID NO: 46 | SEQ ID NO: 146 | 1 | 55 | 0.74 |
| 47 | FH3072 | SEQ ID NO: 47 | SEQ ID NO: 147 | 2 | 55 | 0.63 |
| 48 | FH3802 | SEQ ID NO: 48 | SEQ ID NO: 148 | 2 | 55 | 0.44 |
| 49 | REN06C11 | SEQ ID NO: 49 | SEQ ID NO: 149 | 3 | 58 | 0.79 |
| 50 | REN144M10 | SEQ ID NO: 50 | SEQ ID NO: 150 | 1 | 58 | 0.66 |
| 51 | REN85N14 | SEQ ID NO: 51 | SEQ ID NO: 151 | 1 | 58 | 0.78 |
| 52 | FH3096 | SEQ ID NO: 52 | SEQ ID NO: 152 | 2 | 55 | 0.79 |
| 53 | C17.402 | SEQ ID NO: 53 | SEQ ID NO: 153 | 1 | 58 | 0.75 |
| 54 | REN50B03 | SEQ ID NO: 54 | SEQ ID NO: 154 | 3 | 58 | 0.74 |
| 55 | REN112G10 | SEQ ID NO: 55 | SEQ ID NO: 155 | 1 | 55 | 0.7 |
| 56 | REN186N13 | SEQ ID NO: 56 | SEQ ID NO: 156 | 1 | 58 | 0.66 |
| 57 | FH2795 | SEQ ID NO: 57 | SEQ ID NO: 157 | 2 | 58 | 0.71 |
| 58 | C18.460 | SEQ ID NO: 58 | SEQ ID NO: 158 | 1 | 58 | 0.53 |
| 59 | FH2783 | SEQ ID NO: 59 | SEQ ID NO: 159 | 2 | 55 | NA |
| 60 | REN91I14 | SEQ ID NO: 60 | SEQ ID NO: 160 | 1 | 58 | 0.72 |
| 61 | REN274F18 | SEQ ID NO: 61 | SEQ ID NO: 161 | 1 | 58 | 0.66 |
| 62 | FH2887 | SEQ ID NO: 62 | SEQ ID NO: 162 | 2 | 55 | 0.77 |
| 63 | FH3109 | SEQ ID NO: 63 | SEQ ID NO: 163 | 2 | 58 | 0.62 |
| 64 | REN293N22 | SEQ ID NO: 64 | SEQ ID NO: 164 | 1 | 58 | 0.48 |
| 65 | FH2914 | SEQ ID NO: 65 | SEQ ID NO: 165 | 2 | 55 | 0.61 |
| 66 | FH3069 | SEQ ID NO: 66 | SEQ ID NO: 166 | 2 | 55 | 0.53 |
| 67 | REN49F22 | SEQ ID NO: 67 | SEQ ID NO: 167 | 3 | 55 | 0.66 |
| 68 | REN107H05 | SEQ ID NO: 68 | SEQ ID NO: 168 | 1 | 55 | 0.86 |
| 69 | REN78I16 | SEQ ID NO: 69 | SEQ ID NO: 169 | 1 | 55 | 0.63 |
| 70 | FH3078 | SEQ ID NO: 70 | SEQ ID NO: 170 | 2 | 55 | 0.67 |
| 71 | C23.277 | SEQ ID NO: 71 | SEQ ID NO: 171 | 1 | 55 | 0.54 |
| 72 | REN181K04 | SEQ ID NO: 72 | SEQ ID NO: 172 | 1 | 58 | 0.64 |
| 73 | REN106I06 | SEQ ID NO: 73 | SEQ ID NO: 173 | 1 | 55 | 0.58 |
| 74 | FH3083 | SEQ ID NO: 74 | SEQ ID NO: 174 | 2 | 55 | 0.61 |
| 75 | REN54E19 | SEQ ID NO: 75 | SEQ ID NO: 175 | 1 | 55 | 0.54 |
| 76 | C25.213 | SEQ ID NO: 76 | SEQ ID NO: 176 | 1 | | 0.78 |
| 77 | REN87O21 | SEQ ID NO: 77 | SEQ ID NO: 177 | 1 | 55 | 0.62 |
| 78 | C26.733 | SEQ ID NO: 78 | SEQ ID NO: 178 | 1 | 55 | 0.61 |
| 79 | C27.442 | SEQ ID NO: 79 | SEQ ID NO: 179 | 1 | 55 | 0.74 |
| 80 | C27.436 | SEQ ID NO: 80 | SEQ ID NO: 180 | 1 | 55 | 0.51 |
| 81 | REN72K15 | SEQ ID NO: 81 | SEQ ID NO: 181 | 1 | 55 | 0.66 |
| 82 | FH2759 | SEQ ID NO: 82 | SEQ ID NO: 182 | 2 | 55 | 0.71 |
| 83 | FH2785 | SEQ ID NO: 83 | SEQ ID NO: 183 | 2 | 55 | 0.46 |
| 84 | REN239K24 | SEQ ID NO: 84 | SEQ ID NO: 184 | 1 | 55 | 0.78 |
| 85 | FH3082 | SEQ ID NO: 85 | SEQ ID NO: 185 | 2 | 55 | 0.54 |
| 86 | REN51C16 | SEQ ID NO: 86 | SEQ ID NO: 186 | 4[d] | 55 | 0.8 |
| 87 | FH3053 | SEQ ID NO: 87 | SEQ ID NO: 187 | 2 | 55 | 0.74 |
| 88 | REN43H24 | SEQ ID NO: 88 | SEQ ID NO: 188 | 3 | 55 | 0.66 |
| 89 | FH2712 | SEQ ID NO: 89 | SEQ ID NO: 189 | 2 | 55 | 0.67 |
| 90 | FH2875 | SEQ ID NO: 90 | SEQ ID NO: 190 | 2 | 55 | 0.6 |
| 91 | FH2790 | SEQ ID NO: 91 | SEQ ID NO: 190 | 2 | 55 | 0.58 |
| 92 | REN291M20 | SEQ ID NO: 92 | SEQ ID NO: 192 | 1 | 58 | 0.76 |
| 93 | REN160M18 | SEQ ID NO: 93 | SEQ ID NO: 193 | 1 | 58 | 0.76 |
| 94 | FH3060 | SEQ ID NO: 94 | SEQ ID NO: 194 | 2 | 55 | 0.4 |
| 95 | REN314H10 | SEQ ID NO: 95 | SEQ ID NO: 195 | 1 | 55 | 0.54 |
| 96 | REN01G01 | SEQ ID NO: 96 | SEQ ID NO: 196 | 3 | 55 | 0.54 |
| 97 | REN112C08 | SEQ ID NO: 97 | SEQ ID NO: 197 | 1 | 55 | 0.42 |
| 98 | REN106I07 | SEQ ID NO: 98 | SEQ ID NO: 198 | 1 | 55 | 0.78 |
| 99 | FH2708 | SEQ ID NO: 99 | SEQ ID NO: 199 | 2 | 55 | 0.63 |
| 100 | REN86G15 | SEQ ID NO: 100 | SEQ ID NO: 200 | 1 | 55 | 0.76 |

[a]Breen et al. (2001) Genome Res. 11: 1784–95.
[b]Guyon et al. (2003) Proc. Natl. Acad. Sci. U.S.A. 100(9): 5296–301.
[c]Jouquand et al. (2000) Animal Genetics 31: 266–72.
[d]Mellersh et al. (2000) Mamm. Genome 11: 120–30.

TABLE 2

SNP Markers

| BAC | Forward Primer | Reverse Primer | SNP* | Major Allele | Minor Allele | Minor Allele Frequency** | Heterozygosity** |
|---|---|---|---|---|---|---|---|
| 372-c5t (SEQ ID NO: 202) | SEQ ID NO: 244 | SEQ ID NO: 286 | 82 | C | T | 0.004 | 0.009 |
| | | | 133 | T | C | ND | ND |
| 372-c15t (SEQ ID NO: 203) | SEQ ID NO: 245 | SEQ ID NO: 287 | 285 | G | A | 0.013 | 0.025 |
| 372-e2s (SEQ ID NO: 204) | SEQ ID NO: 246 | SEQ ID NO: 288 | 271 | G | T | 0.029 | 0.057 |
| | | | 257 | C | T | 0.071 | 0.132 |
| | | | 128 | C | G | 0.046 | 0.087 |
| | | | 93 | C | G | 0.021 | 0.041 |
| | | | 50 | A | — | ND | ND |
| 372-e13t (SEQ ID NO: 205) | SEQ ID NO: 247 | SEQ ID NO: 289 | 57 | T | C | 0.004 | 0.008 |
| 372-e15t (SEQ ID NO: 206) | SEQ ID NO: 248 | SEQ ID NO: 290 | 312 | — | A | ND | ND |
| | | | 301 | C | T | ND | ND |
| | | | 258 | C | T | 0.009 | 0.018 |
| | | | 156 | — | T | ND | ND |
| 372-e16s (SEQ ID NO: 207) | SEQ ID NO: 249 | SEQ ID NO: 291 | 254 | G | A | ND | ND |
| 372-e18t (SEQ ID NO: 208) | SEQ ID NO: 250 | SEQ ID NO: 292 | 165 | G | C | 0.254 | 0.379 |
| 372-g17t (SEQ ID NO: 209) | SEQ ID NO: 251 | SEQ ID NO: 293 | 66 | T | A | 0.134 | 0.232 |
| 372-i23s (SEQ ID NO: 210) | SEQ ID NO: 252 | SEQ ID NO: 294 | 384 | A | G | 0.312 | 0.429 |
| 372-m6t (SEQ ID NO: 211) | SEQ ID NO: 253 | SEQ ID NO: 295 | 138 | C | A | 0.275 | 0.399 |
| | | | 88 | T | C | 0.004 | 0.009 |
| | | | 266 | T | G | ND | ND |
| 372-m7s (SEQ ID NO: 212) | SEQ ID NO: 254 | SEQ ID NO: 296 | 317 | T | A | ND | ND |
| 372-m9t (SEQ ID NO: 213) | SEQ ID NO: 255 | SEQ ID NO: 297 | 108 | A | T | 0.368 | 0.465 |
| | | | 58 | G | C | 0.362 | 0.462 |
| 372-m18t (SEQ ID NO: 214) | SEQ ID NO: 256 | SEQ ID NO: 298 | 170 | — | T | ND | ND |
| | | | 129 | G | A | 0.159 | 0.267 |
| 372-m23t (SEQ ID NO: 215) | SEQ ID NO: 257 | SEQ ID NO: 299 | 76 | C | T | 0.017 | 0.034 |
| | | | 108 | G | A | 0.081 | 0.149 |
| | | | 229 | G | A | 0.078 | 0.143 |
| | | | 238 | T | C | 0.078 | 0.143 |
| | | | 263 | A | G | 0.157 | 0.265 |
| 372-o13s (SEQ ID NO: 216) | SEQ ID NO: 258 | SEQ ID NO: 300 | 212 | T | C | 0.316 | 0.433 |
| 373-a10s (SEQ ID NO: 217) | SEQ ID NO: 259 | SEQ ID NO: 301 | 274 | T | C | 0.131 | 0.228 |
| 373-a15t (SEQ ID NO: 218) | SEQ ID NO: 260 | SEQ ID NO: 302 | 112 | G | A | 0.004 | 0.008 |
| 373-a17t (SEQ ID NO: 219) | SEQ ID NO: 261 | SEQ ID NO: 303 | 73 | G | A | ND | ND |
| | | | 136 | A | G | 0.394 | 0.477 |
| 373-a21s (SEQ ID NO: 220) | SEQ ID NO: 262 | SEQ ID NO: 304 | 89 | C | T | 0.017 | 0.034 |
| 373-c13s (SEQ ID NO: 221) | SEQ ID NO: 263 | SEQ ID NO: 305 | 93 | C | T | 0.028 | 0.054 |
| 373-c15t (SEQ ID NO: 222) | SEQ ID NO: 264 | SEQ ID NO: 306 | 242 | C | T | 0.209 | 0.331 |
| | | | 202 | C | T | 0.174 | 0.288 |
| | | | 131 | — | AA | ND | ND |
| 373-e1t (SEQ ID NO: 223) | SEQ ID NO: 265 | SEQ ID NO: 307 | 50 | T | C | 0.009 | 0.019 |
| | | | 102 | | Del. 8 bp | ND | ND |
| | | | 130 | G | A | 0.01 | 0.02 |
| 373-e21t (SEQ ID NO: 224) | SEQ ID NO: 266 | SEQ ID NO: 308 | 282 | A | G | 0.049 | 0.093 |
| | | | 116 | C | T | 0.215 | 0.338 |
| 373-g7t (SEQ ID NO: 225) | SEQ ID NO: 267 | SEQ ID NO: 309 | 243 | C | T | 0.014 | 0.028 |
| | | | 242 | G | A | ND | ND |
| | | | 84 | T | — | ND | ND |
| 373-g19t (SEQ ID NO: 226) | SEQ ID NO: 268 | SEQ ID NO: 310 | 249 | — | A | ND | ND |
| | | | 251 | A | — | ND | ND |
| | | | 246 | G | A | 0.004 | 0.008 |
| | | | 224 | T | C | ND | ND |
| | | | 378 | A | C | 0.082 | 0.15 |
| 373-i8s (SEQ ID NO: 227) | SEQ ID NO: 269 | SEQ ID NO: 311 | 199 | A | C | 0.073 | 0.136 |
| | | | 224 | G | A | 0.004 | 0.009 |
| 373-i16s (SEQ ID NO: 228) | SEQ ID NO: 270 | SEQ ID NO: 312 | 312 | A | G | 0.078 | 0.144 |
| | | | 254 | G | A | 0.24 | 0.365 |
| | | | 250 | C | T | 0.079 | 0.146 |
| | | | 249 | C | T | 0.031 | 0.06 |
| 373-k8s (SEQ ID NO: 229) | SEQ ID NO: 271 | SEQ ID NO: 313 | 181 | C | T | 0.005 | 0.009 |
| | | | 224 | | Del. 2 bp | ND | ND |
| 373-k10t (SEQ ID NO: 230) | SEQ ID NO: 272 | SEQ ID NO: 314 | 261 | A | C | 0.353 | 0.457 |
| | | | 264 | T | C | 0.008 | 0.017 |
| 372-c5s (SEQ ID NO: 231) | SEQ ID NO: 273 | SEQ ID NO: 315 | 112 | A | G | 0.357 | 0.459 |
| | | | 168 | A | G | 0.01 | 0.02 |
| 372-c15s (SEQ ID NO: 232) | SEQ ID NO: 274 | SEQ ID NO: 316 | 121 | T | C | 0.017 | 0.034 |
| | | | 196 | G | A | 0.004 | 0.009 |
| 372-e15s (SEQ ID NO: 233) | SEQ ID NO: 275 | SEQ ID NO: 317 | 67 | A | G | 0.186 | 0.303 |
| | | | 71 | A | C | 0.013 | 0.026 |
| | | | 165 | G | A | 0.105 | 0.188 |
| | | | 221 | C | A | 0.189 | 0.307 |
| 372-i23t (SEQ ID NO: 234) | SEQ ID NO: 276 | SEQ ID NO: 318 | 97 | A | G | 0.119 | 0.21 |
| | | | 224 | — | T | ND | ND |

TABLE 2-continued

SNP Markers

| BAC | Forward Primer | Reverse Primer | SNP* | Major Allele | Minor Allele | Minor Allele Frequency** | Heterozygosity** |
|---|---|---|---|---|---|---|---|
| 372-m6s (SEQ ID NO: 235) | SEQ ID NO: 277 | SEQ ID NO: 319 | 67 | A | G | 0.323 | 0.437 |
| | | | 73 | A | C | 0.042 | 0.081 |
| | | | 100 | T | C | 0.042 | 0.081 |
| | | | 108 | C | T | ND | ND |
| | | | 127 | T | A | ND | ND |
| | | | 147 | T | G | 0.349 | 0.454 |
| | | | 186 | A | G | 0.008 | 0.017 |
| 372-m7t (SEQ ID NO: 236) | SEQ ID NO: 278 | SEQ ID NO: 320 | 100 | C | A | 0.101 | 0.181 |
| | | | 273 | A | G | 0.051 | 0.097 |
| 372-m18s (SEQ ID NO: 237) | SEQ ID NO: 279 | SEQ ID NO: 321 | 131 | T | C | 0.339 | 0.448 |
| 373-a14t (SEQ ID NO: 238) | SEQ ID NO: 280 | SEQ ID NO: 322 | 290 | T | C | 0.224 | 0.347 |
| | | | 197 | C | T | 0.225 | 0.349 |
| | | | 160 | A | T | 0.441 | 0.493 |
| | | | 55 | T | — | ND | ND |
| 373-a21t (SEQ ID NO: 239) | SEQ ID NO: 281 | SEQ ID NO: 323 | 93 | A | G | 0.008 | 0.017 |
| 373-e21s (SEQ ID NO: 240) | SEQ ID NO: 282 | SEQ ID NO: 324 | 136 | C | T | 0.332 | 0.443 |
| | | | 175 | C | T | 0.332 | 0.443 |
| | | | 191 | G | C | 0.33 | 0.442 |
| 373-g7s (SEQ ID NO: 241) | SEQ ID NO: 283 | SEQ ID NO: 325 | 263 | C | T | 0.204 | 0.325 |
| | | | 266 | T | C | 0.201 | 0.321 |
| 373-i16t (SEQ ID NO: 242) | SEQ ID NO: 284 | SEQ ID NO: 326 | 47 | G | A | 0.457 | 0.496 |
| | | | 133 | C | T | ND | ND |
| | | | 173 | G | A | ND | ND |
| | | | 210 | G | A | ND | ND |
| | | | 302 | C | T | 0.476 | 0.499 |
| | | | 319 | C | A | 0.381 | 0.472 |
| 373-k16t (SEQ ID NO: 243) | SEQ ID NO: 285 | SEQ ID NO: 327 | 54 | — | A | ND | ND |

*Position from 5' Forward Primer.
**Based on 120 canids representing 60 breeds.
ND = Not done.

TABLE 5

Abbreviations for Canid Populations

| | |
|---|---|
| ACKR | American Cocker Spaniel |
| AFGH | Afghan Hound |
| AHRT | American Hairless Terrier |
| AIRT | Airedale Terrier |
| AKAB | Akabash |
| AKIT | Akita |
| AMAL | Alaskan Malamute |
| AMWS | American Water Spaniel |
| ASBT | American Staffordshire Bull Terrier |
| AUSS | Australian Shepherd |
| AUST | Australian Terrier |
| BASS | Basset Hound |
| BEAC | Bearded Collie |
| BEAG | Beagle |
| BEDT | Bedlington Terrier |
| BELS | Belgian Sheepdog |
| BICH | Bichon Frise |
| BLDH | Bloodhound |
| BMD | Bernese Mountain Dog |
| BORD | Border Collie |
| BORZ | Borzoi |
| BOST | Boston Terrier |
| BOX | Boxer |
| BOYK | Boykin Spaniel |
| BRIA | Briard |
| BSJI | Basenji |
| BULD | Bulldog |
| BULM | Bullmastiff |
| BULT | Bull Terrier |
| CAIR | Cairn Terrier |
| CHBR | Chesapeak Bay Retriever |
| CHIH | Chihuahua |
| CHOW | Chow Chow |
| CKCS | Cavalier King Charles Spaniel |
| CLSP | Clumber Spaniel |
| COLL | Collie |
| COY | Coyote |
| DACH | Dachshund |
| DALM | Dalmatian |
| DANE | Great Dane |
| DNDT | Dandie Dinmont Terrier |
| DOBP | Doberman Pinscher |
| ECKR | English Cocker Spaniel |
| ESHP | English Shepherd |
| ESPR | English Springer Spaniel |
| EFOX | English Foxhound |
| FCR | Flat-Coated Retriever |
| FBLD | French Bulldog |
| FSP | Field Spaniel |
| GOLD | Golden Retriever |
| GREY | Greyhound |
| GPIN | German Pincher |
| GSD | German Shepherd Dog |
| GSHP | German Short-haired Pointer |
| GSMD | Greater Swiss Mountain Dog |
| GSNZ | Giant Schnauzer |
| HUSK | Siberian Husky |
| IBIZ | Ibizan Hound |
| IRSE | Irish Setter |
| IRTR | Irish Terrier |
| IRWS | Irish Water Spaniel |
| IWOF | Irish Wolfhound |
| ITGR | Italian Greyhound |
| KEES | Keeshond |
| KERY | Kerry Blue Terrier |
| KOMO | Komondor |
| KUVZ | Kuvasz |
| LAB | Labrador Retriever |
| LHSA | Lhasa Apso |
| MAST | Mastiff |

TABLE 5-continued

Abbreviations for Canid Populations

| | |
|---|---|
| MBLT | Miniature Bull Terrier |
| MNTY | Manchester Terrier - toy |
| MSNZ | Miniature Schnauzer |
| NELK | Norwegian Elkhound |
| NEWF | Newfoundland |
| OES | Old English Sheepdog |
| PAPI | Papillon |
| PEKE | Pekingese |
| PBGV | Petit Basset Griffon Vendeen |
| PHAR | Pharaoh Hound |
| PNTR | Pointer |
| POM | Pomeranian |
| PRES | Presa Canario |
| PTWD | Portuguese Water Dog |
| PUG | Pug |
| RHOD | Rhodesian Ridgeback |
| ROTT | Rottweiler |
| SALU | Saluki |
| SAMO | Samoyed |
| SCHP | Schiperke |
| SCDH | Scottish Deerhound |
| SCWT | Soft-coated Wheaten Terrier |
| SFXT | Smooth Fox Terrier |
| SHAR | Shar-Pei |
| SHIB | Shiba Ina |
| SHIH | Shih Tzu |
| SPIN | Spinoni Italiano |
| SPIX | Springer Mix |
| SCOL | Standard Collie |
| SPOO | Standard Poodle |
| SSNZ | Standard Schnauzer |
| SSHP | Shetland Sheepdog |
| STBD | Saint Bernard |
| SUSP | Sussex Spaniel |
| TERV | Belgian Tervuren |
| TIBT | Tibetan Terrier |
| TPOO | Toy Poodle |
| WEIM | Weimaraner |
| WHIP | Whippet |
| WHWT | West Highland White Terrier |
| WOLF | Wolf |
| WSSP | Welsh Springer Spaniel |
| WST | Welsh Terrier |

TABLE 6

94 Canids in Dataset 1

| Population* | Canid Identification Number | | | | |
|---|---|---|---|---|---|
| AHRT | 1120 | 1121 | 1122 | 1123 | 1124 |
| AKIT | 1130 | 1131 | 1132 | 1133 | 1134 |
| BEAG | 994 | 995 | 1323 | 1324 | 1327 |
| BMD | 941 | 943 | 968 | 970 | 971 |
| BOX | 1176 | 1177 | 1178 | 1179 | 1304 |
| BULD | 1193 | 1194 | 1195 | 1197 | 1198 |
| BULM | 1105 | 1106 | 1107 | 1108 | 1109 |
| CHIH | 1202 | 1203 | 1204 | 1205 | 1206 |
| DACH | 1051 | 1052 | 1053 | 1054 | 1055 |
| GOLD | 591 | 592 | 593 | 603 | 604 |
| IBIZ | 1147 | 1148 | 1162 | 1172 | 1280 |
| MAST | 991 | 1015 | 1016 | 1017 | 1066 |
| NEWF | 271 | 274 | 275 | 277 | 278 |
| PEKE | 1143 | 1145 | 1211 | 1212 | 1213 |
| POM | 1190 | 1191 | 1210 | 1238 | 1239 |
| PRES | 1082 | 1093 | 1096 | 1115 | 1127 |
| PUG | 1077 | 1104 | 1183 | 1184 | 1192 |
| ROTT | 1014 | 1028 | 1019 | 1033 | 1034 |
| WOLF | 282135 | 492-8 | 930121 | Iran-1 | |

*See Table 5 for abbreviations of canid populations.

TABLE 7

341 Canids in Dataset 2

| Population* | Canid Identification Number | | | | | |
|---|---|---|---|---|---|---|
| ACKR | 1035 | 2261 | 2310 | | | |
| AFGH | 1812 | 1939 | 2264 | | | |
| AHRT | 1120 | 1121 | 1122 | 1123 | 1124 | |
| AIRT | 1603 | 1604 | 1788 | 1875 | | |
| AKIT | 1130 | 1131 | 1132 | 1133 | 1134 | |
| AMAL | 1629 | 1779 | 1845 | 2132 | 2214 | |
| AMWS | 2168 | 2279 | 2327 | 987 | 988 | |
| AUSS | 1336 | 1337 | 1500 | 1521 | 1683 | |
| AUST | 1387 | 1531 | 1533 | 1564 | 1870 | 1871 |
| BASS | 1341 | 1342 | 1506 | 1917 | | |
| BEAG | 1323 | 1324 | 1327 | 994 | 995 | |
| BEDT | 1422 | 1423 | 1424 | 1426 | | |
| BELS | 1351 | 2111 | 2153 | 2209 | 2210 | |
| BLDH | 1186 | 1223 | 1410 | 1942 | 1957 | |
| BMD | 941 | 943 | 968 | 1763 | 969 | |
| BORD | 1648 | 1828 | 1829 | 2002 | 2003 | |
| BORZ | 1378 | 1401 | 1808 | 2268 | 978 | |
| BOX | 1176 | 1177 | 1178 | 1179 | 1304 | |
| BSJI | 1338 | 1339 | 1645 | 1675 | 1717 | |
| BULD | 1193 | 1194 | 1195 | 1197 | 1198 | |
| BULM | 1105 | 1106 | 1107 | 1108 | 1109 | |
| CAIR | 1405 | 2096 | 2113 | 2125 | 2131 | |
| CHBR | 1546 | 1549 | 1813 | 2091 | 888 | |
| CHIH | 1202 | 1203 | 1204 | 1205 | 1206 | |
| CKCS | 1513 | 1639 | 1640 | 1642 | 2054 | |
| CLSP | 1008 | 1009 | 1802 | 2312 | 2314 | |
| COLL | 1692 | 1701 | 2284 | 373 | 379 | |
| DACH | 1051 | 1052 | 1053 | 1054 | 1055 | |
| DANE | 1574 | 1575 | 1580 | 1700 | 1748 | |
| DNDT | 2204 | 2219 | 2221 | | | |
| DOBP | 1031 | 1749 | 2162 | 2245 | | |
| ECKR | 1376 | 1377 | 1400 | 1404 | 1511 | |
| FCR | 1188 | 2020 | 2042 | 2044 | 2259 | |
| GOLD | 591 | 592 | 593 | 603 | 604 | |
| GREY | 2277 | 2478 | 2479 | 2480 | 2481 | |
| GSD | 1666 | 1776 | 2011 | 2060 | 2086 | |
| GSHP | 1628 | 1708 | 1710 | 1833 | 1892 | |
| GSMD | 1547 | 1659 | 1660 | 1662 | 1663 | |
| HUSK | 1469 | 1883 | 2115 | 2117 | 2118 | |
| IBIZ | 1147 | 1148 | 1162 | 1172 | 1280 | |
| IRSE | 1540 | 1617 | 1896 | 2084 | 2085 | |
| IRTR | 2152 | 2189 | 2238 | 2242 | | |
| IWOF | 1581 | 1761 | 1792 | 1906 | 1993 | |
| KEES | 1501 | 1589 | 1818 | 1819 | 2072 | |
| KOMO | 1484 | 1964 | 2321 | 2323 | 2334 | |
| KUVZ | 1482 | 1551 | 1672 | 1913 | 1994 | |
| LAB | 1310 | 1465 | 1468 | 1754 | 1830 | |
| MAST | 1015 | 1016 | 1017 | 1066 | 991 | |
| MBLT | 1915 | 2253 | 2254 | 2255 | 2256 | |
| MNTY | 1539 | 1732 | 2145 | 2149 | | |
| NELK | 2216 | 2239 | 2240 | 2281 | 2295 | |
| NEWF | 271 | 274 | 275 | 277 | 278 | |
| OES | 1984 | 2171 | 2179 | | | |
| PEKE | 1143 | 1145 | 1211 | 1212 | 1213 | |
| PNTR | 1382 | 1383 | 1869 | 1938 | 1948 | |
| POM | 1190 | 1191 | 1210 | 1238 | 1239 | |
| PRES | 1082 | 1096 | 1115 | 1127 | 1095 | |
| PTWD | P142 | P1 | P238 | P25 | P67 | |
| PUG | 1077 | 1104 | 1183 | 1184 | 1192 | |
| RHOD | 1444 | 1454 | 1505 | 1592 | 1609 | |
| ROTT | 1014 | 1028 | 1029 | 1033 | 1034 | |
| SCHP | 1386 | 1471 | 1814 | 1852 | | |
| SCWT | 1624 | 1770 | 2250 | 2301 | | |
| SFXT | 1550 | 2167 | | | | |
| SHAR | 1573 | 1593 | 1619 | 1998 | 1999 | |
| SPOO | 1530 | 1582 | 1876 | 1877 | 2337 | |
| SSHP | 1379 | 1523 | 1824 | 1921 | 2040 | |
| STBD | 1075 | 1714 | 1750 | 2403 | 2404 | |
| TERV | 1622 | 2194 | 2200 | 2222 | | |
| WHIP | 1355 | 1395 | 1407 | 1409 | 1518 | |
| WHWT | 1388 | 1420 | 1992 | 2100 | 2128 | |
| WSSP | 1955 | 2139 | 2143 | 2195 | 2286 | |

*See Table 5 for abbreviations of canid populations.

TABLE 8

414 Canids in Dataset 3

| Population* | Canid Identification Number | | | | |
|---|---|---|---|---|---|
| ACKR | 1035 | 2261 | 2310 | 1956 | 2260 |
| AFGH | 1812 | 1939 | 2264 | 1936 | 1937 |
| AHRT | 1120 | 1121 | 1122 | 1123 | 1124 |
| AIRT | 1603 | 1604 | 1788 | 1875 | |
| AKIT | 1130 | 1131 | 1132 | 1133 | 1134 |
| AMAL | 1629 | 1779 | 1845 | 2132 | 2214 |
| AMWS | 2168 | 2279 | 2327 | 987 | 988 |
| AUSS | 1336 | 1337 | 1500 | 1521 | 1683 |
| AUST | 1387 | 1531 | 1564 | 1870 | 1871 |
| BASS | 1341 | 1342 | 1506 | 1917 | |
| BEAG | 1323 | 1324 | 1327 | 994 | 995 |
| BEDT | 1422 | 1423 | 1424 | 1426 | |
| BELS | 1351 | 2111 | 2153 | 2209 | 2210 |
| BICH | 1943 | 1954 | 933 | 974 | |
| BLDH | 1186 | 1223 | 1410 | 1942 | 1957 |
| BMD | 941 | 943 | 968 | 1763 | 969 |
| BORD | 1648 | 1828 | 1829 | 2002 | 2003 |
| BORZ | 1378 | 1401 | 1808 | 2268 | 978 |
| BOX | 1176 | 1177 | 1178 | 1179 | 1304 |
| BSJI | 1338 | 1339 | 1645 | 1675 | 1717 |
| BULD | 1193 | 1194 | 1195 | 1197 | 1198 |
| BULM | 1105 | 1106 | 1107 | 1108 | 1109 |
| CAIR | 1405 | 2096 | 2113 | 2125 | 2131 |
| CHBR | 1546 | 1549 | 1813 | 2091 | 888 |
| CHIH | 1202 | 1203 | 1204 | 1205 | 1206 |
| CHOW | 1633 | 1835 | 1837 | 1838 | 1839 |
| CKCS | 1513 | 1639 | 1640 | 1642 | 2054 |
| CLSP | 1008 | 1009 | 1802 | 2312 | 2314 |
| COLL | 1692 | 1701 | 2284 | 373 | 379 |
| DACH | 1051 | 1052 | 1053 | 1054 | 1055 |
| DANE | 1574 | 1575 | 1580 | 1700 | 1748 |
| DOBP | 1031 | 1032 | 1749 | 2162 | 2245 |
| ECKR | 1376 | 1377 | 1400 | 1404 | 1511 |
| FBLD | 1507 | 1508 | 1509 | 2671 | |
| FCR | 1188 | 2020 | 2042 | 2044 | 2259 |
| GOLD | 591 | 592 | 593 | 603 | 604 |
| GREY | 2477 | 2478 | 2479 | 2480 | 2481 |
| GSD | 1666 | 1776 | 2011 | 2060 | 2086 |
| GSHP | 1628 | 1708 | 1710 | 1833 | 1892 |
| GSMD | 1547 | 1659 | 1660 | 1662 | 1663 |
| GSNZ | 1868 | 22739 | 27093 | 27106 | 33390 |
| HUSK | 1469 | 1883 | 2115 | 2117 | 2118 |
| IBIZ | 1147 | 1148 | 1162 | 1172 | 1280 |
| IRSE | 1540 | 1617 | 1896 | 2084 | 2085 |
| IRTR | 2152 | 2189 | 2238 | 2242 | |
| ITGR | 1568 | 1570 | 1862 | 1881 | 1882 |
| IWOF | 1581 | 1761 | 1792 | 1906 | 1993 |
| KEES | 1501 | 1589 | 1818 | 1819 | 2072 |
| KERY | 13878 | 1483 | 1579 | 2014 | 24255 |
| KOMO | 1484 | 1964 | 2321 | 2323 | 2334 |
| KUVZ | 1482 | 1551 | 1672 | 1913 | 1994 |
| LAB | 1310 | 1465 | 1468 | 1754 | 1830 |
| LHSA | 1524 | 1525 | 1526 | 1528 | 2074 |
| MAST | 1015 | 1016 | 1017 | 1066 | 991 |
| MBLT | 1915 | 2253 | 2254 | 2255 | 2256 |
| MNTY | 1539 | 1732 | 2145 | 2149 | |
| MSNZ | 1587 | 1756 | 1851 | 2034 | 2613 |
| NELK | 2216 | 2239 | 2240 | 2281 | 2295 |
| NEWF | 271 | 274 | 275 | 277 | 278 |
| OES | 1984 | 2171 | 2179 | 1914 | 1626 |
| PEKE | 1143 | 1145 | 1211 | 1212 | 1213 |
| PHAR | 1292 | 1947 | 1962 | 1963 | |
| PNTR | 1382 | 1383 | 1869 | 1938 | 1948 |
| POM | 1190 | 1191 | 1210 | 1238 | 1239 |
| PRES | 1082 | 1096 | 1115 | 1127 | 1095 |
| PTWD | P142 | P1 | P238 | P25 | P67 |
| PUG | 1077 | 1104 | 1183 | 1184 | 1192 |
| RHOD | 1444 | 1454 | 1505 | 1592 | 1609 |
| ROTT | 1014 | 1028 | 1029 | 1033 | 1034 |
| SALU | 1491 | 1535 | 1607 | 1873 | 2610 |
| SAMO | 1375 | 1532 | 1560 | 169 | 239 |
| SCHP | 1386 | 1471 | 1814 | 1852 | |
| SCWT | 1624 | 1770 | 2250 | 2301 | |
| SHAR | 1573 | 1593 | 1619 | 1998 | 1999 |
| SHIB | 1769 | 1854 | 1856 | 1860 | 1981 |
| SHIH | 1393 | 1783 | 2068 | 2859 | 2860 |
| SPOO | 1530 | 1582 | 1876 | 1877 | 2337 |
| SSHP | 1379 | 1523 | 1824 | 1921 | 2040 |
| SSNZ | 13352 | 1360 | 1827 | 20457 | 22647 |
| STBD | 1075 | 1714 | 1750 | 2403 | 2404 |
| TIBT | 1466 | 1562 | 1707 | 26078 | 28086 |
| TERV | 1622 | 2194 | 2200 | 2222 | |
| WHIP | 1355 | 1395 | 1407 | 1409 | 1518 |
| WHWT | 1388 | 1420 | 1992 | 2100 | 2128 |
| WSSP | 1955 | 2139 | 2143 | 2195 | 2286 |

*See Table 5 for abbreviations of canid populations.

TABLE 9

85 Canids in Dataset 5

| Population* | Canid Identification Number | | | | |
|---|---|---|---|---|---|
| AHRT | 1120 | 1121 | 1124 | | |
| AKIT | 1130 | 1131 | 1132 | 1133 | 1134 |
| BEAG | 1323 | 1327 | 994 | 995 | |
| BMD | 941 | 943 | 968 | 970 | 971 |
| BOX | 1176 | 1177 | 1178 | 1179 | 1304 |
| BULD | 1193 | 1194 | 1195 | 1197 | 1198 |
| BULM | 1105 | 1106 | 1107 | 1108 | 1109 |
| CHIH | 1202 | 1203 | 1204 | | |
| DACH | 1051 | 1052 | 1053 | 1054 | 1055 |
| GOLD | 591 | 593 | 603 | 604 | |
| IBIZ | 1147 | 1148 | 1162 | 1172 | 1280 |
| MAST | 1015 | 1016 | 1017 | 1066 | 991 |
| NEWF | 271 | 274 | 275 | 277 | 278 |
| PEKE | 1143 | 1145 | 1211 | 1212 | 1213 |
| POM | 1190 | 1191 | 1210 | 1238 | |
| PRES | 1093 | 1096 | 1115 | | |
| PUG | 1077 | 1104 | 1183 | 1184 | 1192 |
| ROTT | 1014 | 1028 | 1029 | 1033 | 1034 |
| WOLF | 282135 | 492-8 | 930121 | Iran-1 | |

*See Table 5 for abbreviations of canid populations.

TABLE 10

Microsatellite Marker Alleles and Heterozygosities in 19 Canid Populations

| Population* | n | P | A | Ap | He | Ho | f |
|---|---|---|---|---|---|---|---|
| AHRT | 4.882353 | 0.835294 | 2.576471 | 2.887324 | 0.439286 | 0.432549 | 0.017577 |
| AKIT | 4.8 | 0.917647 | 3.035294 | 3.217949 | 0.550509 | 0.522157 | 0.058242 |
| BEAG | 4.941176 | 0.929412 | 2.952941 | 3.101266 | 0.560938 | 0.482941 | 0.153823 |
| BMD | 3.938272 | 0.82716 | 2.296296 | 2.552239 | 0.396752 | 0.38642 | 0.095341 |
| BOX | 4.905882 | 0.764706 | 2.141176 | 2.492308 | 0.348287 | 0.308235 | 0.13062 |
| BULD | 4.8 | 0.870588 | 2.6 | 2.837838 | 0.47183 | 0.42902 | 0.104385 |

TABLE 10-continued

Microsatellite Marker Alleles and Heterozygosities in 19 Canid Populations

| Population* | n | P | A | Ap | He | Ho | f |
|---|---|---|---|---|---|---|---|
| BULM | 4.952941 | 0.917647 | 2.752941 | 2.910256 | 0.518151 | 0.488235 | 0.064621 |
| CHIH | 4.811765 | 0.976471 | 3.447059 | 3.506024 | 0.611858 | 0.556667 | 0.101951 |
| DACH | 4.847059 | 0.882353 | 2.658824 | 2.853333 | 0.487712 | 0.482941 | 0.016864 |
| GOLD | 4.905882 | 0.905882 | 2.905882 | 3.103896 | 0.529542 | 0.520784 | 0.018744 |
| IBIZ | 4.682353 | 0.905882 | 2.847059 | 3.038961 | 0.517372 | 0.462745 | 0.118169 |
| MAST | 4.576471 | 0.905882 | 2.541176 | 2.701299 | 0.488389 | 0.466667 | 0.051889 |
| NEWF | 4.882353 | 0.941176 | 2.905882 | 3.025 | 0.516111 | 0.49 | 0.05822 |
| PEKE | 4.917647 | 0.858824 | 2.552941 | 2.808219 | 0.453319 | 0.428824 | 0.062983 |
| POM | 4.717647 | 0.929412 | 3.176471 | 3.341772 | 0.576965 | 0.482941 | 0.17924 |
| PRES | 4.717647 | 0.964706 | 3.435294 | 3.52439 | 0.616111 | 0.558824 | 0.103943 |
| PUG | 4.870588 | 0.776471 | 2.223529 | 2.575758 | 0.397302 | 0.315882 | 0.224817 |
| ROTT | 4.882353 | 0.882353 | 2.670588 | 2.893333 | 0.475864 | 0.44902 | 0.063943 |
| WOLF | 3.847059 | 0.964706 | 3.870588 | 3.97561 | 0.712773 | 0.492157 | 0.345081 |
| Mean | 4.730497 | 0.892451 | 2.820548 | 3.018251 | 0.508899 | 0.460895 | 0.108623 |

*See Table 5 for abbreviations of canid populations.
a = Effective number of individuals sampled from the population (n is smaller than the number of individuals tested due to missing marker data);
P = Proportion of polymorphic loci across all 95 markers for individuals in a population;
A = mean number of alleles per locus;
Ap = mean number of alleles per polymorphic locus;
He = expected heterozygosity;
Ho = observed heterozygosity;
f = estimate of inbreeding coefficient for the population.

TABLE 11

Heterozygosity of 85 Dog Breeds

| Population | Heterozygosity |
|---|---|
| Bedlington Terrier | 0.312842 |
| Miniature Bull Terrier | 0.321619 |
| Boxer | 0.343151 |
| Clumber Spaniel | 0.363595 |
| Greater Swiss Mountain Dog | 0.364943 |
| Airedale Terrier | 0.372793 |
| Soft Coated Wheaten Terrier | 0.37376 |
| Collie | 0.383453 |
| Doberman Pinscher | 0.383763 |
| Irish Terrier | 0.390427 |
| Bloodhound | 0.391559 |
| German Shepherd Dog | 0.397957 |
| Pug Dog | 0.398442 |
| Bernese Mountain Dog | 0.399599 |
| Flat-coated Retriever | 0.402832 |
| Miniature Schnauzer | 0.414528 |
| Irish Wolfhound | 0.418039 |
| Pharaoh Hound | 0.420188 |
| Cavalier King Charles Spaniel | 0.427633 |
| Shetland Sheepdog | 0.43244 |
| Manchester Terrier Toy | 0.432937 |
| French Bulldog | 0.439855 |
| Basset Hound | 0.441171 |
| American Cocker Spaniel | 0.443841 |
| Schipperke | 0.445437 |
| Irish Setter | 0.446656 |
| Basenji | 0.447739 |
| Bulldog | 0.449549 |
| Standard Schnauzer | 0.450041 |
| Whippet | 0.450959 |
| American Hairless Terrier | 0.454113 |
| Mastiff | 0.455126 |
| Rottweiler | 0.45651 |
| Pekingese | 0.459983 |
| English Cocker Spaniel | 0.46565 |
| Saint Bernard | 0.465724 |
| Italian Greyhound | 0.468797 |
| Afghan Hound | 0.468924 |
| Pointer | 0.469444 |
| Shih Tzu | 0.472193 |
| Welsh Springer Spaniel | 0.473917 |
| Kerry Blue Terrier | 0.477836 |
| Dachshund | 0.483817 |
| Borzoi | 0.487909 |
| Great Dane | 0.488697 |
| Alaskan Malamute | 0.489877 |
| Newfoundland | 0.490617 |
| West Highland White Terrier | 0.493936 |
| Belgian Sheepdog | 0.495114 |
| Australian Terrier | 0.499343 |
| Ibizan Hound | 0.503981 |
| Keeshond | 0.505126 |
| Bullmastiff | 0.509243 |
| Akita | 0.510396 |
| Greyhound | 0.513409 |
| Chesapeake Bay Retriever | 0.514166 |
| Golden Retriever | 0.517779 |
| Tibetan Terrier | 0.519535 |
| Chow Chow | 0.52043 |
| Rhodesian Ridgeback | 0.520493 |
| Siberian Husky | 0.527344 |
| Bichon Frise | 0.528271 |
| Standard Poodle | 0.529948 |
| Old English Sheepdog | 0.530192 |
| Norwegian Elkhound | 0.532854 |
| German Shorthaired Pointer | 0.538761 |
| American Water Spaniel | 0.540183 |
| Lhasa Apso | 0.541245 |
| Samoyed | 0.542932 |
| Pomeranian | 0.546007 |
| Beagle | 0.549119 |
| Border Collie | 0.549583 |
| Belgian Tervuren | 0.551091 |
| Kuvasz | 0.553538 |
| Shiba Inu | 0.560543 |
| Labrador Retriever | 0.56059 |
| Giant Schnauzer | 0.56131 |
| Saluki | 0.563037 |
| Portuguese Water Dog | 0.568882 |
| Komondor | 0.57321 |
| Cairn Terrier | 0.575823 |
| Chinese Shar-Pei | 0.584412 |

TABLE 11-continued

Heterozygosity of 85 Dog Breeds

| Population | Heterozygosity |
|---|---|
| Perro de Presa Canario | 0.589397 |
| Chihuahua | 0.592353 |
| Australian Shepherd | 0.609668 |

TABLE 12

Expected Heterozygosity of 60 Breeds Based on Allele Frequencies at 75 SNP Loci

| Breed | Heterozygosity ($\times 10^{-4}$) |
|---|---|
| Scottish Deerhound | 2.0683 |
| Field Spaniel | 2.3165 |
| Flat-coated Retriever | 2.6474 |
| Bernese Mountain Dog | 2.8129 |
| Standard Schnauzer | 2.8129 |
| Boxer | 3.0611 |
| Collie | 3.0611 |
| Bearded Collie | 3.1438 |
| Miniature Bull Terrier | 3.2266 |
| Perro de Presa Canario | 3.392 |
| Bull Terrier | 3.8057 |
| Mastiff | 3.8057 |
| Petite Basset Griffon Vendeen | 3.8884 |
| Bedlington Terrier | 3.9712 |
| Saluki | 4.1366 |
| Standard Poodle | 4.1366 |
| Cavalier King Charles Spaniel | 4.2194 |
| Sussex Spaniel | 4.2194 |
| American Water Spaniel | 4.5503 |
| Ibizan Hound | 4.7158 |
| Beagle | 4.7985 |
| Boston Terrier | 4.7985 |
| German Pinscher | 4.8812 |
| Basset Hound | 4.964 |
| Bichon Frise | 4.964 |
| Rottweiler | 4.964 |
| Bullmastiff | 5.1294 |
| English Springer Spaniel | 5.1294 |
| Greater Swiss Mountain Dog | 5.3776 |
| Pug Dog | 5.3776 |
| Boykin Spaniel | 5.5431 |
| Italian Greyhound | 5.5431 |
| Newfoundland | 5.5431 |
| American Hairless Terrier | 5.7086 |
| Borzoi | 5.7913 |
| German Shepherd Dog | 5.7913 |
| Saint Bernard | 5.7913 |
| Dachshund | 5.874 |
| Akita | 5.9568 |
| Cocker Spaniel | 6.0395 |
| French Bulldog | 6.0395 |
| Greyhound | 6.0395 |
| Irish Water Spaniel | 6.0395 |
| Shetland Sheepdog | 6.205 |
| Papillon | 6.2877 |
| Foxhound (English) | 6.3704 |
| Tibetan Terrier | 6.4532 |
| Welsh Springer Spaniel | 6.4532 |
| German Shorthaired Pointer | 6.6186 |
| Welsh Terrier | 6.6186 |
| Dalmatian | 6.7014 |
| Irish Setter | 6.7014 |
| Alaskan Malamute | 6.8668 |
| Golden Retriever | 7.0323 |
| Portugese Water Dog | 7.115 |
| Weimaraner | 7.6942 |
| Labrador Retriever | 8.4388 |
| Spinoni Italiano | 8.9352 |
| Chesapeak Bay Retriever | 9.1006 |
| English Shepherd | 9.2661 |

TABLE 13

Assignments of 346 Canids to 72 Breeds Using Doh

| Breed* | Correct | Incorrect |
|---|---|---|
| ACKR | 3 | 0 |
| AFGH | 3 | 0 |
| AHRT | 5 | 0 |
| AIRT | 4 | 0 |
| AKIT | 5 | 0 |
| AMAL | 5 | 0 |
| AMWS | 5 | 0 |
| AUSS | 5 | 0 |
| AUST | 5 | 0 |
| BASS | 4 | 0 |
| BEAG | 4 | 1[a] |
| BEDT | 4 | 0 |
| BELS | 3 | 2[b] |
| BLDH | 5 | 0 |
| BMD | 5 | 0 |
| BORD | 5 | 0 |
| BORZ | 5 | 0 |
| BOX | 5 | 0 |
| BSJI | 5 | 0 |
| BULD | 5 | 0 |
| BULM | 5 | 0 |
| CAIR | 5 | 0 |
| CHBR | 5 | 0 |
| CHIH | 4 | 1[c] |
| CKCS | 5 | 0 |
| CLSP | 5 | 0 |
| COLL | 5 | 0 |
| DACH | 5 | 0 |
| DANE | 5 | 0 |
| DNDT | 3 | 0 |
| DOBP | 5 | 0 |
| ECKR | 5 | 0 |
| FCR | 5 | 0 |
| GOLD | 5 | 0 |
| GREY | 5 | 0 |
| GSD | 5 | 0 |
| GSHP | 3 | 2[d] |
| GSMD | 5 | 0 |
| HUSK | 5 | 0 |
| IBIZ | 5 | 0 |
| IRSE | 5 | 0 |
| IRTR | 4 | 0 |
| IWOF | 5 | 0 |
| KEES | 5 | 0 |
| KOMO | 5 | 0 |
| KUVZ | 5 | 0 |
| LAB | 5 | 0 |
| MAST | 5 | 0 |
| MBLT | 5 | 0 |
| MNTY | 4 | 0 |
| NELK | 5 | 0 |
| NEWF | 5 | 0 |
| OES | 3 | 0 |
| PEKE | 5 | 0 |
| PNTR | 5 | 0 |
| POM | 5 | 0 |
| PRES | 5 | 0 |
| PTWD | 5 | 0 |
| PUG | 5 | 0 |
| RHOD | 5 | 0 |
| ROTT | 5 | 0 |

TABLE 13-continued

Assignments of 346 Canids to 72 Breeds Using Doh

| Breed* | Correct | Incorrect |
|---|---|---|
| SCHP | 4 | 0 |
| SCWT | 4 | 0 |
| SFXT | 2 | 0 |
| SHAR | 5 | 0 |
| SPOO | 5 | 0 |
| SSHP | 5 | 0 |
| STBD | 5 | 0 |
| TERV | 1 | 3[e] |
| WHIP | 5 | 0 |
| WHWT | 5 | 0 |
| WSSP | 5 | 0 |

*See Table 5 for abbreviations of canid populations.
[a] 1 dog was misassigned to Presa Canario.
[b] 2 dogs were misassigned to Belgian Tervuren.
[c] 1 dog was misassigned to Cairn Terrier.
[d] 1 dog was misassigned to Kuvasz and 1 dog was misassigned to Standard Poodle.
[e] 3 dogs were misassigned to Belgian Sheepdog.

TABLE 14

| Canid Population[a] | Canid ID No. | Missing Data | 1 | 2 | 3 | 4 | 5 | 6 | 7 | 8 | 9 | 10 |
|---|---|---|---|---|---|---|---|---|---|---|---|---|
| AHRT | 1124 | -2 | 0.001 | 0.001 | 0.001 | 0.001 | 0.002 | 0.001 | 0.003 | 0.001 | 0.002 | 0.001 |
| AHRT | 1120 | -1 | 0.001 | 0.002 | 0.002 | 0.001 | 0.001 | 0.001 | 0.005 | 0.001 | 0.001 | 0.002 |
| AHRT | 1121 | -4 | 0.002 | 0.002 | 0.003 | 0.001 | 0.004 | 0.001 | 0.006 | 0.001 | 0.001 | 0.002 |
| AHRT | 1123 | -2 | 0.004 | 0.009 | 0.038 | 0.002 | 0.004 | 0.005 | 0.004 | 0.005 | 0.003 | 0.018 |
| AHRT | 1122 | 0 | 0.008 | 0.002 | 0.001 | 0.008 | 0.002 | 0.003 | 0.002 | 0.003 | 0.002 | 0.002 |
| AKIT | 1132 | -3 | 0.001 | 0.001 | 0.001 | 0.975 | 0.001 | 0.002 | 0.001 | 0.001 | 0.001 | 0.001 |
| AKIT | 1131 | 0 | 0.002 | 0.003 | 0.001 | 0.962 | 0.002 | 0.003 | 0.002 | 0.006 | 0.002 | 0.001 |
| AKIT | 1130 | -4 | 0.003 | 0.001 | 0.003 | 0.961 | 0.001 | 0.002 | 0.001 | 0.001 | 0.003 | 0.001 |
| AKIT | 1134 | -4 | 0.002 | 0.001 | 0.001 | 0.953 | 0.002 | 0.003 | 0.001 | 0.014 | 0.002 | 0.002 |
| AKIT | 1133 | -5 | 0.002 | 0.001 | 0.001 | 0.949 | 0.001 | 0.003 | 0.001 | 0.001 | 0.002 | 0.002 |
| BEAG | 995 | -1 | 0.001 | 0.002 | 0.003 | 0.001 | 0.002 | 0.001 | 0.002 | 0.006 | 0.001 | 0.96 |
| BEAG | 994 | -2 | 0.001 | 0.001 | 0.002 | 0.001 | 0.001 | 0.001 | 0.014 | 0.003 | 0.001 | 0.939 |
| BEAG | 1323 | -1 | 0.005 | 0.003 | 0.007 | 0.003 | 0.004 | 0.002 | 0.004 | 0.002 | 0.004 | 0.909 |
| BEAG | 1327 | 0 | 0.007 | 0.002 | 0.005 | 0.002 | 0.002 | 0.002 | 0.002 | 0.001 | 0.003 | 0.892 |
| BEAG | 1324 | 0 | 0.015 | 0.014 | 0.002 | 0.002 | 0.065 | 0.016 | 0.057 | 0.004 | 0.015 | 0.42 |
| BMD | 968 | -17 | 0.002 | 0.002 | 0.003 | 0.001 | 0.001 | 0.001 | 0.002 | 0.001 | 0.001 | 0.001 |
| BMD | 970 | -31 | 0.002 | 0.002 | 0.001 | 0.003 | 0.004 | 0.002 | 0.003 | 0.002 | 0.002 | 0.002 |
| BMD | 941 | -11 | 0.005 | 0.002 | 0.002 | 0.001 | 0.006 | 0.002 | 0.006 | 0.004 | 0.002 | 0.006 |
| BMD | 943 | -10 | 0.006 | 0.007 | 0.003 | 0.002 | 0.003 | 0.002 | 0.002 | 0.003 | 0.001 | 0.01 |
| BMD | 971 | -51 | 0.017 | 0.004 | 0.004 | 0.002 | 0.002 | 0.002 | 0.002 | 0.002 | 0.004 | 0.002 |
| BOX | 1304 | -1 | 0.001 | 0.001 | 0.001 | 0.001 | 0.001 | 0.001 | 0.001 | 0.001 | 0.001 | 0.001 |
| BOX | 1179 | -3 | 0.001 | 0.001 | 0.001 | 0.001 | 0.001 | 0.001 | 0.001 | 0.001 | 0.001 | 0.001 |
| BOX | 1178 | -1 | 0.001 | 0.001 | 0.002 | 0.001 | 0.001 | 0.001 | 0.001 | 0.001 | 0.001 | 0.001 |
| BOX | 1176 | -1 | 0.002 | 0.001 | 0.002 | 0.001 | 0.004 | 0.001 | 0.002 | 0.001 | 0.002 | 0.001 |
| BOX | 1177 | 0 | 0.002 | 0.007 | 0.008 | 0.001 | 0.002 | 0.003 | 0.01 | 0.002 | 0.004 | 0.004 |
| BULD | 1195 | -9 | 0.002 | 0.001 | 0.001 | 0.001 | 0.001 | 0.001 | 0.002 | 0.001 | 0.002 | 0.001 |
| BULD | 1193 | -1 | 0.004 | 0.003 | 0.002 | 0.001 | 0.001 | 0.002 | 0.001 | 0.001 | 0.004 | 0.002 |
| BULD | 1197 | -3 | 0.002 | 0.003 | 0.002 | 0.002 | 0.002 | 0.002 | 0.01 | 0.002 | 0.001 | 0.002 |
| BULD | 1194 | -2 | 0.004 | 0.007 | 0.004 | 0.002 | 0.001 | 0.003 | 0.006 | 0.002 | 0.004 | 0.003 |
| BULD | 1198 | 0 | 0.003 | 0.003 | 0.001 | 0.001 | 0.001 | 0.001 | 0.004 | 0.001 | 0.004 | 0.002 |
| PRES | 1082 | -3 | 0.008 | 0.01 | 0.003 | 0.002 | 0.002 | 0.033 | 0.002 | 0.001 | 0.015 | 0.025 |
| BULM | 1107 | -1 | 0.005 | 0.004 | 0.001 | 0.003 | 0.003 | 0.002 | 0.002 | 0.006 | 0.002 | 0.002 |
| BULM | 1109 | 0 | 0.002 | 0.004 | 0.003 | 0.004 | 0.006 | 0.002 | 0.003 | 0.002 | 0.01 | 0.002 |
| BULM | 1108 | 0 | 0.006 | 0.011 | 0.006 | 0.006 | 0.002 | 0.006 | 0.004 | 0.003 | 0.013 | 0.002 |
| BULM | 1105 | 0 | 0.028 | 0.006 | 0.016 | 0.001 | 0.004 | 0.002 | 0.001 | 0.001 | 0.008 | 0.004 |
| BULM | 1106 | -3 | 0.008 | 0.002 | 0.04 | 0.004 | 0.003 | 0.005 | 0.002 | 0.003 | 0.031 | 0.024 |
| MAST | 991 | -14 | 0.002 | 0.001 | 0.001 | 0.004 | 0.002 | 0.001 | 0.001 | 0.001 | 0.002 | 0.003 |
| MAST | 1066 | -2 | 0.003 | 0.002 | 0.002 | 0.002 | 0.001 | 0.002 | 0.004 | 0.003 | 0.003 | 0.003 |
| MAST | 1016 | -1 | 0.003 | 0.003 | 0.003 | 0.001 | 0.005 | 0.002 | 0.002 | 0.002 | 0.002 | 0.001 |
| MAST | 1015 | 0 | 0.002 | 0.005 | 0.008 | 0.001 | 0.001 | 0.002 | 0.003 | 0.001 | 0.002 | 0.004 |
| MAST | 1017 | -22 | 0.002 | 0.002 | 0.004 | 0.001 | 0.002 | 0.002 | 0.001 | 0.001 | 0.059 | 0.001 |
| CHIH | 1203 | -3 | 0.002 | 0.002 | 0.002 | 0.002 | 0.005 | 0.002 | 0.003 | 0.002 | 0.003 | 0.002 |
| CHIH | 1202 | -10 | 0.006 | 0.007 | 0.004 | 0.001 | 0.005 | 0.002 | 0.005 | 0.003 | 0.006 | 0.012 |
| CHIH | 1204 | 0 | 0.023 | 0.037 | 0.003 | 0.001 | 0.004 | 0.003 | 0.004 | 0.004 | 0.004 | 0.008 |
| CHIH | 1205 | -3 | 0.002 | 0.028 | 0.008 | 0.002 | 0.004 | 0.09 | 0.014 | 0.065 | 0.116 | 0.104 |
| CHIH | 1206 | -1 | 0.059 | 0.125 | 0.015 | 0.004 | 0.012 | 0.029 | 0.003 | 0.025 | 0.006 | 0.024 |
| DACH | 1052 | -2 | 0.002 | 0.002 | 0.001 | 0.001 | 0.001 | 0.001 | 0.001 | 0.001 | 0.001 | 0.001 |
| DACH | 1055 | -1 | 0.003 | 0.001 | 0.002 | 0.002 | 0.001 | 0.001 | 0.002 | 0.001 | 0.004 | 0.002 |
| DACH | 1054 | 0 | 0.002 | 0.002 | 0.002 | 0.002 | 0.001 | 0.002 | 0.002 | 0.001 | 0.005 | 0.002 |
| DACH | 1051 | -5 | 0.001 | 0.002 | 0.003 | 0.001 | 0.006 | 0.002 | 0.001 | 0.004 | 0.003 | 0.002 |
| DACH | 1053 | -1 | 0.004 | 0.01 | 0.01 | 0.001 | 0.016 | 0.004 | 0.003 | 0.004 | 0.004 | 0.012 |
| GOLD | 603 | 0 | 0.003 | 0.001 | 0.967 | 0.001 | 0.001 | 0.001 | 0.001 | 0.001 | 0.001 | 0.002 |
| GOLD | 591 | -4 | 0.009 | 0.004 | 0.925 | 0.002 | 0.007 | 0.003 | 0.004 | 0.002 | 0.005 | 0.005 |
| GOLD | 593 | 0 | 0.022 | 0.005 | 0.885 | 0.001 | 0.005 | 0.003 | 0.018 | 0.001 | 0.006 | 0.004 |
| GOLD | 604 | 0 | 0.004 | 0.003 | 0.875 | 0.001 | 0.009 | 0.002 | 0.005 | 0.001 | 0.002 | 0.002 |

TABLE 14-continued

| Canid Population | Canid ID No. | Missing Data | 1 | 2 | 3 | 4 | 5 | 6 | 7 | 8 | 9 | 10 |
|---|---|---|---|---|---|---|---|---|---|---|---|---|
| GOLD | 592 | −4 | 0.006 | 0.006 | 0.733 | 0.006 | 0.009 | 0.016 | 0.003 | 0.002 | 0.04 | 0.098 |
| IBIZ | 1148 | −20 | 0.001 | 0.004 | 0.004 | 0.001 | 0.002 | 0.003 | 0.002 | 0.002 | 0.025 | 0.002 |
| IBIZ | 1172 | 0 | 0.021 | 0.002 | 0.002 | 0.002 | 0.003 | 0.002 | 0.002 | 0.002 | 0.004 | 0.002 |
| IBIZ | 1162 | 0 | 0.003 | 0.005 | 0.013 | 0.002 | 0.003 | 0.003 | 0.002 | 0.003 | 0.002 | 0.002 |
| IBIZ | 1280 | −1 | 0.008 | 0.005 | 0.004 | 0.001 | 0.006 | 0.002 | 0.006 | 0.003 | 0.004 | 0.004 |
| IBIZ | 1147 | −8 | 0.002 | 0.001 | 0.001 | 0.001 | 0.003 | 0.001 | 0.003 | 0.003 | 0.003 | 0.086 |
| NEWF | 275 | −3 | 0.963 | 0.001 | 0.002 | 0.001 | 0.002 | 0.001 | 0.005 | 0.001 | 0.002 | 0.002 |
| NEWF | 274 | −1 | 0.953 | 0.002 | 0.006 | 0.001 | 0.001 | 0.001 | 0.002 | 0.001 | 0.003 | 0.003 |
| NEWF | 277 | 0 | 0.855 | 0.003 | 0.002 | 0.001 | 0.001 | 0.002 | 0.008 | 0.003 | 0.002 | 0.003 |
| NEWF | 271 | −3 | 0.848 | 0.005 | 0.023 | 0.002 | 0.005 | 0.003 | 0.027 | 0.001 | 0.007 | 0.002 |
| NEWF | 278 | −1 | 0.744 | 0.007 | 0.009 | 0.003 | 0.002 | 0.016 | 0.005 | 0.004 | 0.113 | 0.008 |
| PEKE | 1143 | 0 | 0.001 | 0.001 | 0.001 | 0.001 | 0.002 | 0.001 | 0.001 | 0.985 | 0.001 | 0.001 |
| PEKE | 1145 | −1 | 0.001 | 0.004 | 0.002 | 0.001 | 0.003 | 0.002 | 0.001 | 0.964 | 0.001 | 0.002 |
| PEKE | 1211 | 0 | 0.001 | 0.001 | 0.001 | 0.004 | 0.001 | 0.002 | 0.003 | 0.955 | 0.001 | 0.002 |
| PEKE | 1213 | −4 | 0.001 | 0.003 | 0.001 | 0.001 | 0.026 | 0.002 | 0.003 | 0.946 | 0.001 | 0.001 |
| PEKE | 1212 | 0 | 0.003 | 0.005 | 0.017 | 0.001 | 0.001 | 0.002 | 0.001 | 0.932 | 0.002 | 0.003 |
| POM | 1238 | 0 | 0.001 | 0.964 | 0.003 | 0.001 | 0.004 | 0.001 | 0.002 | 0.003 | 0.001 | 0.002 |
| POM | 1190 | 0 | 0.004 | 0.794 | 0.087 | 0.002 | 0.003 | 0.003 | 0.004 | 0.005 | 0.004 | 0.004 |
| POM | 1191 | −2 | 0.051 | 0.785 | 0.003 | 0.002 | 0.001 | 0.002 | 0.005 | 0.001 | 0.003 | 0.003 |
| POM | 1210 | −7 | 0.036 | 0.77 | 0.013 | 0.002 | 0.054 | 0.004 | 0.009 | 0.002 | 0.012 | 0.012 |
| POM | 1239 | −14 | 0.002 | 0.598 | 0.005 | 0.007 | 0.006 | 0.069 | 0.003 | 0.014 | 0.009 | 0.009 |
| PRES | 1093 | −14 | 0.02 | 0.004 | 0.002 | 0.004 | 0.002 | 0.005 | 0.002 | 0.001 | 0.865 | 0.002 |
| PRES | 1115 | −1 | 0.008 | 0.002 | 0.022 | 0.001 | 0.001 | 0.005 | 0.003 | 0.001 | 0.838 | 0.002 |
| PRES | 1127 | −7 | 0.004 | 0.008 | 0.007 | 0.004 | 0.002 | 0.025 | 0.008 | 0.002 | 0.68 | 0.005 |
| PRES | 1096 | 0 | 0.007 | 0.003 | 0.002 | 0.001 | 0.002 | 0.004 | 0.003 | 0.002 | 0.653 | 0.004 |
| PUG | 1184 | −1 | 0.001 | 0.001 | 0.001 | 0.001 | 0.988 | 0.001 | 0.001 | 0.001 | 0.001 | 0.001 |
| PUG | 1077 | −4 | 0.001 | 0.002 | 0.002 | 0.001 | 0.973 | 0.001 | 0.001 | 0.003 | 0.001 | 0.001 |
| PUG | 1104 | −1 | 0.001 | 0.002 | 0.004 | 0.001 | 0.962 | 0.001 | 0.001 | 0.007 | 0.001 | 0.002 |
| PUG | 1183 | −1 | 0.003 | 0.001 | 0.003 | 0.004 | 0.96 | 0.001 | 0.002 | 0.002 | 0.001 | 0.002 |
| PUG | 1192 | −3 | 0.002 | 0.002 | 0.001 | 0.001 | 0.96 | 0.001 | 0.002 | 0.001 | 0.003 | 0.002 |
| ROTT | 1034 | 0 | 0.002 | 0.002 | 0.003 | 0.001 | 0.001 | 0.001 | 0.952 | 0.002 | 0.002 | 0.003 |
| ROTT | 1033 | −1 | 0.004 | 0.002 | 0.002 | 0.001 | 0.001 | 0.002 | 0.951 | 0.001 | 0.003 | 0.002 |
| ROTT | 1028 | −3 | 0.002 | 0.002 | 0.003 | 0.001 | 0.002 | 0.001 | 0.95 | 0.001 | 0.002 | 0.016 |
| ROTT | 1029 | −1 | 0.015 | 0.002 | 0.006 | 0.002 | 0.001 | 0.001 | 0.917 | 0.001 | 0.001 | 0.005 |
| ROTT | 1236 | 0 | 0.004 | 0.022 | 0.002 | 0.001 | 0.002 | 0.003 | 0.901 | 0.002 | 0.007 | 0.007 |
| ROTT | 1014 | −2 | 0.048 | 0.002 | 0.004 | 0.002 | 0.004 | 0.002 | 0.898 | 0.002 | 0.002 | 0.006 |
| WOLF | 282135 | −1 | 0.001 | 0.001 | 0.001 | 0.001 | 0.001 | 0.002 | 0.002 | 0.002 | 0.001 | 0.001 |
| WOLF | 930121 | −3 | 0.001 | 0.002 | 0.001 | 0.008 | 0.001 | 0.002 | 0.001 | 0.003 | 0.001 | 0.001 |
| WOLF | 492 | −1 | 0.001 | 0.002 | 0.001 | 0.002 | 0.002 | 0.559 | 0.001 | 0.002 | 0.005 | 0.001 |
| WOLF | Iran | −7 | 0.001 | 0.001 | 0.002 | 0.002 | 0.002 | 0.741 | 0.001 | 0.003 | 0.002 | 0.002 |

| Canid Population[a] | Canid ID No. | Missing Data | 11 | 12 | 13 | 14 | 15 | 16 | 17 | 18 | 19 | 20 |
|---|---|---|---|---|---|---|---|---|---|---|---|---|
| AHRT | 1124 | −2 | 0.002 | 0.001 | 0.001 | 0.002 | 0.001 | 0.001 | 0.001 | 0.001 | 0.001 | 0.972 |
| AHRT | 1120 | −1 | 0.002 | 0.001 | 0.001 | 0.004 | 0.002 | 0.001 | 0.001 | 0.002 | 0.002 | 0.966 |
| AHRT | 1121 | −4 | 0.002 | 0.001 | 0.003 | 0.001 | 0.002 | 0.001 | 0.001 | 0.001 | 0.002 | 0.963 |
| AHRT | 1123 | −2 | 0.007 | 0.003 | 0.019 | 0.001 | 0.012 | 0.015 | 0.003 | 0.002 | 0.004 | 0.84 |
| AHRT | 1122 | 0 | 0.048 | 0.002 | 0.009 | 0.016 | 0.003 | 0.002 | 0.002 | 0.002 | 0.059 | 0.825 |
| AKIT | 1132 | −3 | 0.002 | 0.001 | 0.002 | 0.001 | 0.002 | 0.001 | 0.001 | 0.002 | 0.001 | 0.002 |
| AKIT | 1131 | 0 | 0.002 | 0.002 | 0.001 | 0.001 | 0.001 | 0.001 | 0.002 | 0.001 | 0.002 | 0.003 |
| AKIT | 1130 | −4 | 0.003 | 0.002 | 0.002 | 0.002 | 0.003 | 0.001 | 0.005 | 0.002 | 0.002 | 0.001 |
| AKIT | 1134 | −4 | 0.002 | 0.001 | 0.003 | 0.001 | 0.001 | 0.001 | 0.003 | 0.001 | 0.001 | 0.004 |
| AKIT | 1133 | −5 | 0.001 | 0.025 | 0.001 | 0.001 | 0.002 | 0.001 | 0.001 | 0.001 | 0.002 | 0.001 |
| BEAG | 995 | −1 | 0.002 | 0.001 | 0.002 | 0.002 | 0.001 | 0.001 | 0.001 | 0.001 | 0.002 | 0.005 |
| BEAG | 994 | −2 | 0.002 | 0.001 | 0.001 | 0.022 | 0.001 | 0.001 | 0.001 | 0.002 | 0.001 | 0.002 |
| BEAG | 1323 | −1 | 0.007 | 0.001 | 0.005 | 0.003 | 0.006 | 0.008 | 0.002 | 0.006 | 0.007 | 0.013 |
| BEAG | 1327 | 0 | 0.004 | 0.002 | 0.002 | 0.005 | 0.002 | 0.048 | 0.002 | 0.008 | 0.006 | 0.002 |
| BEAG | 1324 | 0 | 0.01 | 0.005 | 0.003 | 0.002 | 0.002 | 0.001 | 0.086 | 0.005 | 0.002 | 0.274 |
| BMD | 968 | −17 | 0.001 | 0.001 | 0.001 | 0.002 | 0.002 | 0.001 | 0.001 | 0.002 | 0.972 | 0.001 |
| BMD | 970 | −31 | 0.003 | 0.005 | 0.002 | 0.003 | 0.002 | 0.001 | 0.002 | 0.002 | 0.956 | 0.002 |
| BMD | 941 | −11 | 0.003 | 0.002 | 0.002 | 0.001 | 0.002 | 0.009 | 0.002 | 0.004 | 0.937 | 0.001 |
| BMD | 943 | −10 | 0.004 | 0.001 | 0.005 | 0.007 | 0.002 | 0.002 | 0.001 | 0.002 | 0.934 | 0.003 |
| BMD | 971 | −51 | 0.003 | 0.003 | 0.003 | 0.003 | 0.002 | 0.003 | 0.002 | 0.003 | 0.933 | 0.006 |
| BOX | 1304 | −1 | 0.001 | 0.001 | 0.001 | 0.001 | 0.983 | 0.001 | 0.001 | 0.001 | 0.001 | 0.001 |
| BOX | 1179 | −3 | 0.001 | 0.001 | 0.001 | 0.001 | 0.982 | 0.001 | 0.001 | 0.001 | 0.001 | 0.001 |
| BOX | 1178 | −1 | 0.001 | 0.001 | 0.001 | 0.001 | 0.978 | 0.001 | 0.002 | 0.001 | 0.001 | 0.001 |
| BOX | 1176 | −1 | 0.001 | 0.001 | 0.002 | 0.001 | 0.972 | 0.001 | 0.001 | 0.001 | 0.001 | 0.002 |
| BOX | 1177 | 0 | 0.012 | 0.001 | 0.003 | 0.037 | 0.004 | 0.889 | 0.001 | 0.003 | 0.003 | 0.004 |
| BULD | 1195 | −9 | 0.001 | 0.001 | 0.002 | 0.001 | 0.004 | 0.003 | 0.001 | 0.974 | 0.001 | 0.001 |
| BULD | 1193 | −1 | 0.002 | 0.002 | 0.002 | 0.001 | 0.006 | 0.002 | 0.001 | 0.96 | 0.001 | 0.001 |
| BULD | 1197 | −3 | 0.002 | 0.004 | 0.005 | 0.001 | 0.002 | 0.003 | 0.004 | 0.948 | 0.002 | 0.002 |
| BULD | 1194 | −2 | 0.002 | 0.001 | 0.002 | 0.01 | 0.006 | 0.004 | 0.002 | 0.935 | 0.002 | 0.002 |
| BULD | 1198 | 0 | 0.005 | 0.001 | 0.002 | 0.005 | 0.004 | 0.005 | 0.004 | 0.912 | 0.043 | 0.002 |
| PRES | 1082 | −3 | 0.151 | 0.206 | 0.002 | 0.023 | 0.293 | 0.008 | 0.003 | 0.199 | 0.004 | 0.009 |
| BULM | 1107 | −1 | 0.005 | 0.001 | 0.005 | 0.001 | 0.95 | 0.002 | 0.001 | 0.002 | 0.002 | 0.001 |
| BULM | 1109 | 0 | 0.002 | 0.001 | 0.004 | 0.001 | 0.932 | 0.013 | 0.002 | 0.005 | 0.001 | 0.002 |
| BULM | 1108 | 0 | 0.003 | 0.001 | 0.005 | 0.002 | 0.894 | 0.002 | 0.01 | 0.009 | 0.007 | 0.009 |

TABLE 14-continued

| | | | | | | | | | | | | |
|---|---|---|---|---|---|---|---|---|---|---|---|---|
| BULM | 1105 | 0 | 0.011 | 0.002 | 0.002 | 0.008 | 0.87 | 0.012 | 0.002 | 0.012 | 0.004 | 0.004 |
| BULM | 1106 | -3 | 0.002 | 0.003 | 0.004 | 0.002 | 0.823 | 0.004 | 0.017 | 0.017 | 0.003 | 0.004 |
| MAST | 991 | -14 | 0.002 | 0.001 | 0.002 | 0.006 | 0.963 | 0.001 | 0.001 | 0.001 | 0.002 | 0.002 |
| MAST | 1066 | -2 | 0.003 | 0.001 | 0.002 | 0.003 | 0.948 | 0.003 | 0.001 | 0.007 | 0.003 | 0.005 |
| MAST | 1016 | -1 | 0.004 | 0.002 | 0.003 | 0.003 | 0.93 | 0.001 | 0.002 | 0.025 | 0.006 | 0.001 |
| MAST | 1015 | 0 | 0.002 | 0.001 | 0.002 | 0.019 | 0.929 | 0.002 | 0.001 | 0.003 | 0.006 | 0.004 |
| MAST | 1017 | -22 | 0.002 | 0.001 | 0.025 | 0.001 | 0.885 | 0.001 | 0.001 | 0.002 | 0.003 | 0.003 |
| CHIH | 1203 | -3 | 0.932 | 0.003 | 0.009 | 0.003 | 0.002 | 0.003 | 0.003 | 0.003 | 0.014 | 0.003 |
| CHIH | 1202 | -10 | 0.916 | 0.001 | 0.003 | 0.005 | 0.005 | 0.003 | 0.002 | 0.004 | 0.001 | 0.007 |
| CHIH | 1204 | 0 | 0.868 | 0.002 | 0.004 | 0.002 | 0.003 | 0.002 | 0.002 | 0.003 | 0.018 | 0.005 |
| CHIH | 1205 | -3 | 0.455 | 0.008 | 0.032 | 0.004 | 0.012 | 0.003 | 0.023 | 0.022 | 0.001 | 0.006 |
| CHIH | 1206 | -1 | 0.436 | 0.003 | 0.016 | 0.008 | 0.033 | 0.152 | 0.006 | 0.006 | 0.006 | 0.031 |
| DACH | 1052 | -2 | 0.001 | 0.001 | 0.001 | 0.976 | 0.003 | 0.001 | 0.001 | 0.002 | 0.001 | 0.001 |
| DACH | 1055 | -1 | 0.003 | 0.001 | 0.002 | 0.958 | 0.002 | 0.005 | 0.002 | 0.002 | 0.004 | 0.002 |
| DACH | 1054 | 0 | 0.002 | 0.002 | 0.002 | 0.951 | 0.002 | 0.014 | 0.001 | 0.003 | 0.002 | 0.002 |
| DACH | 1051 | -5 | 0.003 | 0.001 | 0.004 | 0.949 | 0.004 | 0.002 | 0.002 | 0.002 | 0.002 | 0.005 |
| DACH | 1053 | -1 | 0.011 | 0.002 | 0.005 | 0.892 | 0.002 | 0.004 | 0.002 | 0.01 | 0.002 | 0.003 |
| GOLD | 603 | 0 | 0.001 | 0.001 | 0.002 | 0.001 | 0.002 | 0.002 | 0.001 | 0.002 | 0.006 | 0.001 |
| GOLD | 591 | -4 | 0.002 | 0.001 | 0.003 | 0.004 | 0.011 | 0.004 | 0.004 | 0.004 | 0.001 | 0.003 |
| GOLD | 593 | 0 | 0.002 | 0.001 | 0.003 | 0.027 | 0.002 | 0.004 | 0.001 | 0.003 | 0.003 | 0.005 |
| GOLD | 604 | 0 | 0.002 | 0.001 | 0.002 | 0.003 | 0.003 | 0.072 | 0.001 | 0.004 | 0.002 | 0.004 |
| GOLD | 592 | -4 | 0.002 | 0.003 | 0.003 | 0.021 | 0.012 | 0.004 | 0.006 | 0.002 | 0.003 | 0.022 |
| IBIZ | 1148 | -20 | 0.002 | 0.002 | 0.929 | 0.001 | 0.004 | 0.001 | 0.009 | 0.002 | 0.001 | 0.003 |
| IBIZ | 1172 | 0 | 0.004 | 0.001 | 0.917 | 0.016 | 0.003 | 0.002 | 0.001 | 0.003 | 0.009 | 0.004 |
| IBIZ | 1162 | 0 | 0.03 | 0.001 | 0.913 | 0.001 | 0.004 | 0.003 | 0.001 | 0.003 | 0.002 | 0.003 |
| IBIZ | 1280 | -1 | 0.002 | 0.001 | 0.888 | 0.002 | 0.006 | 0.036 | 0.004 | 0.005 | 0.007 | 0.003 |
| IBIZ | 1147 | -8 | 0.007 | 0.001 | 0.871 | 0.001 | 0.003 | 0.002 | 0.001 | 0.005 | 0.002 | 0.002 |
| NEWF | 275 | -3 | 0.002 | 0.001 | 0.002 | 0.002 | 0.002 | 0.004 | 0.001 | 0.002 | 0.004 | 0.001 |
| NEWF | 274 | -1 | 0.002 | 0.001 | 0.007 | 0.001 | 0.003 | 0.003 | 0.001 | 0.003 | 0.001 | 0.003 |
| NEWF | 277 | 0 | 0.002 | 0.002 | 0.001 | 0.002 | 0.076 | 0.028 | 0.001 | 0.002 | 0.002 | 0.003 |
| NEWF | 271 | -3 | 0.034 | 0.002 | 0.004 | 0.003 | 0.002 | 0.003 | 0.001 | 0.016 | 0.008 | 0.003 |
| NEWF | 278 | -1 | 0.011 | 0.002 | 0.011 | 0.018 | 0.029 | 0.003 | 0.004 | 0.004 | 0.006 | 0.001 |
| PEKE | 1143 | 0 | 0.001 | 0.001 | 0.001 | 0.001 | 0.001 | 0.001 | 0.001 | 0.001 | 0.001 | 0.001 |
| PEKE | 1145 | -1 | 0.003 | 0.002 | 0.002 | 0.002 | 0.001 | 0.001 | 0.002 | 0.001 | 0.001 | 0.003 |
| PEKE | 1211 | 0 | 0.007 | 0.004 | 0.002 | 0.002 | 0.002 | 0.004 | 0.001 | 0.002 | 0.002 | 0.003 |
| PEKE | 1213 | -4 | 0.001 | 0.001 | 0.002 | 0.001 | 0.001 | 0.001 | 0.001 | 0.001 | 0.002 | 0.003 |
| PEKE | 1212 | 0 | 0.003 | 0.001 | 0.003 | 0.002 | 0.005 | 0.011 | 0.002 | 0.002 | 0.002 | 0.001 |
| POM | 1238 | 0 | 0.002 | 0.001 | 0.001 | 0.002 | 0.002 | 0.001 | 0.002 | 0.001 | 0.002 | 0.001 |
| POM | 1190 | 0 | 0.018 | 0.003 | 0.003 | 0.001 | 0.003 | 0.004 | 0.003 | 0.005 | 0.034 | 0.015 |
| POM | 1191 | -2 | 0.006 | 0.001 | 0.002 | 0.004 | 0.097 | 0.006 | 0.002 | 0.022 | 0.002 | 0.001 |
| POM | 1210 | -7 | 0.003 | 0.01 | 0.006 | 0.007 | 0.002 | 0.012 | 0.004 | 0.035 | 0.005 | 0.002 |
| POM | 1239 | -14 | 0.004 | 0.002 | 0.232 | 0.007 | 0.004 | 0.003 | 0.004 | 0.007 | 0.005 | 0.01 |
| PRES | 1093 | -14 | 0.004 | 0.008 | 0.01 | 0.002 | 0.028 | 0.022 | 0.003 | 0.01 | 0.002 | 0.004 |
| PRES | 1115 | -1 | 0.003 | 0.002 | 0.002 | 0.003 | 0.01 | 0.066 | 0.009 | 0.01 | 0.001 | 0.01 |
| PRES | 1127 | -7 | 0.008 | 0.002 | 0.067 | 0.016 | 0.008 | 0.012 | 0.006 | 0.123 | 0.003 | 0.01 |
| PRES | 1096 | 0 | 0.003 | 0.002 | 0.004 | 0.105 | 0.019 | 0.019 | 0.006 | 0.145 | 0.008 | 0.007 |
| PUG | 1184 | -1 | 0.001 | 0.001 | 0.001 | 0.001 | 0.001 | 0.001 | 0.001 | 0.001 | 0.001 | 0.001 |
| PUG | 1077 | -4 | 0.001 | 0.001 | 0.001 | 0.001 | 0.001 | 0.001 | 0.001 | 0.001 | 0.001 | 0.004 |
| PUG | 1104 | -1 | 0.001 | 0.001 | 0.002 | 0.001 | 0.003 | 0.002 | 0.001 | 0.001 | 0.002 | 0.002 |
| PUG | 1183 | -1 | 0.001 | 0.001 | 0.008 | 0.001 | 0.002 | 0.001 | 0.001 | 0.001 | 0.002 | 0.002 |
| PUG | 1192 | -3 | 0.002 | 0.001 | 0.003 | 0.001 | 0.001 | 0.006 | 0.002 | 0.003 | 0.003 | 0.002 |
| ROTT | 1034 | 0 | 0.003 | 0.001 | 0.003 | 0.004 | 0.001 | 0.006 | 0.001 | 0.003 | 0.005 | 0.002 |
| ROTT | 1033 | -1 | 0.002 | 0.001 | 0.002 | 0.003 | 0.003 | 0.003 | 0.002 | 0.007 | 0.001 | 0.008 |
| ROTT | 1028 | -3 | 0.001 | 0.001 | 0.001 | 0.007 | 0.001 | 0.005 | 0.001 | 0.001 | 0.001 | 0.001 |
| ROTT | 1029 | -1 | 0.002 | 0.001 | 0.001 | 0.004 | 0.002 | 0.001 | 0.001 | 0.001 | 0.034 | 0.002 |
| ROTT | 1236 | 0 | 0.003 | 0.003 | 0.004 | 0.01 | 0.002 | 0.006 | 0.003 | 0.016 | 0.001 | 0.001 |
| ROTT | 1014 | -2 | 0.004 | 0.002 | 0.004 | 0.001 | 0.004 | 0.001 | 0.002 | 0.003 | 0.006 | 0.003 |
| WOLF | 282135 | -1 | 0.001 | 0.979 | 0.001 | 0.001 | 0.001 | 0.001 | 0.002 | 0.001 | 0.001 | 0.001 |
| WOLF | 930121 | -3 | 0.001 | 0.032 | 0.001 | 0.001 | 0.001 | 0.001 | 0.938 | 0.001 | 0.001 | 0.001 |
| WOLF | 492 | -1 | 0.001 | 0.044 | 0.001 | 0.001 | 0.001 | 0.001 | 0.371 | 0.001 | 0.001 | 0.001 |
| WOLF | Iran | -7 | 0.002 | 0.022 | 0.002 | 0.004 | 0.003 | 0.001 | 0.203 | 0.001 | 0.001 | 0.002 |

[a]See Table 5 for abbreviations of canid populations.
KBB: pbe

TABLE 15A

| Canid Population[a] | Canid ID No. | Missing Data | Groups | | | | | |
|---|---|---|---|---|---|---|---|---|
| | | | 1 | 2 | 3 | 4 | 5 | 6 |
| WOLF | 4928 | -1 | 0 | 0.999 | 0 | 0.001 | 0 | 0 |
| WOLF | 282135 | -1 | 0 | 0.998 | 0 | 0.002 | 0 | 0 |
| WOLF | 930121 | -3 | 0 | 0.997 | 0 | 0.003 | 0 | 0 |
| WOLF | Iran1 | -7 | 0 | 0.999 | 0 | 0.001 | 0 | 0 |
| AKIT | 1130 | -4 | 0 | 0.005 | 0 | 0.995 | 0 | 0 |
| AKIT | 1131 | 0 | 0 | 0.013 | 0 | 0.987 | 0 | 0 |

TABLE 15A-continued

| Canid Population[a] | Canid ID No. | Missing Data | Groups | | | | | |
|---|---|---|---|---|---|---|---|---|
| | | | 1 | 2 | 3 | 4 | 5 | 6 |
| AKIT | 1132 | −3 | 0 | 0.004 | 0 | 0.996 | 0 | 0 |
| AKIT | 1133 | −5 | 0 | 0.005 | 0 | 0.995 | 0 | 0 |
| AKIT | 1134 | −4 | 0 | 0.007 | 0 | 0.993 | 0 | 0 |
| PEKE | 1143 | 0 | 0 | 0 | 0.999 | 0.001 | 0 | 0 |
| PEKE | 1145 | −1 | 0 | 0 | 0.992048 | 0.007952 | 0 | 0 |
| PEKE | 1211 | 0 | 0 | 0 | 0.947818 | 0.052182 | 0 | 0 |
| PEKE | 1212 | 0 | 0 | 0 | 0.961501 | 0.038499 | 0 | 0 |
| PEKE | 1213 | −4 | 0 | 0 | 0.997994 | 0.002006 | 0 | 0 |
| PUG | 1077 | −4 | 0 | 0 | 0 | 0.002 | 0.998 | 0 |
| PUG | 1104 | −1 | 0 | 0 | 0 | 0.006 | 0.994 | 0 |
| PUG | 1183 | −1 | 0 | 0 | 0 | 0.002 | 0.998 | 0 |
| PUG | 1184 | −1 | 0 | 0 | 0 | 0.001 | 0.999 | 0 |
| PUG | 1192 | −3 | 0 | 0 | 0 | 0.001 | 0.999 | 0 |
| GOLD | 591 | −4 | 0.021339 | 0 | 0 | 0.030068 | 0 | 0.948594 |
| GOLD | 592 | −4 | 0.004314 | 0 | 0 | 0.137187 | 0 | 0.858499 |
| GOLD | 593 | 0 | 0.005935 | 0 | 0 | 0.01088 | 0 | 0.983185 |
| GOLD | 603 | 0 | 0.008929 | 0 | 0 | 0.007937 | 0 | 0.983135 |
| GOLD | 604 | 0 | 0.037624 | 0 | 0 | 0.009901 | 0 | 0.952475 |
| AHRT | 1120 | −1 | 0.006289 | 0 | 0 | 0.213836 | 0 | 0.779874 |
| AHRT | 1121 | −4 | 0.003885 | 0 | 0 | 0.222999 | 0 | 0.773116 |
| AHRT | 1122 | 0 | 0.003079 | 0 | 0 | 0.230177 | 0 | 0.766744 |
| AHRT | 1123 | −2 | 0.016419 | 0 | 0 | 0.218139 | 0 | 0.765442 |
| AHRT | 1124 | −2 | 0.004594 | 0 | 0 | 0.234303 | 0 | 0.761103 |
| CHIH | 1202 | −10 | 0.008326 | 0 | 0 | 0.074931 | 0 | 0.916744 |
| CHIH | 1203 | −3 | 0.005578 | 0 | 0 | 0.203187 | 0 | 0.791235 |
| CHIH | 1204 | 0 | 0.004184 | 0 | 0 | 0.16318 | 0 | 0.832636 |
| CHIH | 1205 | −3 | 0.021598 | 0 | 0 | 0.280058 | 0 | 0.698344 |
| CHIH | 1206 | −1 | 0.097854 | 0 | 0 | 0.141631 | 0 | 0.760515 |
| POM | 1190 | 0 | 0.038938 | 0 | 0 | 0.115044 | 0 | 0.846018 |
| POM | 1191 | −2 | 0.480901 | 0 | 0 | 0.020568 | 0 | 0.498531 |
| POM | 1210 | −7 | 0.020236 | 0 | 0 | 0.15683 | 0 | 0.822934 |
| POM | 1238 | 0 | 0.006961 | 0 | 0 | 0.226605 | 0 | 0.766435 |
| POM | 1239 | −14 | 0.006266 | 0 | 0 | 0.373434 | 0 | 0.620301 |
| DACH | 1051 | −5 | 0.008145 | 0 | 0 | 0.095023 | 0 | 0.896833 |
| DACH | 1052 | −2 | 0.013889 | 0 | 0 | 0.007937 | 0 | 0.978175 |
| DACH | 1053 | −1 | 0.009747 | 0 | 0 | 0.025341 | 0 | 0.964912 |
| DACH | 1054 | 0 | 0.006917 | 0 | 0 | 0.011858 | 0 | 0.981225 |
| DACH | 1055 | −1 | 0.010848 | 0 | 0 | 0.013807 | 0 | 0.975345 |
| BEAG | 994 | −2 | 0.004869 | 0 | 0 | 0.02629 | 0 | 0.968841 |
| BEAG | 995 | −1 | 0.002681 | 0 | 0 | 0.106345 | 0 | 0.890974 |
| BEAG | 1323 | −1 | 0.009747 | 0 | 0 | 0.025341 | 0 | 0.964912 |
| BEAG | 1324 | 0 | 0.002839 | 0 | 0 | 0.290277 | 0 | 0.706884 |
| BEAG | 1327 | 0 | 0.01256 | 0 | 0 | 0.033816 | 0 | 0.953623 |
| IBIZ | 1147 | −8 | 0.011867 | 0 | 0 | 0.208861 | 0 | 0.779272 |
| IBIZ | 1148 | −20 | 0.01225 | 0 | 0 | 0.355255 | 0 | 0.632495 |
| IBIZ | 1162 | 0 | 0.019639 | 0 | 0 | 0.214454 | 0 | 0.765907 |
| IBIZ | 1172 | 0 | 0.00639 | 0 | 0 | 0.201278 | 0 | 0.792332 |
| IBIZ | 1280 | −1 | 0.023682 | 0 | 0 | 0.236058 | 0 | 0.74026 |
| BMD | 941 | −11 | 0.009709 | 0 | 0 | 0.029126 | 0 | 0.961165 |
| BMD | 943 | −10 | 0.006686 | 0 | 0 | 0.04489 | 0 | 0.948424 |
| BMD | 968 | −17 | 0.005831 | 0 | 0 | 0.028183 | 0 | 0.965986 |
| BMD | 970 | −31 | 0.011354 | 0 | 0 | 0.18897 | 0 | 0.799676 |
| BMD | 971 | −51 | 0.020568 | 0 | 0 | 0.020568 | 0 | 0.958864 |
| NEWF | 271 | −3 | 0.010913 | 0 | 0 | 0.007937 | 0 | 0.981151 |
| NEWF | 274 | −1 | 0.019881 | 0 | 0 | 0.005964 | 0 | 0.974155 |
| NEWF | 275 | −3 | 0.010934 | 0 | 0 | 0.005964 | 0 | 0.983101 |
| NEWF | 277 | 0 | 0.05859 | 0 | 0 | 0.006951 | 0 | 0.934459 |
| NEWF | 278 | −1 | 0.034213 | 0 | 0 | 0.022483 | 0 | 0.943304 |
| ROTT | 1014 | −2 | 0.0059 | 0 | 0 | 0.016716 | 0 | 0.977384 |
| ROTT | 1028 | −3 | 0.005946 | 0 | 0 | 0.00892 | 0 | 0.985134 |
| ROTT | 1029 | −1 | 0.004955 | 0 | 0 | 0.00892 | 0 | 0.986125 |
| ROTT | 1033 | −1 | 0.009728 | 0 | 0 | 0.027237 | 0 | 0.963035 |
| ROTT | 1034 | 0 | 0.021782 | 0 | 0 | 0.009901 | 0 | 0.968317 |
| PRES | 1082 | −3 | 0.419635 | 0 | 0 | 0.13119 | 0 | 0.449175 |
| PRES | 1093 | −14 | 0.430979 | 0 | 0 | 0.197432 | 0 | 0.371589 |
| PRES | 1096 | 0 | 0.705253 | 0 | 0 | 0.027237 | 0 | 0.26751 |
| PRES | 1115 | −1 | 0.572519 | 0 | 0 | 0.045802 | 0 | 0.381679 |
| PRES | 1127 | −7 | 0.418004 | 0 | 0 | 0.108734 | 0 | 0.473262 |
| BOX | 1176 | −1 | 0.98806 | 0 | 0 | 0.004975 | 0 | 0.006965 |
| BOX | 1177 | 0 | 0.964108 | 0 | 0 | 0.002991 | 0 | 0.032901 |
| BOX | 1178 | −1 | 0.993028 | 0 | 0 | 0.003984 | 0 | 0.002988 |
| BOX | 1179 | −3 | 0.993028 | 0 | 0 | 0.003984 | 0 | 0.002988 |
| BOX | 1304 | −1 | 0.989066 | 0 | 0 | 0.005964 | 0 | 0.00497 |
| BULD | 1193 | −1 | 0.971202 | 0 | 0 | 0.006951 | 0 | 0.021847 |
| BULD | 1194 | −2 | 0.989044 | 0 | 0 | 0.003984 | 0 | 0.006972 |

TABLE 15A-continued

| Canid Population[a] | Canid ID No. | Missing Data | Groups | | | | | |
|---|---|---|---|---|---|---|---|---|
| | | | 1 | 2 | 3 | 4 | 5 | 6 |
| BULD | 1195 | −9 | 0.99005 | 0 | 0 | 0.004975 | 0 | 0.004975 |
| BULD | 1197 | −3 | 0.879648 | 0 | 0 | 0.021526 | 0 | 0.098826 |
| BULD | 1198 | 0 | 0.983051 | 0 | 0 | 0.002991 | 0 | 0.013958 |
| MAST | 991 | −14 | 0.97931 | 0 | 0 | 0.014778 | 0 | 0.005911 |
| MAST | 1015 | 0 | 0.983085 | 0 | 0 | 0.004975 | 0 | 0.01194 |
| MAST | 1016 | −1 | 0.981188 | 0 | 0 | 0.009901 | 0 | 0.008911 |
| MAST | 1017 | −22 | 0.94294 | 0 | 0 | 0.032882 | 0 | 0.024178 |
| MAST | 1066 | −2 | 0.983168 | 0 | 0 | 0.009901 | 0 | 0.006931 |
| BULM | 1105 | 0 | 0.985075 | 0 | 0 | 0.004975 | 0 | 0.00995 |
| BULM | 1106 | −3 | 0.971429 | 0 | 0 | 0.014778 | 0 | 0.013793 |
| BULM | 1107 | −1 | 0.973529 | 0 | 0 | 0.019608 | 0 | 0.006863 |
| BULM | 1108 | 0 | 0.970559 | 0 | 0 | 0.018646 | 0 | 0.010795 |
| BULM | 1109 | 0 | 0.974535 | 0 | 0 | 0.020568 | 0 | 0.004897 |

TABLE 15B

| Canid Population[a] | Canid ID No. | Missing Data | Groups | | | | | |
|---|---|---|---|---|---|---|---|---|
| | | | 1 | 2 | 3 | 4 | 5 | 6 |
| WOLF | 4928 | −1 | 0 | 0.999 | 0 | 0.001 | 0 | 0 |
| WOLF | 282135 | −1 | 0 | 0.998 | 0 | 0.002 | 0 | 0 |
| WOLF | 930121 | −3 | 0 | 0.997 | 0 | 0.003 | 0 | 0 |
| WOLF | Iran1 | −7 | 0 | 0.999 | 0 | 0.001 | 0 | 0 |
| AKIT | 1130 | −4 | 0 | 0.005 | 0 | 0.995 | 0 | 0 |
| AKIT | 1131 | 0 | 0 | 0.013 | 0 | 0.987 | 0 | 0 |
| AKIT | 1132 | −3 | 0 | 0.004 | 0 | 0.996 | 0 | 0 |
| AKIT | 1133 | −5 | 0 | 0.005 | 0 | 0.995 | 0 | 0 |
| AKIT | 1134 | −4 | 0 | 0.007 | 0 | 0.993 | 0 | 0 |
| PEKE | 1143 | 0 | 0 | 0 | 0.999 | 0.001 | 0 | 0 |
| PEKE | 1145 | −1 | 0 | 0 | 0.992048 | 0.007952 | 0 | 0 |
| PEKE | 1211 | 0 | 0 | 0 | 0.947818 | 0.052182 | 0 | 0 |
| PEKE | 1212 | 0 | 0 | 0 | 0.961501 | 0.038499 | 0 | 0 |
| PEKE | 1213 | −4 | 0 | 0 | 0.997994 | 0.002006 | 0 | 0 |
| PUG | 1077 | −4 | 0 | 0 | 0 | 0.002 | 0.998 | 0 |
| PUG | 1104 | −1 | 0 | 0 | 0 | 0.006 | 0.994 | 0 |
| PUG | 1183 | −1 | 0 | 0 | 0 | 0.002 | 0.998 | 0 |
| PUG | 1184 | −1 | 0 | 0 | 0 | 0.001 | 0.999 | 0 |
| PUG | 1192 | −3 | 0 | 0 | 0 | 0.001 | 0.999 | 0 |
| GOLD | 591 | −4 | 0.021339 | 0 | 0 | 0.030068 | 0 | 0.948594 |
| GOLD | 592 | −4 | 0.004314 | 0 | 0 | 0.137187 | 0 | 0.858499 |
| GOLD | 593 | 0 | 0.005935 | 0 | 0 | 0.01088 | 0 | 0.983185 |
| GOLD | 603 | 0 | 0.008929 | 0 | 0 | 0.007937 | 0 | 0.983135 |
| GOLD | 604 | 0 | 0.037624 | 0 | 0 | 0.009901 | 0 | 0.952475 |
| AHRT | 1120 | −1 | 0.006289 | 0 | 0 | 0.213836 | 0 | 0.779874 |
| AHRT | 1121 | −4 | 0.003885 | 0 | 0 | 0.222999 | 0 | 0.773116 |
| AHRT | 1122 | 0 | 0.003079 | 0 | 0 | 0.230177 | 0 | 0.766744 |
| AHRT | 1123 | −2 | 0.016419 | 0 | 0 | 0.218139 | 0 | 0.765442 |
| AHRT | 1124 | −2 | 0.004594 | 0 | 0 | 0.234303 | 0 | 0.761103 |
| CHIH | 1202 | −10 | 0.008326 | 0 | 0 | 0.074931 | 0 | 0.916744 |
| CHIH | 1203 | −3 | 0.005578 | 0 | 0 | 0.203187 | 0 | 0.791235 |
| CHIH | 1204 | 0 | 0.004184 | 0 | 0 | 0.16318 | 0 | 0.832636 |
| CHIH | 1205 | −3 | 0.021598 | 0 | 0 | 0.280058 | 0 | 0.698344 |
| CHIH | 1206 | −1 | 0.097854 | 0 | 0 | 0.141631 | 0 | 0.760515 |
| POM | 1190 | 0 | 0.038938 | 0 | 0 | 0.115044 | 0 | 0.846018 |
| POM | 1191 | −2 | 0.480901 | 0 | 0 | 0.020568 | 0 | 0.498531 |
| POM | 1210 | −7 | 0.020236 | 0 | 0 | 0.15683 | 0 | 0.822934 |
| POM | 1238 | 0 | 0.006961 | 0 | 0 | 0.226605 | 0 | 0.766435 |
| POM | 1239 | −14 | 0.006266 | 0 | 0 | 0.373434 | 0 | 0.620301 |
| DACH | 1051 | −5 | 0.008145 | 0 | 0 | 0.095023 | 0 | 0.896833 |
| DACH | 1052 | −2 | 0.013889 | 0 | 0 | 0.007937 | 0 | 0.978175 |
| DACH | 1053 | −1 | 0.009747 | 0 | 0 | 0.025341 | 0 | 0.964912 |
| DACH | 1054 | 0 | 0.006917 | 0 | 0 | 0.011858 | 0 | 0.981225 |
| DACH | 1055 | −1 | 0.010848 | 0 | 0 | 0.013807 | 0 | 0.975345 |
| BEAG | 994 | −2 | 0.004869 | 0 | 0 | 0.02629 | 0 | 0.968841 |
| BEAG | 995 | −1 | 0.002681 | 0 | 0 | 0.106345 | 0 | 0.890974 |
| BEAG | 1323 | −1 | 0.009747 | 0 | 0 | 0.025341 | 0 | 0.964912 |
| BEAG | 1324 | 0 | 0.002839 | 0 | 0 | 0.290277 | 0 | 0.706884 |
| BEAG | 1327 | 0 | 0.01256 | 0 | 0 | 0.033816 | 0 | 0.953623 |
| IBIZ | 1147 | −8 | 0.011867 | 0 | 0 | 0.208861 | 0 | 0.779272 |
| IBIZ | 1148 | −20 | 0.01225 | 0 | 0 | 0.355255 | 0 | 0.632495 |
| IBIZ | 1162 | 0 | 0.019639 | 0 | 0 | 0.214454 | 0 | 0.765907 |

TABLE 15B-continued

| Canid Population[a] | Canid ID No. | Missing Data | Groups | | | | | |
|---|---|---|---|---|---|---|---|---|
| | | | 1 | 2 | 3 | 4 | 5 | 6 |
| IBIZ | 1172 | 0 | 0.00639 | 0 | 0 | 0.201278 | 0 | 0.792332 |
| IBIZ | 1280 | −1 | 0.023682 | 0 | 0 | 0.236058 | 0 | 0.74026 |
| BMD | 941 | −11 | 0.009709 | 0 | 0 | 0.029126 | 0 | 0.961165 |
| BMD | 943 | −10 | 0.006686 | 0 | 0 | 0.04489 | 0 | 0.948424 |
| BMD | 968 | −17 | 0.005831 | 0 | 0 | 0.028183 | 0 | 0.965986 |
| BMD | 970 | −31 | 0.011354 | 0 | 0 | 0.18897 | 0 | 0.799676 |
| BMD | 971 | −51 | 0.020568 | 0 | 0 | 0.020568 | 0 | 0.958864 |
| NEWF | 271 | −3 | 0.010913 | 0 | 0 | 0.007937 | 0 | 0.981151 |
| NEWF | 274 | −1 | 0.019881 | 0 | 0 | 0.005964 | 0 | 0.974155 |
| NEWF | 275 | −3 | 0.010934 | 0 | 0 | 0.005964 | 0 | 0.983101 |
| NEWF | 277 | 0 | 0.05859 | 0 | 0 | 0.006951 | 0 | 0.934459 |
| NEWF | 278 | −1 | 0.034213 | 0 | 0 | 0.022483 | 0 | 0.943304 |
| ROTT | 1014 | −2 | 0.0059 | 0 | 0 | 0.016716 | 0 | 0.977384 |
| ROTT | 1028 | −3 | 0.005946 | 0 | 0 | 0.00892 | 0 | 0.985134 |
| ROTT | 1029 | −1 | 0.004955 | 0 | 0 | 0.00892 | 0 | 0.986125 |
| ROTT | 1033 | −1 | 0.009728 | 0 | 0 | 0.027237 | 0 | 0.963035 |
| ROTT | 1034 | 0 | 0.021782 | 0 | 0 | 0.009901 | 0 | 0.968317 |
| PRES | 1082 | −3 | 0.419635 | 0 | 0 | 0.13119 | 0 | 0.449175 |
| PRES | 1093 | −14 | 0.430979 | 0 | 0 | 0.197432 | 0 | 0.371589 |
| PRES | 1096 | 0 | 0.705253 | 0 | 0 | 0.027237 | 0 | 0.26751 |
| PRES | 1115 | −1 | 0.572519 | 0 | 0 | 0.045802 | 0 | 0.381679 |
| PRES | 1127 | −7 | 0.418004 | 0 | 0 | 0.108734 | 0 | 0.473262 |
| BOX | 1176 | −1 | 0.002964 | 0 | 0 | 0.004941 | 0 | 0.006917 |
| BOX | 1177 | 0 | 0.046332 | 0 | 0 | 0.002896 | 0 | 0.031853 |
| BOX | 1178 | −1 | 0.002979 | 0 | 0 | 0.003972 | 0 | 0.002979 |
| BOX | 1179 | −3 | 0.000993 | 0 | 0 | 0.003972 | 0 | 0.002979 |
| BOX | 1304 | −1 | 0.001978 | 0 | 0 | 0.005935 | 0 | 0.004946 |
| BULD | 1193 | −1 | 0.968902 | 0 | 0 | 0.006803 | 0 | 0.02138 |
| BULD | 1194 | −2 | 0.986152 | 0 | 0 | 0.003956 | 0 | 0.006924 |
| BULD | 1195 | −9 | 0.988119 | 0 | 0 | 0.00495 | 0 | 0.00495 |
| BULD | 1197 | −3 | 0.887801 | 0 | 0 | 0.01959 | 0 | 0.089938 |
| BULD | 1198 | 0 | 0.979351 | 0 | 0 | 0.00295 | 0 | 0.013766 |
| MAST | 991 | −14 | 0.978452 | 0 | 0 | 0.014691 | 0 | 0.005877 |
| MAST | 1015 | 0 | 0.981318 | 0 | 0 | 0.004916 | 0 | 0.011799 |
| MAST | 1016 | −1 | 0.980373 | 0 | 0 | 0.009814 | 0 | 0.008832 |
| MAST | 1017 | −22 | 0.943343 | 0 | 0 | 0.032106 | 0 | 0.023607 |
| MAST | 1066 | −2 | 0.981318 | 0 | 0 | 0.009833 | 0 | 0.006883 |
| BULM | 1105 | 0 | 0.981281 | 0 | 0 | 0.004926 | 0 | 0.009852 |
| BULM | 1106 | −3 | 0.969874 | 0 | 0 | 0.014577 | 0 | 0.013605 |
| BULM | 1107 | −1 | 0.971762 | 0 | 0 | 0.019474 | 0 | 0.006816 |
| BULM | 1108 | 0 | 0.969903 | 0 | 0 | 0.018447 | 0 | 0.01068 |
| BULM | 1109 | 0 | 0.971735 | 0 | 0 | 0.020468 | 0 | 0.004873 |

TABLE 15C

| Canid Population[a] | Canid ID No. | Missing Data | Groups | | | | | |
|---|---|---|---|---|---|---|---|---|
| | | | 1 | 2 | 3 | 4 | 5 | 6 |
| WOLF | 4928 | −1 | 0 | 0.999 | 0 | 0.001 | 0 | 0 |
| WOLF | 282135 | −1 | 0 | 0.998 | 0 | 0.002 | 0 | 0 |
| WOLF | 930121 | −3 | 0 | 0.997 | 0 | 0.003 | 0 | 0 |
| WOLF | Iran1 | −7 | 0 | 0.999 | 0 | 0.001 | 0 | 0 |
| AKIT | 1130 | −4 | 0 | 0.005 | 0 | 0.995 | 0 | 0 |
| AKIT | 1131 | 0 | 0 | 0.013 | 0 | 0.987 | 0 | 0 |
| AKIT | 1132 | −3 | 0 | 0.004 | 0 | 0.996 | 0 | 0 |
| AKIT | 1133 | −5 | 0 | 0.005 | 0 | 0.995 | 0 | 0 |
| AKIT | 1134 | −4 | 0 | 0.007 | 0 | 0.993 | 0 | 0 |
| PEKE | 1143 | 0 | 0 | 0 | 0.999 | 0.001 | 0 | 0 |
| PEKE | 1145 | −1 | 0 | 0 | 0.992048 | 0.007952 | 0 | 0 |
| PEKE | 1211 | 0 | 0 | 0 | 0.947818 | 0.052182 | 0 | 0 |
| PEKE | 1212 | 0 | 0 | 0 | 0.961501 | 0.038499 | 0 | 0 |
| PEKE | 1213 | −4 | 0 | 0 | 0.997994 | 0.002006 | 0 | 0 |
| PUG | 1077 | −4 | 0 | 0 | 0 | 0.002 | 0.998 | 0 |
| PUG | 1104 | −1 | 0 | 0 | 0 | 0.006 | 0.994 | 0 |
| PUG | 1183 | −1 | 0 | 0 | 0 | 0.002 | 0.998 | 0 |
| PUG | 1184 | −1 | 0 | 0 | 0 | 0.001 | 0.999 | 0 |
| PUG | 1192 | −3 | 0 | 0 | 0 | 0.001 | 0.999 | 0 |
| GOLD | 591 | −4 | 0.021339 | 0 | 0 | 0.030068 | 0 | 0.948594 |
| GOLD | 592 | −4 | 0.004314 | 0 | 0 | 0.137187 | 0 | 0.858499 |
| GOLD | 593 | 0 | 0.005935 | 0 | 0 | 0.01088 | 0 | 0.983185 |
| GOLD | 603 | 0 | 0.008929 | 0 | 0 | 0.007937 | 0 | 0.983135 |

TABLE 15C-continued

| Canid Population[a] | Canid ID No. | Missing Data | Groups | | | | | |
|---|---|---|---|---|---|---|---|---|
| | | | 1 | 2 | 3 | 4 | 5 | 6 |
| GOLD | 604 | 0 | 0.037624 | 0 | 0 | 0.009901 | 0 | 0.952475 |
| AHRT | 1120 | −1 | 0.006289 | 0 | 0 | 0.213836 | 0 | 0.779874 |
| AHRT | 1121 | −4 | 0.003885 | 0 | 0 | 0.222999 | 0 | 0.773116 |
| AHRT | 1122 | 0 | 0.003079 | 0 | 0 | 0.230177 | 0 | 0.766744 |
| AHRT | 1123 | −2 | 0.016419 | 0 | 0 | 0.218139 | 0 | 0.765442 |
| AHRT | 1124 | −2 | 0.004594 | 0 | 0 | 0.234303 | 0 | 0.761103 |
| CHIH | 1202 | −10 | 0.008326 | 0 | 0 | 0.074931 | 0 | 0.916744 |
| CHIH | 1203 | −3 | 0.005578 | 0 | 0 | 0.203187 | 0 | 0.791235 |
| CHIH | 1204 | 0 | 0.004184 | 0 | 0 | 0.16318 | 0 | 0.832636 |
| CHIH | 1205 | −3 | 0.021598 | 0 | 0 | 0.280058 | 0 | 0.698344 |
| CHIH | 1206 | −1 | 0.097854 | 0 | 0 | 0.141631 | 0 | 0.760515 |
| POM | 1190 | 0 | 0.038938 | 0 | 0 | 0.115044 | 0 | 0.846018 |
| POM | 1191 | −2 | 0.480901 | 0 | 0 | 0.020568 | 0 | 0.498531 |
| POM | 1210 | −7 | 0.020236 | 0 | 0 | 0.15683 | 0 | 0.822934 |
| POM | 1238 | 0 | 0.006961 | 0 | 0 | 0.226605 | 0 | 0.766435 |
| POM | 1239 | −14 | 0.006266 | 0 | 0 | 0.373434 | 0 | 0.620301 |
| DACH | 1051 | −5 | 0.008145 | 0 | 0 | 0.095023 | 0 | 0.896833 |
| DACH | 1052 | −2 | 0.013889 | 0 | 0 | 0.007937 | 0 | 0.978175 |
| DACH | 1053 | −1 | 0.009747 | 0 | 0 | 0.025341 | 0 | 0.964912 |
| DACH | 1054 | 0 | 0.006917 | 0 | 0 | 0.011858 | 0 | 0.981225 |
| DACH | 1055 | −1 | 0.010848 | 0 | 0 | 0.013807 | 0 | 0.975345 |
| BEAG | 994 | −2 | 0.004869 | 0 | 0 | 0.02629 | 0 | 0.968841 |
| BEAG | 995 | −1 | 0.002681 | 0 | 0 | 0.106345 | 0 | 0.890974 |
| BEAG | 1323 | −1 | 0.009747 | 0 | 0 | 0.025341 | 0 | 0.964912 |
| BEAG | 1324 | 0 | 0.002839 | 0 | 0 | 0.290277 | 0 | 0.706884 |
| BEAG | 1327 | 0 | 0.01256 | 0 | 0 | 0.033816 | 0 | 0.953623 |
| IBIZ | 1147 | −8 | 0.011867 | 0 | 0 | 0.208861 | 0 | 0.779272 |
| IBIZ | 1148 | −20 | 0.01225 | 0 | 0 | 0.355255 | 0 | 0.632495 |
| IBIZ | 1162 | 0 | 0.019639 | 0 | 0 | 0.214454 | 0 | 0.765907 |
| IBIZ | 1172 | 0 | 0.00639 | 0 | 0 | 0.201278 | 0 | 0.792332 |
| IBIZ | 1280 | −1 | 0.023682 | 0 | 0 | 0.236058 | 0 | 0.74026 |
| BMD | 941 | −11 | 0.009709 | 0 | 0 | 0.029126 | 0 | 0.961165 |
| BMD | 943 | −10 | 0.006686 | 0 | 0 | 0.04489 | 0 | 0.948424 |
| BMD | 968 | −17 | 0.005831 | 0 | 0 | 0.028183 | 0 | 0.965986 |
| BMD | 970 | −31 | 0.011354 | 0 | 0 | 0.18897 | 0 | 0.799676 |
| BMD | 971 | −51 | 0.020568 | 0 | 0 | 0.020568 | 0 | 0.958864 |
| NEWF | 271 | −3 | 0.010913 | 0 | 0 | 0.007937 | 0 | 0.981151 |
| NEWF | 274 | −1 | 0.019881 | 0 | 0 | 0.005964 | 0 | 0.974155 |
| NEWF | 275 | −3 | 0.010934 | 0 | 0 | 0.005964 | 0 | 0.983101 |
| NEWF | 277 | 0 | 0.05859 | 0 | 0 | 0.006951 | 0 | 0.934459 |
| NEWF | 278 | −1 | 0.034213 | 0 | 0 | 0.022483 | 0 | 0.943304 |
| ROTT | 1014 | −2 | 0.0059 | 0 | 0 | 0.016716 | 0 | 0.977384 |
| ROTT | 1028 | −3 | 0.005946 | 0 | 0 | 0.00892 | 0 | 0.985134 |
| ROTT | 1029 | −1 | 0.004955 | 0 | 0 | 0.00892 | 0 | 0.986125 |
| ROTT | 1033 | −1 | 0.009728 | 0 | 0 | 0.027237 | 0 | 0.963035 |
| ROTT | 1034 | 0 | 0.021782 | 0 | 0 | 0.009901 | 0 | 0.968317 |
| PRES | 1082 | −3 | 0.419635 | 0 | 0 | 0.13119 | 0 | 0.449175 |
| PRES | 1093 | −14 | 0.430979 | 0 | 0 | 0.197432 | 0 | 0.371589 |
| PRES | 1096 | 0 | 0.705253 | 0 | 0 | 0.027237 | 0 | 0.26751 |
| PRES | 1115 | −1 | 0.572519 | 0 | 0 | 0.045802 | 0 | 0.381679 |
| PRES | 1127 | −7 | 0.418004 | 0 | 0 | 0.108734 | 0 | 0.473262 |
| BOX | 1176 | −1 | 0.002964 | 0 | 0 | 0.004941 | 0 | 0.006917 |
| BOX | 1177 | 0 | 0.046332 | 0 | 0 | 0.002896 | 0 | 0.031853 |
| BOX | 1178 | −1 | 0.002979 | 0 | 0 | 0.003972 | 0 | 0.002979 |
| BOX | 1179 | −3 | 0.000993 | 0 | 0 | 0.003972 | 0 | 0.002979 |
| BOX | 1304 | −1 | 0.001978 | 0 | 0 | 0.005935 | 0 | 0.004946 |
| BULD | 1193 | −1 | 0.001938 | 0 | 0 | 0.006783 | 0 | 0.021318 |
| BULD | 1194 | −2 | 0.004931 | 0 | 0 | 0.003945 | 0 | 0.006903 |
| BULD | 1195 | −9 | 0.000988 | 0 | 0 | 0.004941 | 0 | 0.004941 |
| BULD | 1197 | −3 | 0.003552 | 0 | 0 | 0.019538 | 0 | 0.089698 |
| BULD | 1198 | 0 | 0.003918 | 0 | 0 | 0.002938 | 0 | 0.013712 |
| MAST | 991 | −14 | 0.976517 | 0 | 0 | 0.014677 | 0 | 0.005871 |
| MAST | 1015 | 0 | 0.979392 | 0 | 0 | 0.004907 | 0 | 0.011776 |
| MAST | 1016 | −1 | 0.972549 | 0 | 0 | 0.009804 | 0 | 0.008824 |
| MAST | 1017 | −22 | 0.941509 | 0 | 0 | 0.032075 | 0 | 0.023585 |
| MAST | 1066 | −2 | 0.975466 | 0 | 0 | 0.009814 | 0 | 0.006869 |
| BULM | 1105 | 0 | 0.976447 | 0 | 0 | 0.004907 | 0 | 0.009814 |
| BULM | 1106 | −3 | 0.964113 | 0 | 0 | 0.014549 | 0 | 0.013579 |
| BULM | 1107 | −1 | 0.969874 | 0 | 0 | 0.019436 | 0 | 0.006803 |
| BULM | 1108 | 0 | 0.967022 | 0 | 0 | 0.018429 | 0 | 0.010669 |
| BULM | 1109 | 0 | 0.968902 | 0 | 0 | 0.020408 | 0 | 0.004859 |

TABLE 15D

| Canid Population[a] | Canid ID No. | Missing Data | Groups | | | | | | | | |
|---|---|---|---|---|---|---|---|---|---|---|---|
| | | | 1 | 2 | 3 | 4 | 5 | 6 | 7 | 8 | 9 |
| WOLF | 4928 | −1 | 0 | 0.999 | 0 | 0.001 | 0 | 0 | 0 | 0 | 0 |
| WOLF | 282135 | −1 | 0 | 0.998 | 0 | 0.002 | 0 | 0 | 0 | 0 | 0 |
| WOLF | 930121 | −3 | 0 | 0.997 | 0 | 0.003 | 0 | 0 | 0 | 0 | 0 |
| WOLF | Iran1 | −7 | 0 | 0.999 | 0 | 0.001 | 0 | 0 | 0 | 0 | 0 |
| AKIT | 1130 | −4 | 0 | 0.005 | 0 | 0.995 | 0 | 0 | 0 | 0 | 0 |
| AKIT | 1131 | 0 | 0 | 0.013 | 0 | 0.987 | 0 | 0 | 0 | 0 | 0 |
| AKIT | 1132 | −3 | 0 | 0.004 | 0 | 0.996 | 0 | 0 | 0 | 0 | 0 |
| AKIT | 1133 | −5 | 0 | 0.005 | 0 | 0.995 | 0 | 0 | 0 | 0 | 0 |
| AKIT | 1134 | −4 | 0 | 0.007 | 0 | 0.993 | 0 | 0 | 0 | 0 | 0 |
| PEKE | 1143 | 0 | 0 | 0 | 0.999 | 0.001 | 0 | 0 | 0 | 0 | 0 |
| PEKE | 1145 | −1 | 0 | 0 | 0.992048 | 0.007952 | 0 | 0 | 0 | 0 | 0 |
| PEKE | 1211 | 0 | 0 | 0 | 0.947818 | 0.052182 | 0 | 0 | 0 | 0 | 0 |
| PEKE | 1212 | 0 | 0 | 0 | 0.961501 | 0.038499 | 0 | 0 | 0 | 0 | 0 |
| PEKE | 1213 | −4 | 0 | 0 | 0.997994 | 0.002006 | 0 | 0 | 0 | 0 | 0 |
| PUG | 1077 | −4 | 0 | 0 | 0 | 0.002 | 0.998 | 0 | 0 | 0 | 0 |
| PUG | 1104 | −1 | 0 | 0 | 0 | 0.006 | 0.994 | 0 | 0 | 0 | 0 |
| PUG | 1183 | −1 | 0 | 0 | 0 | 0.002 | 0.998 | 0 | 0 | 0 | 0 |
| PUG | 1184 | −1 | 0 | 0 | 0 | 0.001 | 0.999 | 0 | 0 | 0 | 0 |
| PUG | 1192 | −3 | 0 | 0 | 0 | 0.001 | 0.999 | 0 | 0 | 0 | 0 |
| GOLD | 591 | −4 | 0.021339 | 0 | 0 | 0.030068 | 0 | 0.948594 | 0 | 0 | 0 |
| GOLD | 592 | −4 | 0.004314 | 0 | 0 | 0.137187 | 0 | 0.858499 | 0 | 0 | 0 |
| GOLD | 593 | 0 | 0.005935 | 0 | 0 | 0.01088 | 0 | 0.983185 | 0 | 0 | 0 |
| GOLD | 603 | 0 | 0.008929 | 0 | 0 | 0.007937 | 0 | 0.983135 | 0 | 0 | 0 |
| GOLD | 604 | 0 | 0.037624 | 0 | 0 | 0.009901 | 0 | 0.952475 | 0 | 0 | 0 |
| AHRT | 1120 | −1 | 0.006289 | 0 | 0 | 0.213836 | 0 | 0.779874 | 0 | 0 | 0 |
| AHRT | 1121 | −4 | 0.003885 | 0 | 0 | 0.222999 | 0 | 0.773116 | 0 | 0 | 0 |
| AHRT | 1122 | 0 | 0.003079 | 0 | 0 | 0.230177 | 0 | 0.766744 | 0 | 0 | 0 |
| AHRT | 1123 | −2 | 0.016419 | 0 | 0 | 0.218139 | 0 | 0.765442 | 0 | 0 | 0 |
| AHRT | 1124 | −2 | 0.004594 | 0 | 0 | 0.234303 | 0 | 0.761103 | 0 | 0 | 0 |
| CHIH | 1202 | −10 | 0.008326 | 0 | 0 | 0.074931 | 0 | 0.916744 | 0 | 0 | 0 |
| CHIH | 1203 | −3 | 0.005578 | 0 | 0 | 0.203187 | 0 | 0.791235 | 0 | 0 | 0 |
| CHIH | 1204 | 0 | 0.004184 | 0 | 0 | 0.16318 | 0 | 0.832636 | 0 | 0 | 0 |
| CHIH | 1205 | −3 | 0.021598 | 0 | 0 | 0.280058 | 0 | 0.698344 | 0 | 0 | 0 |
| CHIH | 1206 | −1 | 0.097854 | 0 | 0 | 0.141631 | 0 | 0.760515 | 0 | 0 | 0 |
| POM | 1190 | 0 | 0.038938 | 0 | 0 | 0.115044 | 0 | 0.846018 | 0 | 0 | 0 |
| POM | 1191 | −2 | 0.480901 | 0 | 0 | 0.020568 | 0 | 0.498531 | 0 | 0 | 0 |
| POM | 1210 | −7 | 0.020236 | 0 | 0 | 0.15683 | 0 | 0.822934 | 0 | 0 | 0 |
| POM | 1238 | 0 | 0.006961 | 0 | 0 | 0.226605 | 0 | 0.766435 | 0 | 0 | 0 |
| POM | 1239 | −14 | 0.006266 | 0 | 0 | 0.373434 | 0 | 0.620301 | 0 | 0 | 0 |
| DACH | 1051 | −5 | 0.008145 | 0 | 0 | 0.095023 | 0 | 0.896833 | 0 | 0 | 0 |
| DACH | 1052 | −2 | 0.013889 | 0 | 0 | 0.007937 | 0 | 0.978175 | 0 | 0 | 0 |
| DACH | 1053 | −1 | 0.009747 | 0 | 0 | 0.025341 | 0 | 0.964912 | 0 | 0 | 0 |
| DACH | 1054 | 0 | 0.006917 | 0 | 0 | 0.011858 | 0 | 0.981225 | 0 | 0 | 0 |
| DACH | 1055 | −1 | 0.010848 | 0 | 0 | 0.013807 | 0 | 0.975345 | 0 | 0 | 0 |
| BEAG | 994 | −2 | 0.004869 | 0 | 0 | 0.02629 | 0 | 0.968841 | 0 | 0 | 0 |
| BEAG | 995 | −1 | 0.002681 | 0 | 0 | 0.106345 | 0 | 0.890974 | 0 | 0 | 0 |
| BEAG | 1323 | −1 | 0.009747 | 0 | 0 | 0.025341 | 0 | 0.964912 | 0 | 0 | 0 |
| BEAG | 1324 | 0 | 0.002839 | 0 | 0 | 0.290277 | 0 | 0.706884 | 0 | 0 | 0 |
| BEAG | 1327 | 0 | 0.01256 | 0 | 0 | 0.033816 | 0 | 0.953623 | 0 | 0 | 0 |
| IBIZ | 1147 | −8 | 0.011867 | 0 | 0 | 0.208861 | 0 | 0.779273 | 0 | 0 | 0 |
| IBIZ | 1148 | −20 | 0.01225 | 0 | 0 | 0.355255 | 0 | 0.632495 | 0 | 0 | 0 |
| IBIZ | 1162 | 0 | 0.019639 | 0 | 0 | 0.214454 | 0 | 0.765907 | 0 | 0 | 0 |
| IBIZ | 1172 | 0 | 0.00639 | 0 | 0 | 0.201278 | 0 | 0.792332 | 0 | 0 | 0 |
| IBIZ | 1280 | −1 | 0.023682 | 0 | 0 | 0.236058 | 0 | 0.74026 | 0 | 0 | 0 |
| BMD | 941 | −11 | 0.009709 | 0 | 0 | 0.029126 | 0 | 0.961165 | 0 | 0 | 0 |
| BMD | 943 | −10 | 0.006686 | 0 | 0 | 0.04489 | 0 | 0.948424 | 0 | 0 | 0 |
| BMD | 968 | −17 | 0.005831 | 0 | 0 | 0.028183 | 0 | 0.965986 | 0 | 0 | 0 |
| BMD | 970 | −31 | 0.011354 | 0 | 0 | 0.18897 | 0 | 0.799676 | 0 | 0 | 0 |
| BMD | 971 | −51 | 0.020568 | 0 | 0 | 0.020568 | 0 | 0.958864 | 0 | 0 | 0 |
| NEWF | 271 | −3 | 0.010913 | 0 | 0 | 0.007937 | 0 | 0.981151 | 0 | 0 | 0 |
| NEWF | 274 | −1 | 0.019881 | 0 | 0 | 0.005964 | 0 | 0.974155 | 0 | 0 | 0 |
| NEWF | 275 | −3 | 0.010934 | 0 | 0 | 0.005964 | 0 | 0.983101 | 0 | 0 | 0 |
| NEWF | 277 | 0 | 0.05859 | 0 | 0 | 0.006951 | 0 | 0.934459 | 0 | 0 | 0 |
| NEWF | 278 | −1 | 0.034213 | 0 | 0 | 0.022483 | 0 | 0.943304 | 0 | 0 | 0 |
| ROTT | 1014 | −2 | 0.0059 | 0 | 0 | 0.016716 | 0 | 0.977384 | 0 | 0 | 0 |
| ROTT | 1028 | −3 | 0.005946 | 0 | 0 | 0.00892 | 0 | 0.985134 | 0 | 0 | 0 |
| ROTT | 1029 | −1 | 0.004955 | 0 | 0 | 0.00892 | 0 | 0.986125 | 0 | 0 | 0 |
| ROTT | 1033 | −1 | 0.009728 | 0 | 0 | 0.027237 | 0 | 0.963035 | 0 | 0 | 0 |
| ROTT | 1034 | 0 | 0.021782 | 0 | 0 | 0.009901 | 0 | 0.968317 | 0 | 0 | 0 |
| PRES | 1082 | −3 | 0.419635 | 0 | 0 | 0.13119 | 0 | 0.449167 | 0 | 0 | 0 |
| PRES | 1093 | −14 | 0.430979 | 0 | 0 | 0.197432 | 0 | 0.371589 | 0 | 0 | 0 |
| PRES | 1096 | 0 | 0.705253 | 0 | 0 | 0.027237 | 0 | 0.26751 | 0 | 0 | 0 |
| PRES | 1115 | −1 | 0.572519 | 0 | 0 | 0.045802 | 0 | 0.381679 | 0 | 0 | 0 |
| PRES | 1127 | −7 | 0.418004 | 0 | 0 | 0.108734 | 0 | 0.473262 | 0 | 0 | 0 |
| BOX | 1176 | −1 | 0.002964 | 0 | 0 | 0.004941 | 0 | 0.006917 | 0.985178 | 0 | 0 |

TABLE 15D-continued

| Canid Population[a] | Canid ID No. | Missing Data | Groups | | | | | | | | |
|---|---|---|---|---|---|---|---|---|---|---|---|
| | | | 1 | 2 | 3 | 4 | 5 | 6 | 7 | 8 | 9 |
| BOX | 1177 | 0 | 0.046332 | 0 | 0 | 0.002896 | 0 | 0.031853 | 0.918919 | 0 | 0 |
| BOX | 1178 | -1 | 0.002979 | 0 | 0 | 0.003972 | 0 | 0.002979 | 0.99007 | 0 | 0 |
| BOX | 1179 | -3 | 0.000993 | 0 | 0 | 0.003972 | 0 | 0.002979 | 0.992056 | 0 | 0 |
| BOX | 1304 | -1 | 0.001978 | 0 | 0 | 0.005935 | 0 | 0.004946 | 0.987141 | 0 | 0 |
| BULD | 1193 | -1 | 0.001938 | 0 | 0 | 0.006783 | 0 | 0.021318 | 0.002907 | 0.967054 | 0 |
| BULD | 1194 | -2 | 0.004931 | 0 | 0 | 0.003945 | 0 | 0.006903 | 0.002959 | 0.981262 | 0 |
| BULD | 1195 | -9 | 0.000988 | 0 | 0 | 0.004941 | 0 | 0.004941 | 0.001976 | 0.987154 | 0 |
| BULD | 1197 | -3 | 0.003552 | 0 | 0 | 0.019538 | 0 | 0.089698 | 0.002664 | 0.884547 | 0 |
| BULD | 1198 | 0 | 0.003918 | 0 | 0 | 0.002938 | 0 | 0.013712 | 0.003918 | 0.975514 | 0 |
| MAST | 991 | -14 | 0.984143 | 0 | 0 | 0 | 0 | 0.005946 | 0.000991 | 0.001982 | 0.006938 |
| MAST | 1015 | 0 | 0.979331 | 0 | 0 | 0 | 0 | 0.011811 | 0.001969 | 0.001969 | 0.004921 |
| MAST | 1016 | -1 | 0.978389 | 0 | 0 | 0 | 0 | 0.008841 | 0.000982 | 0.007859 | 0.003929 |
| MAST | 1017 | -22 | 0.966926 | 0 | 0 | 0 | 0 | 0.024319 | 0.000973 | 0.001946 | 0.005837 |
| MAST | 1066 | -2 | 0.982266 | 0 | 0 | 0 | 0 | 0.006897 | 0.00197 | 0.005911 | 0.002956 |
| BULM | 1105 | 0 | 0.003925 | 0 | 0 | 0 | 0 | 0.009814 | 0.003925 | 0.004907 | 0.977429 |
| BULM | 1106 | -3 | 0.002935 | 0 | 0 | 0 | 0 | 0.013569 | 0.001957 | 0.005871 | 0.975538 |
| BULM | 1107 | -1 | 0.003956 | 0 | 0 | 0 | 0 | 0.006924 | 0.001978 | 6.001978 | 0.985163 |
| BULM | 1108 | 0 | 0.009852 | 0 | 0 | 0 | 0 | 0.010837 | 0.000985 | 0.002956 | 0.975369 |
| BULM | 1109 | 0 | 0.003956 | 0 | 0 | 0 | 0 | 0.004946 | 0.002967 | 0.002967 | 0.985163 |

[a]See Table 5 for abbreviations of canid populations.
KBB: pbe

TABLE 16

Average Membership Coefficient for Each Breed From the K = 4 Cluster Results

| Breed | Number of Individuals | Inferred Clusters | | | |
|---|---|---|---|---|---|
| | | 1 | 2 | 3 | 4 |
| Shiba Inu | 5 | 0.974 | 0.007 | 0.010 | 0.009 |
| Chow Chow | 5 | 0.983 | 0.006 | 0.005 | 0.006 |
| Akita | 5 | 0.977 | 0.005 | 0.013 | 0.006 |
| Alaskan Malamute | 5 | 0.884 | 0.029 | 0.023 | 0.064 |
| Basenji | 5 | 0.925 | 0.030 | 0.012 | 0.033 |
| Chinese Shar-Pei | 5 | 0.894 | 0.050 | 0.029 | 0.027 |
| Siberian Husky | 5 | 0.828 | 0.021 | 0.071 | 0.080 |
| Afghan Hound | 5 | 0.634 | 0.041 | 0.068 | 0.256 |
| Saluki | 5 | 0.392 | 0.041 | 0.058 | 0.509 |
| Tibetan Terrier | 5 | 0.368 | 0.120 | 0.141 | 0.371 |
| Lhasa Apso | 5 | 0.402 | 0.030 | 0.444 | 0.125 |
| Samoyed | 5 | 0.404 | 0.017 | 0.501 | 0.078 |
| Pekingese | 5 | 0.210 | 0.026 | 0.603 | 0.161 |
| Shih Tzu | 5 | 0.199 | 0.026 | 0.616 | 0.159 |
| Irish Wolfhound | 5 | 0.011 | 0.165 | 0.650 | 0.173 |
| Saint Bernard | 5 | 0.016 | 0.201 | 0.557 | 0.226 |
| Greyhound | 5 | 0.017 | 0.091 | 0.740 | 0.152 |
| Belgian Sheepdog | 5 | 0.013 | 0.009 | 0.962 | 0.016 |
| Belgian Tervuren | 4 | 0.018 | 0.022 | 0.856 | 0.103 |
| Borzoi | 5 | 0.041 | 0.024 | 0.720 | 0.215 |
| Collie | 5 | 0.007 | 0.019 | 0.766 | 0.208 |
| Shetland Sheepdog | 5 | 0.017 | 0.105 | 0.684 | 0.193 |
| Pug Dog | 5 | 0.022 | 0.017 | 0.466 | 0.494 |
| Komondor | 5 | 0.039 | 0.101 | 0.206 | 0.653 |
| Whippet | 5 | 0.007 | 0.087 | 0.480 | 0.426 |
| Standard Poodle | 5 | 0.032 | 0.144 | 0.370 | 0.454 |
| Bichon Frise | 4 | 0.074 | 0.087 | 0.362 | 0.477 |
| Keeshond | 5 | 0.016 | 0.043 | 0.479 | 0.462 |
| Manchester Terrier, Toy | 4 | 0.024 | 0.161 | 0.303 | 0.513 |
| Norwegian Elkhound | 5 | 0.104 | 0.090 | 0.329 | 0.477 |
| Kuvasz | 5 | 0.077 | 0.043 | 0.378 | 0.502 |
| Great Dane | 5 | 0.067 | 0.085 | 0.240 | 0.608 |
| Welsh Springer Spaniel | 5 | 0.007 | 0.083 | 0.255 | 0.654 |
| Doberman Pinscher | 5 | 0.015 | 0.103 | 0.194 | 0.688 |
| Standard Schnauzer | 5 | 0.006 | 0.149 | 0.165 | 0.681 |
| Italian Greyhound | 5 | 0.074 | 0.068 | 0.096 | 0.762 |
| Old English Sheepdog | 5 | 0.024 | 0.086 | 0.122 | 0.768 |
| American Water Spaniel | 5 | 0.023 | 0.127 | 0.131 | 0.719 |
| Miniature Schnauzer | 5 | 0.009 | 0.136 | 0.129 | 0.726 |
| Australian Terrier | 5 | 0.022 | 0.107 | 0.104 | 0.767 |
| English Cocker Spaniel | 5 | 0.004 | 0.088 | 0.182 | 0.725 |
| Irish Setter | 5 | 0.005 | 0.074 | 0.117 | 0.804 |
| West Highland White Terrier | 5 | 0.019 | 0.079 | 0.058 | 0.844 |
| Pointer | 5 | 0.019 | 0.067 | 0.105 | 0.809 |
| Basset Hound | 4 | 0.020 | 0.086 | 0.077 | 0.818 |
| Cavalier King Charles Spaniel | 5 | 0.013 | 0.078 | 0.122 | 0.787 |
| Giant Schnauzer | 5 | 0.106 | 0.082 | 0.060 | 0.752 |
| Pharaoh Hound | 4 | 0.102 | 0.081 | 0.025 | 0.792 |
| Golden Retriever | 5 | 0.009 | 0.184 | 0.019 | 0.789 |
| Beagle | 5 | 0.016 | 0.175 | 0.058 | 0.751 |
| Bloodhound | 5 | 0.009 | 0.203 | 0.014 | 0.775 |
| Airedale Terrier | 4 | 0.016 | 0.127 | 0.109 | 0.748 |
| American Cocker Spaniel | 5 | 0.010 | 0.103 | 0.053 | 0.834 |
| American Hairless Rat Terrier | 5 | 0.009 | 0.149 | 0.064 | 0.778 |
| Chesapeake Bay Retriever | 5 | 0.019 | 0.173 | 0.032 | 0.776 |
| Cairn Terrier | 5 | 0.015 | 0.123 | 0.073 | 0.790 |
| Portuguese Water Dog | 5 | 0.007 | 0.134 | 0.139 | 0.720 |
| German Shorthaired Pointer | 5 | 0.015 | 0.172 | 0.094 | 0.719 |
| Border Collie | 5 | 0.037 | 0.116 | 0.101 | 0.746 |
| Bedlington Terrier | 4 | 0.010 | 0.233 | 0.145 | 0.613 |
| Clumber Spaniel | 5 | 0.005 | 0.355 | 0.066 | 0.573 |
| Ibizan Hound | 5 | 0.015 | 0.149 | 0.120 | 0.716 |
| Rhodesian Ridgeback | 5 | 0.010 | 0.215 | 0.150 | 0.625 |
| Dachshund | 5 | 0.015 | 0.315 | 0.192 | 0.479 |
| Australian Shepherd | 5 | 0.068 | 0.221 | 0.170 | 0.540 |
| Chihuahua | 5 | 0.028 | 0.229 | 0.161 | 0.582 |
| Kerry Blue Terrier | 5 | 0.008 | 0.257 | 0.147 | 0.588 |
| Schipperke | 4 | 0.011 | 0.195 | 0.078 | 0.717 |
| Irish Terrier | 4 | 0.009 | 0.277 | 0.070 | 0.644 |
| Flat-coated Retriever | 5 | 0.005 | 0.207 | 0.084 | 0.704 |
| Soft Coated Wheaten Terrier | 4 | 0.035 | 0.329 | 0.163 | 0.473 |
| Pomeranian | 5 | 0.055 | 0.340 | 0.203 | 0.402 |
| Labrador Retriever | 5 | 0.033 | 0.488 | 0.075 | 0.404 |
| Presa Canario | 5 | 0.036 | 0.762 | 0.044 | 0.158 |
| Rottweiler | 5 | 0.006 | 0.798 | 0.098 | 0.098 |
| Bullmastiff | 5 | 0.008 | 0.873 | 0.032 | 0.087 |

TABLE 16-continued

Average Membership Coefficient for Each Breed
From the K = 4 Cluster Results

| Breed | Number of Individuals | Inferred Clusters | | | |
|---|---|---|---|---|---|
| | | 1 | 2 | 3 | 4 |
| Newfoundland | 5 | 0.020 | 0.923 | 0.018 | 0.040 |
| German Shepherd Dog | 5 | 0.006 | 0.858 | 0.090 | 0.046 |
| French Bulldog | 4 | 0.009 | 0.945 | 0.012 | 0.034 |
| Miniature Bull Terrier | 5 | 0.013 | 0.921 | 0.020 | 0.047 |
| Bulldog | 5 | 0.008 | 0.962 | 0.019 | 0.011 |
| Boxer | 5 | 0.003 | 0.923 | 0.065 | 0.008 |
| Mastiff | 5 | 0.010 | 0.934 | 0.032 | 0.024 |
| Bernese Mountain Dog | 5 | 0.006 | 0.708 | 0.229 | 0.057 |
| Greater Swiss Mountain Dog | 5 | 0.015 | 0.488 | 0.373 | 0.124 |

TABLE 17A

| Canid Population[a] | Canid ID No. | Missing Data | Populations* | | | | | | | | | | | | | | | | | | | |
|---|---|---|---|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 | 17 | 18 | 19 | 20 | 21 |
| CHOW | 1633 | -10 | 0.006 | 0.001 | 0.001 | 0.002 | 0.001 | 0.023 | 0.003 | 0.002 | 0.001 | 0.001 | 0.001 | 0.001 | 0.001 | 0.915 | 0.002 | 0.004 | 0.002 | 0.021 | 0.006 | 0.002 | 0.003 |
| CHOW | 1835 | -9 | 0.001 | 0.001 | 0.001 | 0.001 | 0.002 | 0.001 | 0.001 | 0.001 | 0.001 | 0.001 | 0.001 | 0.001 | 0.001 | 0.981 | 0.001 | 0.001 | 0.003 | 0.001 | 0.001 | 0.001 | 0.001 |
| CHOW | 1837 | -18 | 0.001 | 0.001 | 0.005 | 0.001 | 0.003 | 0.001 | 0.001 | 0.001 | 0.001 | 0.001 | 0.001 | 0.001 | 0 | 0.978 | 0.001 | 0.001 | 0.001 | 0.001 | 0 | 0.001 | 0.001 |
| CHOW | 1838 | -19 | 0.001 | 0.001 | 0.001 | 0.001 | 0.001 | 0.013 | 0.016 | 0.001 | 0.001 | 0.001 | 0.001 | 0 | 0.001 | 0.936 | 0.004 | 0.003 | 0.001 | 0.002 | 0.003 | 0.001 | 0.002 |
| CHOW | 1839 | -1 | 0.002 | 0.001 | 0.001 | 0.002 | 0.002 | 0.964 | 0.002 | 0.001 | 0.001 | 0.001 | 0.001 | 0.002 | 0.002 | 0.009 | 0.001 | 0.003 | 0.012 | 0.009 | 0.001 | 0.001 | 0.001 |
| SHAR | 1573 | -5 | 0.001 | 0.001 | 0.001 | 0.001 | 0.003 | 0.935 | 0.002 | 0.001 | 0.001 | 0.001 | 0.008 | 0.004 | 0 | 0.001 | 0.001 | 0.003 | 0.001 | 0.006 | 0.001 | 0.001 | 0.006 |
| SHAR | 1593 | -11 | 0.011 | 0.001 | 0.001 | 0.002 | 0.003 | 0.982 | 0.003 | 0.001 | 0.003 | 0.001 | 0.006 | 0.004 | 0.003 | 0.001 | 0.001 | 0.003 | 0.002 | 0.001 | 0.001 | 0.001 | 0.001 |
| SHAR | 1619 | -6 | 0.001 | 0.001 | 0.001 | 0.001 | 0.043 | 0.72 | 0.003 | 0.002 | 0.005 | 0.01 | 0.001 | 0.001 | 0.003 | 0.049 | 0.001 | 0.01 | 0.002 | 0.003 | 0.001 | 0.005 | 0.005 |
| SHAR | 1998 | -2 | 0.016 | 0.025 | 0.002 | 0.004 | 0.098 | 0.713 | 0.062 | 0.003 | 0.002 | 0.003 | 0.001 | 0.004 | 0.004 | 0.025 | 0.001 | 0.001 | 0.004 | 0.001 | 0.001 | 0.094 | 0.026 |
| SHAR | 1999 | -4 | 0.031 | 0 | 0.001 | 0.001 | 0.001 | 0.001 | 0.001 | 0.001 | 0.001 | 0.001 | 0.001 | 0.001 | 0.001 | 0.002 | 0.001 | 0.001 | 0.98 | 0.001 | 0 | 0.001 | 0.001 |
| SHIB | 1769 | -22 | 0.001 | 0.001 | 0.002 | 0.001 | 0.003 | 0.001 | 0.002 | 0.001 | 0.004 | 0.001 | 0.001 | 0.005 | 0.001 | 0.006 | 0.002 | 0.013 | 0.958 | 0.001 | 0.011 | 0.001 | 0.001 |
| SHIB | 1854 | -11 | 0.002 | 0.001 | 0.001 | 0.003 | 0.008 | 0.035 | 0.001 | 0.002 | 0.001 | 0.002 | 0.005 | 0.001 | 0.001 | 0.021 | 0.001 | 0.003 | 0.837 | 0.002 | 0.001 | 0.001 | 0.064 |
| SHIB | 1856 | -6 | 0.003 | 0.001 | 0.001 | 0.001 | 0.01 | 0.008 | 0.002 | 0.001 | 0.001 | 0.002 | 0.007 | 0.005 | 0.002 | 0.005 | 0.001 | 0.003 | 0.958 | 0.001 | 0.001 | 0.001 | 0.002 |
| SHIB | 1860 | -7 | 0.002 | 0.001 | 0.001 | 0.001 | 0.026 | 0.01 | 0.001 | 0.001 | 0.001 | 0.001 | 0.001 | 0.006 | 0.001 | 0.053 | 0.001 | 0.003 | 0.875 | 0.001 | 0.001 | 0.001 | 0.002 |
| SHIB | 1981 | -1 | 0.004 | 0.001 | 0.002 | 0.001 | 0.976 | 0.001 | 0.002 | 0.001 | 0.002 | 0.001 | 0.005 | 0.006 | 0 | 0.001 | 0.001 | 0.001 | 0.005 | 0.001 | 0.002 | 0.001 | 0.003 |
| AKIT | 1130 | -5 | 0.002 | 0.001 | 0.001 | 0.001 | 0.969 | 0.001 | 0.001 | 0.002 | 0.001 | 0.001 | 0.001 | 0.001 | 0 | 0.001 | 0.001 | 0.001 | 0.002 | 0.001 | 0.001 | 0.001 | 0.001 |
| AKIT | 1131 | 0 | 0.003 | 0.001 | 0.001 | 0.002 | 0.97 | 0.001 | 0.001 | 0.003 | 0.001 | 0.005 | 0.001 | 0 | 0.001 | 0.005 | 0.001 | 0.001 | 0.002 | 0.001 | 0 | 0.001 | 0.001 |
| AKIT | 1132 | -3 | 0.001 | 0 | 0.001 | 0.001 | 0.981 | 0.002 | 0.003 | 0.001 | 0.003 | 0.001 | 0.001 | 0 | 0.002 | 0.002 | 0.001 | 0.001 | 0.001 | 0.001 | 0 | 0.001 | 0.001 |
| AKIT | 1133 | -5 | 0.002 | 0.001 | 0.001 | 0 | 0.974 | 0.003 | 0.001 | 0.001 | 0.001 | 0.001 | 0 | 0.001 | 0.003 | 0.003 | 0.001 | 0.001 | 0.003 | 0.002 | 0.011 | 0.001 | 0.064 |
| AKIT | 1134 | -3 | 0.001 | 0.001 | 0.004 | 0.001 | 0.976 | 0.001 | 0.002 | 0.001 | 0.001 | 0.002 | 0.001 | 0.001 | 0.001 | 0.001 | 0.001 | 0.001 | 0.001 | 0.001 | 0.001 | 0.001 | 0.001 |
| AMAL | 1629 | -3 | 0.003 | 0.002 | 0.001 | 0.015 | 0 | 0.002 | 0.952 | 0.001 | 0.004 | 0.002 | 0.002 | 0.003 | 0.002 | 0.003 | 0.001 | 0.001 | 0.002 | 0.001 | 0.001 | 0.001 | 0.002 |
| AMAL | 1779 | -3 | 0.002 | 0.005 | 0.003 | 0.004 | 0.001 | 0.002 | 0.938 | 0.001 | 0.001 | 0.003 | 0.012 | 0.004 | 0.002 | 0.005 | 0.001 | 0.013 | 0.001 | 0.001 | 0.001 | 0.004 | 0.008 |
| AMAL | 1845 | -3 | 0.003 | 0.003 | 0.003 | 0.001 | 0.003 | 0.002 | 0.964 | 0.001 | 0.001 | 0.002 | 0.004 | 0.001 | 0.004 | 0.001 | 0.001 | 0.001 | 0.001 | 0.001 | 0.001 | 0.001 | 0.001 |
| AMAL | 2132 | -6 | 0.005 | 0.004 | 0.002 | 0.001 | 0.003 | 0.001 | 0.925 | 0.01 | 0.002 | 0.008 | 0.013 | 0.001 | 0.001 | 0.001 | 0.001 | 0.001 | 0.001 | 0.001 | 0.001 | 0.011 | 0.004 |
| AMAL | 2214 | -1 | 0.003 | 0.002 | 0.01 | 0.004 | 0.004 | 0.001 | 0.943 | 0.004 | 0.008 | 0.002 | 0.001 | 0.007 | 0.001 | 0.001 | 0.001 | 0.001 | 0.002 | 0.001 | 0.001 | 0.003 | 0.002 |
| HUSK | 1469 | -12 | 0.002 | 0.001 | 0.01 | 0.001 | 0.001 | 0.001 | 0.96 | 0.001 | 0.003 | 0.001 | 0 | 0 | 0.003 | 0.013 | 0.001 | 0.001 | 0.001 | 0.001 | 0.001 | 0.001 | 0.002 |
| HUSK | 1883 | -2 | 0.002 | 0.001 | 0.011 | 0.001 | 0.001 | 0.001 | 0.956 | 0.003 | 0.003 | 0.001 | 0.001 | 0.004 | 0.002 | 0.001 | 0.002 | 0.001 | 0.001 | 0.002 | 0.001 | 0.005 | 0.002 |
| HUSK | 2115 | -6 | 0.003 | 0.001 | 0.001 | 0.006 | 0.001 | 0.002 | 0.947 | 0.004 | 0.003 | 0.003 | 0.004 | 0.004 | 0.001 | 0.003 | 0.005 | 0.003 | 0.001 | 0.001 | 0.001 | 0.002 | 0.007 |
| HUSK | 2117 | -1 | 0.019 | 0.041 | 0.002 | 0.001 | 0.002 | 0.003 | 0.778 | 0.007 | 0.003 | 0.002 | 0.002 | 0.003 | 0.002 | 0.009 | 0.001 | 0.004 | 0.002 | 0.003 | 0.001 | 0.11 | 0.006 |
| HUSK | 2118 | -3 | 0.013 | 0.001 | 0.004 | 0.031 | 0.001 | 0.003 | 0.838 | 0.025 | 0.003 | 0.003 | 0.004 | 0.008 | 0.001 | 0.003 | 0.002 | 0.016 | 0.002 | 0.004 | 0.014 | 0.027 | 0.005 |
| SAMO | 1375 | 0 | 0.001 | 0.001 | 0.001 | 0.001 | 0.001 | 0.001 | 0.002 | 0.001 | 0.001 | 0.001 | 0.001 | 0.001 | 0 | 0.001 | 0.001 | 0.001 | 0.001 | 0.001 | 0.001 | 0.004 | 0.001 |
| SAMO | 1532 | -5 | 0.001 | 0.001 | 0.001 | 0.001 | 0.001 | 0.001 | 0.002 | 0.002 | 0.002 | 0.001 | 0.002 | 0.001 | 0.976 | 0.001 | 0 | 0.001 | 0.001 | 0.001 | 0.001 | 0.003 | 0.001 |
| SAMO | 1560 | -1 | 0.002 | 0.007 | 0.001 | 0.001 | 0.001 | 0.001 | 0.002 | 0.001 | 0.003 | 0.001 | 0.001 | 0.001 | 0.981 | 0.001 | 0.002 | 0.001 | 0.001 | 0.001 | 0.001 | 0.002 | 0.001 |
| SAMO | 169 | 0 | 0.001 | 0.002 | 0.97 | 0.002 | 0.002 | 0.002 | 0.002 | 0.001 | 0.001 | 0.001 | 0.003 | 0.001 | 0.983 | 0 | 0.001 | 0.001 | 0.001 | 0.001 | 0.002 | 0.002 | 0.007 |
| SAMO | 239 | 0 | 0.002 | 0.002 | 0.97 | 0.001 | 0.001 | 0.001 | 0.003 | 0.001 | 0.002 | 0.001 | 0.003 | 0.003 | 0 | 0 | 0.001 | 0.001 | 0.001 | 0.001 | 0.001 | 0.001 | 0.001 |
| AFGH | 1812 | -3 | 0.002 | 0.001 | 0.961 | 0.001 | 0.001 | 0.001 | 0.001 | 0.017 | 0.001 | 0.011 | 0.001 | 0.001 | 0.02 | 0 | 0 | 0.001 | 0.001 | 0.001 | 0.001 | 0.001 | 0.001 |
| AFGH | 1939 | -3 | 0.001 | 0.004 | 0.973 | 0.001 | 0.001 | 0.001 | 0.019 | 0.002 | 0.001 | 0.001 | 0.002 | 0.001 | 0.02 | 0 | 0.001 | 0.001 | 0.001 | 0.001 | 0 | 0.001 | 0.001 |
| AFGH | 2264 | -7 | 0.001 | 0.001 | 0.928 | 0.001 | 0.001 | 0.001 | 0.002 | 0.001 | 0.001 | 0.002 | 0.001 | 0.002 | 0.017 | 0 | 0.001 | 0.001 | 0.001 | 0.001 | 0.001 | 0.001 | 0.001 |
| AFGH | 1936 | -9 | 0.001 | 0.001 | 0.981 | 0.001 | 0 | 0.001 | 0.002 | 0.001 | 0.001 | 0.001 | 0.001 | 0.002 | 0.019 | 0.001 | 0 | 0.001 | 0.001 | 0.001 | 0 | 0.001 | 0.001 |
| AFGH | 1937 | -13 | 0.002 | 0.001 | 0.001 | 0 | 0.001 | 0.001 | 0.007 | 0.01 | 0.002 | 0.007 | 0.002 | 0.004 | 0.075 | 0.005 | 0.004 | 0.002 | 0.004 | 0.009 | 0.001 | 0.009 | 0.009 |
| SALU | 1491 | 0 | 0.004 | 0.001 | 0.006 | 0.005 | 0.001 | 0.001 | 0.001 | 0.1 | 0.002 | 0.026 | 0.003 | 0.003 | 0.002 | 0.001 | 0.922 | 0.032 | 0.001 | 0.001 | 0 | 0.001 | 0.002 |
| SALU | 1535 | -5 | 0.002 | 0.002 | 0.001 | 0.002 | 0.003 | 0.005 | 0.019 | 0.002 | 0.002 | 0.007 | 0.005 | 0.004 | 0.017 | 0.001 | 0.931 | 0.001 | 0.001 | 0.001 | 0.001 | 0.001 | 0.001 |
| SALU | 1607 | -14 | 0.001 | 0.001 | 0.001 | 0.002 | 0.001 | 0 | 0.002 | 0.001 | 0.001 | 0.001 | 0.002 | 0.001 | 0.001 | 0.001 | 0.961 | 0.001 | 0.001 | 0.001 | 0.001 | 0.001 | 0.002 |
| SALU | 1873 | -2 | 0.001 | 0.001 | 0.001 | 0.001 | 0.003 | 0.006 | 0.005 | 0.001 | 0.001 | 0.001 | 0.001 | 0.004 | 0.001 | 0.001 | 0.939 | 0.002 | 0.001 | 0.001 | 0.001 | 0.001 | 0.002 |
| SALU | 2610 | -20 | 0.078 | 0.004 | 0.001 | 0.011 | 0.005 | 0.005 | 0.002 | 0.002 | 0.002 | 0.007 | 0.005 | 0.003 | 0.002 | 0.005 | 0.579 | 0.032 | 0.001 | 0.001 | 0.032 | 0.006 | 0.046 |
| BSJI | 1338 | -9 | 0.281 | 0.001 | 0.001 | 0.002 | 0.001 | 0.003 | 0.001 | 0.1 | 0.001 | 0.026 | 0.002 | 0.003 | 0 | 0.001 | 0.017 | 0.03 | 0.004 | 0.002 | 0.548 | 0.003 | 0.064 |
| BSJI | 1339 | -3 | 0.001 | 0.002 | 0.001 | 0.001 | 0.001 | 0.001 | 0.001 | 0.001 | 0.001 | 0 | 0.001 | 0.001 | 0.001 | 0 | 0 | 0.001 | 0 | 0.001 | 0.986 | 0.001 | 0.001 |

TABLE 17A-continued

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 | 17 | 18 | 19 | 20 | 21 |
| BSJI | 1645 | −12 | 0 | 0 | 0 | 0 | 0 | 0 | 0 | 0 | 0 | 0 | 0 | 0 | 0 | 0 | 0 | 0 | 0 | 0 | 0.992 | 0 | 0 |
| BSJI | 1675 | 0 | 0.001 | 0.001 | 0.001 | 0.001 | 0 | 0.001 | 0.001 | 0.001 | 0.001 | 0.001 | 0.001 | 0.001 | 0.004 | 0.001 | 0.001 | 0.001 | 0.001 | 0.001 | 0.988 | 0.001 | 0.001 |
| BSJI | 1717 | −2 | 0.002 | 0 | 0.005 | 0.001 | 0.005 | 0.002 | 0.001 | 0.001 | 0 | 0.009 | 0.007 | 0.008 | 0.004 | 0.002 | 0.004 | 0 | 0.005 | 0.001 | 0.976 | 0.005 | 0.001 |
| TIBT | 1466 | −8 | 0.006 | 0.003 | 0.005 | 0.003 | 0.005 | 0.002 | 0.003 | 0.014 | 0.002 | 0.009 | 0.001 | 0.001 | 0 | 0.002 | 0.004 | 0.003 | 0.004 | 0.904 | 0.002 | 0.005 | 0.005 |
| TIBT | 1562 | −9 | 0.001 | 0.001 | 0.001 | 0.001 | 0 | 0 | 0.001 | 0.001 | 0.001 | 0.001 | 0.001 | 0.001 | 0.001 | 0.001 | 0 | 0.002 | 0.001 | 0.985 | 0.001 | 0.001 | 0.001 |
| TIBT | 1707 | −12 | 0.001 | 0.01 | 0.001 | 0.001 | 0.001 | 0 | 0.001 | 0.001 | 0.001 | 0.002 | 0.001 | 0.002 | 0.001 | 0.001 | 0.001 | 0.001 | 0.001 | 0.974 | 0 | 0.001 | 0.001 |
| TIBT | 26078 | −2 | 0.012 | 0.004 | 0.004 | 0.003 | 0.005 | 0.002 | 0.006 | 0.008 | 0.023 | 0.076 | 0.009 | 0.004 | 0.003 | 0.002 | 0.031 | 0.009 | 0.015 | 0.756 | 0.001 | 0.001 | 0.027 |
| TIBT | 28086 | 0 | 0.001 | 0.001 | 0.001 | 0.001 | 0 | 0.001 | 0.001 | 0.004 | 0 | 0.001 | 0.002 | 0.002 | 0.001 | 0.001 | 0.001 | 0.001 | 0.001 | 0.967 | 0.001 | 0.012 | 0.001 |
| LHSA | 1524 | −1 | 0.002 | 0.002 | 0.002 | 0.086 | 0.001 | 0.001 | 0.002 | 0.002 | 0.081 | 0.005 | 0.002 | 0.001 | 0.001 | 0.001 | 0.001 | 0.269 | 0.003 | 0.001 | 0.001 | 0.003 | 0.537 |
| LHSA | 1525 | −41 | 0.003 | 0.002 | 0.004 | 0.043 | 0.001 | 0.001 | 0.001 | 0.002 | 0.245 | 0.003 | 0.003 | 0.001 | 0.003 | 0.002 | 0.002 | 0.138 | 0.002 | 0.001 | 0.003 | 0.004 | 0.535 |
| LHSA | 1526 | −18 | 0.006 | 0.001 | 0.005 | 0.085 | 0.001 | 0.002 | 0.001 | 0.002 | 0.007 | 0.003 | 0.004 | 0.005 | 0.004 | 0.001 | 0.001 | 0.22 | 0.001 | 0.001 | 0.001 | 0.002 | 0.647 |
| LHSA | 1528 | −2 | 0.003 | 0.002 | 0.004 | 0.051 | 0.001 | 0.001 | 0.004 | 0.238 | 0.166 | 0.004 | 0.001 | 0.009 | 0.001 | 0.006 | 0.01 | 0.157 | 0.002 | 0.009 | 0.001 | 0.003 | 0.325 |
| LHSA | 2074 | −3 | 0.004 | 0.002 | 0.001 | 0.079 | 0.001 | 0.001 | 0.004 | 0.004 | 0.009 | 0.001 | 0.001 | 0.002 | 0.001 | 0.001 | 0.005 | 0.203 | 0.001 | 0.003 | 0.002 | 0.001 | 0.672 |
| PEKE | 1143 | 0 | 0 | 0.001 | 0 | 0 | 0 | 0 | 0 | 0 | 0.99 | 0 | 0 | 0 | 0 | 0 | 0 | 0.001 | 0 | 0 | 0 | 0 | 0.001 |
| PEKE | 1145 | −2 | 0.001 | 0.002 | 0.001 | 0.004 | 0.001 | 0.001 | 0.001 | 0.001 | 0.974 | 0.001 | 0.002 | 0.001 | 0.001 | 0.002 | 0.002 | 0.002 | 0.001 | 0.001 | 0.001 | 0.001 | 0.002 |
| PEKE | 1211 | 0 | 0.003 | 0.012 | 0.002 | 0.005 | 0.001 | 0.001 | 0.001 | 0.002 | 0.951 | 0.002 | 0.003 | 0.001 | 0.003 | 0.001 | 0.006 | 0.023 | 0 | 0.001 | 0.003 | 0.002 | 0.003 |
| PEKE | 1212 | −1 | 0.003 | 0.014 | 0.001 | 0.008 | 0.002 | 0.002 | 0.001 | 0.001 | 0.919 | 0.002 | 0.004 | 0.001 | 0.003 | 0.001 | 0.001 | 0.026 | 0.001 | 0.001 | 0.004 | 0.002 | 0.003 |
| PEKE | 1213 | −3 | 0.001 | 0.001 | 0.001 | 0.001 | 0.001 | 0.001 | 0.001 | 0.001 | 0.963 | 0.001 | 0.002 | 0.001 | 0.004 | 0.001 | 0.001 | 0.002 | 0.005 | 0.001 | 0.001 | 0.001 | 0.003 |
| SHIH | 1393 | 0 | 0.001 | 0.001 | 0.001 | 0.166 | 0.001 | 0.001 | 0.002 | 0.001 | 0.106 | 0.001 | 0.001 | 0.002 | 0 | 0.001 | 0.001 | 0.71 | 0.001 | 0.001 | 0 | 0.001 | 0.001 |
| SHIH | 1783 | −11 | 0.001 | 0.002 | 0.001 | 0.186 | 0.001 | 0.002 | 0.001 | 0.006 | 0.018 | 0.001 | 0.001 | 0.002 | 0.001 | 0.002 | 0.001 | 0.769 | 0.001 | 0.001 | 0.001 | 0.001 | 0.005 |
| SHIH | 2068 | −3 | 0.001 | 0.001 | 0.001 | 0.188 | 0.001 | 0.001 | 0.002 | 0.002 | 0.021 | 0.005 | 0.002 | 0.001 | 0.003 | 0.001 | 0.001 | 0.772 | 0.002 | 0.001 | 0.001 | 0.001 | 0.005 |
| SHIH | 2859 | −44 | 0.001 | 0.001 | 0.001 | 0.198 | 0.001 | 0.001 | 0.001 | 0.002 | 0.002 | 0.001 | 0.003 | 0.001 | 0.003 | 0.002 | 0.001 | 0.777 | 0.002 | 0.001 | 0.001 | 0.001 | 0.001 |
| SHIH | 2860 | −12 | 0.002 | 0.002 | 0.001 | 0.151 | 0.007 | 0.001 | 0.002 | 0.002 | 0.124 | 0.001 | 0.003 | 0.003 | 0.001 | 0.005 | 0.001 | 0.624 | 0.005 | 0.001 | 0.001 | 0.001 | 0.068 |
| PUG | 1077 | −5 | 0.001 | 0.001 | 0.001 | 0.001 | 0.001 | 0.002 | 0.001 | 0.001 | 0.001 | 0.001 | 0.001 | 0.001 | 0.001 | 0.001 | 0.001 | 0.001 | 0.001 | 0.001 | 0 | 0.001 | 0.001 |
| PUG | 1104 | 0 | 0.001 | 0.954 | 0.001 | 0.004 | 0.001 | 0.002 | 0.002 | 0.001 | 0.005 | 0.004 | 0.001 | 0.942 | 0.001 | 0 | 0.001 | 0.014 | 0.001 | 0.003 | 0.001 | 0.001 | 0.002 |
| PUG | 1183 | −2 | 0.001 | 0.986 | 0.001 | 0.001 | 0.002 | 0.001 | 0.001 | 0.001 | 0.001 | 0.001 | 0.001 | 0.954 | 0.001 | 0.001 | 0.001 | 0.001 | 0.001 | 0.001 | 0.001 | 0.001 | 0.001 |
| PUG | 1184 | −1 | 0 | 0.993 | 0 | 0 | 0 | 0 | 0 | 0 | 0 | 0 | 0 | 0.818 | 0 | 0 | 0 | 0 | 0 | 0 | 0 | 0 | 0 |
| PUG | 1192 | −3 | 0.001 | 0.986 | 0.001 | 0.001 | 0.001 | 0 | 0.001 | 0.001 | 0 | 0.001 | 0.003 | 0.964 | 0.001 | 0.001 | 0.001 | 0.003 | 0.001 | 0.001 | 0.001 | 0.001 | 0.001 |
| BICH | 1943 | −17 | 0.002 | 0.002 | 0.007 | 0.003 | 0.007 | 0.002 | 0.001 | 0.917 | 0.002 | 0.007 | 0.003 | 0.003 | 0.001 | 0.003 | 0.001 | 0.003 | 0.001 | 0.023 | 0.001 | 0.008 | 0.004 |
| BICH | 1954 | −7 | 0.002 | 0.001 | 0.001 | 0.004 | 0 | 0.001 | 0.001 | 0.963 | 0.001 | 0.001 | 0.001 | 0.003 | 0.002 | 0.001 | 0.005 | 0.004 | 0.003 | 0.003 | 0.001 | 0.002 | 0.001 |
| BICH | 933 | −4 | 0.002 | 0.002 | 0.003 | 0.001 | 0 | 0.001 | 0.001 | 0.954 | 0.001 | 0.003 | 0.001 | 0.003 | 0.002 | 0.001 | 0.003 | 0.003 | 0.001 | 0.006 | 0.001 | 0.002 | 0.005 |
| BICH | 974 | −2 | 0.002 | 0.091 | 0.002 | 0.001 | 0.001 | 0.002 | 0.003 | 0.87 | 0.001 | 0.001 | 0.005 | 0.004 | 0.004 | 0.001 | 0.001 | 0.004 | 0.002 | 0.001 | 0.002 | 0.005 | 0.002 |
| SPOO | 1530 | −3 | 0.004 | 0.001 | 0.003 | 0.003 | 0.001 | 0.002 | 0.005 | 0.006 | 0.001 | 0.003 | 0.002 | 0.002 | 0.001 | 0.002 | 0.004 | 0.002 | 0.001 | 0.011 | 0.001 | 0.003 | 0.003 |
| SPOO | 1582 | −1 | 0.002 | 0.001 | 0.001 | 0.004 | 0.001 | 0.001 | 0.001 | 0.003 | 0.001 | 0.003 | 0.001 | 0.001 | 0.001 | 0.001 | 0.001 | 0.003 | 0.001 | 0.001 | 0.004 | 0.005 | 0.006 |
| SPOO | 1876 | −18 | 0.01 | 0.001 | 0.003 | 0.054 | 0.001 | 0.001 | 0.002 | 0.005 | 0.001 | 0.012 | 0.003 | 0.818 | 0.003 | 0.001 | 0.004 | 0.047 | 0.001 | 0.002 | 0.003 | 0.022 | 0.006 |
| SPOO | 1877 | −5 | 0.002 | 0.001 | 0.002 | 0.002 | 0.001 | 0.001 | 0.001 | 0.002 | 0.002 | 0.009 | 0.001 | 0.964 | 0.002 | 0.001 | 0.004 | 0.001 | 0.002 | 0.001 | 0.001 | 0.001 | 0.002 |

TABLE 17A-continued

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 | 17 | 18 | 19 | 20 | 21 |
| SPOO | 2337 | −13 | 0.001 | 0.002 | 0.001 | 0.003 | 0.001 | 0.001 | 0.001 | 0.002 | 0.001 | 0.002 | 0.002 | 0.961 | 0.004 | 0.001 | 0.001 | 0.002 | 0.001 | 0.007 | 0.001 | 0.002 | 0.001 |
| KOMO | 1484 | −13 | 0.001 | 0.001 | 0.003 | 0.001 | 0.001 | 0.001 | 0.003 | 0.001 | 0.002 | 0.967 | 0.002 | 0.002 | 0.001 | 0.001 | 0.002 | 0.001 | 0.001 | 0.004 | 0.001 | 0.003 | 0.002 |
| KOMO | 1964 | −17 | 0.014 | 0.001 | 0.001 | 0.003 | 0.001 | 0.001 | 0.001 | 0.003 | 0.001 | 0.851 | 0.025 | 0.007 | 0.011 | 0.002 | 0.047 | 0.002 | 0.002 | 0.003 | 0.003 | 0.014 | 0.007 |
| KOMO | 2321 | −1 | 0.002 | 0.017 | 0.002 | 0.012 | 0.001 | 0.001 | 0.003 | 0.019 | 0.001 | 0.899 | 0.001 | 0.003 | 0.002 | 0.001 | 0.001 | 0.005 | 0.001 | 0.008 | 0.001 | 0.021 | 0.002 |
| KOMO | 2323 | −1 | 0.004 | 0.014 | 0.003 | 0.003 | 0.001 | 0.001 | 0.001 | 0.002 | 0.009 | 0.859 | 0.002 | 0.083 | 0.004 | 0.001 | 0.001 | 0.004 | 0.001 | 0.002 | 0.001 | 0.001 | 0.003 |
| KOMO | 2334 | −2 | 0.001 | 0.004 | 0.002 | 0.002 | 0.002 | 0.001 | 0.001 | 0.002 | 0.003 | 0.968 | 0.002 | 0.001 | 0.002 | 0.001 | 0.001 | 0.001 | 0.001 | 0.001 | 0.001 | 0.003 | 0.001 |
| KOMO | 1482 | −3 | 0.002 | 0.009 | 0.013 | 0.047 | 0.001 | 0.001 | 0.006 | 0.009 | 0.001 | 0.002 | 0.001 | 0.006 | 0.001 | 0.001 | 0.001 | 0.001 | 0 | 0.001 | 0.001 | 0.889 | 0.001 |
| KUVZ | 1551 | 0 | 0.004 | 0.001 | 0.002 | 0.002 | 0.001 | 0.003 | 0.002 | 0.015 | 0.001 | 0.001 | 0.013 | 0.027 | 0.001 | 0.001 | 0.005 | 0.002 | 0.002 | 0.007 | 0.002 | 0.905 | 0.003 |
| KUVZ | 1672 | −23 | 0.002 | 0.004 | 0.001 | 0.005 | 0.011 | 0.001 | 0.002 | 0.001 | 0.001 | 0.007 | 0.001 | 0.007 | 0.002 | 0.001 | 0.001 | 0.002 | 0.001 | 0.001 | 0.001 | 0.942 | 0.003 |
| KUVZ | 1913 | −2 | 0.004 | 0.001 | 0.006 | 0.007 | 0.001 | 0.003 | 0.002 | 0.007 | 0.004 | 0.01 | 0.012 | 0.003 | 0.026 | 0.001 | 0.003 | 0.005 | 0.001 | 0.003 | 0.001 | 0.896 | 0.003 |
| KUVZ | 1994 | −2 | 0.005 | 0.002 | 0.006 | 0.003 | 0.001 | 0.003 | 0.001 | 0.006 | 0.003 | 0.008 | 0.005 | 0.014 | 0.002 | 0.002 | 0.002 | 0.003 | 0.001 | 0.003 | 0.006 | 0.916 | 0.006 |
| KEES | 1501 | 0 | 0.001 | 0.003 | 0.188 | 0.771 | 0.001 | 0.001 | 0.003 | 0.002 | 0.001 | 0.001 | 0.008 | 0.003 | 0.002 | 0.001 | 0.001 | 0.004 | 0.001 | 0.002 | 0.004 | 0.002 | 0.001 |
| KEES | 1589 | −2 | 0.002 | 0.008 | 0.155 | 0.77 | 0.001 | 0.002 | 0.001 | 0.002 | 0.002 | 0.004 | 0.017 | 0.003 | 0.003 | 0.001 | 0.021 | 0.001 | 0.001 | 0.001 | 0.001 | 0.002 | 0.002 |
| KEES | 1818 | −41 | 0.001 | 0.001 | 0.19 | 0.778 | 0.001 | 0.001 | 0.001 | 0.001 | 0.001 | 0.002 | 0.004 | 0.006 | 0.001 | 0.001 | 0.002 | 0.001 | 0.001 | 0.001 | 0.001 | 0.001 | 0.001 |
| KEES | 1819 | −1 | 0.002 | 0.002 | 0.174 | 0.767 | 0.002 | 0.001 | 0.001 | 0.02 | 0.001 | 0.002 | 0.002 | 0.009 | 0.001 | 0.002 | 0.001 | 0.002 | 0.001 | 0.003 | 0.002 | 0.004 | 0.002 |
| KEES | 2072 | −4 | 0.003 | 0.003 | 0.168 | 0.749 | 0.001 | 0.001 | 0.002 | 0.035 | 0.005 | 0.003 | 0.001 | 0.008 | 0.002 | 0.001 | 0.002 | 0.002 | 0.001 | 0.001 | 0.002 | 0.006 | 0.004 |
| NELK | 2216 | −4 | 0.039 | 0.003 | 0.018 | 0.017 | 0.001 | 0.002 | 0.005 | 0.004 | 0.003 | 0.008 | 0.846 | 0.005 | 0.002 | 0.01 | 0.002 | 0.006 | 0.001 | 0.011 | 0.004 | 0.004 | 0.01 |
| NELK | 2239 | −2 | 0.001 | 0.001 | 0.001 | 0.002 | 0 | 0.001 | 0.001 | 0.001 | 0.001 | 0.001 | 0.984 | 0.001 | 0 | 0.001 | 0.001 | 0.001 | 0.001 | 0.001 | 0.001 | 0.008 | 0.001 |
| NELK | 2240 | −2 | 0.002 | 0.001 | 0.005 | 0.008 | 0.001 | 0.001 | 0.002 | 0.001 | 0.007 | 0.003 | 0.948 | 0.002 | 0.001 | 0.001 | 0.003 | 0.002 | 0.001 | 0.002 | 0.001 | 0.008 | 0.001 |
| NELK | 2281 | −1 | 0.001 | 0.003 | 0.002 | 0.008 | 0.001 | 0.001 | 0.001 | 0.002 | 0.001 | 0.001 | 0.949 | 0.001 | 0.005 | 0.001 | 0.008 | 0.001 | 0.001 | 0.01 | 0.001 | 0.001 | 0.001 |
| NELK | 2295 | −15 | 0.001 | 0.002 | 0.002 | 0.002 | 0.002 | 0.001 | 0.002 | 0.002 | 0.001 | 0.001 | 0.957 | 0.001 | 0.001 | 0.001 | 0.004 | 0.004 | 0.001 | 0.007 | 0.001 | 0.003 | 0.002 |

TABLE 17B

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 44 | 45 | 46 | 47 | 48 | 49 | 50 | 51 | 52 | 53 | 54 | 55 | 56 | 57 | 58 | 59 | 60 | 61 | 62 | 63 | 64 |
| ECKR | 1376 | −1 | 0.002 | 0.001 | 0.01 | 0.002 | 0.003 | 0.001 | 0.863 | 0.007 | 0.001 | 0.001 | 0.002 | 0.008 | 0.001 | 0.001 | 0.001 | 0.006 | 0.003 | 0.004 | 0.002 | 0.072 | 0.009 |
| ECKR | 1377 | −2 | 0.001 | 0.056 | 0.012 | 0.003 | 0.003 | 0.002 | 0.859 | 0.001 | 0.007 | 0.002 | 0.004 | 0.003 | 0.003 | 0.001 | 0.002 | 0.001 | 0.003 | 0.005 | 0.003 | 0.023 | 0.002 |
| ECKR | 1400 | −2 | 0.001 | 0.001 | 0 | 0.001 | 0.001 | 0.001 | 0.983 | 0.002 | 0.001 | 0.001 | 0.001 | 0.001 | 0.002 | 0 | 0.001 | 0.001 | 0.001 | 0 | 0.001 | 0.002 | 0 |
| ECKR | 1404 | −7 | 0.001 | 0.001 | 0.002 | 0.001 | 0.001 | 0.001 | 0.977 | 0.001 | 0.001 | 0.002 | 0.004 | 0.001 | 0.001 | 0.001 | 0.003 | 0.001 | 0.002 | 0.001 | 0.001 | 0.001 | 0.001 |
| ECKR | 1511 | −6 | 0.002 | 0.004 | 0.003 | 0.001 | 0.001 | 0.001 | 0.959 | 0.001 | 0.003 | 0.001 | 0.004 | 0.007 | 0.003 | 0.005 | 0.003 | 0.001 | 0.007 | 0.002 | 0.004 | 0.001 | 0.001 |
| ACKR | 1035 | −2 | 0.002 | 0.001 | 0.001 | 0.739 | 0.003 | 0.186 | 0.009 | 0.001 | 0.001 | 0.002 | 0.006 | 0.001 | 0.001 | 0.023 | 0.003 | 0.001 | 0.001 | 0.001 | 0.001 | 0.004 | 0.001 |
| ACKR | 2261 | −2 | 0.003 | 0.001 | 0.001 | 0.961 | 0.001 | 0.001 | 0.006 | 0.003 | 0.001 | 0.001 | 0.001 | 0.002 | 0.001 | 0.001 | 0.002 | 0.001 | 0.001 | 0.002 | 0.002 | 0.001 | 0.001 |
| ACKR | 2310 | −1 | 0.004 | 0.001 | 0.001 | 0.949 | 0.019 | 0.003 | 0.002 | 0.004 | 0.001 | 0.001 | 0.001 | 0.001 | 0.001 | 0.001 | 0.002 | 0.001 | 0.001 | 0.001 | 0.001 | 0.006 | 0.001 |
| ACKR | 1956 | −18 | 0.001 | 0.001 | 0.001 | 0.983 | 0.001 | 0.001 | 0.002 | 0.001 | 0.001 | 0.001 | 0.002 | 0.001 | 0.003 | 0.001 | 0.001 | 0.001 | 0.001 | 0.001 | 0.001 | 0.001 | 0.002 |
| ACKR | 2260 | −2 | 0.001 | 0.001 | 0.001 | 0.983 | 0.001 | 0.002 | 0.002 | 0.001 | 0.001 | 0.001 | 0.001 | 0.001 | 0.001 | 0.001 | 0.001 | 0.001 | 0.001 | 0.001 | 0.001 | 0 | 0.001 |
| CKCS | 1513 | −6 | 0.001 | 0.004 | 0.001 | 0.001 | 0.002 | 0.002 | 0.002 | 0.965 | 0.001 | 0.001 | 0.002 | 0.004 | 0.003 | 0.001 | 0.001 | 0.001 | 0.002 | 0.003 | 0.002 | 0.001 | 0.001 |
| CKCS | 1639 | −2 | 0.001 | 0.003 | 0.001 | 0.001 | 0.001 | 0.002 | 0.001 | 0.98 | 0.001 | 0.001 | 0.001 | 0.001 | 0.001 | 0.001 | 0.001 | 0.001 | 0.001 | 0.001 | 0.001 | 0.001 | 0.001 |
| CKCS | 1640 | −15 | 0.001 | 0.001 | 0.034 | 0 | 0.001 | 0.001 | 0.001 | 0.941 | 0.002 | 0.001 | 0.006 | 0.001 | 0 | 0.001 | 0.001 | 0.001 | 0.001 | 0.003 | 0.001 | 0.001 | 0.001 |
| CKCS | 1642 | −4 | 0.005 | 0.001 | 0.001 | 0 | 0.001 | 0.001 | 0.002 | 0.975 | 0.001 | 0.001 | 0.001 | 0.001 | 0 | 0.001 | 0.001 | 0.001 | 0.001 | 0.003 | 0.001 | 0.001 | 0.002 |
| CKCS | 2054 | −5 | 0.001 | 0.001 | 0 | 0.003 | 0 | 0.002 | 0 | 0.991 | 0 | 0 | 0 | 0 | 0 | 0 | 0.001 | 0 | 0.001 | 0 | 0 | 0 | 0 |
| DOBP | 1031 | −1 | 0.002 | 0.003 | 0.004 | 0.002 | 0.001 | 0.001 | 0.001 | 0.002 | 0.001 | 0.003 | 0.002 | 0.003 | 0.001 | 0.966 | 0.001 | 0.001 | 0.001 | 0.002 | 0.001 | 0.001 | 0.001 |
| DOBP | 1032 | −3 | 0.001 | 0.001 | 0.001 | 0.002 | 0.004 | 0.011 | 0.004 | 0.001 | 0.026 | 0.002 | 0.001 | 0.001 | 0.001 | 0.929 | 0.001 | 0.001 | 0.005 | 0.001 | 0.001 | 0.003 | 0.002 |
| DOBP | 1749 | −2 | 0.001 | 0.001 | 0.001 | 0.002 | 0.001 | 0.001 | 0 | 0 | 0.002 | 0.001 | 0.001 | 0.001 | 0.001 | 0.979 | 0.002 | 0.001 | 0.001 | 0.001 | 0.001 | 0 | 0.002 |
| DOBP | 2162 | −5 | 0.009 | 0.001 | 0.004 | 0.001 | 0.001 | 0.002 | 0.001 | 0.002 | 0.002 | 0.001 | 0.001 | 0.001 | 0.002 | 0.964 | 0.001 | 0.001 | 0.001 | 0.001 | 0.001 | 0.001 | 0.002 |
| DOBP | 2245 | −2 | 0.001 | 0.001 | 0 | 0 | 0.001 | 0.001 | 0 | 0 | 0 | 0 | 0 | 0.001 | 0.001 | 0.989 | 0.001 | 0 | 0.001 | 0 | 0 | 0 | 0 |
| MNTY | 1539 | −1 | 0.002 | 0.003 | 0.001 | 0.013 | 0.001 | 0.007 | 0.002 | 0.003 | 0.002 | 0.003 | 0.008 | 0.003 | 0.001 | 0.006 | 0.007 | 0.001 | 0.005 | 0.001 | 0.001 | 0.007 | 0.003 |
| MNTY | 1732 | −15 | 0.978 | 0.001 | 0.001 | 0.002 | 0.001 | 0.001 | 0.002 | 0.001 | 0.001 | 0.002 | 0.001 | 0.001 | 0.001 | 0.004 | 0.001 | 0.001 | 0.001 | 0.001 | 0.001 | 0.001 | 0.001 |
| MNTY | 2145 | −19 | 0.983 | 0.001 | 0.002 | 0.002 | 0.001 | 0.001 | 0.001 | 0.001 | 0.001 | 0.001 | 0.001 | 0 | 0.001 | 0.002 | 0.002 | 0.001 | 0.001 | 0.001 | 0.001 | 0.001 | 0.001 |
| MNTY | 2149 | −47 | 0.945 | 0.002 | 0 | 0.003 | 0.001 | 0.002 | 0.014 | 0.002 | 0.003 | 0.002 | 0.001 | 0.003 | 0.008 | 0.001 | 0.001 | 0.001 | 0.003 | 0.001 | 0.001 | 0.004 | 0.003 |
| IRSE | 1540 | −5 | 0.001 | 0.001 | 0.001 | 0.005 | 0.006 | 0.002 | 0.001 | 0.001 | 0.001 | 0.001 | 0.001 | 0.006 | 0.001 | 0.001 | 0.002 | 0.001 | 0.001 | 0.001 | 0.001 | 0.001 | 0.978 |
| IRSE | 1617 | −4 | 0.001 | 0.001 | 0.001 | 0.003 | 0.001 | 0.001 | 0 | 0.001 | 0.001 | 0.001 | 0.001 | 0.001 | 0.001 | 0.001 | 0.002 | 0.001 | 0.001 | 0.001 | 0.001 | 0.001 | 0.983 |
| IRSE | 1896 | 0 | 0.002 | 0.003 | 0.004 | 0.001 | 0.002 | 0.001 | 0.003 | 0.001 | 0.001 | 0.001 | 0.001 | 0.015 | 0.001 | 0.001 | 0.004 | 0.001 | 0.001 | 0.001 | 0.002 | 0.002 | 0.94 |
| IRSE | 2084 | −6 | 0.017 | 0.002 | 0.008 | 0.008 | 0.001 | 0.001 | 0.015 | 0.001 | 0.005 | 0.001 | 0.001 | 0.015 | 0.003 | 0.001 | 0.005 | 0.001 | 0.002 | 0.014 | 0.008 | 0.001 | 0.927 |
| IRSE | 2085 | −17 | 0.002 | 0.001 | 0.001 | 0.003 | 0.001 | 0.002 | 0.001 | 0.006 | 0.004 | 0.002 | 0.001 | 0.965 | 0.001 | 0.001 | 0.005 | 0.004 | 0.001 | 0.003 | 0.001 | 0.005 | 0.936 |
| PNTR | 1382 | 0 | 0.001 | 0.002 | 0.001 | 0.001 | 0.001 | 0.008 | 0.003 | 0.001 | 0.003 | 0.001 | 0.002 | 0.967 | 0.003 | 0.001 | 0.002 | 0.001 | 0.001 | 0.001 | 0.001 | 0.001 | 0.003 |
| PNTR | 1383 | −2 | 0.002 | 0.003 | 0.002 | 0.001 | 0.001 | 0.002 | 0.001 | 0.001 | 0.004 | 0.001 | 0.002 | 0.942 | 0.001 | 0.001 | 0.001 | 0.001 | 0.001 | 0.002 | 0.001 | 0.001 | 0.002 |
| PNTR | 1869 | −2 | 0.001 | 0.003 | 0.003 | 0.005 | 0.006 | 0.002 | 0.001 | 0.001 | 0.002 | 0.001 | 0.008 | 0.965 | 0.001 | 0.001 | 0.002 | 0.004 | 0.001 | 0.011 | 0.001 | 0.004 | 0.002 |
| PNTR | 1938 | −6 | 0.001 | 0.001 | 0.001 | 0.003 | 0.001 | 0.001 | 0.002 | 0.001 | 0.001 | 0.001 | 0.002 | 0.933 | 0.003 | 0.001 | 0.002 | 0.001 | 0.002 | 0.002 | 0.001 | 0.001 | 0.003 |
| PNTR | 1948 | −31 | 0.004 | 0.001 | 0.005 | 0.002 | 0.005 | 0 | 0.003 | 0.027 | 0.002 | 0.003 | 0.011 | 0.005 | 0.003 | 0.087 | 0.001 | 0.003 | 0.003 | 0.001 | 0.002 | 0.006 | 0.002 |
| GSHP | 1628 | −5 | 0.025 | 0.002 | 0.009 | 0.008 | 0.005 | 0.808 | 0.002 | 0.001 | 0.003 | 0.003 | 0.011 | 0.012 | 0.005 | 0.001 | 0.042 | 0.001 | 0.004 | 0.001 | 0.012 | 0.003 | 0.003 |
| GSHP | 1708 | −22 | 0.001 | 0.001 | 0.001 | 0.003 | 0.002 | 0.929 | 0.001 | 0.001 | 0.016 | 0.001 | 0.001 | 0.005 | 0.003 | 0.001 | 0.001 | 0.001 | 0.002 | 0.003 | 0.008 | 0.001 | 0.001 |
| GSHP | 1710 | −28 | 0.002 | 0.001 | 0.001 | 0.002 | 0.002 | 0.959 | 0.002 | 0.001 | 0.001 | 0.001 | 0.001 | 0.005 | 0.001 | 0.001 | 0.001 | 0.001 | 0.001 | 0.002 | 0.001 | 0.001 | 0.001 |
| GSHP | 1833 | −26 | 0.335 | 0.013 | 0.008 | 0.155 | 0.003 | 0.146 | 0.003 | 0.001 | 0.013 | 0.002 | 0.001 | 0.072 | 0.003 | 0.001 | 0.01 | 0.044 | 0.025 | 0.067 | 0.095 | 0.001 | 0.003 |
| GSHP | 1892 | −4 | 0.012 | 0.001 | 0.003 | 0.004 | 0.104 | 0.398 | 0.001 | 0.002 | 0.016 | 0.003 | 0.001 | 0.012 | 0.002 | 0.001 | 0.004 | 0.182 | 0.011 | 0.004 | 0.028 | 0.003 | 0.203 |
| MSNZ | 1587 | −9 | 0.001 | 0.001 | 0.984 | 0.001 | 0.001 | 0.001 | 0.001 | 0.001 | 0.001 | 0.001 | 0.001 | 0.001 | 0.002 | 0.001 | 0.001 | 0.001 | 0.001 | 0.001 | 0.001 | 0.001 | 0.001 |
| MSNZ | 1756 | −6 | 0.001 | 0.001 | 0.982 | 0.001 | 0.001 | 0.001 | 0.001 | 0.001 | 0.002 | 0.001 | 0.001 | 0.001 | 0.003 | 0 | 0 | 0.001 | 0.003 | 0.001 | 0.095 | 0.001 | 0.001 |
| MSNZ | 1851 | −7 | 0.001 | 0.001 | 0.976 | 0.001 | 0.001 | 0.001 | 0.001 | 0.001 | 0.013 | 0.002 | 0.001 | 0.002 | 0.003 | 0.001 | 0.002 | 0.001 | 0.001 | 0.004 | 0.028 | 0.001 | 0.001 |
| MSNZ | 2034 | −1 | 0.001 | 0.001 | 0.919 | 0.001 | 0.001 | 0.003 | 0.001 | 0.005 | 0.005 | 0.002 | 0.001 | 0.002 | 0.001 | 0.001 | 0.027 | 0.001 | 0.011 | 0.01 | 0.004 | 0.001 | 0.001 |
| MSNZ | 2613 | −16 | 0.001 | 0.001 | 0.912 | 0.006 | 0.001 | 0.002 | 0.028 | 0.001 | 0.002 | 0.003 | 0.001 | 0.001 | 0.023 | 0.003 | 0.003 | 0.001 | 0.001 | 0.001 | 0.001 | 0.003 | 0.002 |
| SSNZ | 13352 | 0 | 0.001 | 0.001 | 0.001 | 0.001 | 0.001 | 0.001 | 0.005 | 0.009 | 0.01 | 0.001 | 0.003 | 0.001 | 0.002 | 0.001 | 0.968 | 0.001 | 0.001 | 0.001 | 0.001 | 0.001 | 0.003 |
| SSNZ | 1360 | −3 | 0.008 | 0.003 | 0.075 | 0.004 | 0.001 | 0.002 | 0.005 | 0.001 | 0.001 | 0.001 | 0.001 | 0.001 | 0.002 | 0.002 | 0.855 | 0.002 | 0.006 | 0.002 | 0.004 | 0.005 | 0.001 |
| SSNZ | 1827 | −9 | 0.001 | 0 | 0.001 | 0.001 | 0.001 | 0.001 | 0 | 0.001 | 0.001 | 0.001 | 0.003 | 0.001 | 0.001 | 0.001 | 0.988 | 0.001 | 0.001 | 0 | 0.001 | 0 | 0.001 |

TABLE 17B-continued

| Canid Population[a] | Canid ID No. | Missing Data | 44 | 45 | 46 | 47 | 48 | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|---|---|---|---|---|---|---|
| SSNZ | 20457 | −1 | 0.001 | 0.001 | 0.001 | 0.002 | 0.001 | 0.002 | 0.001 | 0.001 | 0.001 | 0.002 | 0.001 | 0.002 | 0.002 | 0 | 0.97 | 0.001 | 0.002 | 0.001 | 0.001 | 0.001 | 0.004 |
| SSNZ | 22647 | −3 | 0.001 | 0.001 | 0.002 | 0.001 | 0.001 | 0.001 | 0.001 | 0.005 | 0.001 | 0.001 | 0.001 | 0.001 | 0.001 | 0.001 | 0.976 | 0.001 | 0.001 | 0.001 | 0.001 | 0.001 | 0.001 |
| GSNZ | 1868 | −6 | 0.009 | 0.003 | 0.002 | 0.01 | 0.14 | 0.006 | 0.002 | 0.006 | 0.597 | 0.01 | 0.003 | 0.015 | 0.012 | 0.005 | 0.035 | 0.012 | 0.007 | 0.008 | 0.106 | 0.004 | 0.008 |
| GSNZ | 22739 | 0 | 0.001 | 0.001 | 0.006 | 0.002 | 0.042 | 0.002 | 0.001 | 0.003 | 0.928 | 0.001 | 0.001 | 0.001 | 0.001 | 0.002 | 0.001 | 0.001 | 0.001 | 0.001 | 0.001 | 0.001 | 0.003 |
| GSNZ | 27093 | 0 | 0.003 | 0.005 | 0.002 | 0.001 | 0.002 | 0.002 | 0.003 | 0.003 | 0.948 | 0.002 | 0.006 | 0.002 | 0.001 | 0.001 | 0.002 | 0.001 | 0.004 | 0.008 | 0.001 | 0.002 | 0.002 |
| GSNZ | 27106 | −1 | 0.001 | 0.009 | 0.001 | 0.002 | 0.002 | 0.002 | 0.008 | 0.001 | 0.863 | 0.002 | 0.001 | 0.004 | 0.001 | 0.002 | 0.093 | 0.002 | 0.002 | 0.001 | 0.001 | 0.001 | 0.003 |
| GSNZ | 33390 | 0 | 0.007 | 0.003 | 0.007 | 0.003 | 0.002 | 0.004 | 0.004 | 0.002 | 0.775 | 0.004 | 0.04 | 0.001 | 0.104 | 0.002 | 0.016 | 0.012 | 0.004 | 0.002 | 0.005 | 0.001 | 0.001 |
| AHRT | 1120 | −1 | 0.001 | 0.002 | 0.001 | 0.001 | 0.001 | 0.001 | 0.001 | 0.001 | 0.001 | 0.001 | 0.001 | 0.001 | 0.001 | 0.001 | 0.002 | 0.977 | 0.001 | 0.002 | 0.001 | 0.001 | 0.001 |
| AHRT | 1121 | −3 | 0.001 | 0.001 | 0.002 | 0.001 | 0.001 | 0.001 | 0.001 | 0.002 | 0.001 | 0.001 | 0.001 | 0.002 | 0.001 | 0 | 0.001 | 0.979 | 0.001 | 0.002 | 0.002 | 0.001 | 0.001 |
| AHRT | 1122 | 0 | 0.004 | 0.004 | 0.002 | 0.006 | 0.061 | 0.004 | 0.002 | 0.002 | 0.003 | 0.001 | 0.001 | 0.001 | 0.016 | 0.003 | 0.001 | 0.854 | 0.009 | 0.002 | 0.008 | 0.008 | 0.005 |
| AHRT | 1123 | −1 | 0.001 | 0.001 | 0.002 | 0.003 | 0.003 | 0.03 | 0.002 | 0.003 | 0.004 | 0.001 | 0.023 | 0.001 | 0.004 | 0.003 | 0.003 | 0.888 | 0.004 | 0.011 | 0.004 | 0.007 | 0.002 |
| AHRT | 1124 | −2 | 0.001 | 0 | 0.001 | 0.001 | 0.001 | 0.001 | 0.001 | 0 | 0.001 | 0.001 | 0.001 | 0.001 | 0.001 | 0.001 | 0.001 | 0.984 | 0.001 | 0.001 | 0.001 | 0.001 | 0.001 |
| AIRT | 1603 | −3 | 0.001 | 0 | 0 | 0.001 | 0.001 | 0.001 | 0.001 | 0 | 0 | 0 | 0.99 | 0.001 | 0.005 | 0 | 0 | 0.001 | 0.001 | 0.001 | 0 | 0.001 | 0 |
| AIRT | 1604 | −7 | 0.001 | 0.001 | 0.001 | 0.001 | 0.001 | 0.001 | 0.001 | 0.002 | 0.001 | 0.001 | 0.975 | 0.001 | 0.001 | 0.003 | 0.002 | 0.001 | 0.001 | 0.001 | 0.001 | 0.001 | 0.001 |
| AIRT | 1788 | −2 | 0.001 | 0.001 | 0.001 | 0.001 | 0.001 | 0.001 | 0.001 | 0.001 | 0.001 | 0.001 | 0.981 | 0.001 | 0.001 | 0.003 | 0.001 | 0.001 | 0.001 | 0.001 | 0.001 | 0.001 | 0.002 |
| AIRT | 1875 | −1 | 0.001 | 0.001 | 0.001 | 0.001 | 0.001 | 0.001 | 0.006 | 0.001 | 0.001 | 0.001 | 0.982 | 0.001 | 0.001 | 0.003 | 0.001 | 0.001 | 0.001 | 0.001 | 0.001 | 0.001 | 0.001 |
| BASS | 1341 | 0 | 0.001 | 0.003 | 0.001 | 0.001 | 0.981 | 0.002 | 0.001 | 0.001 | 0.001 | 0.001 | 0.001 | 0.001 | 0 | 0.001 | 0 | 0.001 | 0.001 | 0.001 | 0.001 | 0.001 | 0.001 |
| BASS | 1342 | −5 | 0.001 | 0.001 | 0.003 | 0.001 | 0.966 | 0.002 | 0.001 | 0.001 | 0.001 | 0.001 | 0.001 | 0.001 | 0.001 | 0.001 | 0.001 | 0.001 | 0.001 | 0.001 | 0.001 | 0.003 | 0.005 |
| BASS | 1506 | 0 | 0.001 | 0.002 | 0.001 | 0.001 | 0.951 | 0.001 | 0.004 | 0.001 | 0.001 | 0.004 | 0.001 | 0.001 | 0.001 | 0.001 | 0.001 | 0.001 | 0.002 | 0.002 | 0.005 | 0.011 | 0.001 |
| BEAG | 1917 | −4 | 0.001 | 0.003 | 0.001 | 0.001 | 0.971 | 0.007 | 0.002 | 0.001 | 0.002 | 0.001 | 0.001 | 0.001 | 0.002 | 0.001 | 0 | 0.001 | 0.003 | 0.003 | 0.001 | 0.001 | 0.001 |
| BEAG | 1323 | −2 | 0.001 | 0.059 | 0.011 | 0.019 | 0.002 | 0.002 | 0.002 | 0.001 | 0.002 | 0.003 | 0.001 | 0.001 | 0.017 | 0.001 | 0.001 | 0.007 | 0.004 | 0.859 | 0.003 | 0.002 | 0.002 |
| BEAG | 1324 | −1 | 0.003 | 0.001 | 0.004 | 0.002 | 0.005 | 0.04 | 0.001 | 0.012 | 0.004 | 0.003 | 0.001 | 0.001 | 0.001 | 0.231 | 0.001 | 0.244 | 0.008 | 0.421 | 0.012 | 0.002 | 0.001 |
| BEAG | 1327 | −2 | 0.003 | 0.017 | 0.002 | 0.001 | 0.003 | 0.006 | 0.001 | 0.001 | 0.003 | 0.001 | 0.002 | 0.002 | 0.011 | 0.001 | 0.001 | 0.002 | 0.007 | 0.928 | 0.002 | 0.002 | 0.001 |
| BEAG | 994 | −3 | 0.002 | 0.001 | 0.001 | 0.001 | 0.001 | 0.001 | 0.002 | 0.001 | 0.001 | 0.002 | 0.001 | 0.001 | 0.001 | 0.001 | 0.001 | 0.001 | 0.001 | 0.98 | 0.001 | 0.001 | 0.001 |
| BEAG | 995 | −2 | 0.001 | 0.001 | 0.001 | 0.001 | 0.001 | 0.001 | 0.001 | 0.002 | 0.001 | 0.002 | 0.001 | 0.001 | 0.002 | 0.001 | 0.002 | 0.001 | 0.001 | 0.972 | 0.001 | 0.001 | 0.002 |
| BLDH | 1186 | 0 | 0.001 | 0.989 | 0 | 0.001 | 0.001 | 0.001 | 0.001 | 0.001 | 0 | 0.001 | 0.001 | 0 | 0.001 | 0 | 0 | 0 | 0.001 | 0.006 | 0 | 0.001 | 0 |
| BLDH | 1223 | −2 | 0.01 | 0.945 | 0.001 | 0.002 | 0.002 | 0.002 | 0.003 | 0.006 | 0.001 | 0.001 | 0.001 | 0.001 | 0.002 | 0.001 | 0.001 | 0.001 | 0.001 | 0.006 | 0.001 | 0.006 | 0.007 |
| BLDH | 1410 | −8 | 0.001 | 0.978 | 0.001 | 0.001 | 0.001 | 0.04 | 0.001 | 0.002 | 0.001 | 0.001 | 0.001 | 0.001 | 0.001 | 0.001 | 0.001 | 0.001 | 0.001 | 0.002 | 0.001 | 0.001 | 0.001 |
| BLDH | 1942 | −6 | 0.001 | 0.981 | 0.001 | 0.001 | 0.001 | 0.001 | 0.001 | 0.001 | 0.004 | 0.003 | 0.001 | 0.001 | 0.004 | 0.001 | 0.003 | 0.001 | 0.001 | 0.001 | 0.004 | 0.001 | 0.001 |
| BLDH | 1957 | 0 | 0.001 | 0.973 | 0.001 | 0.001 | 0.002 | 0.001 | 0.001 | 0.001 | 0.001 | 0.002 | 0.001 | 0.001 | 0.003 | 0.001 | 0.001 | 0.001 | 0.002 | 0.008 | 0.003 | 0.002 | 0.001 |
| IBIZ | 1147 | −8 | 0.001 | 0.001 | 0.001 | 0.001 | 0.001 | 0.001 | 0.017 | 0.001 | 0.002 | 0.097 | 0.002 | 0.001 | 0.01 | 0.001 | 0.003 | 0.001 | 0.001 | 0.008 | 0.84 | 0.001 | 0.002 |
| IBIZ | 1148 | −19 | 0.002 | 0.001 | 0.011 | 0.001 | 0.003 | 0.002 | 0.002 | 0.001 | 0.002 | 0.109 | 0.004 | 0.001 | 0.002 | 0.001 | 0.001 | 0.002 | 0.002 | 0.001 | 0.852 | 0.001 | 0.001 |
| IBIZ | 1162 | 0 | 0.001 | 0.002 | 0.002 | 0.002 | 0.001 | 0.001 | 0.003 | 0.001 | 0.002 | 0.247 | 0.001 | 0.001 | 0.001 | 0.001 | 0.001 | 0.001 | 0.001 | 0.001 | 0.725 | 0.001 | 0.003 |

TABLE 17B-continued

| Canid Population[a] | Canid ID No. | Missing Data | Populations* | | | | | | | | | | | | | | | | | | | |
|---|---|---|---|---|---|---|---|---|---|---|---|---|---|---|---|---|---|---|---|---|---|---|
| | | | 44 | 45 | 46 | 47 | 48 | 49 | 50 | 51 | 52 | 53 | 54 | 55 | 56 | 57 | 58 | 59 | 60 | 61 | 62 | 63 | 64 |
| IBIZ | 1172 | 0 | 0.002 | 0.075 | 0.001 | 0.007 | 0.001 | 0.001 | 0.001 | 0.001 | 0.003 | 0.098 | 0.001 | 0.001 | 0.002 | 0.001 | 0.002 | 0.002 | 0.002 | 0.002 | 0.795 | 0.001 | 0.002 |
| IBIZ | 1280 | 0 | 0.002 | 0.001 | 0.001 | 0.003 | 0.004 | 0.005 | 0.004 | 0.001 | 0.001 | 0.102 | 0.007 | 0.001 | 0.001 | 0.001 | 0.001 | 0.003 | 0.004 | 0.001 | 0.85 | 0.002 | 0.002 |
| PHAR | 1292 | −3 | 0.001 | 0.001 | 0.001 | 0.001 | 0.002 | 0.001 | 0.001 | 0.001 | 0.001 | 0.977 | 0.001 | 0.001 | 0.001 | 0.001 | 0.001 | 0.001 | 0.004 | 0.001 | 0.002 | 0.001 | 0.002 |
| PHAR | 1947 | −14 | 0.001 | 0 | 0.002 | 0.001 | 0.001 | 0.009 | 0.001 | 0.001 | 0.006 | 0.968 | 0.001 | 0.001 | 0.001 | 0.001 | 0.002 | 0.001 | 0.001 | 0.002 | 0.002 | 0.001 | 0.001 |
| PHAR | 1962 | −14 | 0.001 | 0.001 | 0.001 | 0.002 | 0.001 | 0.002 | 0.001 | 0.001 | 0.001 | 0.969 | 0 | 0.001 | 0.001 | 0.001 | 0.001 | 0.001 | 0.005 | 0.001 | 0.003 | 0.003 | 0.001 |
| PHAR | 1963 | −10 | 0.002 | 0.001 | 0.001 | 0.001 | 0.008 | 0.001 | 0.001 | 0.001 | 0.001 | 0.956 | 0.001 | 0.003 | 0.005 | 0.001 | 0.001 | 0.001 | 0.001 | 0.001 | 0.003 | 0.001 | 0.016 |
| PTWD | P142 | −3 | 0.002 | 0.001 | 0.009 | 0.001 | 0.001 | 0.001 | 0.002 | 0.001 | 0.002 | 0.002 | 0.007 | 0.001 | 0.001 | 0.002 | 0.002 | 0.005 | 0.942 | 0.002 | 0.003 | 0.005 | 0.002 |
| PTWD | P1 | −6 | 0.001 | 0.008 | 0.003 | 0.001 | 0.002 | 0.002 | 0.001 | 0.021 | 0.035 | 0.001 | 0.001 | 0.001 | 0.001 | 0.002 | 0.023 | 0.002 | 0.929 | 0.002 | 0.002 | 0.015 | 0.002 |
| PTWD | P238 | −3 | 0.003 | 0.002 | 0.005 | 0.005 | 0.004 | 0.025 | 0.002 | 0.021 | 0.035 | 0.024 | 0.008 | 0.007 | 0.002 | 0.002 | 0.003 | 0.003 | 0.503 | 0.301 | 0.018 | 0.022 | 0.005 |
| PTWD | P25 | −2 | 0.006 | 0.002 | 0.016 | 0.005 | 0.002 | 0.031 | 0.028 | 0.005 | 0.004 | 0.003 | 0.003 | 0.007 | 0.005 | 0.054 | 0.004 | 0.01 | 0.767 | 0.008 | 0.014 | 0.025 | 0.003 |
| PTWD | P67 | 0 | 0.002 | 0.001 | 0.001 | 0.001 | 0.003 | 0.003 | 0.001 | 0.001 | 0.002 | 0.009 | 0.001 | 0.001 | 0.001 | 0.001 | 0.001 | 0.005 | 0.957 | 0.003 | 0.002 | 0.002 | 0.002 |
| AMWS | 2168 | 0 | 0.004 | 0.001 | 0.09 | 0.007 | 0.002 | 0.005 | 0.002 | 0.204 | 0.002 | 0.001 | 0.002 | 0.001 | 0.626 | 0.001 | 0.002 | 0.004 | 0.002 | 0.005 | 0.002 | 0.036 | 0.003 |
| AMWS | 2279 | −4 | 0.005 | 0.016 | 0.001 | 0.025 | 0.003 | 0.01 | 0.039 | 0.009 | 0.012 | 0.004 | 0.002 | 0.013 | 0.706 | 0.069 | 0.005 | 0.042 | 0.005 | 0.014 | 0.009 | 0.002 | 0.011 |
| AMWS | 2327 | −36 | 0.002 | 0.001 | 0.001 | 0.001 | 0.001 | 0.001 | 0.003 | 0.003 | 0.001 | 0.001 | 0.003 | 0.001 | 0.975 | 0.001 | 0.003 | 0.001 | 0.001 | 0.001 | 0.003 | 0.001 | 0.001 |
| AMWS | 987 | −1 | 0.001 | 0.002 | 0.001 | 0.001 | 0.001 | 0.001 | 0.001 | 0.001 | 0.001 | 0.001 | 0.001 | 0.001 | 0.974 | 0.001 | 0.001 | 0.001 | 0.001 | 0.003 | 0.003 | 0.003 | 0.001 |
| AMWS | 988 | 0 | 0.004 | 0.001 | 0.019 | 0.002 | 0.004 | 0.003 | 0.002 | 0.007 | 0.006 | 0.007 | 0.002 | 0.002 | 0.897 | 0.001 | 0.003 | 0.025 | 0.007 | 0.002 | 0.004 | 0.002 | 0.001 |
| WSSP | 1955 | −14 | 0.001 | 0.001 | 0.001 | 0.001 | 0.004 | 0.001 | 0.001 | 0.001 | 0.001 | 0.001 | 0.001 | 0.001 | 0.001 | 0.001 | 0.002 | 0.001 | 0.001 | 0.001 | 0.002 | 0.977 | 0.001 |
| WSSP | 2139 | −1 | 0.002 | 0.002 | 0.001 | 0.001 | 0.001 | 0.002 | 0.01 | 0.017 | 0.002 | 0.001 | 0.001 | 0.001 | 0.001 | 0.001 | 0.001 | 0.003 | 0.001 | 0.001 | 0.001 | 0.948 | 0.001 |
| WSSP | 2143 | 0 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 | 0.977 | 0.001 |
| WSSP | 2195 | −27 | 0.003 | 0.002 | 0.003 | 0.001 | 0.001 | 0.001 | 0.001 | 0.001 | 0.002 | 0.001 | 0.004 | 0.002 | 0.004 | 0.002 | 0.001 | 0.001 | 0.003 | 0.002 | 0.001 | 0.962 | 0.002 |
| WSSP | 2286 | −5 | 0.002 | 0.02 | 0.001 | 0.005 | 0.002 | 0.001 | 0.004 | 0.002 | 0.001 | 0.002 | 0.002 | 0.001 | 0.002 | 0.001 | 0.002 | 0.002 | 0.003 | 0.002 | 0.001 | 0.943 | 0.001 |

TABLE 17C

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 22 | 23 | 24 | 25 | 26 | 27 | 28 | 29 | 30 | 31 | 32 | 33 | 34 | 35 | 36 | 37 | 38 | 39 | 40 | 41 | 42 |
| TURV | 1622 | −1 | 0.001 | 0.002 | 0.001 | 0.002 | 0.004 | 0.003 | 0.002 | 0.001 | 0.003 | 0.002 | 0.001 | 0.005 | 0.001 | 0.002 | 0.002 | 0.002 | 0.001 | 0.002 | 0.002 | 0.958 | 0.004 |
| TURV | 2194 | −1 | 0.003 | 0.001 | 0.001 | 0.008 | 0.001 | 0.001 | 0.001 | 0.001 | 0.005 | 0.005 | 0.005 | 0.002 | 0.001 | 0.009 | 0.005 | 0.016 | 0.002 | 0.01 | 0.004 | 0.881 | 0.019 |
| TURV | 2200 | 0 | 0.003 | 0.001 | 0.001 | 0.002 | 0.001 | 0.001 | 0.001 | 0.001 | 0.004 | 0.005 | 0.003 | 0.002 | 0.001 | 0.003 | 0.013 | 0.008 | 0.001 | 0.003 | 0.001 | 0.951 | 0.002 |
| TURV | 2222 | 0 | 0.003 | 0.003 | 0.008 | 0.004 | 0.009 | 0.006 | 0.006 | 0.001 | 0.003 | 0.004 | 0.003 | 0.002 | 0.001 | 0.005 | 0.001 | 0.001 | 0.002 | 0.005 | 0.007 | 0.907 | 0.004 |
| BELS | 1351 | −1 | 0.001 | 0.001 | 0.001 | 0.003 | 0.001 | 0.001 | 0.001 | 0.003 | 0.002 | 0.004 | 0.003 | 0.001 | 0.001 | 0.001 | 0.002 | 0.001 | 0.002 | 0.001 | 0.001 | 0.967 | 0.002 |
| BELS | 2111 | −6 | 0.001 | 0.004 | 0.006 | 0.001 | 0.001 | 0.001 | 0.001 | 0.001 | 0.001 | 0.003 | 0.002 | 0.002 | 0.001 | 0.001 | 0.001 | 0.001 | 0.008 | 0.002 | 0.001 | 0.954 | 0.002 |
| BELS | 2153 | 0 | 0.001 | 0.001 | 0.001 | 0.001 | 0.001 | 0 | 0.001 | 0.002 | 0.001 | 0.002 | 0.001 | 0.001 | 0.001 | 0.001 | 0.002 | 0.001 | 0.001 | 0.002 | 0.001 | 0.981 | 0.001 |
| BELS | 2209 | −1 | 0.001 | 0.001 | 0.001 | 0.001 | 0.001 | 0.001 | 0.011 | 0.001 | 0.001 | 0.002 | 0.002 | 0.001 | 0.001 | 0.001 | 0.001 | 0.001 | 0.004 | 0.001 | 0 | 0.973 | 0.001 |
| BELS | 2210 | 0 | 0.001 | 0.001 | 0.001 | 0.002 | 0.001 | 0.001 | 0.004 | 0.002 | 0.001 | 0.002 | 0.001 | 0.004 | 0.001 | 0.006 | 0.002 | 0.001 | 0.001 | 0.001 | 0.001 | 0.976 | 0.001 |
| OES | 1984 | −1 | 0.905 | 0.004 | 0.006 | 0.002 | 0.006 | 0.002 | 0.001 | 0.002 | 0.004 | 0.001 | 0.001 | 0.004 | 0.002 | 0.006 | 0.019 | 0.001 | 0.003 | 0.021 | 0.001 | 0.002 | 0.009 |
| OES | 2171 | −4 | 0.85 | 0.004 | 0.002 | 0.002 | 0.003 | 0.001 | 0.001 | 0.007 | 0.003 | 0.001 | 0.003 | 0.019 | 0.003 | 0.018 | 0.01 | 0.002 | 0.004 | 0.023 | 0.002 | 0.001 | 0.018 |
| OES | 2179 | −9 | 0.881 | 0.025 | 0.004 | 0.004 | 0.002 | 0.001 | 0.001 | 0.001 | 0.001 | 0.007 | 0.012 | 0.008 | 0.006 | 0.004 | 0.001 | 0.005 | 0.006 | 0.004 | 0.002 | 0.005 | 0.004 |
| OES | 1914 | −5 | 0.966 | 0.001 | 0.001 | 0.001 | 0.002 | 0.001 | 0.003 | 0.001 | 0.002 | 0.003 | 0.001 | 0.001 | 0.001 | 0.002 | 0.002 | 0.001 | 0.002 | 0.001 | 0.001 | 0.001 | 0.002 |
| OES | 2626 | −38 | 0.965 | 0.001 | 0.001 | 0.001 | 0.001 | 0.001 | 0.001 | 0.001 | 0.001 | 0.002 | 0.001 | 0.001 | 0.001 | 0.001 | 0.002 | 0.003 | 0.001 | 0.002 | 0.002 | 0.001 | 0.002 |
| BORD | 1648 | −26 | 0.003 | 0.001 | 0.001 | 0.001 | 0.001 | 0.01 | 0.002 | 0.001 | 0.005 | 0.004 | 0.003 | 0.004 | 0.001 | 0.002 | 0.958 | 0.006 | 0.001 | 0.003 | 0.006 | 0.001 | 0.002 |
| BORD | 1828 | −17 | 0.002 | 0.005 | 0.003 | 0.001 | 0.001 | 0.01 | 0.001 | 0.001 | 0.001 | 0.017 | 0.003 | 0.002 | 0.008 | 0.003 | 0.749 | 0.001 | 0.168 | 0.002 | 0.001 | 0.001 | 0.004 |
| BORD | 1829 | −1 | 0.009 | 0.003 | 0.023 | 0.012 | 0.021 | 0.002 | 0.004 | 0.003 | 0.005 | 0.005 | 0.001 | 0.002 | 0.008 | 0.018 | 0.823 | 0.002 | 0.002 | 0.02 | 0.002 | 0.005 | 0.014 |
| BORD | 2002 | −3 | 0.006 | 0.002 | 0.012 | 0.003 | 0.978 | 0.001 | 0.002 | 0.001 | 0.005 | 0.001 | 0.002 | 0.001 | 0.001 | 0.002 | 0.955 | 0.001 | 0.005 | 0.003 | 0.001 | 0.001 | 0.003 |
| BORD | 2003 | −3 | 0.008 | 0.021 | 0.002 | 0.004 | 0.002 | 0.004 | 0.002 | 0.008 | 0.002 | 0.001 | 0.002 | 0.005 | 0.007 | 0.006 | 0.886 | 0.002 | 0.005 | 0.005 | 0.003 | 0.008 | 0.011 |
| AUSS | 1336 | −2 | 0.011 | 0.003 | 0.002 | 0.009 | 0.039 | 0.008 | 0.003 | 0.002 | 0.004 | 0.01 | 0.015 | 0.002 | 0.003 | 0.26 | 0.034 | 0.001 | 0.005 | 0.347 | 0.016 | 0.005 | 0.064 |
| AUSS | 1337 | −2 | 0.005 | 0.006 | 0.001 | 0.005 | 0.013 | 0.004 | 0.001 | 0.001 | 0.096 | 0.003 | 0.002 | 0.032 | 0.003 | 0.015 | 0.022 | 0.001 | 0.002 | 0.342 | 0.002 | 0.003 | 0.2 |
| AUSS | 1500 | −15 | 0.002 | 0.001 | 0.003 | 0.003 | 0.015 | 0.002 | 0.002 | 0.003 | 0.004 | 0.009 | 0.001 | 0.001 | 0.003 | 0.003 | 0.005 | 0.001 | 0.002 | 0.021 | 0.003 | 0.001 | 0.472 |
| AUSS | 1521 | −3 | 0.128 | 0.003 | 0.002 | 0.08 | 0.074 | 0.035 | 0.001 | 0.001 | 0.007 | 0.002 | 0.003 | 0.003 | 0.002 | 0.073 | 0.004 | 0.003 | 0.002 | 0.382 | 0.002 | 0.001 | 0.085 |
| AUSS | 1683 | −4 | 0.031 | 0.004 | 0.001 | 0.013 | 0.005 | 0.001 | 0.001 | 0.001 | 0.003 | 0.006 | 0.008 | 0.014 | 0.001 | 0.128 | 0.078 | 0.029 | 0.002 | 0.060 | 0.003 | 0.002 | 0.344 |
| COLL | 1692 | −2 | 0.001 | 0.001 | 0.001 | 0.002 | 0.001 | 0.001 | 0.001 | 0.001 | 0.001 | 0.002 | 0.001 | 0.004 | 0.002 | 0.001 | 0.003 | 0.005 | 0.001 | 0.001 | 0.001 | 0.001 | 0.001 |
| COLL | 1701 | −11 | 0.001 | 0.001 | 0.001 | 0.001 | 0 | 0.001 | 0.004 | 0.003 | 0.002 | 0.001 | 0.001 | 0.001 | 0.001 | 0.002 | 0.001 | 0.001 | 0.001 | 0.004 | 0.002 | 0.001 | 0.003 |
| COLL | 2284 | −16 | 0.001 | 0.001 | 0.001 | 0.001 | 0.002 | 0.004 | 0.002 | 0.008 | 0.001 | 0.001 | 0.001 | 0.001 | 0.007 | 0.002 | 0.001 | 0.001 | 0.001 | 0.005 | 0.005 | 0.001 | 0.002 |
| COLL | 373 | −2 | 0.001 | 0 | 0.001 | 0.001 | 0.983 | 0.008 | 0.003 | 0.002 | 0.002 | 0.01 | 0.015 | 0.001 | 0.003 | 0.006 | 0.001 | 0.001 | 0.005 | 0.001 | 0.003 | 0.001 | 0.001 |
| COLL | 379 | −3 | 0.001 | 0.001 | 0.001 | 0.001 | 0.978 | 0.004 | 0.001 | 0.001 | 0.001 | 0.003 | 0.002 | 0.032 | 0.003 | 0.015 | 0.022 | 0.001 | 0.002 | 0.001 | 0 | 0.003 | 0.001 |
| SSHP | 1379 | 0 | 0.005 | 0.002 | 0.002 | 0.01 | 0.878 | 0.003 | 0.006 | 0.003 | 0.002 | 0.012 | 0.001 | 0.018 | 0.003 | 0.003 | 0.005 | 0.001 | 0.013 | 0.004 | 0.001 | 0.002 | 0.012 |
| SSHP | 1523 | −1 | 0.001 | 0.008 | 0.003 | 0.002 | 0.868 | 0.035 | 0.002 | 0.001 | 0.003 | 0.003 | 0.008 | 0.002 | 0.004 | 0.006 | 0.004 | 0.029 | 0.005 | 0.004 | 0.003 | 0.003 | 0.006 |
| SSHP | 1824 | −6 | 0.004 | 0.001 | 0.006 | 0.003 | 0.869 | 0.001 | 0.002 | 0.003 | 0.001 | 0.004 | 0.001 | 0.011 | 0.001 | 0.002 | 0.001 | 0.005 | 0.004 | 0.003 | 0.008 | 0.066 | 0.003 |
| SSHP | 1921 | −30 | 0.002 | 0.002 | 0.004 | 0.001 | 0.971 | 0.001 | 0.001 | 0.001 | 0.001 | 0.002 | 0.002 | 0.003 | 0.001 | 0.002 | 0.001 | 0.001 | 0.001 | 0.002 | 0.001 | 0.001 | 0.002 |
| SSHP | 2040 | −19 | 0.004 | 0.002 | 0.001 | 0.001 | 0.907 | 0.002 | 0.006 | 0.001 | 0.003 | 0.004 | 0.001 | 0.003 | 0.002 | 0.013 | 0.004 | 0.002 | 0.002 | 0.009 | 0.001 | 0.018 | 0.007 |
| DACH | 1051 | −5 | 0.002 | 0.001 | 0.001 | 0.001 | 0.001 | 0.001 | 0.001 | 0.003 | 0.002 | 0.001 | 0.001 | 0.001 | 0.001 | 0.001 | 0.004 | 0.001 | 0.001 | 0.001 | 0.968 | 0.018 | 0.001 |
| DACH | 1052 | −2 | 0.001 | 0.001 | 0.002 | 0.001 | 0.002 | 0.014 | 0.001 | 0.001 | 0.001 | 0.001 | 0.001 | 0.001 | 0.001 | 0.001 | 0.001 | 0.001 | 0.001 | 0.001 | 0.984 | 0.001 | 0.001 |
| DACH | 1053 | −2 | 0.001 | 0.005 | 0.001 | 0.002 | 0.001 | 0.032 | 0.002 | 0.016 | 0.001 | 0.001 | 0.001 | 0.001 | 0.003 | 0.005 | 0.002 | 0.001 | 0.004 | 0.003 | 0.915 | 0.002 | 0.005 |
| DACH | 1054 | 0 | 0.001 | 0.001 | 0.001 | 0.001 | 0.002 | 0.001 | 0.001 | 0.001 | 0.001 | 0.001 | 0.001 | 0.001 | 0.001 | 0.001 | 0.001 | 0.001 | 0.001 | 0.002 | 0.961 | 0.001 | 0.001 |
| DACH | 1055 | −1 | 0.001 | 0.001 | 0.001 | 0.002 | 0.001 | 0.001 | 0.001 | 0.001 | 0.001 | 0.001 | 0.001 | 0.001 | 0.001 | 0.001 | 0.002 | 0.001 | 0.001 | 0.001 | 0.971 | 0.001 | 0.001 |
| DANE | 1574 | −5 | 0.004 | 0.002 | 0.002 | 0.002 | 0.003 | 0.002 | 0.001 | 0.001 | 0.001 | 0.001 | 0.003 | 0.001 | 0.003 | 0.006 | 0.001 | 0.005 | 0.037 | 0.001 | 0.002 | 0.001 | 0.005 |
| DANE | 1575 | −11 | 0.004 | 0.9 | 0.002 | 0.001 | 0.001 | 0 | 0.001 | 0.001 | 0 | 0.001 | 0.001 | 0.001 | 0.001 | 0.001 | 0.002 | 0.001 | 0.02 | 0.005 | 0.006 | 0.001 | 0.001 |
| DANE | 1580 | −2 | 0.002 | 0.977 | 0.001 | 0.001 | 0.001 | 0.001 | 0.001 | 0.001 | 0.001 | 0.001 | 0.001 | 0.001 | 0.001 | 0.002 | 0.001 | 0.001 | 0.001 | 0.001 | 0.001 | 0.002 | 0.001 |
| DANE | 1700 | −7 | 0.002 | 0.934 | 0.003 | 0.002 | 0.004 | 0.001 | 0.002 | 0.004 | 0.002 | 0.012 | 0.001 | 0.001 | 0.002 | 0.002 | 0.002 | 0.013 | 0.001 | 0.001 | 0.001 | 0.006 | 0.002 |
| DANE | 1748 | −3 | 0.001 | 0.973 | 0.001 | 0.001 | 0.001 | 0 | 0.002 | 0.001 | 0.001 | 0.001 | 0.001 | 0.001 | 0.001 | 0.001 | 0.001 | 0.001 | 0.001 | 0.001 | 0.001 | 0.001 | 0.001 |
| IWOF | 1581 | −21 | 0.001 | 0.001 | 0.001 | 0.001 | 0 | 0.001 | 0.001 | 0.001 | 0.001 | 0.001 | 0.001 | 0.001 | 0.001 | 0.001 | 0.001 | 0.985 | 0.001 | 0.001 | 0 | 0.001 | 0.001 |
| IWOF | 1761 | −12 | 0.001 | 0.001 | 0.003 | 0.001 | 0.001 | 0.001 | 0.001 | 0.001 | 0.001 | 0.001 | 0.001 | 0.001 | 0.001 | 0.001 | 0.001 | 0.981 | 0.001 | 0.001 | 0.001 | 0.001 | 0.001 |
| IWOF | 1792 | −4 | 0.001 | 0.001 | 0.003 | 0.002 | 0.001 | 0.001 | 0.001 | 0.001 | 0.001 | 0.002 | 0.001 | 0.001 | 0.001 | 0.001 | 0.001 | 0.972 | 0.003 | 0.001 | 0.002 | 0.001 | 0.001 |

TABLE 17C-continued

| Canid Population[a] | Canid ID No. | Missing Data | \multicolumn{21}{c}{Populations*} |
|---|---|---|---|---|---|---|---|---|---|---|---|---|---|---|---|---|---|---|---|---|---|
| | | | 22 | 23 | 24 | 25 | 26 | 27 | 28 | 29 | 30 | 31 | 32 | 33 | 34 | 35 | 36 | 37 | 38 | 39 | 40 | 41 | 42 |
| IWOF | 1906 | −6 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 | 0.982 | 0.002 | 0.001 | 0.001 | 0.001 | 0.001 |
| IWOF | 1993 | −3 | 0.002 | 0.001 | 0.001 | 0.001 | 0.001 | 0.001 | 0.001 | 0.003 | 0.001 | 0.002 | 0.001 | 0.001 | 0.001 | 0.001 | 0 | 0.972 | 0.001 | 0.001 | 0.001 | 0.006 | 0.001 |
| BORZ | 1378 | 0 | 0.004 | 0.001 | 0.001 | 0.002 | 0.004 | 0.001 | 0.944 | 0.007 | 0.001 | 0.003 | 0.002 | 0.007 | 0.003 | 0.003 | 0.002 | 0.001 | 0.001 | 0.004 | 0.002 | 0.001 | 0.003 |
| BORZ | 1401 | −4 | 0.001 | 0.001 | 0.002 | 0.001 | 0.001 | 0.001 | 0.979 | 0.001 | 0 | 0.001 | 0.001 | 0.001 | 0.002 | 0.001 | 0.001 | 0.003 | 0.001 | 0.001 | 0.001 | 0 | 0.001 |
| BORZ | 1808 | −2 | 0.001 | 0.004 | 0.001 | 0.003 | 0.001 | 0.002 | 0.959 | 0.001 | 0.001 | 0.001 | 0.004 | 0.001 | 0.002 | 0.002 | 0.001 | 0.001 | 0.003 | 0.003 | 0.002 | 0.001 | 0.003 |
| BORZ | 2268 | 0 | 0.003 | 0.003 | 0.002 | 0.002 | 0.008 | 0.004 | 0.858 | 0.004 | 0.002 | 0.012 | 0.005 | 0.001 | 0.002 | 0.007 | 0.002 | 0.058 | 0.001 | 0.005 | 0.004 | 0.004 | 0.006 |
| BORZ | 978 | −1 | 0.003 | 0.008 | 0.001 | 0.004 | 0.002 | 0.001 | 0.936 | 0.001 | 0.011 | 0.006 | 0.006 | 0.003 | 0.003 | 0.002 | 0.001 | 0.001 | 0.001 | 0.002 | 0.001 | 0.005 | 0.001 |
| GREY | 2477 | −1 | 0.002 | 0.001 | 0.01 | 0.001 | 0.001 | 0.001 | 0.019 | 0.023 | 0.001 | 0.864 | 0.008 | 0.002 | 0.001 | 0.012 | 0.001 | 0.018 | 0.005 | 0.011 | 0.001 | 0.003 | 0.015 |
| GREY | 2478 | 0 | 0.001 | 0.004 | 0.001 | 0.002 | 0.002 | 0.002 | 0.001 | 0.002 | 0.006 | 0.951 | 0.001 | 0.001 | 0.003 | 0.002 | 0.001 | 0.001 | 0.001 | 0.002 | 0.002 | 0.001 | 0.002 |
| GREY | 2479 | 0 | 0.004 | 0.002 | 0.001 | 0.007 | 0.003 | 0.002 | 0.005 | 0.001 | 0.004 | 0.932 | 0.009 | 0.002 | 0.003 | 0.004 | 0.002 | 0.004 | 0.002 | 0.005 | 0.001 | 0.001 | 0.004 |
| GREY | 2480 | −3 | 0.002 | 0.001 | 0.001 | 0.004 | 0.004 | 0.011 | 0.004 | 0.001 | 0.001 | 0.929 | 0.002 | 0.001 | 0.002 | 0.006 | 0.001 | 0.012 | 0.002 | 0.005 | 0.001 | 0.003 | 0.003 |
| GREY | 2481 | −3 | 0.001 | 0.004 | 0.002 | 0.013 | 0.002 | 0.004 | 0.012 | 0.045 | 0.006 | 0.829 | 0.004 | 0.008 | 0.001 | 0.011 | 0.005 | 0.017 | 0.001 | 0.006 | 0.002 | 0.003 | 0.012 |
| WHIP | 1355 | −1 | 0.003 | 0.001 | 0.002 | 0.001 | 0.001 | 0.001 | 0.002 | 0.001 | 0.002 | 0.96 | 0.004 | 0.001 | 0.001 | 0.002 | 0.001 | 0.002 | 0.001 | 0.002 | 0.001 | 0.001 | 0.001 |
| WHIP | 1395 | −42 | 0.003 | 0.002 | 0.004 | 0.006 | 0.001 | 0.001 | 0.022 | 0.005 | 0.003 | 0.61 | 0.004 | 0.008 | 0.002 | 0.006 | 0.02 | 0.148 | 0.004 | 0.02 | 0.004 | 0.002 | 0.067 |
| WHIP | 1407 | −2 | 0.001 | 0.001 | 0.001 | 0.001 | 0.001 | 0.002 | 0.002 | 0.002 | 0.002 | 0.881 | 0.002 | 0.005 | 0.001 | 0.003 | 0.002 | 0.083 | 0.001 | 0.002 | 0.002 | 0.002 | 0.002 |
| WHIP | 1409 | −2 | 0.001 | 0.001 | 0.001 | 0.001 | 0.001 | 0.001 | 0.004 | 0.001 | 0.001 | 0.97 | 0.001 | 0.001 | 0.001 | 0.001 | 0.001 | 0.007 | 0.001 | 0.002 | 0.001 | 0.001 | 0.001 |
| WHIP | 1518 | −14 | 0.001 | 0.001 | 0.001 | 0.003 | 0.003 | 0.001 | 0.002 | 0.002 | 0.002 | 0.942 | 0.006 | 0.012 | 0.001 | 0.003 | 0.001 | 0.001 | 0.005 | 0.003 | 0.001 | 0.001 | 0.006 |
| ITGR | 1568 | −1 | 0.001 | 0.004 | 0.008 | 0.002 | 0.001 | 0.004 | 0.001 | 0.001 | 0.008 | 0.002 | 0.95 | 0.002 | 0.001 | 0.003 | 0.001 | 0.002 | 0.001 | 0.002 | 0.001 | 0.003 | 0.001 |
| ITGR | 1570 | −25 | 0.001 | 0.001 | 0.001 | 0.001 | 0.001 | 0.004 | 0.002 | 0.001 | 0.001 | 0.001 | 0.975 | 0.002 | 0.001 | 0.002 | 0.001 | 0.003 | 0.001 | 0.003 | 0.001 | 0.001 | 0.001 |
| ITGR | 1862 | −5 | 0.001 | 0.001 | 0.001 | 0.001 | 0.001 | 0.001 | 0.001 | 0 | 0.001 | 0.001 | 0.978 | 0.004 | 0.001 | 0.003 | 0.001 | 0.002 | 0.001 | 0.002 | 0.001 | 0.001 | 0.001 |
| ITGR | 1881 | −12 | 0.001 | 0.001 | 0.001 | 0.002 | 0.001 | 0.001 | 0.001 | 0.001 | 0.006 | 0.002 | 0.949 | 0.002 | 0.001 | 0.003 | 0.003 | 0.001 | 0.005 | 0.002 | 0.004 | 0.003 | 0.003 |
| ITGR | 1882 | −3 | 0.001 | 0.002 | 0.001 | 0.001 | 0.001 | 0.001 | 0.001 | 0.001 | 0 | 0.002 | 0.972 | 0.004 | 0.001 | 0.001 | 0.001 | 0.002 | 0.001 | 0.002 | 0.001 | 0.001 | 0.001 |
| RHOD | 1444 | −16 | 0.002 | 0.001 | 0.006 | 0.003 | 0.001 | 0.001 | 0.001 | 0.001 | 0.006 | 0.002 | 0.002 | 0.004 | 0.001 | 0.002 | 0.004 | 0.001 | 0.908 | 0.003 | 0.002 | 0.002 | 0.003 |
| RHOD | 1454 | −2 | 0.035 | 0.003 | 0.01 | 0.014 | 0.043 | 0.001 | 0.004 | 0.001 | 0.002 | 0.001 | 0.014 | 0.002 | 0.01 | 0.011 | 0.002 | 0.001 | 0.695 | 0.008 | 0.003 | 0.002 | 0.071 |
| RHOD | 1505 | −3 | 0.03 | 0.023 | 0.003 | 0.036 | 0.004 | 0.014 | 0.002 | 0.001 | 0.03 | 0.003 | 0.002 | 0.008 | 0.005 | 0.01 | 0.003 | 0.009 | 0.774 | 0.023 | 0.002 | 0.002 | 0.009 |
| RHOD | 1592 | −14 | 0.001 | 0.001 | 0.002 | 0.001 | 0.002 | 0.001 | 0.001 | 0.001 | 0.001 | 0.001 | 0.001 | 0.004 | 0.001 | 0.001 | 0.001 | 0.001 | 0.979 | 0.001 | 0.002 | 0.001 | 0.001 |
| RHOD | 1609 | −50 | 0.001 | 0.001 | 0.005 | 0.001 | 0.001 | 0.001 | 0.001 | 0.003 | 0.001 | 0.001 | 0.001 | 0.001 | 0.001 | 0.001 | 0.001 | 0.001 | 0.977 | 0.001 | 0.001 | 0.001 | 0.001 |
| STBD | 1075 | −1 | 0.006 | 0.005 | 0.005 | 0.026 | 0.003 | 0.005 | 0.002 | 0.838 | 0.017 | 0.005 | 0.001 | 0.002 | 0.012 | 0.02 | 0.004 | 0.002 | 0.001 | 0.011 | 0.001 | 0.017 | 0.01 |
| STBD | 1714 | −5 | 0.001 | 0.001 | 0.001 | 0.002 | 0.001 | 0.001 | 0.001 | 0.98 | 0.001 | 0.001 | 0.001 | 0.001 | 0.001 | 0.001 | 0.001 | 0.001 | 0.001 | 0.001 | 0.001 | 0 | 0.001 |
| STBD | 1750 | −22 | 0.001 | 0.001 | 0.001 | 0.001 | 0.001 | 0.001 | 0.001 | 0.982 | 0.001 | 0.001 | 0.001 | 0.001 | 0.001 | 0.001 | 0.001 | 0.001 | 0.001 | 0.001 | 0.001 | 0.001 | 0.001 |
| STBD | 2403 | −17 | 0.001 | 0.002 | 0.001 | 0.001 | 0.003 | 0.001 | 0.005 | 0.967 | 0.001 | 0.001 | 0.001 | 0.005 | 0.001 | 0.001 | 0.001 | 0.003 | 0.002 | 0.001 | 0.002 | 0.002 | 0.001 |
| STBD | 2404 | −2 | 0.001 | 0.001 | 0.002 | 0.001 | 0.002 | 0.001 | 0.001 | 0.975 | 0.001 | 0.001 | 0.001 | 0.001 | 0.001 | 0.001 | 0.001 | 0.003 | 0.001 | 0.001 | 0.002 | 0.001 | 0.001 |
| CLSP | 1008 | −1 | 0.001 | 0.003 | 0.003 | 0.001 | 0.001 | 0.976 | 0 | 0.001 | 0.001 | 0.001 | 0.001 | 0.001 | 0.001 | 0.001 | 0.001 | 0.003 | 0.001 | 0.001 | 0.001 | 0.001 | 0.001 |
| CLSP | 1009 | 0 | 0 | 0.001 | 0 | 0.001 | 0.001 | 0.988 | 0 | 0.001 | 0.001 | 0.001 | 0.001 | 0 | 0.001 | 0.001 | 0.001 | 0.001 | 0 | 0.001 | 0.001 | 0 | 0 |
| CLSP | 1802 | −2 | 0 | 0.001 | 0 | 0.001 | 0.001 | 0.992 | 0 | 0.001 | 0 | 0.001 | 0.001 | 0 | 0.001 | 0 | 0 | 0.001 | 0 | 0.001 | 0.001 | 0 | 0.001 |
| CLSP | 2312 | −1 | 0.001 | 0.001 | 0.001 | 0.002 | 0.001 | 0.978 | 0.001 | 0.001 | 0.001 | 0.001 | 0.001 | 0.001 | 0.001 | 0.001 | 0.001 | 0.001 | 0.001 | 0.001 | 0.001 | 0.001 | 0.001 |

TABLE 17C-continued

| Canid Population[a] | Canid ID No. | Missing Data | Populations* | | | | | | | | | | | | | | | | | | | |
|---|---|---|---|---|---|---|---|---|---|---|---|---|---|---|---|---|---|---|---|---|---|---|
| | | | 22 | 23 | 24 | 25 | 26 | 27 | 28 | 29 | 30 | 31 | 32 | 33 | 34 | 35 | 36 | 37 | 38 | 39 | 40 | 41 | 42 |
| CLSP | 2314 | 0 | 0 | 0 | 0.001 | 0.001 | 0.001 | 0.988 | 0 | 0.001 | 0 | 0.001 | 0.001 | 0 | 0 | 0.001 | 0.001 | 0 | 0.001 | 0.001 | 0 | 0 | 0.001 |
| AUST | 1387 | −3 | 0.006 | 0.006 | 0.002 | 0.003 | 0.006 | 0.001 | 0.003 | 0.001 | 0.002 | 0.004 | 0.011 | 0.91 | 0.004 | 0.003 | 0.002 | 0.015 | 0.002 | 0.005 | 0.003 | 0.002 | 0.005 |
| AUST | 1531 | −1 | 0.003 | 0.004 | 0.002 | 0.002 | 0.004 | 0.007 | 0.005 | 0.002 | 0.018 | 0.002 | 0.001 | 0.899 | 0.004 | 0.005 | 0.017 | 0.003 | 0.002 | 0.005 | 0.005 | 0.002 | 0.004 |
| AUST | 1564 | −7 | 0.001 | 0.001 | 0.001 | 0.002 | 0.003 | 0 | 0.001 | 0.001 | 0.001 | 0.001 | 0.003 | 0.973 | 0.002 | 0.001 | 0.002 | 0.001 | 0.001 | 0.002 | 0.001 | 0.001 | 0.002 |
| AUST | 1870 | −5 | 0.001 | 0.001 | 0.002 | 0.002 | 0.003 | 0.003 | 0.011 | 0.003 | 0.001 | 0.001 | 0.001 | 0.95 | 0.001 | 0.003 | 0.002 | 0.001 | 0.083 | 0.004 | 0.003 | 0.001 | 0.003 |
| AUST | 1871 | 0 | 0.012 | 0.009 | 0.005 | 0.016 | 0.002 | 0.002 | 0.002 | 0.003 | 0.002 | 0.014 | 0.001 | 0.806 | 0.007 | 0.006 | 0.004 | 0.002 | 0.001 | 0.007 | 0.003 | 0.003 | 0.007 |
| WHWT | 1388 | −13 | 0.002 | 0.001 | 0.001 | 0.001 | 0.002 | 0.007 | 0.004 | 0.001 | 0.954 | 0.002 | 0.007 | 0.002 | 0.002 | 0.002 | 0.001 | 0.001 | 0.001 | 0.002 | 0.001 | 0.002 | 0.002 |
| WHWT | 1420 | −7 | 0.001 | 0.001 | 0.001 | 0.001 | 0.001 | 0.001 | 0.001 | 0.113 | 0.856 | 0.003 | 0.001 | 0.001 | 0.001 | 0.001 | 0.001 | 0.003 | 0.001 | 0.001 | 0.001 | 0.001 | 0.002 |
| WHWT | 1992 | −5 | 0.002 | 0.001 | 0.001 | 0.003 | 0.001 | 0.006 | 0.001 | 0.001 | 0.968 | 0.001 | 0.001 | 0.001 | 0.001 | 0.001 | 0.001 | 0.001 | 0.001 | 0.001 | 0.001 | 0.002 | 0.001 |
| WHWT | 2100 | −4 | 0.002 | 0.003 | 0.005 | 0.003 | 0.006 | 0.001 | 0.001 | 0.003 | 0.948 | 0.002 | 0.002 | 0.001 | 0.001 | 0.003 | 0.002 | 0.001 | 0.001 | 0.003 | 0.005 | 0.003 | 0.002 |
| WHWT | 2128 | 0 | 0.002 | 0.001 | 0.001 | 0.002 | 0.001 | 0 | 0.001 | 0.001 | 0.979 | 0.001 | 0.001 | 0.001 | 0.001 | 0.001 | 0.001 | 0.001 | 0.001 | 0.001 | 0.001 | 0.001 | 0.001 |
| CAIR | 1405 | −1 | 0.002 | 0.002 | 0.002 | 0.638 | 0.002 | 0.007 | 0.001 | 0.004 | 0.28 | 0.006 | 0.001 | 0.002 | 0.011 | 0.008 | 0.004 | 0.003 | 0.002 | 0.008 | 0.002 | 0.004 | 0.004 |
| CAIR | 2096 | −28 | 0.001 | 0.001 | 0.003 | 0.857 | 0.002 | 0.002 | 0.002 | 0.001 | 0.076 | 0.005 | 0.011 | 0.002 | 0.003 | 0.004 | 0.001 | 0.001 | 0.002 | 0.005 | 0.003 | 0.001 | 0.007 |
| CAIR | 2113 | −4 | 0.003 | 0.003 | 0.003 | 0.693 | 0.001 | 0.001 | 0.004 | 0.001 | 0.242 | 0.004 | 0.004 | 0.002 | 0.004 | 0.005 | 0.002 | 0.001 | 0.002 | 0.006 | 0.003 | 0.003 | 0.006 |
| CAIR | 2125 | −1 | 0.005 | 0.001 | 0.005 | 0.619 | 0.001 | 0.001 | 0.001 | 0.001 | 0.332 | 0.004 | 0.002 | 0.002 | 0.002 | 0.004 | 0.001 | 0.001 | 0.004 | 0.003 | 0.001 | 0.005 | 0.003 |
| CAIR | 2131 | −8 | 0.009 | 0.003 | 0.002 | 0.917 | 0.005 | 0.003 | 0.003 | 0.002 | 0.007 | 0.005 | 0.002 | 0.004 | 0.003 | 0.004 | 0.01 | 0.001 | 0.001 | 0.005 | 0.001 | 0.002 | 0.006 |
| BEDT | 1422 | −5 | 0.001 | 0 | 0.987 | 0.001 | 0.001 | 0.001 | 0 | 0.001 | 0.001 | 0.001 | 0.001 | 0.001 | 0.001 | 0.001 | 0.001 | 0.001 | 0.001 | 0.001 | 0.001 | 0 | 0.001 |
| BEDT | 1423 | −8 | 0 | 0.001 | 0.986 | 0.001 | 0.001 | 0.006 | 0.001 | 0 | 0.001 | 0.005 | 0.011 | 0.002 | 0.001 | 0.001 | 0 | 0.001 | 0.001 | 0.001 | 0.001 | 0 | 0.001 |
| BEDT | 1424 | −21 | 0.001 | 0.001 | 0.982 | 0.001 | 0.001 | 0.001 | 0.001 | 0.001 | 0.001 | 0.001 | 0.004 | 0.001 | 0.001 | 0.001 | 0.001 | 0.001 | 0.001 | 0.001 | 0.001 | 0.001 | 0.001 |
| BEDT | 1426 | −30 | 0.001 | 0.001 | 0.981 | 0.001 | 0.003 | 0.001 | 0.001 | 0.003 | 0.001 | 0.001 | 0.002 | 0.001 | 0.001 | 0.002 | 0.001 | 0.001 | 0.003 | 0.002 | 0.002 | 0.002 | 0.001 |
| CHIH | 1202 | −8 | 0.002 | 0.002 | 0.002 | 0.002 | 0.001 | 0.001 | 0.001 | 0.001 | 0.001 | 0.001 | 0.001 | 0.001 | 0.963 | 0.002 | 0.001 | 0.002 | 0.003 | 0.002 | 0.001 | 0.002 | 0.001 |
| CHIH | 1203 | −4 | 0.001 | 0.001 | 0.001 | 0.003 | 0.001 | 0.001 | 0.001 | 0.002 | 0.001 | 0.001 | 0.002 | 0.002 | 0.969 | 0.002 | 0.001 | 0.002 | 0.001 | 0.001 | 0.002 | 0.001 | 0.001 |
| CHIH | 1204 | 0 | 0.003 | 0.002 | 0.002 | 0.005 | 0.001 | 0.002 | 0.009 | 0.001 | 0.002 | 0.013 | 0.001 | 0.006 | 0.921 | 0.006 | 0.003 | 0.002 | 0.001 | 0.007 | 0.001 | 0.001 | 0.005 |
| CHIH | 1205 | −2 | 0.013 | 0.003 | 0.001 | 0.007 | 0.003 | 0.004 | 0.001 | 0.001 | 0.002 | 0.002 | 0.001 | 0.001 | 0.417 | 0.176 | 0.018 | 0.001 | 0.005 | 0.113 | 0.004 | 0.005 | 0.118 |
| CHIH | 1206 | −1 | 0.001 | 0.001 | 0.003 | 0.409 | 0.002 | 0.007 | 0.001 | 0.003 | 0.002 | 0.018 | 0.005 | 0.029 | 0.405 | 0.013 | 0.018 | 0.012 | 0.006 | 0.011 | 0.005 | 0.007 | 0.021 |

TABLE 17D

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 65 | 66 | 67 | 68 | 69 | 70 | 71 | 72 | 73 | 74 | 75 | 76 | 77 | 78 | 79 | 80 | 81 | 82 | 83 | 84 | 85 |
| CHBR | 1546 | −4 | 0.002 | 0.832 | 0.008 | 0.001 | 0.006 | 0.003 | 0.002 | 0.004 | 0.004 | 0.006 | 0.031 | 0.008 | 0.003 | 0.007 | 0.044 | 0.005 | 0.014 | 0.009 | 0.002 | 0.002 | 0.006 |
| CHBR | 1549 | −4 | 0.001 | 0.955 | 0.001 | 0.002 | 0.001 | 0.001 | 0.004 | 0.003 | 0.002 | 0.003 | 0.002 | 0.001 | 0.002 | 0.002 | 0.003 | 0.002 | 0.002 | 0.004 | 0.002 | 0.003 | 0.001 |
| CHBR | 1813 | −3 | 0.001 | 0.951 | 0.002 | 0.001 | 0.003 | 0.003 | 0.002 | 0.003 | 0.002 | 0.002 | 0.002 | 0.001 | 0.005 | 0.003 | 0.006 | 0.002 | 0.002 | 0.001 | 0.003 | 0.003 | 0.001 |
| CHBR | 2091 | −1 | 0.003 | 0.868 | 0.005 | 0.001 | 0.003 | 0.003 | 0.001 | 0.004 | 0.022 | 0.021 | 0.002 | 0.007 | 0.002 | 0.001 | 0.007 | 0.007 | 0.004 | 0.027 | 0.001 | 0.002 | 0.009 |
| CHBR | 888 | −12 | 0.002 | 0.959 | 0.001 | 0.009 | 0.001 | 0.003 | 0.001 | 0.001 | 0.001 | 0.001 | 0.005 | 0.001 | 0.002 | 0.001 | 0.001 | 0.002 | 0.002 | 0.001 | 0.002 | 0.001 | 0.01 |
| FCR | 1188 | −1 | 0.002 | 0.005 | 0.001 | 0.001 | 0.221 | 0.001 | 0.001 | 0.002 | 0.001 | 0.001 | 0.001 | 0.001 | 0.004 | 0.001 | 0.001 | 0.001 | 0.001 | 0.748 | 0.001 | 0.001 | 0.004 |
| FCR | 2020 | −11 | 0.001 | 0.001 | 0.001 | 0.001 | 0.215 | 0.001 | 0.002 | 0.001 | 0.002 | 0.001 | 0.001 | 0.001 | 0.001 | 0.002 | 0.002 | 0.001 | 0.001 | 0.759 | 0.001 | 0.001 | 0.001 |
| FCR | 2042 | −7 | 0.002 | 0.001 | 0.001 | 0.001 | 0.221 | 0.001 | 0.007 | 0.002 | 0.002 | 0.001 | 0.001 | 0.001 | 0.004 | 0.001 | 0.001 | 0.001 | 0.001 | 0.759 | 0.001 | 0.001 | 0.001 |
| FCR | 2044 | 0 | 0.002 | 0.009 | 0.001 | 0.001 | 0.193 | 0.002 | 0.002 | 0.002 | 0.002 | 0.001 | 0.003 | 0.001 | 0.003 | 0.001 | 0.002 | 0.001 | 0.002 | 0.746 | 0.001 | 0.004 | 0.004 |
| FCR | 2259 | 0 | 0.005 | 0.001 | 0.001 | 0.001 | 0.213 | 0.008 | 0.004 | 0.002 | 0.001 | 0.001 | 0.001 | 0.001 | 0.001 | 0.002 | 0.001 | 0.001 | 0.001 | 0.754 | 0.001 | 0.011 | 0.002 |
| GOLD | 591 | −3 | 0.003 | 0.002 | 0.003 | 0.002 | 0.001 | 0.002 | 0.004 | 0.005 | 0.001 | 0.005 | 0.027 | 0.003 | 0.001 | 0.001 | 0.002 | 0.002 | 0.003 | 0.01 | 0.001 | 0.001 | 0.001 |
| GOLD | 592 | −3 | 0.001 | 0.009 | 0.001 | 0.002 | 0.01 | 0.001 | 0.002 | 0.005 | 0.004 | 0.01 | 0.144 | 0.07 | 0.003 | 0.001 | 0.925 | 0.005 | 0.019 | 0.063 | 0.001 | 0.002 | 0.003 |
| GOLD | 593 | −1 | 0.002 | 0.003 | 0.001 | 0.001 | 0.001 | 0.007 | 0.003 | 0.001 | 0.002 | 0.003 | 0.006 | 0.003 | 0.004 | 0.001 | 0.642 | 0.001 | 0.003 | 0.002 | 0.001 | 0.002 | 0.003 |
| GOLD | 603 | 0 | 0.001 | 0.001 | 0.001 | 0.002 | 0.001 | 0.001 | 0.001 | 0.001 | 0.001 | 0.001 | 0.001 | 0.001 | 0.001 | 0.001 | 0.95 | 0.001 | 0.001 | 0.001 | 0.001 | 0.001 | 0.01 |
| GOLD | 604 | 0 | 0.001 | 0.002 | 0.001 | 0.001 | 0.001 | 0.002 | 0.001 | 0.002 | 0.001 | 0.001 | 0.001 | 0.001 | 0.004 | 0.001 | 0.979 | 0.001 | 0.002 | 0.005 | 0.002 | 0.001 | 0 |
| LAB | 1310 | −2 | 0.001 | 0.002 | 0.001 | 0.001 | 0.009 | 0.002 | 0.002 | 0.004 | 0.002 | 0.001 | 0.001 | 0.045 | 0.004 | 0.011 | 0.939 | 0.003 | 0.002 | 0.005 | 0.003 | 0.003 | 0.003 |
| LAB | 1465 | −2 | 0.008 | 0.002 | 0.005 | 0.102 | 0.003 | 0.016 | 0.002 | 0.019 | 0.01 | 0.012 | 0.547 | 0.001 | 0.003 | 0.008 | 0.002 | 0.004 | 0.029 | 0.179 | 0.001 | 0.003 | 0.002 |
| LAB | 1468 | −2 | 0.001 | 0.003 | 0.001 | 0.001 | 0.002 | 0.001 | 0.001 | 0.001 | 0.01 | 0.002 | 0.745 | 0.001 | 0.003 | 0.002 | 0.002 | 0.002 | 0.001 | 0.23 | 0.001 | 0.001 | 0.001 |
| LAB | 1754 | −12 | 0.001 | 0.004 | 0.001 | 0.003 | 0.005 | 0.002 | 0.005 | 0.001 | 0.001 | 0.002 | 0.728 | 0.004 | 0.002 | 0.003 | 0.006 | 0.001 | 0.002 | 0.222 | 0.001 | 0.005 | 0.001 |
| LAB | 1830 | −12 | 0.023 | 0.002 | 0.002 | 0.001 | 0.001 | 0.001 | 0.001 | 0.009 | 0.005 | 0.004 | 0.703 | 0.004 | 0.002 | 0.003 | 0.006 | 0.002 | 0.007 | 0.214 | 0.006 | 0.001 | 0.001 |
| LAB | 1666 | −17 | 0.001 | 0.003 | 0.005 | 0.021 | 0.003 | 0.009 | 0.003 | 0.013 | 0.003 | 0.002 | 0.359 | 0.082 | 0.001 | 0.006 | 0.027 | 0.001 | 0.363 | 0.095 | 0.002 | 0.001 | 0.002 |
| GSD | 1776 | −23 | 0.002 | 0.001 | 0.001 | 0 | 0 | 0.001 | 0.001 | 0.019 | 0.01 | 0.012 | 0.001 | 0.001 | 0.006 | 0.977 | 0.002 | 0.001 | 0.001 | 0.001 | 0.001 | 0.001 | 0.001 |
| GSD | 2011 | −9 | 0.001 | 0.001 | 0.001 | 0.001 | 0.002 | 0.001 | 0.001 | 0.001 | 0.001 | 0.002 | 0.001 | 0.001 | 0.003 | 0.98 | 0.002 | 0.001 | 0.001 | 0.001 | 0.001 | 0.002 | 0.001 |
| GSD | 2060 | −2 | 0.001 | 0.001 | 0.001 | 0.003 | 0.005 | 0.001 | 0.005 | 0.001 | 0.001 | 0.002 | 0.004 | 0.004 | 0.002 | 0.975 | 0.001 | 0.001 | 0.002 | 0.001 | 0.001 | 0.001 | 0.001 |
| GSD | 2086 | −2 | 0.003 | 0.003 | 0.005 | 0.001 | 0.001 | 0.002 | 0.001 | 0.002 | 0.002 | 0.001 | 0.003 | 0.001 | 0.003 | 0.977 | 0.004 | 0.001 | 0.001 | 0.001 | 0.001 | 0.001 | 0.001 |
| GSD | 2152 | −6 | 0.055 | 0.001 | 0.008 | 0.053 | 0.007 | 0.002 | 0.001 | 0.002 | 0.002 | 0.001 | 0.008 | 0.002 | 0.002 | 0.961 | 0.001 | 0.001 | 0.003 | 0.002 | 0.001 | 0.001 | 0.002 |
| IRTR | 2189 | −4 | 0.001 | 0.001 | 0.001 | 0.001 | 0.001 | 0.001 | 0.001 | 0.013 | 0.004 | 0.003 | 0.001 | 0.034 | 0.001 | 0.002 | 0.005 | 0.003 | 0.009 | 0.036 | 0.001 | 0.002 | 0.002 |
| IRTR | 2238 | −4 | 0.001 | 0.001 | 0.001 | 0.001 | 0.001 | 0 | 0 | 0 | 0.004 | 0.001 | 0.001 | 0.001 | 0.001 | 0.001 | 0 | 0.001 | 0.001 | 0.001 | 0.001 | 0 | 0.001 |
| IRTR | 2242 | −1 | 0.001 | 0.001 | 0.001 | 0.001 | 0.001 | 0.001 | 0.001 | 0.001 | 0.002 | 0.001 | 0.002 | 0.001 | 0.002 | 0.001 | 0.001 | 0.001 | 0.001 | 0.003 | 0.001 | 0.001 | 0.004 |
| KERY | 13878 | 0 | 0.007 | 0.042 | 0.006 | 0.003 | 0.001 | 0 | 0 | 0.001 | 0.001 | 0.002 | 0.003 | 0.003 | 0.005 | 0 | 0.001 | 0.001 | 0.001 | 0.001 | 0.003 | 0.001 | 0.001 |
| KERY | 1483 | −11 | 0.001 | 0.001 | 0.001 | 0.001 | 0.001 | 0.001 | 0.002 | 0.001 | 0.001 | 0.002 | 0.001 | 0.001 | 0.002 | 0.001 | 0.008 | 0.001 | 0.001 | 0.002 | 0.001 | 0.001 | 0.003 |
| KERY | 1579 | −2 | 0.001 | 0.001 | 0.001 | 0.004 | 0.001 | 0.001 | 0.004 | 0.02 | 0.004 | 0.001 | 0.003 | 0.005 | 0.026 | 0.001 | 0.002 | 0.001 | 0.022 | 0.003 | 0.003 | 0.003 | 0.006 |
| KERY | 2014 | 0 | 0.003 | 0.058 | 0.003 | 0.002 | 0.001 | 0.004 | 0.007 | 0.001 | 0.004 | 0.006 | 0.006 | 0.004 | 0.003 | 0.009 | 0.003 | 0.028 | 0.003 | 0.007 | 0.011 | 0.008 | 0.007 |
| KERY | 24255 | −1 | 0.001 | 0.001 | 0.001 | 0.001 | 0.002 | 0.001 | 0.001 | 0.001 | 0.002 | 0.001 | 0.004 | 0.002 | 0.007 | 0.001 | 0.003 | 0.003 | 0.004 | 0.002 | 0.001 | 0.013 | 0.005 |
| SCWT | 1624 | −30 | 0.001 | 0.001 | 0.002 | 0.134 | 0.001 | 0.001 | 0.001 | 0.001 | 0.003 | 0.002 | 0.001 | 0.352 | 0.001 | 0.001 | 0.005 | 0.003 | 0.002 | 0.001 | 0.002 | 0.003 | 0.001 |
| SCWT | 1770 | −4 | 0.001 | 0.001 | 0.001 | 0.978 | 0.001 | 0.001 | 0.001 | 0.001 | 0.002 | 0.001 | 0.03 | 0.001 | 0.001 | 0.001 | 0.001 | 0.001 | 0.002 | 0.001 | 0.004 | 0.001 | 0.001 |
| SCWT | 2250 | −6 | 0.004 | 0.001 | 0.001 | 0.973 | 0.001 | 0.001 | 0.001 | 0.001 | 0.005 | 0.001 | 0.001 | 0.004 | 0.001 | 0 | 0.001 | 0.001 | 0.002 | 0.001 | 0.001 | 0.001 | 0.001 |
| SCWT | 2301 | −15 | 0.003 | 0.002 | 0.001 | 0.982 | 0.001 | 0.001 | 0 | 0.001 | 0.001 | 0.001 | 0.001 | 0.002 | 0.001 | 0 | 0.001 | 0.001 | 0.001 | 0.002 | 0.003 | 0.001 | 0.002 |
| POM | 1190 | −2 | 0.001 | 0.001 | 0.001 | 0.975 | 0.001 | 0 | 0.001 | 0.001 | 0.001 | 0.002 | 0.004 | 0.005 | 0.002 | 0.001 | 0 | 0.895 | 0.001 | 0.002 | 0.001 | 0.001 | 0.002 |
| POM | 1191 | −2 | 0.001 | 0.002 | 0.001 | 0.975 | 0.004 | 0.001 | 0.004 | 0.02 | 0.004 | 0.002 | 0.004 | 0.004 | 0.026 | 0.001 | 0.008 | 0.892 | 0.022 | 0.003 | 0.001 | 0.003 | 0.006 |
| POM | 1210 | −8 | 0.001 | 0.002 | 0.003 | 0.005 | 0.005 | 0.009 | 0.007 | 0.001 | 0.004 | 0.002 | 0.005 | 0.007 | 0.003 | 0.009 | 0.002 | 0.908 | 0.003 | 0.007 | 0.011 | 0.008 | 0.002 |
| POM | 1238 | −1 | 0.007 | 0.003 | 0.003 | 0.007 | 0.004 | 0.007 | 0.001 | 0.001 | 0.001 | 0.007 | 0.004 | 0.002 | 0.007 | 0.001 | 0.003 | 0.975 | 0.001 | 0.001 | 0.001 | 0.001 | 0.005 |
| POM | 1239 | −14 | 0.003 | 0.001 | 0.001 | 0.001 | 0.001 | 0.001 | 0.001 | 0.001 | 0.002 | 0.002 | 0.001 | 0.002 | 0.001 | 0.002 | 0.005 | 0.553 | 0.025 | 0.001 | 0.002 | 0.001 | 0.001 |
| SCHP | 1386 | −9 | 0.004 | 0.005 | 0.002 | 0.003 | 0.001 | 0.001 | 0.001 | 0.001 | 0.003 | 0.002 | 0.001 | 0.001 | 0.002 | 0.001 | 0.002 | 0.001 | 0.001 | 0.001 | 0.002 | 0.001 | 0.002 |
| SCHP | 1471 | −13 | 0.008 | 0.001 | 0.001 | 0.001 | 0.001 | 0.001 | 0.028 | 0.001 | 0.001 | 0.001 | 0.001 | 0.001 | 0.001 | 0 | 0.001 | 0.001 | 0.001 | 0.002 | 0.001 | 0.001 | 0.969 |
| SCHP | 1814 | −1 | 0.002 | 0.001 | 0.001 | 0.001 | 0.001 | 0.002 | 0.001 | 0.001 | 0.001 | 0.001 | 0.001 | 0.002 | 0.006 | 0.002 | 0.004 | 0.002 | 0.001 | 0.003 | 0.001 | 0.001 | 0.972 |
| SCHP | 1852 | 0 | 0.001 | 0.001 | 0.001 | 0.004 | 0.001 | 0.001 | 0.001 | 0.001 | 0.001 | 0.003 | 0.002 | 0.001 | 0.002 | 0.001 | 0.001 | 0.002 | 0.001 | 0.004 | 0.001 | 0.002 | 0.966 |

TABLE 17D-continued

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 65 | 66 | 67 | 68 | 69 | 70 | 71 | 72 | 73 | 74 | 75 | 76 | 77 | 78 | 79 | 80 | 81 | 82 | 83 | 84 | 85 |
| BMD | 941 | −11 | 0.001 | 0.003 | 0.001 | 0.002 | 0.004 | 0.014 | 0.007 | 0.002 | 0.002 | 0.002 | 0.001 | 0.002 | 0.94 | 0.001 | 0.003 | 0.003 | 0.004 | 0.001 | 0.001 | 0.005 | 0.001 |
| BMD | 943 | −10 | 0.002 | 0.002 | 0.001 | 0.002 | 0.002 | 0.005 | 0.002 | 0.001 | 0.002 | 0.002 | 0.005 | 0.005 | 0.869 | 0.002 | 0.002 | 0.087 | 0.004 | 0.002 | 0.001 | 0.002 | 0.001 |
| BMD | 968 | −15 | 0.001 | 0.001 | 0.001 | 0.001 | 0.001 | 0.002 | 0.002 | 0.001 | 0.001 | 0.001 | 0.001 | 0.002 | 0.973 | 0.001 | 0.004 | 0.001 | 0.001 | 0.002 | 0.01 | 0.001 | 0.001 |
| BMD | 1763 | −10 | 0.012 | 0.003 | 0.002 | 0.002 | 0.005 | 0.003 | 0.003 | 0.012 | 0.001 | 0.001 | 0.002 | 0.001 | 0.916 | 0.005 | 0.007 | 0.005 | 0.002 | 0.002 | 0.001 | 0.001 | 0.003 |
| BMD | 969 | −2 | 0.001 | 0.001 | 0.001 | 0.001 | 0.013 | 0.002 | 0.001 | 0.003 | 0.004 | 0.001 | 0.002 | 0.001 | 0.954 | 0.002 | 0.002 | 0.001 | 0.001 | 0.002 | 0.002 | 0.003 | 0.001 |
| GSMD | 1547 | −4 | 0.001 | 0.001 | 0.001 | 0.001 | 0 | 0.001 | 0.001 | 0 | 0.001 | 0.001 | 0.001 | 0.001 | 0.986 | 0.001 | 0.001 | 0.001 | 0.001 | 0.001 | 0.001 | 0.001 | 0.001 |
| GSMD | 1659 | 0 | 0.002 | 0.001 | 0.007 | 0.005 | 0.001 | 0.002 | 0.003 | 0.001 | 0.002 | 0.001 | 0.002 | 0.002 | 0.976 | 0.023 | 0.001 | 0.002 | 0.001 | 0.001 | 0.001 | 0.001 | 0.001 |
| GSMD | 1660 | −4 | 0.003 | 0.003 | 0.001 | 0.001 | 0.001 | 0.001 | 0.002 | 0.001 | 0.001 | 0.001 | 0.001 | 0.002 | 0.932 | 0.001 | 0.002 | 0.001 | 0.002 | 0.001 | 0.001 | 0.001 | 0.001 |
| GSMD | 1662 | −42 | 0.001 | 0.004 | 0.001 | 0.001 | 0.001 | 0.001 | 0.001 | 0.001 | 0.001 | 0 | 0.001 | 0.001 | 0.97 | 0.001 | 0.002 | 0.001 | 0.004 | 0.001 | 0.002 | 0.001 | 0.001 |
| GSMD | 1663 | −5 | 0.001 | 0.001 | 0 | 0.001 | 0 | 0.001 | 0 | 0.001 | 0.001 | 0 | 0 | 0.001 | 0.988 | 0.001 | 0.001 | 0.001 | 0 | 0.001 | 0.001 | 0 | 0.001 |
| BOX | 1176 | 0 | 0.001 | 0.001 | 0 | 0 | 0.981 | 0.001 | 0.001 | 0.001 | 0.001 | 0.002 | 0.001 | 0.001 | 0.002 | 0.001 | 0.001 | 0.001 | 0.001 | 0.001 | 0.002 | 0.001 | 0.001 |
| BOX | 1177 | −1 | 0.004 | 0.021 | 0.002 | 0.002 | 0.912 | 0.001 | 0.006 | 0.002 | 0.002 | 0.003 | 0.002 | 0.003 | 0.002 | 0 | 0.006 | 0.014 | 0.003 | 0.005 | 0.002 | 0.002 | 0.003 |
| BOX | 1178 | 0 | 0.001 | 0.001 | 0.003 | 0.001 | 0.978 | 0.001 | 0.001 | 0.001 | 0.001 | 0.001 | 0.001 | 0.001 | 0 | 0 | 0.001 | 0.001 | 0.001 | 0.001 | 0.001 | 0.001 | 0.001 |
| BOX | 1179 | −3 | 0.001 | 0 | 0.001 | 0 | 0.988 | 0.001 | 0.001 | 0.001 | 0 | 0 | 0 | 0.001 | 0.001 | 0 | 0 | 0.001 | 0.001 | 0 | 0 | 0 | 0.001 |
| BOX | 1304 | −1 | 0.001 | 0.001 | 0.001 | 0.001 | 0.984 | 0.001 | 0.001 | 0.001 | 0.001 | 0.001 | 0.001 | 0.001 | 0.002 | 0.001 | 0.001 | 0.001 | 0.001 | 0.001 | 0.001 | 0.001 | 0.001 |
| MBLT | 1915 | −5 | 0.003 | 0.001 | 0.956 | 0.001 | 0.002 | 0.001 | 0.001 | 0.001 | 0.003 | 0.001 | 0.002 | 0.001 | 0.001 | 0.001 | 0.001 | 0.001 | 0.001 | 0.004 | 0.002 | 0.004 | 0.01 |
| MBLT | 2253 | −12 | 0.001 | 0.001 | 0.979 | 0.002 | 0.001 | 0.001 | 0.001 | 0.001 | 0.009 | 0.001 | 0.005 | 0.001 | 0.001 | 0.001 | 0.001 | 0.002 | 0.006 | 0.001 | 0.001 | 0.001 | 0.001 |
| MBLT | 2254 | −33 | 0.001 | 0.001 | 0.989 | 0.001 | 0.001 | 0.001 | 0.001 | 0.001 | 0.002 | 0.001 | 0.001 | 0.001 | 0.001 | 0 | 0 | 0.001 | 0.001 | 0.001 | 0.001 | 0.001 | 0.001 |
| MBLT | 2255 | −23 | 0.002 | 0.001 | 0.98 | 0.001 | 0.001 | 0.001 | 0.001 | 0 | 0.002 | 0.002 | 0.001 | 0.001 | 0 | 0.001 | 0.001 | 0.001 | 0.001 | 0.004 | 0.001 | 0.001 | 0.001 |
| MBLT | 2256 | −34 | 0.001 | 0.001 | 0.981 | 0.001 | 0.001 | 0.001 | 0.001 | 0.001 | 0 | 0.001 | 0.005 | 0.001 | 0.001 | 0 | 0.001 | 0.001 | 0.001 | 0.001 | 0.001 | 0.002 | 0.001 |
| BULD | 193 | −1 | 0.001 | 0.002 | 0.003 | 0.001 | 0.002 | 0.002 | 0.001 | 0.003 | 0.003 | 0.003 | 0.002 | 0.002 | 0.001 | 0.001 | 0.001 | 0.001 | 0.006 | 0.002 | 0.001 | 0.001 | 0.002 |
| BULD | 1194 | −2 | 0.001 | 0.001 | 0.001 | 0.009 | 0.001 | 0.002 | 0.001 | 0.001 | 0.002 | 0.001 | 0.001 | 0.001 | 0.001 | 0 | 0.001 | 0.003 | 0.001 | 0.001 | 0.009 | 0.952 | 0.001 |
| BULD | 1195 | −8 | 0.005 | 0.001 | 0.001 | 0.001 | 0.001 | 0.001 | 0.001 | 0.003 | 0.008 | 0.002 | 0.001 | 0.001 | 0.001 | 0.001 | 0 | 0.001 | 0.001 | 0.001 | 0.001 | 0.952 | 0.002 |
| BULD | 1197 | −3 | 0.001 | 0.003 | 0.003 | 0.004 | 0.004 | 0.002 | 0.001 | 0.001 | 0.002 | 0.003 | 0.003 | 0.001 | 0.001 | 0.001 | 0.002 | 0.001 | 0.002 | 0.002 | 0.001 | 0.974 | 0.001 |
| BULD | 1198 | 0 | 0.001 | 0.001 | 0.002 | 0.002 | 0.001 | 0.001 | 0.005 | 0.005 | 0.003 | 0.001 | 0.003 | 0.002 | 0.002 | 0.001 | 0.001 | 0.001 | 0.002 | 0.001 | 0.001 | 0.97 | 0.001 |
| FBLD | 1507 | −9 | 0.001 | 0.004 | 0.001 | 0.001 | 0.001 | 0.001 | 0.001 | 0.001 | 0.001 | 0.003 | 0.002 | 0.001 | 0.001 | 0.001 | 0.001 | 0.001 | 0.001 | 0.001 | 0.013 | 0.944 | 0.001 |
| FBLD | 1508 | −7 | 0.001 | 0.001 | 0.003 | 0.004 | 0.012 | 0.006 | 0.002 | 0.016 | 0.05 | 0.748 | 0.043 | 0.015 | 0.002 | 0.032 | 0.002 | 0.01 | 0.002 | 0.005 | 0.984 | 0.001 | 0.001 |
| FBLD | 1509 | −7 | 0.001 | 0.003 | 0.003 | 0.002 | 0.007 | 0.002 | 0.001 | 0.007 | 0.05 | 0.926 | 0.002 | 0.008 | 0.001 | 0.001 | 0.001 | 0.001 | 0.014 | 0.001 | 0.939 | 0.002 | 0.004 |
| FBLD | 2671 | −5 | 0.001 | 0.001 | 0.015 | 0.001 | 0.016 | 0.002 | 0.001 | 0.003 | 0.002 | 0.817 | 0.01 | 0.003 | 0.001 | 0.001 | 0.002 | 0.001 | 0.001 | 0.001 | 0.95 | 0.029 | 0.001 |
| PRES | 1082 | −15 | 0.017 | 0.001 | 0.05 | 0.003 | 0.011 | 0.002 | 0.001 | 0.014 | 0.001 | 0.909 | 0.01 | 0.017 | 0.004 | 0.009 | 0.001 | 0.003 | 0.757 | 0.001 | 0.9 | 0.001 | 0.004 |
| PRES | 1096 | −4 | 0.002 | 0.003 | 0.12 | 0.001 | 0.012 | 0.002 | 0.006 | 0.002 | 0.05 | 0.748 | 0.002 | 0.008 | 0.002 | 0.032 | 0.001 | 0.003 | 0.014 | 0.002 | 0.002 | 0.013 | 0.002 |
| PRES | 1115 | 0 | 0.003 | 0.018 | 0.003 | 0.002 | 0.007 | 0.006 | 0.002 | 0.007 | 0.05 | 0.926 | 0.002 | 0.008 | 0.002 | 0.001 | 0.001 | 0.01 | 0.082 | 0.005 | 0.001 | 0.082 | 0.008 |
| PRES | 1127 | −7 | 0.001 | 0.002 | 0.015 | 0.002 | 0.016 | 0.002 | 0.001 | 0.003 | 0.002 | 0.817 | 0.01 | 0.003 | 0.001 | 0.001 | 0.009 | 0.001 | 0.003 | 0.002 | 0.003 | 0.003 | 0.001 |
| PRES | 1095 | −5 | 0.002 | 0.021 | 0.003 | 0.001 | 0.011 | 0.002 | 0.006 | 0.002 | 0.001 | 0.909 | 0.01 | 0.017 | 0.004 | 0.002 | 0.004 | 0.006 | 0.004 | 0.003 | 0.02 | 0.059 | 0.005 |
| PRES | | | 0.005 | 0.003 | 0.009 | 0.013 | 0.006 | 0.002 | 0.002 | 0.014 | 0.007 | | 0.003 | 0.004 | 0.002 | 0.002 | 0.002 | 0.002 | 0.003 | 0.001 | 0.005 | 0.003 | 0.002 |

TABLE 17D-continued

| Canid Population[a] | Canid ID No. | Missing Data | Populations* | | | | | | | | | | | | | | | | | | | | |
|---|---|---|---|---|---|---|---|---|---|---|---|---|---|---|---|---|---|---|---|---|---|---|---|
| | | | 65 | 66 | 67 | 68 | 69 | 70 | 71 | 72 | 73 | 74 | 75 | 76 | 77 | 78 | 79 | 80 | 81 | 82 | 83 | 84 | 85 |
| BULM | 1105 | 0 | 0.008 | 0.003 | 0.003 | 0.002 | 0.008 | 0.011 | 0.001 | 0.922 | 0.001 | 0.005 | 0.002 | 0.003 | 0.003 | 0.001 | 0.005 | 0.002 | 0.004 | 0.002 | 0.004 | 0.006 | 0.002 |
| BULM | 1106 | -3 | 0.002 | 0.009 | 0.003 | 0.002 | 0.001 | 0.004 | 0.001 | 0.902 | 0.002 | 0.007 | 0.007 | 0.004 | 0.002 | 0.001 | 0.024 | 0.002 | 0.006 | 0.002 | 0.003 | 0.006 | 0.007 |
| BULM | 1107 | -1 | 0.002 | 0.002 | 0.001 | 0.001 | 0.003 | 0.001 | 0.001 | 0.972 | 0.001 | 0.001 | 0.001 | 0.002 | 0.001 | 0.001 | 0.001 | 0.002 | 0.002 | 0.002 | 0.001 | 0.001 | 0.001 |
| BULM | 1108 | 0 | 0.016 | 0.01 | 0.065 | 0.005 | 0.001 | 0.002 | 0.001 | 0.844 | 0.004 | 0.015 | 0.003 | 0.004 | 0.002 | 0.008 | 0.002 | 0.003 | 0.003 | 0.003 | 0.002 | 0.003 | 0.004 |
| BULM | 1109 | 0 | 0.005 | 0.001 | 0.007 | 0.004 | 0.007 | 0.001 | 0.002 | 0.915 | 0.002 | 0.01 | 0.003 | 0.003 | 0.001 | 0.005 | 0.002 | 0.003 | 0.003 | 0.006 | 0.001 | 0.018 | 0.001 |
| MAST | 1015 | 0 | 0.001 | 0.001 | 0.001 | 0.002 | 0.001 | 0.001 | 0.001 | 0.968 | 0.004 | 0.001 | 0.001 | 0.003 | 0.003 | 0.001 | 0.001 | 0.002 | 0.001 | 0.001 | 0.001 | 0.001 | 0.001 |
| MAST | 1016 | 0 | 0.002 | 0.001 | 0.001 | 0.001 | 0.001 | 0.001 | 0.001 | 0.911 | 0.003 | 0.001 | 0.001 | 0.002 | 0.003 | 0.001 | 0.003 | 0.002 | 0.004 | 0.001 | 0.002 | 0.001 | 0.001 |
| MAST | 1017 | -25 | 0.002 | 0.001 | 0.001 | 0.002 | 0.002 | 0.002 | 0.001 | 0.964 | 0.002 | 0.002 | 0.001 | 0.001 | 0.002 | 0.001 | 0.001 | 0.001 | 0.002 | 0.002 | 0.001 | 0.055 | 0.003 |
| MAST | 1066 | -3 | 0.001 | 0.002 | 0.002 | 0.001 | 0.001 | 0.001 | 0.002 | 0.962 | 0.002 | 0.001 | 0.002 | 0.003 | 0.001 | 0.001 | 0.002 | 0.001 | 0.007 | 0.001 | 0.003 | 0.002 | 0.001 |
| MAST | 991 | -18 | 0.002 | 0.001 | 0.001 | 0.001 | 0.001 | 0.001 | 0.001 | 0.977 | 0.003 | 0.001 | 0.001 | 0.001 | 0.001 | 0.002 | 0.001 | 0.001 | 0.001 | 0.001 | 0.003 | 0.003 | 0.001 |
| NEWF | 271 | -2 | 0.002 | 0.004 | 0.001 | 0.001 | 0.005 | 0.874 | 0.01 | 0.002 | 0.002 | 0.016 | 0.006 | 0.009 | 0.006 | 0.002 | 0.01 | 0.015 | 0.006 | 0.014 | 0.005 | 0.005 | 0.004 |
| NEWF | 274 | -1 | 0.001 | 0.001 | 0.002 | 0.001 | 0.001 | 0.968 | 0.001 | 0.002 | 0.002 | 0.001 | 0.005 | 0.002 | 0.002 | 0.002 | 0.002 | 0.001 | 0.002 | 0.002 | 0.001 | 0.001 | 0.001 |
| NEWF | 275 | -2 | 0.002 | 0.002 | 0.001 | 0.001 | 0.001 | 0.979 | 0.002 | 0.001 | 0.001 | 0.001 | 0.001 | 0.001 | 0.001 | 0.003 | 0.001 | 0.001 | 0.001 | 0.001 | 0.001 | 0.001 | 0 |
| NEWF | 277 | 0 | 0.002 | 0.001 | 0.001 | 0.001 | 0.006 | 0.904 | 0.005 | 0.02 | 0.001 | 0.002 | 0.034 | 0.002 | 0.001 | 0.004 | 0.001 | 0.001 | 0.003 | 0.011 | 0.001 | 0.001 | 0.001 |
| NEWF | 278 | -2 | 0.002 | 0.003 | 0.001 | 0.001 | 0.002 | 0.667 | 0.003 | 0.005 | 0.002 | 0.203 | 0.013 | 0.057 | 0.001 | 0.015 | 0.003 | 0.004 | 0.01 | 0.004 | 0.002 | 0.002 | 0.001 |
| ROTT | 1014 | -2 | 0.003 | 0.005 | 0.001 | 0.004 | 0.001 | 0.011 | 0.933 | 0.002 | 0.001 | 0.001 | 0.002 | 0.004 | 0.008 | 0.004 | 0.002 | 0.004 | 0.005 | 0.001 | 0.004 | 0.002 | 0.002 |
| ROTT | 1028 | -3 | 0.001 | 0.001 | 0 | 0 | 0.001 | 0.003 | 0.981 | 0 | 0 | 0.001 | 0.001 | 0.001 | 0.001 | 0.001 | 0.002 | 0.001 | 0.001 | 0.001 | 0.001 | 0.001 | 0.001 |
| ROTT | 1029 | -1 | 0.001 | 0.002 | 0.002 | 0.006 | 0.001 | 0.007 | 0.939 | 0.001 | 0.001 | 0.001 | 0.004 | 0.003 | 0.007 | 0.008 | 0.004 | 0.001 | 0.002 | 0.003 | 0.001 | 0.002 | 0.001 |
| ROTT | 1033 | -4 | 0.002 | 0.002 | 0.003 | 0.001 | 0.001 | 0.003 | 0.963 | 0.002 | 0.001 | 0.003 | 0.002 | 0.003 | 0.001 | 0.001 | 0.002 | 0.001 | 0.004 | 0.001 | 0.001 | 0.002 | 0.002 |
| ROTT | 1034 | 0 | 0.001 | 0.002 | 0.001 | 0.001 | 0.004 | 0.001 | 0.967 | 0.001 | 0.002 | 0.001 | 0.001 | 0.001 | 0.004 | 0.003 | 0.001 | 0.001 | 0.001 | 0.001 | 0.004 | 0.001 | 0.001 |

[a]See Table 5 for abbreviations of canid populations.
*All values for the populations that are not shown are zero.
KBB: pbe

TABLE 18A-F

| Population | Canid ID No. | | |
|---|---|---|---|
| AMAL | 1629 | 0.998 | 0.002 |
| AMAL | 1779 | 0.997 | 0.003 |
| AMAL | 1845 | 0.997 | 0.003 |
| AMAL | 2132 | 0.987 | 0.013 |
| AMAL | 2214 | 0.997 | 0.003 |
| HUSK | 1469 | 0.003 | 0.997 |
| HUSK | 1883 | 0.001 | 0.999 |
| HUSK | 2115 | 0.003 | 0.997 |
| HUSK | 2117 | 0.006 | 0.994 |
| HUSK | 2118 | 0.005 | 0.995 |
| BULM | 1105 | 0.003 | 0.997 |
| BULM | 1106 | 0.002 | 0.998 |
| BULM | 1107 | 0.002 | 0.998 |
| BULM | 1108 | 0.006 | 0.994 |
| BULM | 1109 | 0.003 | 0.997 |
| MAST | 1015 | 0.998 | 0.002 |
| MAST | 1016 | 0.997 | 0.003 |
| MAST | 1017 | 0.995 | 0.005 |
| MAST | 1066 | 0.997 | 0.003 |
| MAST | 991 | 0.995 | 0.005 |
| BMD | 941 | 0.002 | 0.998 |
| BMD | 943 | 0.003 | 0.997 |
| BMD | 968 | 0.001 | 0.999 |
| BMD | 1763 | 0.002 | 0.998 |
| BMD | 969 | 0.002 | 0.998 |
| GSMD | 1547 | 0.998 | 0.002 |
| GSMD | 1659 | 0.997 | 0.003 |
| GSMD | 1660 | 0.999 | 0.001 |
| GSMD | 1662 | 0.997 | 0.003 |
| GSMD | 1663 | 0.998 | 0.002 |
| GREY | 2477 | 0.005 | 0.995 |
| GREY | 2478 | 0.007 | 0.993 |
| GREY | 2479 | 0.003 | 0.997 |
| GREY | 2480 | 0.003 | 0.997 |
| GREY | 2481 | 0.005 | 0.995 |
| WHIP | 1355 | 0.993 | 0.007 |
| WHIP | 1395 | 0.992 | 0.008 |
| WHIP | 1407 | 0.919 | 0.081 |
| WHIP | 1409 | 0.997 | 0.003 |
| WHIP | 1518 | 0.976 | 0.024 |
| BELS | 1351 | 0.515 | 0.485 |
| BELS | 2111 | 0.515 | 0.485 |
| BELS | 22153 | 0.504 | 0.496 |
| BELS | 2209 | 0.504 | 0.496 |
| BELS | 2210 | 0.522 | 0.478 |
| TURV | 1622 | 0.517 | 0.483 |
| TURV | 2194 | 0.521 | 0.479 |
| TURV | 2200 | 0.527 | 0.473 |
| TURV | 2222 | 0.514 | 0.486 |
| COLL | 1692 | 0.003 | 0.997 |
| COLL | 1701 | 0.005 | 0.995 |
| COLL | 2284 | 0.002 | 0.998 |
| COLL | 373 | 0.003 | 0.997 |
| COLL | 379 | 0.003 | 0.997 |
| SSHP | 1379 | 0.996 | 0.004 |
| SSHP | 1523 | 0.998 | 0.002 |
| SSHP | 1824 | 0.998 | 0.002 |
| SSHP | 1921 | 0.998 | 0.002 |
| SSHP | 2040 | 0.997 | 0.003 |

\* See Table 5 for abbreviations of canid populations.

TABLE 19A

| Canid Population[a] | Canid ID No. | k = 4, 15 Run Average | | | |
|---|---|---|---|---|---|
| | | Pop1 | Pop2 | Pop3 | Pop4 |
| SHIB | 1769 | 0.9862 | 0.00393333 | 0.00473333 | 0.00493333 |
| SHIB | 1854 | 0.9806 | 0.0052 | 0.00626667 | 0.00793333 |
| SHIB | 1856 | 0.94133333 | 0.01373333 | 0.02513333 | 0.02 |
| SHIB | 1860 | 0.98093333 | 0.0056 | 0.00733333 | 0.00653333 |
| SHIB | 1981 | 0.98026667 | 0.00573333 | 0.00753333 | 0.00653333 |
| CHOW | 1633 | 0.98393333 | 0.00593333 | 0.0052 | 0.005 |
| CHOW | 1835 | 0.986 | 0.00473333 | 0.00366667 | 0.00546667 |
| CHOW | 1837 | 0.9802 | 0.00813333 | 0.00606667 | 0.00553333 |
| CHOW | 1838 | 0.98626667 | 0.0044 | 0.0048 | 0.0048 |
| CHOW | 1839 | 0.97853333 | 0.0088 | 0.00573333 | 0.0068 |
| AKIT | 1130 | 0.94546667 | 0.0058 | 0.0374 | 0.01133333 |
| AKIT | 1131 | 0.97693333 | 0.00486667 | 0.0144 | 0.0038 |
| AKIT | 1132 | 0.9882 | 0.00453333 | 0.00333333 | 0.00393333 |
| AKIT | 1133 | 0.98713333 | 0.00546667 | 0.00393333 | 0.00366667 |
| AKIT | 1134 | 0.98873333 | 0.00266667 | 0.00353333 | 0.00526667 |
| AMAL | 1629 | 0.87893333 | 0.06 | 0.0244 | 0.03693333 |
| AMAL | 1779 | 0.7818 | 0.01673333 | 0.01706667 | 0.1842 |
| AMAL | 1845 | 0.9252 | 0.02833333 | 0.02626667 | 0.0202 |
| AMAL | 2132 | 0.91766667 | 0.02413333 | 0.01786667 | 0.04006667 |
| AMAL | 2214 | 0.91493333 | 0.01646667 | 0.03 | 0.0388 |
| BSJI | 1338 | 0.7572 | 0.0864 | 0.02133333 | 0.1354 |
| BSJI | 1339 | 0.96393333 | 0.01353333 | 0.0158 | 0.00686667 |
| BSJI | 1645 | 0.97746667 | 0.00886667 | 0.00626667 | 0.00733333 |
| BSJI | 1675 | 0.95526667 | 0.02933333 | 0.00886667 | 0.00673333 |
| BSJI | 1717 | 0.97253333 | 0.00953333 | 0.00733333 | 0.01033333 |
| SHAR | 1573 | 0.95946667 | 0.0204 | 0.00653333 | 0.01366667 |
| SHAR | 1593 | 0.85086667 | 0.111 | 0.02073333 | 0.0172 |
| SHAR | 1619 | 0.90013333 | 0.0718 | 0.01546667 | 0.0128 |
| SHAR | 1998 | 0.8014 | 0.02793333 | 0.09453333 | 0.07633333 |
| SHAR | 1999 | 0.956 | 0.01933333 | 0.0078 | 0.01686667 |
| HUSK | 1469 | 0.90333333 | 0.02393333 | 0.0232 | 0.04973333 |
| HUSK | 1883 | 0.8904 | 0.00786667 | 0.07193333 | 0.02953333 |
| HUSK | 2115 | 0.77493333 | 0.0192 | 0.09933333 | 0.1074 |
| HUSK | 2117 | 0.67213333 | 0.027 | 0.1188 | 0.18193333 |
| HUSK | 2118 | 0.90086667 | 0.02786667 | 0.04093333 | 0.03006667 |
| AFGH | 1812 | 0.56573333 | 0.02113333 | 0.06673333 | 0.3464 |

TABLE 19A-continued

|  | Canid ID | k = 4, 15 Run Average | | | |
|---|---|---|---|---|---|
| Canid Population[a] | No. | Pop1 | Pop2 | Pop3 | Pop4 |
| AFGH | 1939 | 0.6262 | 0.03553333 | 0.1018 | 0.23666667 |
| AFGH | 2264 | 0.55926667 | 0.05073333 | 0.0692 | 0.3208 |
| AFGH | 1936 | 0.74713333 | 0.05586667 | 0.05413333 | 0.14273333 |
| AFGH | 1937 | 0.67166667 | 0.0436 | 0.04986667 | 0.23486667 |
| SALU | 1491 | 0.4006 | 0.04506667 | 0.06466667 | 0.4898 |
| SALU | 1535 | 0.49886667 | 0.01166667 | 0.05393333 | 0.4354 |
| SALU | 1607 | 0.45526667 | 0.02433333 | 0.04333333 | 0.477 |
| SALU | 1873 | 0.2272 | 0.06186667 | 0.08613333 | 0.62433333 |
| SALU | 2610 | 0.37806667 | 0.0618 | 0.0416 | 0.5184 |
| TIBT | 1466 | 0.49693333 | 0.0552 | 0.18146667 | 0.26653333 |
| TIBT | 1562 | 0.36673333 | 0.1172 | 0.24446667 | 0.27173333 |
| TIBT | 1707 | 0.38166667 | 0.2034 | 0.04906667 | 0.36593333 |
| TIBT | 26078 | 0.43486667 | 0.0804 | 0.101 | 0.38373333 |
| TIBT | 28086 | 0.16093333 | 0.14593333 | 0.12653333 | 0.56666667 |
| LHSA | 1524 | 0.35406667 | 0.01493333 | 0.55546667 | 0.0756 |
| LHSA | 1525 | 0.44253333 | 0.01693333 | 0.4188 | 0.12166667 |
| LHSA | 1526 | 0.331 | 0.03193333 | 0.42106667 | 0.21606667 |
| LHSA | 1528 | 0.28613333 | 0.07026667 | 0.5356 | 0.10806667 |
| LHSA | 2074 | 0.59526667 | 0.01573333 | 0.28666667 | 0.1024 |
| SAMO | 1375 | 0.23546667 | 0.01233333 | 0.6444 | 0.1078 |
| SAMO | 1532 | 0.46653333 | 0.0064 | 0.48693333 | 0.04046667 |
| SAMO | 1560 | 0.51173333 | 0.02726667 | 0.37386667 | 0.08686667 |
| SAMO | 169 | 0.3968 | 0.0122 | 0.50726667 | 0.0838 |
| SAMO | 239 | 0.40986667 | 0.02673333 | 0.49193333 | 0.07133333 |
| PEKE | 1143 | 0.30666667 | 0.0062 | 0.5552 | 0.13173333 |
| PEKE | 1145 | 0.1708 | 0.00693333 | 0.60313333 | 0.2192 |
| PEKE | 1211 | 0.1872 | 0.0086 | 0.65013333 | 0.15393333 |
| PEKE | 1212 | 0.14846667 | 0.1002 | 0.59466667 | 0.15693333 |
| PEKE | 1213 | 0.23773333 | 0.0056 | 0.6136 | 0.14306667 |
| SHIH | 1393 | 0.15306667 | 0.08493333 | 0.61986667 | 0.14206667 |
| SHIH | 1783 | 0.14486667 | 0.00826667 | 0.70373333 | 0.14333333 |
| SHIH | 2068 | 0.15553333 | 0.0106 | 0.66613333 | 0.16773333 |
| SHIH | 2859 | 0.20993333 | 0.01053333 | 0.69053333 | 0.08913333 |
| SHIH | 2860 | 0.3304 | 0.01586667 | 0.40086667 | 0.2528 |
| IWOF | 1581 | 0.0168 | 0.3314 | 0.57773333 | 0.0742 |
| IWOF | 1761 | 0.00506667 | 0.11346667 | 0.66893333 | 0.2124 |
| IWOF | 1792 | 0.01426667 | 0.1258 | 0.641 | 0.21893333 |
| IWOF | 1906 | 0.01446667 | 0.13733333 | 0.70666667 | 0.14166667 |
| IWOF | 1993 | 0.00586667 | 0.11806667 | 0.65613333 | 0.22006667 |
| STBD | 1075 | 0.0306 | 0.2296 | 0.40906667 | 0.33073333 |
| STBD | 1714 | 0.01853333 | 0.08833333 | 0.6668 | 0.2266 |
| STBD | 1750 | 0.01566667 | 0.22233333 | 0.48973333 | 0.27226667 |
| STBD | 2403 | 0.00846667 | 0.0614 | 0.69553333 | 0.23453333 |
| STBD | 2404 | 0.0078 | 0.40166667 | 0.524 | 0.0666 |
| GREY | 2477 | 0.0444 | 0.09686667 | 0.765 | 0.0938 |
| GREY | 2478 | 0.01273333 | 0.05146667 | 0.75186667 | 0.18393333 |
| GREY | 2479 | 0.0094 | 0.17826667 | 0.6994 | 0.11306667 |
| GREY | 2480 | 0.01386667 | 0.04133333 | 0.8324 | 0.1126 |
| GREY | 2481 | 0.00573333 | 0.0872 | 0.65273333 | 0.2544 |
| BELS | 1351 | 0.00686667 | 0.0086 | 0.96793333 | 0.0168 |
| BELS | 2111 | 0.0314 | 0.00953333 | 0.94333333 | 0.0158 |
| BELS | 2153 | 0.00373333 | 0.00453333 | 0.98086667 | 0.0108 |
| BELS | 2209 | 0.01126667 | 0.0056 | 0.9696 | 0.01353333 |
| BELS | 2210 | 0.01166667 | 0.01566667 | 0.94853333 | 0.02413333 |
| TURV | 1622 | 0.00333333 | 0.0054 | 0.97573333 | 0.01573333 |
| TURV | 2194 | 0.01046667 | 0.05633333 | 0.799 | 0.13413333 |
| TURV | 2200 | 0.01726667 | 0.01913333 | 0.90673333 | 0.05713333 |
| TURV | 2222 | 0.00473333 | 0.01653333 | 0.84253333 | 0.13633333 |
| BORZ | 1378 | 0.05593333 | 0.01486667 | 0.7554 | 0.17386667 |
| BORZ | 1401 | 0.0358 | 0.03173333 | 0.68146667 | 0.25066667 |
| BORZ | 1808 | 0.064 | 0.0278 | 0.66526667 | 0.2428 |
| BORZ | 2268 | 0.02186667 | 0.0252 | 0.81853333 | 0.13446667 |
| BORZ | 978 | 0.0262 | 0.02046667 | 0.68133333 | 0.2722 |
| COLL | 1692 | 0.00513333 | 0.0512 | 0.718 | 0.22553333 |
| COLL | 1701 | 0.01646667 | 0.01206667 | 0.76006667 | 0.21133333 |
| COLL | 2284 | 0.0048 | 0.01013333 | 0.786 | 0.19926667 |
| COLL | 373 | 0.00393333 | 0.01066667 | 0.78246667 | 0.2028 |
| COLL | 379 | 0.00393333 | 0.0094 | 0.7856 | 0.20113333 |
| SSHP | 1379 | 0.02233333 | 0.19673333 | 0.5936 | 0.18726667 |
| SSHP | 1523 | 0.02086667 | 0.04446667 | 0.73086667 | 0.20373333 |
| SSHP | 1824 | 0.0084 | 0.168 | 0.65733333 | 0.16646667 |
| SSHP | 1921 | 0.00573333 | 0.08706667 | 0.6808 | 0.22633333 |
| SSHP | 2040 | 0.0296 | 0.03046667 | 0.7582 | 0.18166667 |
| PUG | 1077 | 0.00746667 | 0.0072 | 0.4794 | 0.50606667 |
| PUG | 1104 | 0.0188 | 0.0076 | 0.49706667 | 0.47646667 |

TABLE 19A-continued

| Canid Population[a] | Canid ID No. | k = 4, 15 Run Average | | | |
|---|---|---|---|---|---|
| | | Pop1 | Pop2 | Pop3 | Pop4 |
| PUG | 1183 | 0.07146667 | 0.01226667 | 0.4226 | 0.49393333 |
| PUG | 1184 | 0.0082 | 0.00713333 | 0.495 | 0.48966667 |
| PUG | 1192 | 0.006 | 0.05273333 | 0.438 | 0.50326667 |
| KOMO | 1484 | 0.02893333 | 0.08226667 | 0.29953333 | 0.5892 |
| KOMO | 1964 | 0.03166667 | 0.1022 | 0.2362 | 0.63 |
| KOMO | 2321 | 0.04006667 | 0.13546667 | 0.2222 | 0.6022 |
| KOMO | 2323 | 0.08526667 | 0.10286667 | 0.14026667 | 0.67173333 |
| KOMO | 2334 | 0.00913333 | 0.08426667 | 0.1342 | 0.77246667 |
| WHIP | 1355 | 0.0062 | 0.05526667 | 0.4162 | 0.52246667 |
| WHIP | 1395 | 0.00873333 | 0.09993333 | 0.4982 | 0.39313333 |
| WHIP | 1407 | 0.00713333 | 0.12913333 | 0.30046667 | 0.56313333 |
| WHIP | 1409 | 0.00566667 | 0.05026667 | 0.72593333 | 0.218 |
| WHIP | 1518 | 0.0056 | 0.10146667 | 0.45786667 | 0.435 |
| SPOO | 1530 | 0.05693333 | 0.25666667 | 0.36106667 | 0.3252 |
| SPOO | 1582 | 0.07346667 | 0.11826667 | 0.38393333 | 0.42473333 |
| SPOO | 1876 | 0.0106 | 0.12953333 | 0.50726667 | 0.35246667 |
| SPOO | 1877 | 0.0136 | 0.16693333 | 0.37186667 | 0.44753333 |
| SPOO | 2337 | 0.00593333 | 0.0468 | 0.2268 | 0.7206 |
| BICH | 1943 | 0.0758 | 0.0702 | 0.35546667 | 0.4986 |
| BICH | 1954 | 0.14973333 | 0.05386667 | 0.31746667 | 0.47873333 |
| BICH | 933 | 0.03653333 | 0.1844 | 0.31173333 | 0.46746667 |
| BICH | 974 | 0.07046667 | 0.0902 | 0.29946667 | 0.53993333 |
| KEES | 1501 | 0.03973333 | 0.03486667 | 0.5276 | 0.39786667 |
| KEES | 1589 | 0.00533333 | 0.03853333 | 0.44706667 | 0.5092 |
| KEES | 1818 | 0.02126667 | 0.0422 | 0.4594 | 0.47733333 |
| KEES | 1819 | 0.00526667 | 0.0386 | 0.54426667 | 0.41153333 |
| KEES | 2072 | 0.0064 | 0.06153333 | 0.4162 | 0.51586667 |
| MNTY | 1539 | 0.01293333 | 0.2696 | 0.13173333 | 0.5856 |
| MNTY | 1732 | 0.0262 | 0.15633333 | 0.1496 | 0.66773333 |
| MNTY | 2145 | 0.01133333 | 0.20213333 | 0.35033333 | 0.4362 |
| MNTY | 2149 | 0.01066667 | 0.06813333 | 0.57466667 | 0.34666667 |
| NELK | 2216 | 0.05673333 | 0.1076 | 0.30873333 | 0.52693333 |
| NELK | 2239 | 0.18626667 | 0.03333333 | 0.4914 | 0.289 |
| NELK | 2240 | 0.02666667 | 0.1904 | 0.44286667 | 0.34013333 |
| NELK | 2281 | 0.012 | 0.0752 | 0.10806667 | 0.80493333 |
| NELK | 2295 | 0.24066667 | 0.04506667 | 0.29186667 | 0.42233333 |
| KUVZ | 1482 | 0.0566 | 0.0156 | 0.52573333 | 0.4018 |
| KUVZ | 1551 | 0.18713333 | 0.02206667 | 0.41506667 | 0.3758 |
| KUVZ | 1672 | 0.07186667 | 0.05426667 | 0.20386667 | 0.66993333 |
| KUVZ | 1913 | 0.02453333 | 0.06113333 | 0.34526667 | 0.56926667 |
| KUVZ | 1994 | 0.04446667 | 0.06193333 | 0.40193333 | 0.49186667 |
| DANE | 1574 | 0.01126667 | 0.086 | 0.17386667 | 0.72873333 |
| DANE | 1575 | 0.1096 | 0.12853333 | 0.19233333 | 0.5696 |
| DANE | 1580 | 0.0112 | 0.0698 | 0.21413333 | 0.705 |
| DANE | 1700 | 0.00773333 | 0.06426667 | 0.41106667 | 0.51706667 |
| DANE | 1748 | 0.19526667 | 0.07813333 | 0.20826667 | 0.51826667 |
| WSSP | 1955 | 0.00506667 | 0.0726 | 0.3252 | 0.59726667 |
| WSSP | 2139 | 0.01333333 | 0.0658 | 0.24086667 | 0.67993333 |
| WSSP | 2143 | 0.00386667 | 0.07613333 | 0.20346667 | 0.71646667 |
| WSSP | 2195 | 0.0078 | 0.10353333 | 0.29773333 | 0.59093333 |
| WSSP | 2286 | 0.0054 | 0.09933333 | 0.20973333 | 0.68546667 |
| DOBP | 1031 | 0.007 | 0.08406667 | 0.18426667 | 0.7248 |
| DOBP | 1032 | 0.03506667 | 0.09113333 | 0.1938 | 0.68006667 |
| DOBP | 1749 | 0.01766667 | 0.17506667 | 0.19726667 | 0.60986667 |
| DOBP | 2162 | 0.00786667 | 0.08273333 | 0.19973333 | 0.70986667 |
| DOBP | 2245 | 0.0054 | 0.0814 | 0.1972 | 0.71593333 |
| SSNZ | 13352 | 0.00353333 | 0.26246667 | 0.1206 | 0.61326667 |
| SSNZ | 1360 | 0.00353333 | 0.12506667 | 0.1222 | 0.74906667 |
| SSNZ | 1827 | 0.00653333 | 0.092 | 0.19446667 | 0.70726667 |
| SSNZ | 20457 | 0.0084 | 0.07666667 | 0.22706667 | 0.6882 |
| SSNZ | 22647 | 0.00753333 | 0.18713333 | 0.16033333 | 0.64526667 |
| ITGY | 1568 | 0.03193333 | 0.076 | 0.1174 | 0.77473333 |
| ITGY | 1570 | 0.01333333 | 0.0768 | 0.0818 | 0.82806667 |
| ITGY | 1862 | 0.10826667 | 0.06413333 | 0.08133333 | 0.74633333 |
| ITGY | 1881 | 0.042 | 0.06533333 | 0.0726 | 0.82 |
| ITGY | 1882 | 0.172 | 0.05926667 | 0.12893333 | 0.6398 |
| OES | 1984 | 0.0208 | 0.0792 | 0.06466667 | 0.83533333 |
| OES | 2171 | 0.0094 | 0.07693333 | 0.17926667 | 0.7344 |
| OES | 2179 | 0.01033333 | 0.08166667 | 0.1854 | 0.72273333 |
| OES | 1914 | 0.02013333 | 0.12153333 | 0.10093333 | 0.75773333 |
| OES | 2626 | 0.05893333 | 0.0684 | 0.0808 | 0.79173333 |
| AMWS | 2168 | 0.01106667 | 0.07626667 | 0.16186667 | 0.7508 |
| AMWS | 2279 | 0.01213333 | 0.13833333 | 0.1118 | 0.73766667 |
| AMWS | 2327 | 0.06306667 | 0.14373333 | 0.07946667 | 0.71366667 |
| AMWS | 987 | 0.0132 | 0.09766667 | 0.17166667 | 0.71766667 |

TABLE 19A-continued

| | Canid ID | k = 4, 15 Run Average | | | |
|---|---|---|---|---|---|
| Canid Population[a] | No. | Pop1 | Pop2 | Pop3 | Pop4 |
| AMWS | 988 | 0.0164 | 0.17813333 | 0.12913333 | 0.6764 |
| MSNZ | 1587 | 0.00553333 | 0.15366667 | 0.11553333 | 0.72533333 |
| MSNZ | 1756 | 0.00593333 | 0.07446667 | 0.16326667 | 0.75586667 |
| MSNZ | 1851 | 0.00406667 | 0.09013333 | 0.1284 | 0.77753333 |
| MSNZ | 2034 | 0.026 | 0.2376 | 0.1144 | 0.62193333 |
| MSNZ | 2613 | 0.00513333 | 0.12266667 | 0.12486667 | 0.74726667 |
| AUST | 1387 | 0.04046667 | 0.11066667 | 0.20053333 | 0.6482 |
| AUST | 1531 | 0.0178 | 0.139 | 0.06606667 | 0.77713333 |
| AUST | 1564 | 0.00726667 | 0.0902 | 0.0582 | 0.8444 |
| AUST | 1870 | 0.0388 | 0.1046 | 0.13213333 | 0.7246 |
| AUST | 1871 | 0.00673333 | 0.0902 | 0.06326667 | 0.84006667 |
| ECKR | 1376 | 0.004 | 0.11126667 | 0.0808 | 0.8038 |
| ECKR | 1377 | 0.00406667 | 0.08373333 | 0.14606667 | 0.76593333 |
| ECKR | 1400 | 0.0034 | 0.06993333 | 0.26133333 | 0.66546667 |
| ECKR | 1404 | 0.0034 | 0.09186667 | 0.23986667 | 0.66486667 |
| ECKR | 1511 | 0.0068 | 0.08413333 | 0.18326667 | 0.72573333 |
| IRSE | 1540 | 0.00333333 | 0.0736 | 0.08586667 | 0.83726667 |
| IRSE | 1617 | 0.0038 | 0.072 | 0.07486667 | 0.8494 |
| IRSE | 1896 | 0.00906667 | 0.07533333 | 0.11866667 | 0.79666667 |
| IRSE | 2084 | 0.00406667 | 0.06606667 | 0.2228 | 0.70706667 |
| IRSE | 2085 | 0.00326667 | 0.0842 | 0.0818 | 0.831 |
| WHWT | 1388 | 0.0142 | 0.0704 | 0.05473333 | 0.86053333 |
| WHWT | 1420 | 0.0452 | 0.0842 | 0.08166667 | 0.7888 |
| WHWT | 1992 | 0.0108 | 0.08613333 | 0.07613333 | 0.82693333 |
| WHWT | 2100 | 0.01053333 | 0.0824 | 0.04333333 | 0.86353333 |
| WHWT | 2128 | 0.0158 | 0.0728 | 0.03166667 | 0.87973333 |
| PNTR | 1382 | 0.00826667 | 0.07166667 | 0.07566667 | 0.8442 |
| PNTR | 1383 | 0.01426667 | 0.07086667 | 0.0714 | 0.84353333 |
| PNTR | 1869 | 0.00726667 | 0.0582 | 0.12293333 | 0.81146667 |
| PNTR | 1938 | 0.0098 | 0.07566667 | 0.15733333 | 0.75693333 |
| PNTR | 1948 | 0.05646667 | 0.0598 | 0.0958 | 0.78773333 |
| BASS | 1341 | 0.02966667 | 0.1016 | 0.04426667 | 0.82446667 |
| BASS | 1342 | 0.01053333 | 0.0758 | 0.09866667 | 0.81473333 |
| BASS | 1506 | 0.0078 | 0.08493333 | 0.0752 | 0.8318 |
| BASS | 1917 | 0.00926667 | 0.10106667 | 0.04406667 | 0.84593333 |
| CKCS | 1513 | 0.0408 | 0.0656 | 0.12133333 | 0.77233333 |
| CKCS | 1639 | 0.00753333 | 0.07806667 | 0.12053333 | 0.794 |
| CKCS | 1640 | 0.00806667 | 0.0998 | 0.1152 | 0.77686667 |
| CKCS | 1642 | 0.0048 | 0.07466667 | 0.13413333 | 0.78653333 |
| CKCS | 2054 | 0.00553333 | 0.07133333 | 0.1202 | 0.80293333 |
| GSNZ | 1868 | 0.27746667 | 0.06873333 | 0.06233333 | 0.5912 |
| GSNZ | 22739 | 0.1848 | 0.06566667 | 0.06806667 | 0.68133333 |
| GSNZ | 27093 | 0.05206667 | 0.08053333 | 0.06046667 | 0.807 |
| GSNZ | 27106 | 0.0098 | 0.10226667 | 0.0224 | 0.8656 |
| GSNZ | 33390 | 0.0082 | 0.09093333 | 0.0874 | 0.81346667 |
| PHAR | 1292 | 0.12533333 | 0.05726667 | 0.0088 | 0.80886667 |
| PHAR | 1947 | 0.1386 | 0.05446667 | 0.01913333 | 0.78773333 |
| PHAR | 1962 | 0.13706667 | 0.0674 | 0.06313333 | 0.7326 |
| PHAR | 1963 | 0.10473333 | 0.0708 | 0.012 | 0.81246667 |
| GOLD | 591 | 0.00453333 | 0.15633333 | 0.02266667 | 0.8164 |
| GOLD | 592 | 0.02186667 | 0.2448 | 0.0112 | 0.72213333 |
| GOLD | 593 | 0.00693333 | 0.1734 | 0.01473333 | 0.80526667 |
| GOLD | 603 | 0.0058 | 0.148 | 0.009 | 0.83726667 |
| GOLD | 604 | 0.00386667 | 0.19653333 | 0.03653333 | 0.76313333 |
| BEAG | 1323 | 0.012 | 0.169 | 0.01126667 | 0.80753333 |
| BEAG | 1324 | 0.01733333 | 0.09226667 | 0.126 | 0.7644 |
| BEAG | 1327 | 0.00813333 | 0.2708 | 0.0204 | 0.70093333 |
| BEAG | 994 | 0.029 | 0.25213333 | 0.06993333 | 0.64906667 |
| BEAG | 995 | 0.01573333 | 0.0918 | 0.06013333 | 0.83213333 |
| BLDH | 1186 | 0.0088 | 0.224 | 0.0264667 | 0.7406 |
| BLDH | 1223 | 0.0126 | 0.15126667 | 0.01466667 | 0.82126667 |
| BLDH | 1410 | 0.0056 | 0.3068 | 0.00726667 | 0.68026667 |
| BLDH | 1942 | 0.00893333 | 0.17273333 | 0.00906667 | 0.80933333 |
| BLDH | 1957 | 0.00693333 | 0.16 | 0.01146667 | 0.82153333 |
| AIRT | 1603 | 0.03993333 | 0.15466667 | 0.11033333 | 0.69526667 |
| AIRT | 1604 | 0.00613333 | 0.08966667 | 0.12693333 | 0.7772 |
| AIRT | 1788 | 0.00466667 | 0.20253333 | 0.09266667 | 0.70013333 |
| AIRT | 1875 | 0.01793333 | 0.09733333 | 0.13313333 | 0.7516 |
| ACKR | 1035 | 0.0102 | 0.09006667 | 0.08406667 | 0.8156 |
| ACKR | 2261 | 0.02313333 | 0.0972 | 0.1014 | 0.77833333 |
| ACKR | 2310 | 0.0038 | 0.09926667 | 0.026 | 0.87086667 |
| ACKR | 1956 | 0.00913333 | 0.1278 | 0.02146667 | 0.84173333 |
| ACKR | 2260 | 0.00533333 | 0.10193333 | 0.03026667 | 0.86233333 |
| AHRT | 1120 | 0.00986667 | 0.12326667 | 0.0524 | 0.8144 |
| AHRT | 1121 | 0.0104 | 0.18726667 | 0.04926667 | 0.753 |

TABLE 19A-continued

| | Canid ID | k = 4, 15 Run Average | | | |
|---|---|---|---|---|---|
| Canid Population[a] | No. | Pop1 | Pop2 | Pop3 | Pop4 |
| AHRT | 1122 | 0.00853333 | 0.1532 | 0.089 | 0.74886667 |
| AHRT | 1123 | 0.00866667 | 0.14433333 | 0.07606667 | 0.77093333 |
| AHRT | 1124 | 0.0076 | 0.1374 | 0.05166667 | 0.80346667 |
| CHBR | 1546 | 0.01113333 | 0.13993333 | 0.05573333 | 0.7932 |
| CHBR | 1549 | 0.06426667 | 0.33173333 | 0.01326667 | 0.5908 |
| CHBR | 1813 | 0.00446667 | 0.17893333 | 0.02786667 | 0.7888 |
| CHBR | 2091 | 0.0086 | 0.1008 | 0.038 | 0.85266667 |
| CHBR | 888 | 0.00506667 | 0.11486667 | 0.02473333 | 0.8552 |
| CAIR | 1405 | 0.00846667 | 0.277 | 0.0828 | 0.6316 |
| CAIR | 2096 | 0.0146 | 0.07973333 | 0.03353333 | 0.87213333 |
| CAIR | 2113 | 0.01413333 | 0.1012 | 0.10746667 | 0.77733333 |
| CAIR | 2125 | 0.0062 | 0.0752 | 0.07646667 | 0.8422 |
| CAIR | 2131 | 0.0292 | 0.08106667 | 0.0632 | 0.82666667 |
| PTWD | P142 | 0.0074 | 0.1588 | 0.11633333 | 0.71733333 |
| PTWD | P1 | 0.00453333 | 0.192 | 0.1194 | 0.68413333 |
| PTWD | P238 | 0.01333333 | 0.1686 | 0.17253333 | 0.64566667 |
| PTWD | P25 | 0.00413333 | 0.07453333 | 0.1428 | 0.77853333 |
| PTWD | P67 | 0.00613333 | 0.07766667 | 0.1434 | 0.77266667 |
| GSHP | 1628 | 0.00506667 | 0.13306667 | 0.08306667 | 0.77886667 |
| GSHP | 1708 | 0.02013333 | 0.08246667 | 0.20713333 | 0.69033333 |
| GSHP | 1710 | 0.02533333 | 0.08533333 | 0.072 | 0.8172 |
| GSHP | 1833 | 0.00806667 | 0.44793333 | 0.03073333 | 0.5134 |
| GSHP | 1892 | 0.01533333 | 0.1122 | 0.07586667 | 0.79673333 |
| BORD | 1648 | 0.11253333 | 0.07173333 | 0.0404 | 0.77573333 |
| BORD | 1828 | 0.01326667 | 0.07473333 | 0.09166667 | 0.82006667 |
| BORD | 1829 | 0.00546667 | 0.24266667 | 0.13626667 | 0.61566667 |
| BORD | 2002 | 0.01993333 | 0.10706667 | 0.12306667 | 0.75 |
| BORD | 2003 | 0.03286667 | 0.08433333 | 0.11186667 | 0.77086667 |
| BEDT | 1422 | 0.00793333 | 0.32966667 | 0.12893333 | 0.5334 |
| BEDT | 1423 | 0.00626667 | 0.1544 | 0.15853333 | 0.68086667 |
| BEDT | 1424 | 0.01353333 | 0.12806667 | 0.2118 | 0.64666667 |
| BEDT | 1426 | 0.0142 | 0.2006 | 0.16206667 | 0.62333333 |
| CLSP | 1008 | 0.00746667 | 0.3506 | 0.06153333 | 0.5802 |
| CLSP | 1009 | 0.00386667 | 0.316 | 0.075 | 0.60473333 |
| CLSP | 1802 | 0.00646667 | 0.32126667 | 0.07473333 | 0.59733333 |
| CLSP | 2312 | 0.00413333 | 0.3918 | 0.06026667 | 0.5438 |
| CLSP | 2314 | 0.00473333 | 0.395 | 0.06026667 | 0.53973333 |
| IBIZ | 1147 | 0.0094 | 0.09326667 | 0.0498 | 0.84746667 |
| IBIZ | 1148 | 0.0076 | 0.2762 | 0.12373333 | 0.59233333 |
| IBIZ | 1162 | 0.00813333 | 0.07513333 | 0.0816 | 0.8354 |
| IBIZ | 1172 | 0.02393333 | 0.09233333 | 0.1424 | 0.7416 |
| IBIZ | 1280 | 0.027 | 0.20926667 | 0.20173333 | 0.56186667 |
| RHOD | 1444 | 0.0056 | 0.13373333 | 0.17626667 | 0.68426667 |
| RHOD | 1454 | 0.02113333 | 0.17686667 | 0.17033333 | 0.63213333 |
| RHOD | 1505 | 0.01006667 | 0.11066667 | 0.0728 | 0.80653333 |
| RHOD | 1592 | 0.00833333 | 0.4782 | 0.06833333 | 0.44506667 |
| RHOD | 1609 | 0.00606667 | 0.1752 | 0.2602 | 0.55853333 |
| DACH | 1051 | 0.01053333 | 0.25333333 | 0.23673333 | 0.49933333 |
| DACH | 1052 | 0.00893333 | 0.2756 | 0.21553333 | 0.49993333 |
| DACH | 1053 | 0.0174 | 0.33433333 | 0.12966667 | 0.5186 |
| DACH | 1054 | 0.02753333 | 0.43573333 | 0.13406667 | 0.40273333 |
| DACH | 1055 | 0.00966667 | 0.27553333 | 0.24213333 | 0.47253333 |
| AUSS | 1336 | 0.19213333 | 0.16606667 | 0.19266667 | 0.449 |
| AUSS | 1337 | 0.01626667 | 0.218 | 0.16453333 | 0.60106667 |
| AUSS | 1500 | 0.00893333 | 0.06726667 | 0.2208 | 0.70266667 |
| AUSS | 1521 | 0.11106667 | 0.43073333 | 0.18213333 | 0.27613333 |
| AUSS | 1683 | 0.01366667 | 0.2222 | 0.091 | 0.67313333 |
| CHIH | 1202 | 0.0064 | 0.22773333 | 0.1 | 0.66586667 |
| CHIH | 1203 | 0.0148 | 0.09106667 | 0.30626667 | 0.58766667 |
| CHIH | 1204 | 0.01226667 | 0.12713333 | 0.14806667 | 0.71253333 |
| CHIH | 1205 | 0.0992 | 0.32273333 | 0.15366667 | 0.42466667 |
| CHIH | 1206 | 0.0062 | 0.37573333 | 0.09806667 | 0.51986667 |
| KERY | 13878 | 0.00706667 | 0.22393333 | 0.15313333 | 0.61586667 |
| KERY | 1483 | 0.00713333 | 0.2578 | 0.16 | 0.57506667 |
| KERY | 1579 | 0.0126 | 0.10493333 | 0.18953333 | 0.69286667 |
| KERY | 2014 | 0.0036 | 0.342 | 0.07906667 | 0.5752 |
| KERY | 24255 | 0.00853333 | 0.35613333 | 0.15386667 | 0.48133333 |
| SCHP | 1386 | 0.0076 | 0.19293333 | 0.036 | 0.76353333 |
| SCHP | 1471 | 0.00766667 | 0.20733333 | 0.02273333 | 0.76213333 |
| SCHP | 1814 | 0.01046667 | 0.289 | 0.0824 | 0.6182 |
| SCHP | 1852 | 0.0162 | 0.13586667 | 0.15466667 | 0.69326667 |
| IRTR | 2152 | 0.01113333 | 0.14993333 | 0.093 | 0.746 |
| IRTR | 2189 | 0.01146667 | 0.36666667 | 0.08746667 | 0.53433333 |
| IRTR | 2238 | 0.0052 | 0.36626667 | 0.043 | 0.58546667 |
| IRTR | 2242 | 0.00893333 | 0.27573333 | 0.06926667 | 0.64613333 |

TABLE 19A-continued

|  |  | k = 4, 15 Run Average | | | |
| --- | --- | --- | --- | --- | --- |
| Canid Population[a] | Canid ID No. | Pop1 | Pop2 | Pop3 | Pop4 |
| FCR | 1188 | 0.0062 | 0.22606667 | 0.05746667 | 0.7102 |
| FCR | 2020 | 0.00506667 | 0.1566 | 0.08913333 | 0.749 |
| FCR | 2042 | 0.0048 | 0.23086667 | 0.0638 | 0.70053333 |
| FCR | 2044 | 0.00613333 | 0.17806667 | 0.16073333 | 0.65506667 |
| FCR | 2259 | 0.0036 | 0.24293333 | 0.048 | 0.70526667 |
| SCWT | 1624 | 0.0506 | 0.4248 | 0.08933333 | 0.4352 |
| SCWT | 1770 | 0.00433333 | 0.2824 | 0.31153333 | 0.40166667 |
| SCWT | 2250 | 0.00513333 | 0.22033333 | 0.04646667 | 0.7282 |
| SCWT | 2301 | 0.0162 | 0.36513333 | 0.03973333 | 0.57913333 |
| POM | 1190 | 0.09806667 | 0.35386667 | 0.32793333 | 0.22 |
| POM | 1191 | 0.00926667 | 0.7472 | 0.04853333 | 0.19473333 |
| POM | 1210 | 0.04093333 | 0.3494 | 0.1288 | 0.48053333 |
| POM | 1238 | 0.00613333 | 0.16306667 | 0.26906667 | 0.56173333 |
| POM | 1239 | 0.1202 | 0.08513333 | 0.2394 | 0.555 |
| LAB | 1310 | 0.11153333 | 0.54806667 | 0.0612 | 0.2794 |
| LAB | 1465 | 0.01346667 | 0.33846667 | 0.05966667 | 0.5884 |
| LAB | 1468 | 0.02113333 | 0.40553333 | 0.09626667 | 0.477 |
| LAB | 1754 | 0.01206667 | 0.6368 | 0.01 | 0.34093333 |
| LAB | 1830 | 0.00533333 | 0.5134 | 0.14593333 | 0.33526667 |
| PRES | 1082 | 0.00793333 | 0.73346667 | 0.0294 | 0.22913333 |
| PRES | 1096 | 0.00493333 | 0.7488 | 0.05413333 | 0.19193333 |
| PRES | 1115 | 0.00993333 | 0.64406667 | 0.086 | 0.2604 |
| PRES | 1127 | 0.10286667 | 0.85446667 | 0.01946667 | 0.0234 |
| PRES | 1095 | 0.05353333 | 0.82886667 | 0.03246667 | 0.08533333 |
| ROTT | 1014 | 0.01153333 | 0.72453333 | 0.13553333 | 0.12833333 |
| ROTT | 1028 | 0.00553333 | 0.712 | 0.13746667 | 0.1448 |
| ROTT | 1029 | 0.0042 | 0.8398 | 0.05386667 | 0.10193333 |
| ROTT | 1033 | 0.006 | 0.85826667 | 0.04853333 | 0.08746667 |
| ROTT | 1034 | 0.00453333 | 0.85426667 | 0.11393333 | 0.02726667 |
| BULM | 1105 | 0.0056 | 0.94446667 | 0.01333333 | 0.03626667 |
| BULM | 1106 | 0.00486667 | 0.61486667 | 0.0896 | 0.2908 |
| BULM | 1107 | 0.01853333 | 0.90133333 | 0.026 | 0.05413333 |
| BULM | 1108 | 0.00653333 | 0.93873333 | 0.02386667 | 0.03073333 |
| BULM | 1109 | 0.00513333 | 0.96613333 | 0.00746667 | 0.0212 |
| NEWF | 271 | 0.0132 | 0.866 | 0.0532 | 0.0676 |
| NEWF | 274 | 0.00526667 | 0.94806667 | 0.00966667 | 0.03706667 |
| NEWF | 275 | 0.00733333 | 0.97226667 | 0.0052 | 0.01533333 |
| NEWF | 277 | 0.00586667 | 0.97893333 | 0.00673333 | 0.00833333 |
| NEWF | 278 | 0.06706667 | 0.8476 | 0.01493333 | 0.07053333 |
| GSD | 1666 | 0.00613333 | 0.88413333 | 0.08013333 | 0.02946667 |
| GSD | 1776 | 0.00306667 | 0.89873333 | 0.07173333 | 0.0264 |
| GSD | 2011 | 0.00773333 | 0.853 | 0.0962 | 0.04313333 |
| GSD | 2060 | 0.00613333 | 0.81526667 | 0.10273333 | 0.07626667 |
| GSD | 2086 | 0.00573333 | 0.84086667 | 0.10013333 | 0.05313333 |
| FBUL | 1507 | 0.0104 | 0.96366667 | 0.0158 | 0.00986667 |
| FBUL | 1508 | 0.00626667 | 0.96013333 | 0.01466667 | 0.0188 |
| FBUL | 1509 | 0.00493333 | 0.97453333 | 0.0106 | 0.01006667 |
| FBUL | 2671 | 0.01693333 | 0.91053333 | 0.01173333 | 0.0608 |
| MBLT | 1915 | 0.00553333 | 0.9154 | 0.008 | 0.071 |
| MBLT | 2253 | 0.0068 | 0.89166667 | 0.045 | 0.0564 |
| MBLT | 2254 | 0.036 | 0.9132 | 0.03073333 | 0.02006667 |
| MBLT | 2255 | 0.0098 | 0.90326667 | 0.00946667 | 0.0772 |
| MBLT | 2256 | 0.0062 | 0.97946667 | 0.00573333 | 0.0086 |
| BULD | 1193 | 0.01906667 | 0.95466667 | 0.01473333 | 0.01153333 |
| BULD | 1194 | 0.00513333 | 0.9824 | 0.00626667 | 0.00593333 |
| BULD | 1195 | 0.0036 | 0.98433333 | 0.00473333 | 0.00726667 |
| BULD | 1197 | 0.0052 | 0.92026667 | 0.05506667 | 0.0194 |
| BULD | 1198 | 0.00553333 | 0.96853333 | 0.0138 | 0.01206667 |
| BOX | 1176 | 0.00313333 | 0.91446667 | 0.07333333 | 0.009 |
| BOX | 1177 | 0.00366667 | 0.92693333 | 0.05286667 | 0.01653333 |
| BOX | 1178 | 0.00446667 | 0.93326667 | 0.05726667 | 0.00513333 |
| BOX | 1179 | 0.00233333 | 0.92526667 | 0.06886667 | 0.0036 |
| BOX | 1304 | 0.00266667 | 0.9162 | 0.07473333 | 0.00593333 |
| MAST | 1015 | 0.004 | 0.9386 | 0.0162 | 0.04126667 |
| MAST | 1016 | 0.009 | 0.90766667 | 0.06406667 | 0.01933333 |
| MAST | 1017 | 0.0046 | 0.9216 | 0.0498 | 0.024 |
| MAST | 1066 | 0.0158 | 0.94853333 | 0.018 | 0.01753333 |
| MAST | 991 | 0.01866667 | 0.95213333 | 0.0108 | 0.0186 |
| BMD | 941 | 0.00406667 | 0.76213333 | 0.21013333 | 0.02386667 |
| BMD | 943 | 0.0094 | 0.58306667 | 0.2496 | 0.1578 |
| BMD | 968 | 0.0062 | 0.74973333 | 0.21286667 | 0.03113333 |
| BMD | 1763 | 0.0046 | 0.74813333 | 0.20066667 | 0.04646667 |
| BMD | 969 | 0.00373333 | 0.69866667 | 0.2714 | 0.02653333 |
| GSMD | 1547 | 0.0066 | 0.41546667 | 0.36546667 | 0.21266667 |
| GSMD | 1659 | 0.0052 | 0.5908 | 0.34013333 | 0.0638 |

TABLE 19A-continued

| Canid Population[a] | Canid ID No. | k = 4, 15 Run Average | | | |
|---|---|---|---|---|---|
| | | Pop1 | Pop2 | Pop3 | Pop4 |
| GSMD | 1660 | 0.013 | 0.41086667 | 0.435 | 0.14126667 |
| GSMD | 1662 | 0.04386667 | 0.51266667 | 0.304 | 0.13973333 |
| GSMD | 1663 | 0.00653333 | 0.50973333 | 0.42086667 | 0.063 |

TABLE 19B

| Canid Population[a] | Canid ID No. | k = 3, 15 Run Average | | |
|---|---|---|---|---|
| | | Pop1 | Pop2 | Pop3 |
| SHIB | 1769 | 0.989667 | 0.004667 | 0.005667 |
| SHIB | 1854 | 0.982933 | 0.006867 | 0.0102 |
| SHIB | 1856 | 0.9584 | 0.016067 | 0.025667 |
| SHIB | 1860 | 0.9852 | 0.0066 | 0.008267 |
| SHIB | 1981 | 0.983733 | 0.0078 | 0.008133 |
| CHOW | 1633 | 0.985533 | 0.008133 | 0.0064 |
| CHOW | 1835 | 0.988133 | 0.006133 | 0.0058 |
| CHOW | 1837 | 0.982067 | 0.0094 | 0.0084 |
| CHOW | 1838 | 0.9884 | 0.0056 | 0.006 |
| CHOW | 1839 | 0.978667 | 0.0116 | 0.009867 |
| AKIT | 1130 | 0.9576 | 0.007467 | 0.035 |
| AKIT | 1131 | 0.988933 | 0.0052 | 0.005733 |
| AKIT | 1132 | 0.989133 | 0.005867 | 0.004933 |
| AKIT | 1133 | 0.988133 | 0.0072 | 0.004667 |
| AKIT | 1134 | 0.991 | 0.003667 | 0.005467 |
| AMAL | 1629 | 0.8604 | 0.083867 | 0.055733 |
| AMAL | 1779 | 0.7986 | 0.020667 | 0.1806 |
| AMAL | 1845 | 0.9078 | 0.047 | 0.045067 |
| AMAL | 2132 | 0.920333 | 0.0362 | 0.043533 |
| AMAL | 2214 | 0.908333 | 0.0218 | 0.069733 |
| BSJI | 1338 | 0.762067 | 0.122333 | 0.1156 |
| BSJI | 1339 | 0.973267 | 0.018 | 0.0088 |
| BSJI | 1645 | 0.977733 | 0.012933 | 0.009467 |
| BSJI | 1675 | 0.945333 | 0.0468 | 0.007933 |
| BSJI | 1717 | 0.972533 | 0.013667 | 0.013867 |
| SHAR | 1573 | 0.9602 | 0.028267 | 0.0116 |
| SHAR | 1593 | 0.845667 | 0.138 | 0.016533 |
| SHAR | 1619 | 0.870933 | 0.1136 | 0.015467 |
| SHAR | 1998 | 0.7902 | 0.031533 | 0.178267 |
| SHAR | 1999 | 0.957 | 0.029067 | 0.014 |
| HUSK | 1469 | 0.915533 | 0.037133 | 0.0474 |
| HUSK | 1883 | 0.907867 | 0.0104 | 0.0818 |
| HUSK | 2115 | 0.748733 | 0.013533 | 0.237867 |
| HUSK | 2117 | 0.632333 | 0.013333 | 0.3544 |
| HUSK | 2118 | 0.905133 | 0.042133 | 0.052533 |
| AFGH | 1812 | 0.601933 | 0.0432 | 0.3548 |
| AFGH | 1939 | 0.6604 | 0.084067 | 0.255467 |
| AFGH | 2264 | 0.6198 | 0.122933 | 0.2574 |
| AFGH | 1936 | 0.785067 | 0.0934 | 0.121467 |
| AFGH | 1937 | 0.717867 | 0.070933 | 0.2112 |
| SALU | 1491 | 0.4102 | 0.017667 | 0.5722 |
| SALU | 1535 | 0.542067 | 0.007067 | 0.450867 |
| SALU | 1607 | 0.500067 | 0.020533 | 0.479467 |
| SALU | 1873 | 0.292667 | 0.031667 | 0.675733 |
| SALU | 2610 | 0.4434 | 0.055533 | 0.501 |
| TIBT | 1466 | 0.479867 | 0.027867 | 0.492333 |
| TIBT | 1562 | 0.355667 | 0.0502 | 0.594 |
| TIBT | 1707 | 0.397133 | 0.240333 | 0.362333 |
| TIBT | 26078 | 0.431867 | 0.0466 | 0.521533 |
| TIBT | 28086 | 0.163867 | 0.103733 | 0.733067 |
| LHSA | 1524 | 0.558933 | 0.034333 | 0.4066 |
| LHSA | 1525 | 0.5262 | 0.023 | 0.451 |
| LHSA | 1526 | 0.463467 | 0.020533 | 0.5162 |
| LHSA | 1528 | 0.3624 | 0.0748 | 0.562667 |
| LHSA | 2074 | 0.705 | 0.023 | 0.272067 |
| SAMO | 1375 | 0.271267 | 0.011733 | 0.716867 |
| SAMO | 1532 | 0.553067 | 0.0086 | 0.438267 |
| SAMO | 1560 | 0.5902 | 0.0374 | 0.372533 |
| SAMO | 169 | 0.436867 | 0.016867 | 0.546267 |
| SAMO | 239 | 0.458933 | 0.038267 | 0.502867 |
| PEKE | 1143 | 0.696267 | 0.013267 | 0.2904 |
| PEKE | 1145 | 0.445133 | 0.011533 | 0.543333 |
| PEKE | 1211 | 0.457267 | 0.010667 | 0.532133 |
| PEKE | 1212 | 0.380333 | 0.2828 | 0.336733 |
| PEKE | 1213 | 0.61 | 0.012933 | 0.377067 |
| SHIH | 1393 | 0.390067 | 0.1362 | 0.473867 |
| SHIH | 1783 | 0.3624 | 0.011267 | 0.626333 |
| SHIH | 2068 | 0.379533 | 0.009533 | 0.610867 |
| SHIH | 2859 | 0.4456 | 0.0228 | 0.531667 |
| SHIH | 2860 | 0.5422 | 0.0238 | 0.433933 |
| IWOF | 1581 | 0.0226 | 0.2552 | 0.7222 |
| IWOF | 1761 | 0.0088 | 0.020333 | 0.970733 |
| IWOF | 1792 | 0.026267 | 0.069467 | 0.904467 |
| IWOF | 1906 | 0.052267 | 0.033933 | 0.914 |
| IWOF | 1993 | 0.007267 | 0.026733 | 0.966067 |
| STBD | 1075 | 0.0464 | 0.139933 | 0.813733 |
| STBD | 1714 | 0.059 | 0.030333 | 0.910733 |
| STBD | 1750 | 0.047733 | 0.2466 | 0.705533 |
| STBD | 2403 | 0.013333 | 0.0294 | 0.9572 |
| STBD | 2404 | 0.0206 | 0.376867 | 0.602533 |
| GREY | 2477 | 0.1562 | 0.0356 | 0.808267 |
| GREY | 2478 | 0.017867 | 0.018267 | 0.963733 |
| GREY | 2479 | 0.0112 | 0.063333 | 0.925333 |
| GREY | 2480 | 0.059467 | 0.011467 | 0.929067 |
| GREY | 2481 | 0.009133 | 0.02 | 0.970867 |
| BELS | 1351 | 0.0132 | 0.007333 | 0.979467 |
| BELS | 2111 | 0.0744 | 0.013133 | 0.912267 |
| BELS | 2153 | 0.0058 | 0.006067 | 0.988 |
| BELS | 2209 | 0.031467 | 0.005733 | 0.962933 |
| BELS | 2210 | 0.034733 | 0.026267 | 0.938867 |
| TURV | 1622 | 0.009067 | 0.010133 | 0.980667 |
| TURV | 2194 | 0.013067 | 0.057467 | 0.929333 |
| TURV | 2200 | 0.020267 | 0.010467 | 0.969133 |
| TURV | 2222 | 0.0056 | 0.009133 | 0.985133 |
| BORZ | 1378 | 0.136 | 0.007733 | 0.856333 |
| BORZ | 1401 | 0.114733 | 0.024133 | 0.861133 |
| BORZ | 1808 | 0.1772 | 0.014467 | 0.8084 |
| BORZ | 2268 | 0.063467 | 0.015867 | 0.920867 |
| BORZ | 978 | 0.042 | 0.014733 | 0.9434 |
| COLL | 1692 | 0.011933 | 0.020667 | 0.9674 |
| COLL | 1701 | 0.0218 | 0.011 | 0.967 |
| COLL | 2284 | 0.0116 | 0.021867 | 0.9666 |
| COLL | 373 | 0.008933 | 0.013 | 0.977933 |
| COLL | 379 | 0.0058 | 0.011267 | 0.9828 |
| SSHP | 1379 | 0.032667 | 0.1834 | 0.783933 |
| SSHP | 1523 | 0.050067 | 0.043333 | 0.9064 |
| SSHP | 1824 | 0.016067 | 0.141133 | 0.842867 |
| SSHP | 1921 | 0.0062 | 0.118733 | 0.875 |
| SSHP | 2040 | 0.08 | 0.152 | 0.768133 |
| PUG | 1077 | 0.010667 | 0.008933 | 0.9804 |
| PUG | 1104 | 0.048267 | 0.017733 | 0.933933 |
| PUG | 1183 | 0.121733 | 0.0116 | 0.866667 |
| PUG | 1184 | 0.013467 | 0.011733 | 0.975 |
| PUG | 1192 | 0.009333 | 0.098867 | 0.8916 |
| KOMO | 1484 | 0.035 | 0.041867 | 0.923067 |
| KOMO | 1964 | 0.036133 | 0.055333 | 0.908333 |
| KOMO | 2321 | 0.036 | 0.099533 | 0.8644 |
| KOMO | 2323 | 0.086267 | 0.096333 | 0.817467 |
| KOMO | 2334 | 0.0092 | 0.036467 | 0.9544 |
| WHIP | 1355 | 0.006867 | 0.0162 | 0.9768 |
| WHIP | 1395 | 0.010667 | 0.0362 | 0.953067 |
| WHIP | 1407 | 0.0076 | 0.073267 | 0.9192 |

TABLE 19B-continued

| Canid Population[a] | Canid ID No. | k = 3, 15 Run Average | | |
|---|---|---|---|---|
| | | Pop1 | Pop2 | Pop3 |
| WHIP | 1409 | 0.006333 | 0.014267 | 0.9794 |
| WHIP | 1518 | 0.005933 | 0.039267 | 0.9546 |
| SPOO | 1530 | 0.0676 | 0.185267 | 0.747067 |
| SPOO | 1582 | 0.0744 | 0.064333 | 0.8612 |
| SPOO | 1876 | 0.015 | 0.155 | 0.830067 |
| SPOO | 1877 | 0.018467 | 0.190133 | 0.791333 |
| SPOO | 2337 | 0.006867 | 0.016533 | 0.976667 |
| BICH | 1943 | 0.0654 | 0.019933 | 0.9146 |
| BICH | 1954 | 0.239867 | 0.018 | 0.741933 |
| BICH | 933 | 0.050933 | 0.159467 | 0.789467 |
| BICH | 974 | 0.109533 | 0.092333 | 0.798067 |
| KEES | 1501 | 0.060867 | 0.013067 | 0.925933 |
| KEES | 1589 | 0.006467 | 0.007267 | 0.986267 |
| KEES | 1818 | 0.015467 | 0.027133 | 0.9572 |
| KEES | 1819 | 0.007133 | 0.012733 | 0.980067 |
| KEES | 2072 | 0.008 | 0.0212 | 0.970667 |
| MNTY | 1539 | 0.0138 | 0.264733 | 0.7214 |
| MNTY | 1732 | 0.0298 | 0.1218 | 0.8486 |
| MNTY | 2145 | 0.014333 | 0.155133 | 0.830333 |
| MNTY | 2149 | 0.010533 | 0.014533 | 0.974933 |
| NELK | 2216 | 0.0872 | 0.0802 | 0.832467 |
| NELK | 2239 | 0.214533 | 0.02 | 0.765467 |
| NELK | 2240 | 0.0426 | 0.1888 | 0.768667 |
| NELK | 2281 | 0.0142 | 0.027533 | 0.958333 |
| NELK | 2295 | 0.293 | 0.025867 | 0.681467 |
| KUVZ | 1482 | 0.0854 | 0.0086 | 0.906 |
| KUVZ | 1551 | 0.198533 | 0.008533 | 0.793 |
| KUVZ | 1672 | 0.075467 | 0.032267 | 0.8924 |
| KUVZ | 1913 | 0.033333 | 0.073267 | 0.8936 |
| KUVZ | 1994 | 0.0498 | 0.042467 | 0.907867 |
| DANE | 1574 | 0.016533 | 0.026467 | 0.957 |
| DANE | 1575 | 0.1558 | 0.1312 | 0.713 |
| DANE | 1580 | 0.011 | 0.007067 | 0.982 |
| DANE | 1700 | 0.0088 | 0.016933 | 0.9742 |
| DANE | 1748 | 0.1982 | 0.034533 | 0.767333 |
| WSSP | 1955 | 0.0066 | 0.015867 | 0.977533 |
| WSSP | 2139 | 0.018667 | 0.028867 | 0.952533 |
| WSSP | 2143 | 0.0056 | 0.033333 | 0.961133 |
| WSSP | 2195 | 0.014467 | 0.065667 | 0.920133 |
| WSSP | 2286 | 0.007133 | 0.102133 | 0.890867 |
| DOBP | 1031 | 0.012667 | 0.102067 | 0.8852 |
| DOBP | 1032 | 0.047733 | 0.092733 | 0.859267 |
| DOBP | 1749 | 0.0394 | 0.2362 | 0.724467 |
| DOBP | 2162 | 0.013133 | 0.0862 | 0.9008 |
| DOBP | 2245 | 0.008467 | 0.085933 | 0.9056 |
| SSNZ | 13352 | 0.004733 | 0.290333 | 0.705133 |
| SSNZ | 1360 | 0.004267 | 0.093667 | 0.902133 |
| SSNZ | 1827 | 0.007067 | 0.034467 | 0.958533 |
| SSNZ | 20457 | 0.009267 | 0.021267 | 0.969267 |
| SSNZ | 22647 | 0.0088 | 0.203133 | 0.7878 |
| ITGY | 1568 | 0.022933 | 0.012267 | 0.965067 |
| ITGY | 1570 | 0.019333 | 0.061067 | 0.919533 |
| ITGY | 1862 | 0.1134 | 0.021067 | 0.865533 |
| ITGY | 1881 | 0.0564 | 0.017467 | 0.9262 |
| ITGY | 1882 | 0.1768 | 0.014467 | 0.808667 |
| OES | 1984 | 0.022133 | 0.022067 | 0.955667 |
| OES | 2171 | 0.009 | 0.028867 | 0.962067 |
| OES | 2179 | 0.011267 | 0.022 | 0.966867 |
| OES | 1914 | 0.020467 | 0.0566 | 0.9232 |
| OES | 2626 | 0.062467 | 0.013267 | 0.924333 |
| AMWS | 2168 | 0.012 | 0.020333 | 0.967667 |
| AMWS | 2279 | 0.012 | 0.195533 | 0.792467 |
| AMWS | 2327 | 0.0978 | 0.257667 | 0.6446 |
| AMWS | 987 | 0.018933 | 0.108533 | 0.8722 |
| AMWS | 988 | 0.019667 | 0.155133 | 0.825333 |
| MSNZ | 1587 | 0.0078 | 0.129067 | 0.8634 |
| MSNZ | 1756 | 0.006733 | 0.011 | 0.9824 |
| MSNZ | 1851 | 0.005067 | 0.029733 | 0.9652 |
| MSNZ | 2034 | 0.0352 | 0.1964 | 0.7686 |
| MSNZ | 2613 | 0.0062 | 0.0746 | 0.919333 |
| AUST | 1387 | 0.046333 | 0.052533 | 0.9012 |
| AUST | 1531 | 0.0178 | 0.145467 | 0.836933 |
| AUST | 1564 | 0.008067 | 0.045867 | 0.946 |
| AUST | 1870 | 0.051933 | 0.069333 | 0.878667 |
| AUST | 1871 | 0.008533 | 0.072 | 0.9196 |
| ECKR | 1376 | 0.005467 | 0.0664 | 0.928 |
| ECKR | 1377 | 0.005133 | 0.032267 | 0.962333 |
| ECKR | 1400 | 0.003867 | 0.036667 | 0.9594 |
| ECKR | 1404 | 0.004067 | 0.042933 | 0.952867 |
| ECKR | 1511 | 0.008333 | 0.081333 | 0.910267 |
| IRSE | 1540 | 0.0042 | 0.0116 | 0.984133 |
| IRSE | 1617 | 0.005267 | 0.010867 | 0.9838 |
| IRSE | 1896 | 0.009267 | 0.017133 | 0.9736 |
| IRSE | 2084 | 0.004333 | 0.008133 | 0.9876 |
| IRSE | 2085 | 0.004267 | 0.029467 | 0.966067 |
| WHWT | 1388 | 0.013 | 0.013667 | 0.973533 |
| WHWT | 1420 | 0.037133 | 0.0254 | 0.937267 |
| WHWT | 1992 | 0.0094 | 0.02 | 0.970867 |
| WHWT | 2100 | 0.009933 | 0.033333 | 0.956667 |
| WHWT | 2128 | 0.011533 | 0.009467 | 0.979 |
| PNTR | 1382 | 0.0116 | 0.0096 | 0.978867 |
| PNTR | 1383 | 0.025867 | 0.019933 | 0.9542 |
| PNTR | 1869 | 0.011667 | 0.007867 | 0.980533 |
| PNTR | 1938 | 0.010867 | 0.015533 | 0.973667 |
| PNTR | 1948 | 0.066533 | 0.008533 | 0.925 |
| BASS | 1341 | 0.035333 | 0.0746 | 0.890067 |
| BASS | 1342 | 0.014067 | 0.015467 | 0.970533 |
| BASS | 1506 | 0.008467 | 0.045133 | 0.946533 |
| BASS | 1917 | 0.0118 | 0.065067 | 0.923133 |
| CKCS | 1513 | 0.039067 | 0.011467 | 0.949533 |
| CKCS | 1639 | 0.0096 | 0.034067 | 0.956267 |
| CKCS | 1640 | 0.011467 | 0.1124 | 0.875867 |
| CKCS | 1642 | 0.008133 | 0.017133 | 0.9748 |
| CKCS | 2054 | 0.0076 | 0.014533 | 0.977733 |
| GSNZ | 1868 | 0.2806 | 0.028467 | 0.691 |
| GSNZ | 22739 | 0.187 | 0.026133 | 0.787 |
| GSNZ | 27093 | 0.064533 | 0.027667 | 0.9078 |
| GSNZ | 27106 | 0.0126 | 0.0828 | 0.9048 |
| GSNZ | 33390 | 0.011667 | 0.053533 | 0.9348 |
| PHAR | 1292 | 0.152867 | 0.015267 | 0.831867 |
| PHAR | 1947 | 0.207067 | 0.007933 | 0.785067 |
| PHAR | 1962 | 0.1676 | 0.0442 | 0.788333 |
| PHAR | 1963 | 0.142533 | 0.021667 | 0.8358 |
| GOLD | 591 | 0.006467 | 0.268667 | 0.724933 |
| GOLD | 592 | 0.0284 | 0.465467 | 0.506067 |
| GOLD | 593 | 0.007867 | 0.295733 | 0.696533 |
| GOLD | 603 | 0.0082 | 0.3306 | 0.6614 |
| GOLD | 604 | 0.004533 | 0.283333 | 0.712267 |
| BEAG | 1323 | 0.012467 | 0.292 | 0.695667 |
| BEAG | 1324 | 0.019267 | 0.052133 | 0.928667 |
| BEAG | 1327 | 0.008867 | 0.3602 | 0.630667 |
| BEAG | 994 | 0.0326 | 0.3418 | 0.625467 |
| BEAG | 995 | 0.026333 | 0.1152 | 0.858467 |
| BLDH | 1186 | 0.014133 | 0.626733 | 0.358933 |
| BLDH | 1223 | 0.017133 | 0.404467 | 0.578267 |
| BLDH | 1410 | 0.006467 | 0.772733 | 0.2208 |
| BLDH | 1942 | 0.013 | 0.5678 | 0.419333 |
| BLDH | 1957 | 0.008933 | 0.458133 | 0.532733 |
| AIRT | 1603 | 0.059733 | 0.2394 | 0.701067 |
| AIRT | 1604 | 0.008533 | 0.090133 | 0.901467 |
| AIRT | 1788 | 0.006533 | 0.4282 | 0.5652 |
| AIRT | 1875 | 0.022733 | 0.1192 | 0.857867 |
| ACKR | 1035 | 0.014333 | 0.040733 | 0.944933 |
| ACKR | 2261 | 0.0278 | 0.050867 | 0.921333 |
| ACKR | 2310 | 0.004867 | 0.061133 | 0.9338 |
| ACKR | 1956 | 0.0142 | 0.155667 | 0.830267 |
| ACKR | 2260 | 0.006867 | 0.077 | 0.915867 |
| AHRT | 1120 | 0.016333 | 0.104 | 0.879467 |
| AHRT | 1121 | 0.013733 | 0.185067 | 0.801267 |
| AHRT | 1122 | 0.0096 | 0.190467 | 0.8002 |
| AHRT | 1123 | 0.0118 | 0.097333 | 0.891 |
| AHRT | 1124 | 0.0106 | 0.091933 | 0.8974 |
| CHBR | 1546 | 0.013133 | 0.096333 | 0.890667 |
| CHBR | 1549 | 0.0814 | 0.445533 | 0.473 |
| CHBR | 1813 | 0.0054 | 0.23 | 0.7646 |
| CHBR | 2091 | 0.0118 | 0.073267 | 0.915 |
| CHBR | 888 | 0.0056 | 0.118533 | 0.876 |
| CAIR | 1405 | 0.01 | 0.289333 | 0.7004 |
| CAIR | 2096 | 0.022667 | 0.041733 | 0.935533 |
| CAIR | 2113 | 0.0158 | 0.050867 | 0.933333 |

TABLE 19B-continued

| Canid Population[a] | Canid ID No. | k = 3, 15 Run Average | | |
|---|---|---|---|---|
| | | Pop1 | Pop2 | Pop3 |
| CAIR | 2125 | 0.006333 | 0.0114 | 0.9824 |
| CAIR | 2131 | 0.0202 | 0.027533 | 0.952333 |
| PTWD | P142 | 0.007067 | 0.1418 | 0.8512 |
| PTWD | P1 | 0.005067 | 0.2378 | 0.757 |
| PTWD | P238 | 0.0172 | 0.209333 | 0.773467 |
| PTWD | P25 | 0.005133 | 0.021667 | 0.9732 |
| PTWD | P67 | 0.007067 | 0.023 | 0.97 |
| GSHP | 1628 | 0.006533 | 0.155933 | 0.837533 |
| GSHP | 1708 | 0.042867 | 0.041333 | 0.915867 |
| GSHP | 1710 | 0.0406 | 0.0372 | 0.922133 |
| GSHP | 1833 | 0.012533 | 0.549533 | 0.438133 |
| GSHP | 1892 | 0.0154 | 0.0414 | 0.943267 |
| BORD | 1648 | 0.1348 | 0.036733 | 0.8286 |
| BORD | 1828 | 0.017867 | 0.032733 | 0.949467 |
| BORD | 1829 | 0.006667 | 0.211667 | 0.781733 |
| BORD | 2002 | 0.026467 | 0.061533 | 0.911933 |
| BORD | 2003 | 0.044533 | 0.055467 | 0.9 |
| BEDT | 1422 | 0.009067 | 0.3274 | 0.6634 |
| BEDT | 1423 | 0.007933 | 0.189867 | 0.802333 |
| BEDT | 1424 | 0.017533 | 0.1126 | 0.870133 |
| BEDT | 1426 | 0.014933 | 0.238867 | 0.7462 |
| CLSP | 1008 | 0.01 | 0.7082 | 0.281667 |
| CLSP | 1009 | 0.005333 | 0.637667 | 0.3572 |
| CLSP | 1802 | 0.010467 | 0.666267 | 0.323267 |
| CLSP | 2312 | 0.005 | 0.752 | 0.242867 |
| CLSP | 2314 | 0.006067 | 0.7524 | 0.2416 |
| IBIZ | 1147 | 0.011533 | 0.1148 | 0.8738 |
| IBIZ | 1148 | 0.0164 | 0.235267 | 0.7482 |
| IBIZ | 1162 | 0.013 | 0.055133 | 0.932 |
| IBIZ | 1172 | 0.0232 | 0.1398 | 0.837 |
| IBIZ | 1280 | 0.022333 | 0.175667 | 0.801867 |
| RHOD | 1444 | 0.007267 | 0.143733 | 0.848733 |
| RHOD | 1454 | 0.027467 | 0.127333 | 0.845067 |
| RHOD | 1505 | 0.011 | 0.135467 | 0.853467 |
| RHOD | 1592 | 0.010067 | 0.5242 | 0.4658 |
| RHOD | 1609 | 0.008133 | 0.110267 | 0.881467 |
| DACH | 1051 | 0.0216 | 0.564 | 0.414467 |
| DACH | 1052 | 0.015267 | 0.618867 | 0.365733 |
| DACH | 1053 | 0.015533 | 0.563867 | 0.420667 |
| DACH | 1054 | 0.0254 | 0.728467 | 0.246133 |
| DACH | 1055 | 0.016667 | 0.6114 | 0.3718 |
| AUSS | 1336 | 0.17 | 0.2254 | 0.6046 |
| AUSS | 1337 | 0.016133 | 0.237267 | 0.7464 |
| AUSS | 1500 | 0.012067 | 0.026 | 0.962133 |
| AUSS | 1521 | 0.1014 | 0.3078 | 0.590867 |
| AUSS | 1683 | 0.0128 | 0.210267 | 0.776933 |
| CHIH | 1202 | 0.007267 | 0.219867 | 0.7728 |
| CHIH | 1203 | 0.022 | 0.0794 | 0.898667 |
| CHIH | 1204 | 0.014467 | 0.104733 | 0.880667 |
| CHIH | 1205 | 0.1532 | 0.3324 | 0.514333 |
| CHIH | 1206 | 0.0068 | 0.388867 | 0.6042 |
| KERY | 13878 | 0.007533 | 0.159533 | 0.833067 |
| KERY | 1483 | 0.0064 | 0.175733 | 0.817867 |
| KERY | 1579 | 0.012133 | 0.034067 | 0.953533 |
| KERY | 2014 | 0.004333 | 0.339933 | 0.655933 |
| KERY | 24255 | 0.009733 | 0.294667 | 0.695467 |
| SCHP | 1386 | 0.0092 | 0.0818 | 0.9088 |
| SCHP | 1471 | 0.013867 | 0.077267 | 0.908933 |
| SCHP | 1814 | 0.0104 | 0.090933 | 0.898667 |
| SCHP | 1852 | 0.013067 | 0.013733 | 0.973333 |
| IRTR | 2152 | 0.011533 | 0.1228 | 0.865533 |
| IRTR | 2189 | 0.0128 | 0.413133 | 0.5742 |
| IRTR | 2238 | 0.006667 | 0.4018 | 0.591467 |
| IRTR | 2242 | 0.009667 | 0.282267 | 0.7082 |
| FCR | 1188 | 0.0058 | 0.172933 | 0.821267 |
| FCR | 2020 | 0.006267 | 0.020467 | 0.973267 |
| FCR | 2042 | 0.006067 | 0.123533 | 0.870267 |
| FCR | 2044 | 0.006533 | 0.0468 | 0.946733 |
| FCR | 2259 | 0.004667 | 0.199467 | 0.796 |
| SCWT | 1624 | 0.081533 | 0.640667 | 0.2776 |
| SCWT | 1770 | 0.005933 | 0.3122 | 0.682 |
| SCWT | 2250 | 0.006867 | 0.422133 | 0.571 |
| SCWT | 2301 | 0.021667 | 0.636533 | 0.3418 |
| POM | 1190 | 0.155933 | 0.333533 | 0.5108 |
| POM | 1191 | 0.010667 | 0.731067 | 0.258267 |
| POM | 1210 | 0.050933 | 0.3128 | 0.636333 |
| POM | 1238 | 0.007867 | 0.163933 | 0.827933 |
| POM | 1239 | 0.203467 | 0.0754 | 0.721 |
| LAB | 1310 | 0.119267 | 0.587867 | 0.292733 |
| LAB | 1465 | 0.016267 | 0.392 | 0.591933 |
| LAB | 1468 | 0.022733 | 0.3696 | 0.6078 |
| LAB | 1754 | 0.0192 | 0.791933 | 0.188867 |
| LAB | 1830 | 0.006333 | 0.538667 | 0.454867 |
| PRES | 1082 | 0.009467 | 0.803133 | 0.187667 |
| PRES | 1096 | 0.0064 | 0.797133 | 0.1968 |
| PRES | 1115 | 0.012333 | 0.656733 | 0.330733 |
| PRES | 1127 | 0.0976 | 0.877933 | 0.024533 |
| PRES | 1095 | 0.083267 | 0.823733 | 0.0932 |
| ROTT | 1014 | 0.015867 | 0.725267 | 0.258933 |
| ROTT | 1028 | 0.006667 | 0.7466 | 0.246533 |
| ROTT | 1029 | 0.004867 | 0.9082 | 0.086867 |
| ROTT | 1033 | 0.007133 | 0.946867 | 0.045933 |
| ROTT | 1034 | 0.006467 | 0.921933 | 0.071733 |
| BULM | 1105 | 0.0064 | 0.954333 | 0.0392 |
| BULM | 1106 | 0.005667 | 0.552933 | 0.4414 |
| BULM | 1107 | 0.0256 | 0.9174 | 0.057267 |
| BULM | 1108 | 0.0084 | 0.9536 | 0.038 |
| BULM | 1109 | 0.0064 | 0.9706 | 0.023267 |
| NEWF | 271 | 0.0176 | 0.865867 | 0.116467 |
| NEWF | 274 | 0.006533 | 0.9628 | 0.030333 |
| NEWF | 275 | 0.006467 | 0.983733 | 0.009867 |
| NEWF | 277 | 0.0074 | 0.983867 | 0.008667 |
| NEWF | 278 | 0.086 | 0.862667 | 0.051467 |
| GSD | 1666 | 0.007 | 0.954733 | 0.038133 |
| GSD | 1776 | 0.003733 | 0.958067 | 0.0382 |
| GSD | 2011 | 0.009867 | 0.893933 | 0.096067 |
| GSD | 2060 | 0.0064 | 0.8242 | 0.169467 |
| GSD | 2086 | 0.006933 | 0.917267 | 0.075733 |
| FBUL | 1507 | 0.0122 | 0.975067 | 0.012933 |
| FBUL | 1508 | 0.0082 | 0.970733 | 0.0212 |
| FBUL | 1509 | 0.005 | 0.986333 | 0.008933 |
| FBUL | 2671 | 0.023467 | 0.918267 | 0.0582 |
| MBLT | 1915 | 0.007 | 0.936867 | 0.055933 |
| MBLT | 2253 | 0.008133 | 0.953533 | 0.038467 |
| MBLT | 2254 | 0.060133 | 0.904933 | 0.034933 |
| MBLT | 2255 | 0.010533 | 0.957533 | 0.031867 |
| MBLT | 2256 | 0.0066 | 0.985667 | 0.0078 |
| BULD | 1193 | 0.021133 | 0.964667 | 0.0142 |
| BULD | 1194 | 0.0056 | 0.9872 | 0.007067 |
| BULD | 1195 | 0.003933 | 0.988533 | 0.0074 |
| BULD | 1197 | 0.007133 | 0.9042 | 0.0888 |
| BULD | 1198 | 0.006733 | 0.9778 | 0.0154 |
| BOX | 1176 | 0.0038 | 0.982933 | 0.0132 |
| BOX | 1177 | 0.0044 | 0.9746 | 0.020933 |
| BOX | 1178 | 0.005733 | 0.9872 | 0.007133 |
| BOX | 1179 | 0.002933 | 0.9922 | 0.004733 |
| BOX | 1304 | 0.003733 | 0.9868 | 0.009667 |
| MAST | 1015 | 0.0052 | 0.943267 | 0.0516 |
| MAST | 1016 | 0.0114 | 0.9228 | 0.065867 |
| MAST | 1017 | 0.006133 | 0.913733 | 0.08 |
| MAST | 1066 | 0.0174 | 0.9588 | 0.023733 |
| MAST | 991 | 0.017933 | 0.965933 | 0.016067 |
| BMD | 941 | 0.004867 | 0.9596 | 0.035667 |
| BMD | 943 | 0.013133 | 0.7552 | 0.231733 |
| BMD | 968 | 0.010467 | 0.949133 | 0.040333 |
| BMD | 1763 | 0.005733 | 0.938867 | 0.055267 |
| BMD | 969 | 0.005067 | 0.902933 | 0.092067 |
| GSMD | 1547 | 0.007533 | 0.4592 | 0.533067 |
| GSMD | 1659 | 0.006133 | 0.687133 | 0.3066 |
| GSMD | 1660 | 0.017067 | 0.4854 | 0.4974 |
| GSMD | 1662 | 0.063933 | 0.632667 | 0.303133 |
| GSMD | 1663 | 0.009933 | 0.5714 | 2.93 |

TABLE 19C

| Canid Population[a] | Canid ID No. | k = 2, 15 Run Average | |
|---|---|---|---|
| | | Pop1 | Pop2 |
| SHIB | 1769 | 0.9954 | 0.0046 |
| SHIB | 1854 | 0.991133 | 0.008867 |
| SHIB | 1856 | 0.9642 | 0.0358 |
| SHIB | 1860 | 0.992133 | 0.007867 |
| SHIB | 1981 | 0.989467 | 0.010533 |
| CHOW | 1633 | 0.993733 | 0.006267 |
| CHOW | 1835 | 0:994867 | 0.005133 |
| CHOW | 1837 | 0.991533 | 0.008467 |
| CHOW | 1838 | 0.995 | 0.005 |
| CHOW | 1839 | 0.988 | 0.012 |
| AKIT | 1130 | 0.9788 | 0.0212 |
| AKIT | 1131 | 0.995067 | 0.004933 |
| AKIT | 1132 | 0.995267 | 0.004733 |
| AKIT | 1133 | 0.994933 | 0.005067 |
| AKIT | 1134 | 0.996 | 0.004 |
| AMAL | 1629 | 0.8468 | 0.1532 |
| AMAL | 1779 | 0.816733 | 0.183267 |
| AMAL | 1845 | 0.913667 | 0.086333 |
| AMAL | 2132 | 0.934867 | 0.065133 |
| AMAL | 2214 | 0.9108 | 0.0892 |
| BSJI | 1338 | 0.735267 | 0.264733 |
| BSJI | 1339 | 0.986933 | 0.013067 |
| BSJI | 1645 | 0.989667 | 0.010333 |
| BSJI | 1675 | 0.9814 | 0.0186 |
| BSJI | 1717 | 0.984867 | 0.015133 |
| SHAR | 1573 | 0.9826 | 0.0174 |
| SHAR | 1593 | 0.932 | 0.068 |
| SHAR | 1619 | 0.931133 | 0.068867 |
| SHAR | 1998 | 0.7944 | 0.2056 |
| SHAR | 1999 | 0.9768 | 0.0232 |
| HUSK | 1469 | 0.916333 | 0.083667 |
| HUSK | 1883 | 0.939 | 0.061 |
| HUSK | 2115 | 0.797333 | 0.202667 |
| HUSK | 2117 | 0.642933 | 0.357067 |
| HUSK | 2118 | 0.889267 | 0.110733 |
| AFGH | 1812 | 0.582533 | 0.417467 |
| AFGH | 1939 | 0.6042 | 0.3958 |
| AFGH | 2264 | 0.572067 | 0.427933 |
| AFGH | 1936 | 0.7372 | 0.2628 |
| AFGH | 1937 | 0.666533 | 0.333467 |
| SALU | 1491 | 0.427467 | 0.572533 |
| SALU | 1535 | 0.6256 | 0.3744 |
| SALU | 1607 | 0.548533 | 0.451467 |
| SALU | 1873 | 0.323 | 0.677 |
| SALU | 2610 | 0.452133 | 0.547867 |
| TIBT | 1466 | 0.463867 | 0.536133 |
| TIBT | 1562 | 0.334267 | 0.665733 |
| TIBT | 1707 | 0.369133 | 0.630867 |
| TIBT | 26078 | 0.402067 | 0.597933 |
| TIBT | 28086 | 0.160333 | 0.839667 |
| LHSA | 1524 | 0.547533 | 0.452467 |
| LHSA | 1525 | 0.5422 | 0.4578 |
| LHSA | 1526 | 0.453533 | 0.546467 |
| LHSA | 1528 | 0.339 | 0.661 |
| LHSA | 2074 | 0.688267 | 0.311733 |
| SAMO | 1375 | 0.303933 | 0.696067 |
| SAMO | 1532 | 0.592467 | 0.407533 |
| SAMO | 1560 | 0.5672 | 0.4328 |
| SAMO | 169 | 0.461933 | 0.538067 |
| SAMO | 239 | 0.4442 | 0.5558 |
| PEKE | 1143 | 0.7292 | 0.2708 |
| PEKE | 1145 | 0.4824 | 0.5176 |
| PEKE | 1211 | 0.4778 | 0.5222 |
| PEKE | 1212 | 0.351067 | 0.648933 |
| PEKE | 1213 | 0.638467 | 0.361533 |
| SHIH | 1393 | 0.385467 | 0.614533 |
| SHIH | 1783 | 0.4202 | 0.5798 |
| SHIH | 2068 | 0.433667 | 0.566333 |
| SHIH | 2859 | 0.481267 | 0.518733 |
| SHIH | 2860 | 0.542 | 0.458 |
| IWOF | 1581 | 0.018867 | 0.981133 |
| IWOF | 1761 | 0.0092 | 0.9908 |
| IWOF | 1792 | 0.017467 | 0.982533 |
| IWOF | 1906 | 0.061533 | 0.938467 |
| IWOF | 1993 | 0.0062 | 0.9938 |
| STBD | 1075 | 0.035 | 0.965 |
| STBD | 1714 | 0.056733 | 0.943267 |
| STBD | 1750 | 0.045267 | 0.954733 |
| STBD | 2403 | 0.019667 | 0.980333 |
| STBD | 2404 | 0.021467 | 0.978533 |
| GREY | 2477 | 0.155267 | 0.844733 |
| GREY | 2478 | 0.0156 | 0.9844 |
| GREY | 2479 | 0.0088 | 0.9912 |
| GREY | 2480 | 0.1108 | 0.8892 |
| GREY | 2481 | 0.0092 | 0.9908 |
| BELS | 1351 | 0.030333 | 0.969667 |
| BELS | 2111 | 0.1014 | 0.8986 |
| BELS | 2153 | 0.0072 | 0.9928 |
| BELS | 2209 | 0.053933 | 0.946067 |
| BELS | 2210 | 0.0352 | 0.9648 |
| TURV | 1622 | 0.0158 | 0.9842 |
| TURV | 2194 | 0.0078 | 0.9922 |
| TURV | 2200 | 0.030867 | 0.969133 |
| TURV | 2222 | 0.006133 | 0.993867 |
| BORZ | 1378 | 0.2322 | 0.7678 |
| BORZ | 1401 | 0.170933 | 0.829067 |
| BORZ | 1808 | 0.229267 | 0.770733 |
| BORZ | 2268 | 0.1112 | 0.8888 |
| BORZ | 978 | 0.102267 | 0.897733 |
| COLL | 1692 | 0.011133 | 0.988867 |
| COLL | 1701 | 0.0226 | 0.9774 |
| COLL | 2284 | 0.015333 | 0.984667 |
| COLL | 373 | 0.009267 | 0.990733 |
| COLL | 379 | 0.006133 | 0.993867 |
| SSHP | 1379 | 0.027867 | 0.972133 |
| SSHP | 1523 | 0.054133 | 0.945867 |
| SSHP | 1824 | 0.008133 | 0.991867 |
| SSHP | 1921 | 0.0048 | 0.9952 |
| SSHP | 2040 | 0.0838 | 0.9162 |
| PUG | 1077 | 0.028133 | 0.971867 |
| PUG | 1104 | 0.104933 | 0.895067 |
| PUG | 1183 | 0.159933 | 0.840067 |
| PUG | 1184 | 0.027533 | 0.972467 |
| PUG | 1192 | 0.009467 | 0.990533 |
| KOMO | 1484 | 0.025667 | 0.974333 |
| KOMO | 1964 | 0.0836 | 0.9164 |
| KOMO | 2321 | 0.035333 | 0.964667 |
| KOMO | 2323 | 0.091133 | 0.908867 |
| KOMO | 2334 | 0.0158 | 0.9842 |
| WHIP | 1355 | 0.0084 | 0.9916 |
| WHIP | 1395 | 0.008133 | 0.991867 |
| WHIP | 1407 | 0.005533 | 0.994467 |
| WHIP | 1409 | 0.006 | 0.994 |
| WHIP | 1518 | 0.005267 | 0.994733 |
| SPOO | 1530 | 0.044667 | 0.955333 |
| SPOO | 1582 | 0.050467 | 0.949533 |
| SPOO | 1876 | 0.022133 | 0.977867 |
| SPOO | 1877 | 0.011933 | 0.988067 |
| SPOO | 2337 | 0.0062 | 0.9938 |
| BICH | 1943 | 0.131 | 0.869 |
| BICH | 1954 | 0.286533 | 0.713467 |
| BICH | 933 | 0.056867 | 0.943133 |
| BICH | 974 | 0.142267 | 0.857733 |
| KEES | 1501 | 0.059533 | 0.940467 |
| KEES | 1589 | 0.009067 | 0.990933 |
| KEES | 1818 | 0.018533 | 0.981467 |
| KEES | 1819 | 0.007 | 0.993 |
| KEES | 2072 | 0.0066 | 0.9934 |
| MNTY | 1539 | 0.010933 | 0.989067 |
| MNTY | 1732 | 0.022533 | 0.977467 |
| MNTY | 2145 | 0.012533 | 0.987467 |
| MNTY | 2149 | 0.011333 | 0.988667 |
| NELK | 2216 | 0.107867 | 0.892133 |
| NELK | 2239 | 0.220267 | 0.779733 |
| NELK | 2240 | 0.037333 | 0.962667 |
| NELK | 2281 | 0.0152 | 0.9848 |
| NELK | 2295 | 0.2866 | 0.7134 |
| KUVZ | 1482 | 0.1712 | 0.8288 |
| KUVZ | 1551 | 0.2862 | 0.7138 |
| KUVZ | 1672 | 0.110333 | 0.889667 |

TABLE 19C-continued

| Canid Population[a] | Canid ID No. | k = 2, 15 Run Average | |
|---|---|---|---|
| | | Pop1 | Pop2 |
| KUVZ | 1913 | 0.041067 | 0.958933 |
| KUVZ | 1994 | 0.104667 | 0.895333 |
| DANE | 1574 | 0.018667 | 0.981333 |
| DANE | 1575 | 0.153333 | 0.846667 |
| DANE | 1580 | 0.0202 | 0.9798 |
| DANE | 1700 | 0.007333 | 0.992667 |
| DANE | 1748 | 0.1858 | 0.8142 |
| WSSP | 1955 | 0.006133 | 0.993867 |
| WSSP | 2139 | 0.015867 | 0.984133 |
| WSSP | 2143 | 0.005067 | 0.994933 |
| WSSP | 2195 | 0.020133 | 0.979867 |
| WSSP | 2286 | 0.005333 | 0.994667 |
| DOBP | 1031 | 0.014467 | 0.985533 |
| DOBP | 1032 | 0.062467 | 0.937533 |
| DOBP | 1749 | 0.052933 | 0.947067 |
| DOBP | 2162 | 0.0146 | 0.9854 |
| DOBP | 2245 | 0.0092 | 0.9908 |
| SSNZ | 13352 | 0.003467 | 0.996533 |
| SSNZ | 1360 | 0.003 | 0.997 |
| SSNZ | 1827 | 0.004867 | 0.995133 |
| SSNZ | 20457 | 0.010667 | 0.989333 |
| SSNZ | 22647 | 0.006267 | 0.993733 |
| ITGY | 1568 | 0.025333 | 0.974667 |
| ITGY | 1570 | 0.016533 | 0.983467 |
| ITGY | 1862 | 0.137667 | 0.862333 |
| ITGY | 1881 | 0.0804 | 0.9196 |
| ITGY | 1882 | 0.159933 | 0.840067 |
| OES | 1984 | 0.0414 | 0.9586 |
| OES | 2171 | 0.009067 | 0.990933 |
| OES | 2179 | 0.008133 | 0.991867 |
| OES | 1914 | 0.0212 | 0.9788 |
| OES | 2626 | 0.142733 | 0.857267 |
| AMWS | 2168 | 0.010867 | 0.989133 |
| AMWS | 2279 | 0.007733 | 0.992267 |
| AMWS | 2327 | 0.080333 | 0.919667 |
| AMWS | 987 | 0.014133 | 0.985867 |
| AMWS | 988 | 0.015467 | 0.984533 |
| MSNZ | 1587 | 0.005 | 0.995 |
| MSNZ | 1756 | 0.008267 | 0.991733 |
| MSNZ | 1851 | 0.004667 | 0.995333 |
| MSNZ | 2034 | 0.039 | 0.961 |
| MSNZ | 2613 | 0.004867 | 0.995133 |
| AUST | 1387 | 0.036867 | 0.963133 |
| AUST | 1531 | 0.009 | 0.991 |
| AUST | 1564 | 0.006133 | 0.993867 |
| AUST | 1870 | 0.051467 | 0.948533 |
| AUST | 1871 | 0.0066 | 0.9934 |
| ECKR | 1376 | 0.004133 | 0.995867 |
| ECKR | 1377 | 0.003933 | 0.996067 |
| ECKR | 1400 | 0.002933 | 0.997067 |
| ECKR | 1404 | 0.003133 | 0.996867 |
| ECKR | 1511 | 0.0066 | 0.9934 |
| IRSE | 1540 | 0.003267 | 0.996733 |
| IRSE | 1617 | 0.004133 | 0.995867 |
| IRSE | 1896 | 0.0136 | 0.9864 |
| IRSE | 2084 | 0.004533 | 0.995467 |
| IRSE | 2085 | 0.003533 | 0.996467 |
| WHWT | 1388 | 0.016133 | 0.983867 |
| WHWT | 1420 | 0.031467 | 0.968533 |
| WHWT | 1992 | 0.0064 | 0.9936 |
| WHWT | 2100 | 0.0078 | 0.9922 |
| WHWT | 2128 | 0.010867 | 0.989133 |
| PNTR | 1382 | 0.015 | 0.985 |
| PNTR | 1383 | 0.0574 | 0.9426 |
| PNTR | 1869 | 0.0322 | 0.9678 |
| PNTR | 1938 | 0.009867 | 0.990133 |
| PNTR | 1948 | 0.2778 | 0.7222 |
| BASS | 1341 | 0.024267 | 0.975733 |
| BASS | 1342 | 0.012733 | 0.987267 |
| BASS | 1506 | 0.006667 | 0.993333 |
| BASS | 1917 | 0.0066 | 0.9934 |
| CKCS | 1513 | 0.070867 | 0.929133 |
| CKCS | 1639 | 0.0084 | 0.9916 |
| CKCS | 1640 | 0.0086 | 0.9914 |
| CKCS | 1642 | 0.007267 | 0.992733 |
| CKCS | 2054 | 0.007067 | 0.992933 |
| GSNZ | 1868 | 0.274133 | 0.725867 |
| GSNZ | 22739 | 0.177133 | 0.822867 |
| GSNZ | 27093 | 0.087533 | 0.912467 |
| GSNZ | 27106 | 0.0126 | 0.9874 |
| GSNZ | 33390 | 0.008333 | 0.991667 |
| PHAR | 1292 | 0.1702 | 0.8298 |
| PHAR | 1947 | 0.275533 | 0.724467 |
| PHAR | 1962 | 0.1786 | 0.8214 |
| PHAR | 1963 | 0.158467 | 0.841533 |
| GOLD | 591 | 0.0048 | 0.9952 |
| GOLD | 592 | 0.029667 | 0.970333 |
| GOLD | 593 | 0.005933 | 0.994067 |
| GOLD | 603 | 0.007267 | 0.992733 |
| GOLD | 604 | 0.003333 | 0.996667 |
| BEAG | 1323 | 0.0084 | 0.9916 |
| BEAG | 1324 | 0.037133 | 0.962867 |
| BEAG | 1327 | 0.006667 | 0.993333 |
| BEAG | 994 | 0.0264 | 0.9736 |
| BEAG | 995 | 0.030333 | 0.969667 |
| BLDH | 1186 | 0.007733 | 0.992267 |
| BLDH | 1223 | 0.011667 | 0.988333 |
| BLDH | 1410 | 0.005267 | 0.994733 |
| BLDH | 1942 | 0.008933 | 0.991067 |
| BLDH | 1957 | 0.0058 | 0.9942 |
| AIRT | 1603 | 0.072867 | 0.927133 |
| AIRT | 1604 | 0.007 | 0.993 |
| AIRT | 1788 | 0.005667 | 0.994333 |
| AIRT | 1875 | 0.029867 | 0.970133 |
| ACKR | 1035 | 0.0096 | 0.9904 |
| ACKR | 2261 | 0.023267 | 0.976733 |
| ACKR | 2310 | 0.003667 | 0.996333 |
| ACKR | 1956 | 0.012333 | 0.987667 |
| ACKR | 2260 | 0.0052 | 0.9948 |
| AHRT | 1120 | 0.011133 | 0.988867 |
| AHRT | 1121 | 0.010067 | 0.989933 |
| AHRT | 1122 | 0.007533 | 0.992467 |
| AHRT | 1123 | 0.0102 | 0.9898 |
| AHRT | 1124 | 0.006467 | 0.993533 |
| CHBR | 1546 | 0.009667 | 0.990333 |
| CHBR | 1549 | 0.088867 | 0.911133 |
| CHBR | 1813 | 0.0042 | 0.9958 |
| CHBR | 2091 | 0.011 | 0.989 |
| CHBR | 888 | 0.004267 | 0.995733 |
| CAIR | 1405 | 0.009 | 0.991 |
| CAIR | 2096 | 0.029667 | 0.970333 |
| CAIR | 2113 | 0.0138 | 0.9862 |
| CAIR | 2125 | 0.006333 | 0.993667 |
| CAIR | 2131 | 0.020467 | 0.979533 |
| PTWD | P142 | 0.005333 | 0.994667 |
| PTWD | P1 | 0.0038 | 0.9962 |
| PTWD | P238 | 0.011533 | 0.988467 |
| PTWD | P25 | 0.0044 | 0.9956 |
| PTWD | P67 | 0.006933 | 0.993067 |
| GSHP | 1628 | 0.004733 | 0.995267 |
| GSHP | 1708 | 0.048067 | 0.951933 |
| GSHP | 1710 | 0.040933 | 0.959067 |
| GSHP | 1833 | 0.007667 | 0.992333 |
| GSHP | 1892 | 0.008733 | 0.991267 |
| BORD | 1648 | 0.164267 | 0.835733 |
| BORD | 1828 | 0.0184 | 0.9816 |
| BORD | 1829 | 0.0054 | 0.9946 |
| BORD | 2002 | 0.033 | 0.967 |
| BORD | 2003 | 0.045267 | 0.954733 |
| BEDT | 1422 | 0.006933 | 0.993067 |
| BEDT | 1423 | 0.0062 | 0.9938 |
| BEDT | 1424 | 0.018133 | 0.981867 |
| BEDT | 1426 | 0.01 | 0.99 |
| CLSP | 1008 | 0.0074 | 0.9926 |
| CLSP | 1009 | 0.004067 | 0.995933 |
| CLSP | 1802 | 0.006667 | 0.993333 |
| CLSP | 2312 | 0.004133 | 0.995867 |
| CLSP | 2314 | 0.005067 | 0.994933 |
| IBIZ | 1147 | 0.011467 | 0.988533 |
| IBIZ | 1148 | 0.030933 | 0.969067 |

TABLE 19C-continued

| Canid Population[a] | Canid ID No. | k = 2, 15 Run Average | |
|---|---|---|---|
| | | Pop1 | Pop2 |
| IBIZ | 1162 | 0.0162 | 0.9838 |
| IBIZ | 1172 | 0.017867 | 0.982133 |
| IBIZ | 1280 | 0.018733 | 0.981267 |
| RHOD | 1444 | 0.004333 | 0.995667 |
| RHOD | 1454 | 0.018 | 0.982 |
| RHOD | 1505 | 0.008 | 0.992 |
| RHOD | 1592 | 0.006733 | 0.993267 |
| RHOD | 1609 | 0.005067 | 0.994933 |
| DACH | 1051 | 0.0188 | 0.9812 |
| DACH | 1052 | 0.009067 | 0.990933 |
| DACH | 1053 | 0.016733 | 0.983267 |
| DACH | 1054 | 0.028867 | 0.971133 |
| DACH | 1055 | 0.009933 | 0.990067 |
| AUSS | 1336 | 0.1524 | 0.8476 |
| AUSS | 1337 | 0.013133 | 0.986867 |
| AUSS | 1500 | 0.010667 | 0.989333 |
| AUSS | 1521 | 0.102067 | 0.897933 |
| AUSS | 1683 | 0.008467 | 0.991533 |
| CHIH | 1202 | 0.005267 | 0.994733 |
| CHIH | 1203 | 0.03 | 0.97 |
| CHIH | 1204 | 0.013333 | 0.986667 |
| CHIH | 1205 | 0.166867 | 0.833133 |
| CHIH | 1206 | 0.004867 | 0.995133 |
| KERY | 13878 | 0.0066 | 0.9934 |
| KERY | 1483 | 0.005867 | 0.994133 |
| KERY | 1579 | 0.011133 | 0.988867 |
| KERY | 2014 | 0.0034 | 0.9966 |
| KERY | 24255 | 0.007267 | 0.992733 |
| SCHP | 1386 | 0.0082 | 0.9918 |
| SCHP | 1471 | 0.020933 | 0.979067 |
| SCHP | 1814 | 0.007667 | 0.992333 |
| SCHP | 1852 | 0.0184 | 0.9816 |
| IRTR | 2152 | 0.009333 | 0.990667 |
| IRTR | 2189 | 0.008333 | 0.991667 |
| IRTR | 2238 | 0.005467 | 0.994533 |
| IRTR | 2242 | 0.0076 | 0.9924 |
| FCR | 1188 | 0.004267 | 0.995733 |
| FCR | 2020 | 0.0052 | 0.9948 |
| FCR | 2042 | 0.004333 | 0.995667 |
| FCR | 2044 | 0.005133 | 0.994867 |
| FCR | 2259 | 0.003733 | 0.996267 |
| SCWT | 1624 | 0.051067 | 0.948933 |
| SCWT | 1770 | 0.004467 | 0.995533 |
| SCWT | 2250 | 0.005533 | 0.994467 |
| SCWT | 2301 | 0.0124 | 0.9876 |
| POM | 1190 | 0.181067 | 0.818933 |
| POM | 1191 | 0.006067 | 0.993933 |
| POM | 1210 | 0.049267 | 0.950733 |
| POM | 1238 | 0.010067 | 0.989933 |
| POM | 1239 | 0.298467 | 0.701533 |
| LAB | 1310 | 0.0756 | 0.9244 |
| LAB | 1465 | 0.011 | 0.989 |
| LAB | 1468 | 0.013533 | 0.986467 |
| LAB | 1754 | 0.007067 | 0.992933 |
| LAB | 1830 | 0.0052 | 0.9948 |
| PRES | 1082 | 0.009 | 0.991 |
| PRES | 1096 | 0.004667 | 0.995333 |
| PRES | 1115 | 0.008667 | 0.991333 |
| PRES | 1127 | 0.147867 | 0.852133 |
| PRES | 1095 | 0.115533 | 0.884467 |
| ROTT | 1014 | 0.016467 | 0.983533 |
| ROTT | 1028 | 0.005333 | 0.994667 |
| ROTT | 1029 | 0.003733 | 0.996267 |
| ROTT | 1033 | 0.006933 | 0.993067 |
| ROTT | 1034 | 0.003867 | 0.996133 |
| BULM | 1105 | 0.004067 | 0.995933 |
| BULM | 1106 | 0.004467 | 0.995533 |
| BULM | 1107 | 0.007933 | 0.992067 |
| BULM | 1108 | 0.005533 | 0.994467 |
| BULM | 1109 | 0.004533 | 0.995467 |
| NEWF | 271 | 0.014333 | 0.985667 |
| NEWF | 274 | 0.005867 | 0.994133 |
| NEWF | 275 | 0.006467 | 0.993533 |
| NEWF | 277 | 0.008933 | 0.991067 |
| NEWF | 278 | 0.106 | 0.894 |
| GSD | 1666 | 0.005467 | 0.994533 |
| GSD | 1776 | 0.003 | 0.997 |
| GSD | 2011 | 0.004267 | 0.995733 |
| GSD | 2060 | 0.004467 | 0.995533 |
| GSD | 2086 | 0.005867 | 0.994133 |
| FBUL | 1507 | 0.016867 | 0.983133 |
| FBUL | 1508 | 0.0084 | 0.9916 |
| FBUL | 1509 | 0.0066 | 0.9934 |
| FBUL | 2671 | 0.032867 | 0.967133 |
| MBLT | 1915 | 0.005467 | 0.994533 |
| MBLT | 2253 | 0.007467 | 0.992533 |
| MBLT | 2254 | 0.063667 | 0.936333 |
| MBLT | 2255 | 0.006333 | 0.993667 |
| MBLT | 2256 | 0.0102 | 0.9898 |
| BULD | 1193 | 0.035 | 0.965 |
| BULD | 1194 | 0.010067 | 0.989933 |
| BULD | 1195 | 0.010867 | 0.989133 |
| BULD | 1197 | 0.0042 | 0.9958 |
| BULD | 1198 | 0.005133 | 0.994867 |
| BOX | 1176 | 0.003133 | 0.996867 |
| BOX | 1177 | 0.003467 | 0.996533 |
| BOX | 1178 | 0.005533 | 0.994467 |
| BOX | 1179 | 0.004467 | 0.995533 |
| BOX | 1304 | 0.0046 | 0.9954 |
| MAST | 1015 | 0.003533 | 0.996467 |
| MAST | 1016 | 0.012467 | 0.987533 |
| MAST | 1017 | 0.006933 | 0.993067 |
| MAST | 1066 | 0.011333 | 0.988667 |
| MAST | 991 | 0.0132 | 0.9868 |
| BMD | 941 | 0.0054 | 0.9946 |
| BMD | 943 | 0.0054 | 0.9946 |
| BMD | 968 | 0.005933 | 0.994067 |
| BMD | 1763 | 0.004133 | 0.995867 |
| BMD | 969 | 0.0034 | 0.9966 |
| GSMD | 1547 | 0.004867 | 0.995133 |
| GSMD | 1659 | 0.004467 | 0.995533 |
| GSMD | 1660 | 0.010933 | 0.989067 |
| GSMD | 1662 | 0.0276 | 0.9724 |
| GSMD | 1663 | 0.009267 | 0.990733 |

[a]See Table 5 for abbreviations of canid populations.
KBB: pbe

TABLE 19D

| Canid Population[a] | Canid ID No. | k = 2 with wolf, 15 Run Average | |
|---|---|---|---|
| | | Pop1 | Pop2 |
| WOLF | W511 | 0.994 | 0.006 |
| WOLF | W5131 | 0.982 | 0.018 |
| WOLF | WC3 | 0.995 | 0.005 |
| WOLF | WE10 | 0.995 | 0.005 |
| WOLF | 282135 | 0.9918 | 0.0082 |
| WOLF | 492-8 | 0.9968 | 0.0032 |
| WOLF | 930121 | 0.9858 | 0.0142 |
| WOLF | Iran-1 | 0.9388 | 0.0612 |
| SHIB | 1769 | 0.993 | 0.007 |
| SHIB | 1854 | 0.98 | 0.02 |
| SHIB | 1856 | 0.938 | 0.062 |
| SHIB | 1860 | 0.99 | 0.01 |
| SHIB | 1981 | 0.987 | 0.013 |
| CHOW | 1633 | 0.9904 | 0.0096 |
| CHOW | 1835 | 0.9916 | 0.0084 |
| CHOW | 1837 | 0.9774 | 0.0226 |
| CHOW | 1838 | 0.9918 | 0.0082 |
| CHOW | 1839 | 0.9796 | 0.0204 |
| AKIT | 1130 | 0.9724 | 0.0276 |
| AKIT | 1131 | 0.993 | 0.007 |
| AKIT | 1132 | 0.9934 | 0.0066 |
| AKIT | 1133 | 0.995 | 0.005 |
| AKIT | 1134 | 0.994 | 0.006 |
| AMAL | 1629 | 0.5876 | 0.4124 |

TABLE 19D-continued

| Canid Population[a] | Canid ID No. | k = 2 with wolf, 15 Run Average | |
|---|---|---|---|
| | | Pop1 | Pop2 |
| AMAL | 1779 | 0.516 | 0.484 |
| AMAL | 1845 | 0.6802 | 0.3198 |
| AMAL | 2132 | 0.755 | 0.245 |
| AMAL | 2214 | 0.7298 | 0.2702 |
| BSJI | 1338 | 0.7944 | 0.2056 |
| BSJI | 1339 | 0.976 | 0.024 |
| BSJI | 1645 | 0.9792 | 0.0208 |
| BSJI | 1675 | 0.9718 | 0.0282 |
| BSJI | 1717 | 0.9672 | 0.0328 |
| SHAR | 1573 | 0.9318 | 0.0682 |
| SHAR | 1593 | 0.914 | 0.086 |
| SHAR | 1619 | 0.8048 | 0.1952 |
| SHAR | 1998 | 0.6918 | 0.3082 |
| SHAR | 1999 | 0.9372 | 0.0628 |
| HUSK | 1469 | 0.702 | 0.298 |
| HUSK | 1883 | 0.7878 | 0.2122 |
| HUSK | 2115 | 0.5934 | 0.4066 |
| HUSK | 2117 | 0.5412 | 0.4588 |
| HUSK | 2118 | 0.7718 | 02282 |
| AFGH | 1812 | 0.4642 | 0.5358 |
| AFGH | 1939 | 0.5172 | 0.4828 |
| AFGH | 2264 | 0.4348 | 0.5652 |
| AFGH | 1936 | 0.5942 | 0.4058 |
| AFGH | 1937 | 0.583 | 0.417 |
| SALU | 1491 | 0.3624 | 0.6376 |
| SALU | 1535 | 0.4792 | 0.5208 |
| SALU | 1607 | 0.4234 | 0.5766 |
| SALU | 1873 | 0.2304 | 0.7696 |
| SALU | 2610 | 0.4092 | 0.5908 |
| TIBT | 1466 | 0.3684 | 0.6316 |
| TIBT | 1562 | 0.2896 | 0.7104 |
| TIBT | 1707 | 0.3136 | 0.6864 |
| TIBT | 26078 | 0.3314 | 0.6686 |
| TIBT | 28086 | 0.1316 | 0.8684 |
| LHSA | 1524 | 0.4598 | 0.5402 |
| LHSA | 1525 | 0.4652 | 0.5348 |
| LHSA | 1526 | 0.4 | 0.6 |
| LHSA | 1528 | 0.2798 | 0.7202 |
| LHSA | 2074 | 0.5838 | 0.4162 |
| SAMO | 1375 | 0.1684 | 0.8316 |
| SAMO | 1532 | 0.5154 | 0.4846 |
| SAMO | 1560 | 0.4444 | 0.5556 |
| SAMO | 169 | 0.3686 | 0.6314 |
| SAMO | 239 | 0.3666 | 0.6334 |
| PEKE | 1143 | 0.5856 | 0.4144 |
| PEKE | 1145 | 0.3948 | 0.6052 |
| PEKE | 1211 | 0.416 | 0.584 |
| PEKE | 1212 | 0.2806 | 0.7194 |
| PEKE | 1213 | 0.4832 | 0.5168 |
| SHIH | 1393 | 0.3196 | 0.6804 |
| SHIH | 1783 | 0.3234 | 0.6766 |
| SHIH | 2068 | 0.347 | 0.653 |
| SHIH | 2859 | 0.3476 | 0.6524 |
| SHIH | 2860 | 0.4582 | 0.5418 |
| IWOF | 1581 | 0.0124 | 0.9876 |
| IWOF | 1761 | 0.0054 | 0.9946 |
| IWOF | 1792 | 0.0086 | 0.9914 |
| IWOF | 1906 | 0.026 | 0.974 |
| IWOF | 1993 | 0.0046 | 0.9954 |
| STBD | 1075 | 0.0348 | 0.9652 |
| STBD | 1714 | 0.0484 | 0.9516 |
| STBD | 1750 | 0.028 | 0.972 |
| STBD | 2403 | 0.021 | 0.979 |
| STBD | 2404 | 0.0122 | 0.9878 |
| GREY | 2477 | 0.0992 | 0.9008 |
| GREY | 2478 | 0.0146 | 0.9854 |
| GREY | 2479 | 0.0062 | 0.9938 |
| GREY | 2480 | 0.1026 | 0.8974 |
| GREY | 2481 | 0.0058 | 0.9942 |
| BELS | 1351 | 0.0142 | 0.9858 |
| BELS | 2111 | 0.0206 | 0.9794 |
| BELS | 2153 | 0.0058 | 0.9942 |
| BELS | 2209 | 0.036 | 0.964 |
| BELS | 2210 | 0.0268 | 0.9732 |
| TURV | 1622 | 0.0184 | 0.9816 |
| TURV | 2194 | 0.0062 | 0.9938 |
| TURV | 2200 | 0.0178 | 0.9822 |
| TURV | 2222 | 0.0058 | 0.9942 |
| BORZ | 1378 | 0.1582 | 0.8418 |
| BORZ | 1401 | 0.1348 | 0.8652 |
| BORZ | 1808 | 0.1496 | 0.8504 |
| BORZ | 2268 | 0.0448 | 0.9552 |
| BORZ | 978 | 0.0282 | 0.9718 |
| COLL | 1692 | 0.0102 | 0.9898 |
| COLL | 1701 | 0.0236 | 0.9764 |
| COLL | 2284 | 0.0178 | 0.9822 |
| COLL | 373 | 0.0102 | 0.9898 |
| COLL | 379 | 0.0064 | 0.9936 |
| SSHP | 1379 | 0.0186 | 0.9814 |
| SSHP | 1523 | 0.055 | 0.945 |
| SSHP | 1824 | 0.0058 | 0.9942 |
| SSHP | 1921 | 0.0048 | 0.9952 |
| SSHP | 2040 | 0.0678 | 0.9322 |
| PUG | 1077 | 0.014 | 0.986 |
| PUG | 1104 | 0.0376 | 0.9624 |
| PUG | 1183 | 0.1068 | 0.8932 |
| PUG | 1184 | 0.0102 | 0.9898 |
| PUG | 1192 | 0.0064 | 0.9936 |
| KOMO | 1484 | 0.0138 | 0.9862 |
| KOMO | 1964 | 0.1264 | 0.8736 |
| KOMO | 2321 | 0.0356 | 0.9644 |
| KOMO | 2323 | 0.072 | 0.928 |
| KOMO | 2334 | 0.0368 | 0.9632 |
| WHIP | 1355 | 0.005 | 0.995 |
| WHIP | 1395 | 0.006 | 0.994 |
| WHIP | 1407 | 0.0048 | 0.9952 |
| WHIP | 1409 | 0.0034 | 0.9966 |
| WHIP | 1518 | 0.0038 | 0.9962 |
| SPOO | 1530 | 0.0322 | 0.9678 |
| SPOO | 1582 | 0.033 | 0.967 |
| SPOO | 1876 | 0.0276 | 0.9724 |
| SPOO | 1877 | 0.0108 | 0.9892 |
| SPOO | 2337 | 0.0038 | 0.9962 |
| BICH | 1943 | 0.0252 | 0.9748 |
| BICH | 1954 | 0.2126 | 0.7874 |
| BICH | 933 | 0.0202 | 0.9798 |
| BICH | 974 | 0.09 | 0.91 |
| KEES | 1501 | 0.0352 | 0.9648 |
| KEES | 1589 | 0.012 | 0.988 |
| KEES | 1818 | 0.0182 | 0.9818 |
| KEES | 1819 | 0.005 | 0.995 |
| KEES | 2072 | 0.0054 | 0.9946 |
| MNTY | 1539 | 0.0104 | 0.9896 |
| MNTY | 1732 | 0.013 | 0.987 |
| MNTY | 2145 | 0.0126 | 0.9874 |
| MNTY | 2149 | 0.0068 | 0.9932 |
| NELK | 2216 | 0.0596 | 0.9404 |
| NELK | 2239 | 0.1338 | 0.8662 |
| NELK | 2240 | 0.0184 | 0.9816 |
| NELK | 2281 | 0.0078 | 0.9922 |
| NELK | 2295 | 0.1786 | 0.8214 |
| KUVZ | 1482 | 0.0726 | 0.9274 |
| KUVZ | 1551 | 0.2054 | 0.7946 |
| KUVZ | 1672 | 0.0846 | 0.9154 |
| KUVZ | 1913 | 0.012 | 0.988 |
| KUVZ | 1994 | 0.0654 | 0.9346 |
| DANE | 1574 | 0.0118 | 0.9882 |
| DANE | 1575 | 0.1232 | 0.8768 |
| DANE | 1580 | 0.0138 | 0.9862 |
| DANE | 1700 | 0.0046 | 0.9954 |
| DANE | 1748 | 0.0798 | 0.9202 |
| WSSP | 1955 | 0.004 | 0.996 |
| WSSP | 2139 | 0.0132 | 0.9868 |
| WSSP | 2143 | 0.0068 | 0.9932 |
| WSSP | 2195 | 0.0724 | 0.9276 |
| WSSP | 2286 | 0.0038 | 0.9962 |
| DOBP | 1031 | 0.0126 | 0.9874 |
| DOBP | 1032 | 0.1052 | 0.8948 |
| DOBP | 1749 | 0.0692 | 0.9308 |
| DOBP | 2162 | 0.0136 | 0.9864 |

TABLE 19D-continued

| Canid Population[a] | Canid ID No. | k = 2 with wolf, 15 Run Average | |
|---|---|---|---|
| | | Pop1 | Pop2 |
| DOBP | 2245 | 0.0104 | 0.9896 |
| SSNZ | 13352 | 0.003 | 0.997 |
| SSNZ | 1360 | 0.0024 | 0.9976 |
| SSNZ | 1827 | 0.004 | 0.996 |
| SSNZ | 20457 | 0.0118 | 0.9882 |
| SSNZ | 22647 | 0.0048 | 0.9952 |
| ITGY | 1568 | 0.0098 | 0.9902 |
| ITGY | 1570 | 0.0132 | 0.9868 |
| ITGY | 1862 | 0.0478 | 0.9522 |
| ITGY | 1881 | 0.0746 | 0.9254 |
| ITGY | 1882 | 0.1056 | 0.8944 |
| OES | 1984 | 0.0508 | 0.9492 |
| OES | 2171 | 0.0068 | 0.9932 |
| OES | 2179 | 0.005 | 0.995 |
| OES | 1914 | 0.0148 | 0.9852 |
| OES | 2626 | 0.129 | 0.871 |
| AMWS | 2168 | 0.0194 | 0.9806 |
| AMWS | 2279 | 0.0062 | 0.9938 |
| AMWS | 2327 | 0.036 | 0.964 |
| AMWS | 987 | 0.0054 | 0.9946 |
| AMWS | 988 | 0.0116 | 0.9884 |
| MSNZ | 1587 | 0.004 | 0.996 |
| MSNZ | 1756 | 0.0076 | 0.9924 |
| MSNZ | 1851 | 0.0046 | 0.9954 |
| MSNZ | 2034 | 0.0374 | 0.9626 |
| MSNZ | 2613 | 0.0038 | 0.9962 |
| AUST | 1387 | 0.0208 | 0.9792 |
| AUST | 1531 | 0.0048 | 0.9952 |
| AUST | 1564 | 0.0038 | 0.9962 |
| AUST | 1870 | 0.026 | 0.974 |
| AUST | 1871 | 0.0038 | 0.9962 |
| ECKR | 1376 | 0.0056 | 0.9944 |
| ECKR | 1377 | 0.003 | 0.997 |
| ECKR | 1400 | 0.002 | 0.998 |
| ECKR | 1404 | 0.003 | 0.997 |
| ECKR | 1511 | 0.0048 | 0.9952 |
| IRSE | 1540 | 0.003 | 0.997 |
| IRSE | 1617 | 0.004 | 0.996 |
| IRSE | 1896 | 0.0104 | 0.9896 |
| IRSE | 2084 | 0.0046 | 0.9954 |
| IRSE | 2085 | 0.005 | 0.995 |
| WHWT | 1388 | 0.0084 | 0.9916 |
| WHWT | 1420 | 0.0328 | 0.9672 |
| WHWT | 1992 | 0.0058 | 0.9942 |
| WHWT | 2100 | 0.0054 | 0.9946 |
| WHWT | 2128 | 0.0074 | 0.9926 |
| PNTR | 1382 | 0.0368 | 0.9632 |
| PNTR | 1383 | 0.0748 | 0.9252 |
| PNTR | 1869 | 0.0274 | 0.9726 |
| PNTR | 1938 | 0.0166 | 0.9834 |
| PNTR | 1948 | 0.3046 | 0.6954 |
| BASS | 1341 | 0.0212 | 0.9788 |
| BASS | 1342 | 0.0078 | 0.9922 |
| BASS | 1506 | 0.005 | 0.995 |
| BASS | 1917 | 0.004 | 0.996 |
| CKCS | 1513 | 0.0502 | 0.9498 |
| CKCS | 1639 | 0.0058 | 0.9942 |
| CKCS | 1640 | 0.0068 | 0.9932 |
| CKCS | 1642 | 0.0074 | 0.9926 |
| CKCS | 2054 | 0.0064 | 0.9936 |
| GSNZ | 1868 | 0.224 | 0.776 |
| GSNZ | 22739 | 0.116 | 0.884 |
| GSNZ | 27093 | 0.0496 | 0.9504 |
| GSNZ | 27106 | 0.0094 | 0.9906 |
| GSNZ | 33390 | 0.0048 | 0.9952 |
| PHAR | 1292 | 0.1686 | 0.8314 |
| PHAR | 1947 | 0.3092 | 0.6908 |
| PHAR | 1962 | 0.1454 | 0.8546 |
| PHAR | 1963 | 0.0938 | 0.9062 |
| GOLD | 591 | 0.0058 | 0.9942 |
| GOLD | 592 | 0.0854 | 0.9146 |
| GOLD | 593 | 0.0072 | 0.9928 |
| GOLD | 603 | 0.0092 | 0.9908 |
| GOLD | 604 | 0.003 | 0.997 |
| BEAG | 1323 | 0.0048 | 0.9952 |
| BEAG | 1324 | 0.0458 | 0.9542 |
| BEAG | 1327 | 0.0068 | 0.9932 |
| BEAG | 994 | 0.0198 | 0.9802 |
| BEAG | 995 | 0.012 | 0.988 |
| BLDH | 1186 | 0.005 | 0.995 |
| BLDH | 1223 | 0.0086 | 0.9914 |
| BLDH | 1410 | 0.0038 | 0.9962 |
| BLDH | 1942 | 0.0068 | 0.9932 |
| BLDH | 1957 | 0.004 | 0.996 |
| AIRT | 1603 | 0.0658 | 0.9342 |
| AIRT | 1604 | 0.0052 | 0.9948 |
| AIRT | 1788 | 0.0046 | 0.9954 |
| AIRT | 1875 | 0.0272 | 0.9728 |
| ACKR | 1035 | 0.0066 | 0.9934 |
| ACKR | 2261 | 0.0326 | 0.9674 |
| ACKR | 2310 | 0.003 | 0.997 |
| ACKR | 1956 | 0.0108 | 0.9892 |
| ACKR | 2260 | 0.0038 | 0.9962 |
| AHRT | 1120 | 0.0084 | 0.9916 |
| AHRT | 1121 | 0.0068 | 0.9932 |
| AHRT | 1122 | 0.0054 | 0.9946 |
| AHRT | 1123 | 0.0104 | 0.9896 |
| AHRT | 1124 | 0.0058 | 0.9942 |
| CHBR | 1546 | 0.0058 | 0.9942 |
| CHBR | 1549 | 0.0746 | 0.9254 |
| CHBR | 1813 | 0.003 | 0.997 |
| CHBR | 2091 | 0.0178 | 0.9822 |
| CHBR | 888 | 0.0038 | 0.9962 |
| CAIR | 1405 | 0.0106 | 0.9894 |
| CAIR | 2096 | 0.0402 | 0.9598 |
| CAIR | 2113 | 0.0078 | 0.9922 |
| CAIR | 2125 | 0.0044 | 0.9956 |
| CAIR | 2131 | 0.0132 | 0.9868 |
| PTWD | P142 | 0.0052 | 0.9948 |
| PTWD | P1 | 0.0036 | 0.9964 |
| PTWD | P238 | 0.0082 | 0.9918 |
| PTWD | P25 | 0.004 | 0.996 |
| PTWD | P67 | 0.0062 | 0.9938 |
| GSHP | 1628 | 0.0038 | 0.9962 |
| GSHP | 1708 | 0.0518 | 0.9482 |
| GSHP | 1710 | 0.0456 | 0.9544 |
| GSHP | 1833 | 0.0068 | 0.9932 |
| GSHP | 1892 | 0.0058 | 0.9942 |
| BORD | 1648 | 0.0938 | 0.9062 |
| BORD | 1828 | 0.0114 | 0.9886 |
| BORD | 1829 | 0.0034 | 0.9966 |
| BORD | 2002 | 0.0156 | 0.9844 |
| BORD | 2003 | 0.0452 | 0.9548 |
| BEDT | 1422 | 0.0048 | 0.9952 |
| BEDT | 1423 | 0.005 | 0.995 |
| BEDT | 1424 | 0.0302 | 0.9698 |
| BEDT | 1426 | 0.0072 | 0.9928 |
| CLSP | 1008 | 0.007 | 0.993 |
| CLSP | 1009 | 0.0042 | 0.9958 |
| CLSP | 1802 | 0.006 | 0.994 |
| CLSP | 2312 | 0.0038 | 0.9962 |
| CLSP | 2314 | 0.005 | 0.995 |
| IBIZ | 1147 | 0.011 | 0.989 |
| IBIZ | 1148 | 0.0974 | 0.9026 |
| IBIZ | 1162 | 0.0106 | 0.9894 |
| IBIZ | 1172 | 0.011 | 0.989 |
| IBIZ | 1280 | 0.0148 | 0.9852 |
| RHOD | 1444 | 0.0042 | 0.9958 |
| RHOD | 1454 | 0.0154 | 0.9846 |
| RHOD | 1505 | 0.006 | 0.994 |
| RHOD | 1592 | 0.0082 | 0.9918 |
| RHOD | 1609 | 0.0098 | 0.9902 |
| DACH | 1051 | 0.0166 | 0.9834 |
| DACH | 1052 | 0.0124 | 0.9876 |
| DACH | 1053 | 0.0178 | 0.9822 |
| DACH | 1054 | 0.051 | 0.949 |
| DACH | 1055 | 0.0072 | 0.9928 |
| AUSS | 1336 | 0.093 | 0.907 |
| AUSS | 1337 | 0.0182 | 0.9818 |
| AUSS | 1500 | 0.0206 | 0.9794 |

TABLE 19D-continued

| Canid Population[a] | Canid ID No. | k = 2 with wolf, 15 Run Average Pop1 | Pop2 |
|---|---|---|---|
| AUSS | 1521 | 0.0788 | 0.9212 |
| AUSS | 1683 | 0.0088 | 0.9912 |
| CHIH | 1202 | 0.004 | 0.996 |
| CHIH | 1203 | 0.0298 | 0.9702 |
| CHIH | 1204 | 0.0142 | 0.9858 |
| CHIH | 1205 | 0.1506 | 0.8494 |
| CHIH | 1206 | 0.004 | 0.996 |
| KERY | 13878 | 0.0054 | 0.9946 |
| KERY | 1483 | 0.0048 | 0.9952 |
| KERY | 1579 | 0.0058 | 0.9942 |
| KERY | 2014 | 0.0028 | 0.9972 |
| KERY | 24255 | 0.0052 | 0.9948 |
| SCHP | 1386 | 0.0136 | 0.9864 |
| SCHP | 1471 | 0.0646 | 0.9354 |
| SCHP | 1814 | 0.0076 | 0.9924 |
| SCHP | 1852 | 0.0162 | 0.9838 |
| IRTR | 2152 | 0.0086 | 0.9914 |
| IRTR | 2189 | 0.0048 | 0.9952 |
| IRTR | 2238 | 0.0048 | 0.9952 |
| IRTR | 2242 | 0.0066 | 0.9934 |
| FCR | 1188 | 0.004 | 0.996 |
| FCR | 2020 | 0.004 | 0.996 |
| FCR | 2042 | 0.004 | 0.996 |
| FCR | 2044 | 0.0038 | 0.9962 |
| FCR | 2259 | 0.0028 | 0.9972 |
| SCWT | 1624 | 0.035 | 0.965 |
| SCWT | 1770 | 0.0038 | 0.9962 |
| SCWT | 2250 | 0.004 | 0.996 |
| SCWT | 2301 | 0.0084 | 0.9916 |
| POM | 1190 | 0.1668 | 0.8332 |
| POM | 1191 | 0.0042 | 0.9958 |
| POM | 1210 | 0.0374 | 0.9626 |
| POM | 1238 | 0.0078 | 0.9922 |
| POM | 1239 | 0.3112 | 0.6888 |
| LAB | 1310 | 0.063 | 0.937 |
| LAB | 1465 | 0.0172 | 0.9828 |
| LAB | 1468 | 0.0124 | 0.9876 |
| LAB | 1754 | 0.006 | 0.994 |
| LAB | 1830 | 0.0076 | 0.9924 |
| PRES | 1082 | 0.0108 | 0.9892 |
| PRES | 1096 | 0.0052 | 0.9948 |
| PRES | 1115 | 0.0092 | 0.9908 |
| PRES | 1127 | 0.1526 | 0.8474 |
| PRES | 1095 | 0.0906 | 0.9094 |
| ROTT | 1014 | 0.0124 | 0.9876 |
| ROTT | 1028 | 0.0068 | 0.9932 |
| ROTT | 1029 | 0.0038 | 0.9962 |
| ROTT | 1033 | 0.0204 | 0.9796 |
| ROTT | 1034 | 0.0038 | 0.9962 |
| BULM | 1105 | 0.003 | 0.997 |
| BULM | 1106 | 0.0034 | 0.9966 |
| BULM | 1107 | 0.0082 | 0.9918 |
| BULM | 1108 | 0.005 | 0.995 |
| BULM | 1109 | 0.0066 | 0.9934 |
| NEWF | 271 | 0.0114 | 0.9886 |
| NEWF | 274 | 0.0052 | 0.9948 |
| NEWF | 275 | 0.0048 | 0.9952 |
| NEWF | 277 | 0.0078 | 0.9922 |
| NEWF | 278 | 0.1024 | 0.8976 |
| GSD | 1666 | 0.0058 | 0.9942 |
| GSD | 1776 | 0.003 | 0.997 |
| GSD | 2011 | 0.004 | 0.996 |
| GSD | 2060 | 0.0042 | 0.9958 |
| GSD | 2086 | 0.0046 | 0.9954 |
| FBUL | 1507 | 0.0098 | 0.9902 |
| FBUL | 1508 | 0.0058 | 0.9942 |
| FBUL | 1509 | 0.005 | 0.995 |
| FBUL | 2671 | 0.0464 | 0.9536 |
| MBLT | 1915 | 0.0038 | 0.9962 |
| MBLT | 2253 | 0.0054 | 0.9946 |
| MBLT | 2254 | 0.0454 | 0.9546 |
| MBLT | 2255 | 0.0046 | 0.9954 |
| MBLT | 2256 | 0.0078 | 0.9922 |
| BULD | 1193 | 0.0234 | 0.9766 |
| BULD | 1194 | 0.0098 | 0.9902 |
| BULD | 1195 | 0.0162 | 0.9838 |
| BULD | 1197 | 0.0042 | 0.9958 |
| BULD | 1198 | 0.0038 | 0.9962 |
| BOX | 1176 | 0.003 | 0.997 |
| BOX | 1177 | 0.003 | 0.997 |
| BOX | 1178 | 0.0048 | 0.9952 |
| BOX | 1179 | 0.004 | 0.996 |
| BOX | 1304 | 0.0058 | 0.9942 |
| MAST | 1015 | 0.0038 | 0.9962 |
| MAST | 1016 | 0.0104 | 0.9896 |
| MAST | 1017 | 0.0096 | 0.9904 |
| MAST | 1066 | 0.0078 | 0.9922 |
| MAST | 991 | 0.012 | 0.988 |
| BMD | 941 | 0.0056 | 0.9944 |
| BMD | 943 | 0.004 | 0.996 |
| BMD | 968 | 0.0058 | 0.9942 |
| BMD | 1763 | 0.003 | 0.997 |
| BMD | 969 | 0.0028 | 0.9972 |
| GSMD | 1547 | 0.004 | 0.996 |
| GSMD | 1659 | 0.003 | 0.997 |
| GSMD | 1660 | 0.006 | 0.994 |
| GSMD | 1662 | 0.0204 | 0.9796 |
| GSMD | 1663 | 0.0072 | 0.9928 |

[a]See Table 5 for abbreviations of canid populations.
KBB: pbe

TABLE 21A

| Canid population* | AHRT Canid ID NO (missing genotypes) | | | BASS Canid ID NO (missing genotypes) | | | BEAG Canid ID NO (missing genotypes) | | | | | |
|---|---|---|---|---|---|---|---|---|---|---|---|---|
| | 1119 (8) | 1081 (2) | 1121 (6) | 24039 (19) | 930 (3) | 931 (3) | 18586 (51) | 18424 (13) | 1323 (20) | 1324 (16) | 1325 (8) | 1327 (12) |
| AHTR | 0.19003 | 0 | 0.2457 | 0 | 0 | 0 | 3.00E−05 | 0 | 0 | 0 | 0 | 0 |
| AMWS | 0.00042 | 0 | 0 | 0 | 0 | 0 | 0 | 0 | 0 | 0 | 0 | 0 |
| BASS | 0 | 0 | 0 | 2.00E−05 | 2.00E−05 | 0.36647 | 0 | 0 | 0 | 0 | 0 | 0 |
| BEAG | 0 | 0 | 0 | 0 | 0 | 0.00068 | 0.00859 | 0.00634 | 0.99969 | 0.99504 | 0.99062 | 0.99804 |
| BEAC | 0 | 0 | 0 | 0 | 0 | 0.00014 | 0 | 0 | 0 | 0 | 0 | 0 |
| BMD | 0 | 0 | 0 | 0 | 0 | 0 | 1.00E−05 | 0 | 0 | 0.0049 | 0.00893 | 0 |
| BICH | 0 | 0 | 0 | 0 | 0 | 0 | 0 | 0 | 0 | 2.00E−05 | 0 | 0 |
| BORZ | 0 | 0 | 0 | 9.00E−05 | 0.00021 | 0 | 0.00012 | 0.01475 | 0 | 0 | 0 | 0 |
| BOX | 0 | 0 | 0 | 0 | 0 | 0 | 0 | 0 | 0 | 0 | 0 | 0 |
| BULM | 0 | 0.00023 | 0 | 0 | 1.00E−05 | 0.58998 | 0.00739 | 0 | 0 | 0 | 0 | 0 |
| ACKR | 0.0015 | 0 | 0 | 0 | 0 | 0 | 0 | 0 | 0 | 0 | 0 | 0 |
| DACH | 0.00304 | 0.99974 | 0.0102 | 0.99988 | 0.9996 | 0.03153 | 0.01324 | 0.97888 | 0 | 0 | 0 | 0.00142 |

TABLE 21A-continued

| | AHRT Canid ID NO (missing genotypes) | | | BASS Canid ID NO (missing genotypes) | | | BEAG Canid ID NO (missing genotypes) | | | | | |
|---|---|---|---|---|---|---|---|---|---|---|---|---|
| Canid population* | 1119 (8) | 1081 (2) | 1121 (6) | 24039 (19) | 930 (3) | 931 (3) | 18586 (51) | 18424 (13) | 1323 (20) | 1324 (16) | 1325 (8) | 1327 (12) |
| DALM | 0 | 0 | 0 | 0 | 0 | 0 | 0 | 0 | 0 | 0 | 0 | 0 |
| ESPR | 0 | 0 | 0.00011 | 0 | 0 | 0 | 0 | 0 | 0 | 0 | 0 | 0 |
| FSP | 0 | 0 | 0 | 0 | 0 | 0 | 0 | 0 | 0 | 0 | 0 | 0 |
| FCR | 0 | 0 | 0.2676 | 0 | 0 | 0 | 0.00017 | 0 | 0 | 0 | 0 | 0.00023 |
| EFOX | 0 | 0 | 0 | 0 | 0 | 0 | 7.00E−05 | 0 | 0 | 0 | 0 | 0 |
| FBLD | 0 | 0 | 0 | 0 | 0 | 0 | 0 | 0 | 0 | 0 | 0 | 0 |
| GPIN | 0 | 0 | 0.00039 | 0 | 0 | 0 | 0 | 0 | 0 | 0 | 0 | 0 |
| GSHP | 0.00029 | 0 | 0.00037 | 0 | 0 | 0 | 0 | 0 | 0 | 0 | 0 | 0 |
| GOLD | 0 | 1.00E−05 | 0.4753 | 0 | 0 | 0.00759 | 7.00E−05 | 0 | 0 | 0 | 0 | 0 |
| IBIZ | 0.76932 | 0 | 0.00027 | 0 | 0 | 0 | 0 | 0 | 0 | 0 | 0 | 0 |
| IRSE | 0 | 0 | 0 | 0 | 0 | 0 | 0 | 0 | 0 | 0 | 0 | 0 |
| IRWS | 0 | 0 | 0 | 0 | 0 | 0 | 0.001 | 0 | 0 | 0 | 0 | 0 |
| LAB | 0 | 0 | 0 | 0 | 0.00013 | 6.00E−05 | 0 | 0 | 0 | 0 | 0 | 0 |
| MAST | 0 | 0 | 0 | 0 | 0 | 0 | 0.92848 | 0 | 0 | 0 | 0 | 0 |
| PBGV | 0 | 0 | 0 | 0 | 0 | 0 | 2.00E−05 | 0 | 0 | 0 | 0 | 0 |
| PAPI | 0 | 0 | 0 | 0 | 0 | 0 | 3.00E−05 | 0 | 0 | 0 | 0 | 0 |
| PTWD | 0 | 0 | 0 | 0 | 0 | 0.00346 | 0 | 0 | 0 | 0 | 0 | 0 |
| ROTT | 0 | 0 | 0 | 0 | 0 | 0 | 0.04067 | 0 | 0.00029 | 0 | 0.00043 | 0 |
| STBD | 0.03485 | 0 | 0 | 0 | 0 | 0 | 0 | 0 | 0 | 0 | 0 | 0 |
| SCDH | 0 | 0 | 0 | 0 | 0 | 0 | 1.00E−05 | 0 | 0 | 0 | 0 | 0 |
| SPIN | 0 | 0 | 0 | 0 | 0 | 0 | 0 | 0 | 0 | 0 | 0 | 1.00E−05 |
| SCOL | 0 | 0 | 0 | 0 | 0 | 0 | 0 | 0 | 0 | 0 | 0 | 0 |
| SSCH | 0 | 0 | 0 | 0 | 0 | 0 | 0 | 1.00E−05 | 0 | 0 | 0 | 0.00028 |
| WSSP | 0.0005 | 0 | 0 | 0 | 0 | 1.00E−05 | 0 | 0 | 0 | 0 | 0 | 0 |

TABLE 21B

| | BMD Canid Identification Number (missing genotypes) | | | | | | | | | | Borzoi | | |
|---|---|---|---|---|---|---|---|---|---|---|---|---|---|
| Canid population* | 918 (16) | 883 (6) | 941 (7) | 943 (11) | 21287 (16) | 968 (45) | 970 (17) | 971 (7) | 973 (28) | 976 (9) | 1655 (24) | 978 (0) | 979 (22) |
| AHTR | 0 | 0 | 0 | 0 | 0 | 0 | 0 | 0 | 0 | 0 | 0 | 0 | 0 |
| AMWS | 0 | 0 | 0 | 0 | 0 | 0 | 0 | 0 | 0 | 0 | 0 | 0 | 0 |
| BASS | 0 | 0 | 0 | 0 | 0 | 0 | 0 | 0 | 0 | 0 | 0 | 0.8529 | 0.00981 |
| BEAG | 0 | 0 | 0 | 0 | 0 | 0 | 0 | 0 | 0 | 0 | 0 | 0.00886 | 0 |
| BEAC | 0 | 0 | 0 | 0 | 0 | 0 | 0 | 0 | 0 | 0 | 0 | 0 | 0 |
| BMD | 0.99999 | 0.99999 | 0.99999 | 0.99995 | 0.99999 | 0.99999 | 0.99999 | 0.99999 | 0.99999 | 0.99999 | 0 | 0 | 0 |
| BICH | 0 | 0 | 0 | 0 | 0 | 0 | 0 | 0 | 0 | 0 | 0 | 0 | 0 |
| BORZ | 0 | 0 | 0 | 0 | 0 | 0 | 0 | 0 | 0 | 0 | 0 | 0.06219 | 0 |
| BOX | 0 | 0 | 0 | 0 | 0 | 0 | 0 | 0 | 0 | 0 | 0 | 0 | 0 |
| BULM | 0 | 0 | 0 | 0 | 0 | 0 | 0 | 0 | 0 | 0 | 0 | 0 | 0.0025 |
| ACKR | 0 | 0 | 0 | 0 | 0 | 0 | 0 | 0 | 0 | 0 | 0 | 0 | 0 |
| DACH | 0 | 0 | 0 | 0 | 0 | 0 | 0 | 0 | 0 | 0 | 0.99999 | 0.07511 | 0.98767 |
| DALM | 0 | 0 | 0 | 0 | 0 | 0 | 0 | 0 | 0 | 0 | 0 | 1.00E−05 | 0 |
| ESPR | 0 | 0 | 0 | 0 | 0 | 0 | 0 | 0 | 0 | 0 | 0 | 0 | 0 |
| FSP | 0 | 0 | 0 | 0 | 0 | 0 | 0 | 0 | 0 | 0 | 0 | 0 | 0 |
| FCR | 0 | 0 | 0 | 0 | 0 | 0 | 0 | 0 | 0 | 0 | 0 | 0 | 0 |
| EFOX | 0 | 0 | 0 | 0 | 0 | 0 | 0 | 0 | 0 | 0 | 0 | 4.00E−05 | 0 |
| FBLD | 0 | 0 | 0 | 0 | 0 | 0 | 0 | 0 | 0 | 0 | 0 | 0 | 0 |
| GPIN | 0 | 0 | 0 | 0 | 0 | 0 | 0 | 0 | 0 | 0 | 0 | 0 | 0 |
| GSHP | 0 | 0 | 0 | 0 | 0 | 0 | 0 | 0 | 0 | 0 | 0 | 0 | 0 |
| GOLD | 0 | 0 | 0 | 4.00E−05 | 0 | 0 | 0 | 0 | 0 | 0 | 0 | 0.0001 | 0 |
| IBIZ | 0 | 0 | 0 | 0 | 0 | 0 | 0 | 0 | 0 | 0 | 0 | 0 | 0 |
| IRSE | 0 | 0 | 0 | 0 | 0 | 0 | 0 | 0 | 0 | 0 | 0 | 0 | 0 |
| IRWS | 0 | 0 | 0 | 0 | 0 | 0 | 0 | 0 | 0 | 0 | 0 | 0 | 0 |
| LAB | 0 | 0 | 0 | 0 | 0 | 0 | 0 | 0 | 0 | 0 | 0 | 0.00018 | 0 |
| MAST | 0 | 0 | 0 | 0 | 0 | 0 | 0 | 0 | 0 | 0 | 0 | 4.00E−05 | 0 |
| PBGV | 0 | 0 | 0 | 0 | 0 | 0 | 0 | 0 | 0 | 0 | 0 | 0 | 0 |
| PAPI | 0 | 0 | 0 | 0 | 0 | 0 | 0 | 0 | 0 | 0 | 0 | 0.0005 | 0 |
| PTWD | 0 | 0 | 0 | 0 | 0 | 0 | 0 | 0 | 0 | 0 | 0 | 0 | 0 |
| ROTT | 0 | 0 | 0 | 0 | 0 | 0 | 0 | 0 | 0 | 0 | 0 | 0 | 0 |
| STBD | 0 | 0 | 0 | 0 | 0 | 0 | 0 | 0 | 0 | 0 | 0 | 0 | 0 |
| SCDH | 0 | 0 | 0 | 0 | 0 | 0 | 0 | 0 | 0 | 0 | 0 | 1.00E−05 | 0 |
| SPIN | 0 | 0 | 0 | 0 | 0 | 0 | 0 | 0 | 0 | 0 | 0 | 0 | 0 |
| SCOL | 0 | 0 | 0 | 0 | 0 | 0 | 0 | 0 | 0 | 0 | 0 | 0 | 0 |
| SSCH | 0 | 0 | 0 | 0 | 0 | 0 | 0 | 0 | 0 | 0 | 0 | 0 | 0 |
| WSSP | 0 | 0 | 0 | 0 | 0 | 0 | 0 | 0 | 0 | 0 | 0 | 0 | 0 |

TABLE 21C

| | BOX Canid Identification Number (missing genotypes) | | | | | | | | | | |
|---|---|---|---|---|---|---|---|---|---|---|---|
| Canid population* | 584 (56) | 585 (18) | 583 (14) | 586 (13) | 587 (43) | 588 (0) | 589 (6) | 590 (0) | 997 (0) | 1302 (30) | 1304 (12) |
| AHTR | 0 | 0 | 0 | 0 | 0 | 0 | 0 | 0 | 0 | 0 | 0 |
| AMWS | 0 | 0 | 0 | 0 | 0 | 0 | 0 | 0 | 0 | 0 | 0 |
| BASS | 0 | 0 | 0 | 0 | 0 | 0 | 0 | 0 | 0 | 0 | 0 |
| BEAG | 0 | 0 | 0 | 0 | 0 | 0 | 0 | 0 | 0 | 0 | 0 |
| BEAC | 0 | 0 | 0 | 0 | 0 | 0 | 0 | 0 | 0 | 0 | 0 |
| BMD | 0 | 0 | 0 | 0 | 0 | 0 | 0 | 0 | 0 | 0 | 0 |
| BICH | 0 | 0 | 0 | 0 | 0 | 0 | 0 | 0 | 0 | 0 | 0 |
| BORZ | 0 | 0 | 0 | 0 | 0 | 0 | 0 | 0 | 0 | 0 | 0 |
| BOX | 0.99999 | 0.99999 | 0.99999 | 0.99996 | 0.99996 | 0.99999 | 0.99391 | 0.99999 | 0.99999 | 0.99999 | 0.99999 |
| BULM | 0 | 0 | 0 | 0 | 0 | 0 | 0 | 0 | 0 | 0 | 0 |
| ACKR | 0 | 0 | 0 | 0 | 0 | 0 | 0 | 0 | 0 | 0 | 0 |
| DACH | 0 | 0 | 0 | 0 | 0 | 0 | 0.00153 | 0 | 0 | 0 | 0 |
| DALM | 0 | 0 | 0 | 0 | 0 | 0 | 0 | 0 | 0 | 0 | 0 |
| ESPR | 0 | 0 | 0 | 0 | 0 | 0 | 0 | 0 | 0 | 0 | 0 |
| FSP | 0 | 0 | 0 | 0 | 0 | 0 | 0 | 0 | 0 | 0 | 0 |
| FCR | 0 | 0 | 0 | 0 | 0 | 0 | 0 | 0 | 0 | 0 | 0 |
| EFOX | 0 | 0 | 0 | 0 | 0 | 0 | 0 | 0 | 0 | 0 | 0 |
| FBLD | 0 | 0 | 0 | 0 | 0 | 0 | 0 | 0 | 0 | 0 | 0 |
| GPIN | 0 | 0 | 0 | 0 | 0 | 0 | 0 | 0 | 0 | 0 | 0 |
| GSHP | 0 | 0 | 0 | 0 | 0 | 0 | 0 | 0 | 0 | 0 | 0 |
| GOLD | 0 | 0 | 0 | 3.00E−05 | 0 | 0 | 2.00E−05 | 0 | 0 | 0 | 0 |
| IBIZ | 0 | 0 | 0 | 0 | 0 | 0 | 0 | 0 | 0 | 0 | 0 |
| IRSE | 0 | 0 | 0 | 0 | 0 | 0 | 0 | 0 | 0 | 0 | 0 |
| IRWS | 0 | 0 | 0 | 0 | 0 | 0 | 0 | 0 | 0 | 0 | 0 |
| LAB | 0 | 0 | 0 | 0 | 0 | 0 | 0 | 0 | 0 | 0 | 0 |
| MAST | 0 | 0 | 0 | 0 | 0 | 0 | 0 | 0 | 0 | 0 | 0 |
| PBGV | 0 | 0 | 0 | 0 | 0 | 0 | 0 | 0 | 0 | 0 | 0 |
| PAPI | 0 | 0 | 0 | 0 | 0 | 0 | 0 | 0 | 0 | 0 | 0 |
| PTWD | 0 | 0 | 0 | 0 | 0 | 0 | 0 | 0 | 0 | 0 | 0 |
| ROTT | 0 | 0 | 0 | 0 | 3.00E−05 | 0 | 0.00451 | 0 | 0 | 0 | 0 |
| STBD | 0 | 0 | 0 | 0 | 0 | 0 | 0 | 0 | 0 | 0 | 0 |
| SCDH | 0 | 0 | 0 | 0 | 0 | 0 | 0 | 0 | 0 | 0 | 0 |
| SPIN | 0 | 0 | 0 | 0 | 0 | 0 | 0 | 0 | 0 | 0 | 0 |
| SCOL | 0 | 0 | 0 | 0 | 0 | 0 | 0 | 0 | 0 | 0 | 0 |
| SSCH | 0 | 0 | 0 | 0 | 0 | 0 | 0 | 0 | 0 | 0 | 0 |
| WSSP | 0 | 0 | 0 | 0 | 0 | 0 | 0 | 0 | 0 | 0 | 0 |

TABLE 21D

| | BULM Canid Identification Number (missing genotypes) | | | | | | | | FCR Canid Identification Number (missing genotypes) | | | | |
|---|---|---|---|---|---|---|---|---|---|---|---|---|---|
| Canid population* | 1098 (23) | 1105 (4) | 1106 (16) | 1108 (24) | 1109 (0) | 1110 (5) | 1111 (2) | 1112 (11) | 22417 (29) | 746 (39) | 752 (13) | 839 (33) | 791 (7) |
| AHTR | 0 | 0 | 0 | 0 | 0 | 0 | 0 | 0 | 0 | 0 | 0 | 0 | 0 |
| AMWS | 0 | 0 | 0 | 0 | 0 | 0 | 0 | 0 | 0 | 0 | 0 | 0 | 0 |
| BASS | 0 | 0 | 0 | 0 | 0 | 0 | 0 | 0 | 0 | 0 | 0 | 0 | 0 |
| BEAG | 0 | 0 | 0 | 0 | 0 | 0 | 0 | 0 | 0 | 0 | 0 | 0 | 0 |
| BEAC | 0 | 0 | 0 | 0 | 0 | 0 | 0 | 0 | 0 | 0 | 0 | 0 | 0 |
| BMD | 0 | 0 | 0 | 0 | 0 | 0 | 0 | 0 | 0 | 0 | 0 | 0 | 0 |
| BICH | 0 | 0 | 0 | 0 | 0 | 0 | 0 | 0 | 0 | 0 | 0 | 0 | 0 |
| BORZ | 0 | 0 | 0 | 0 | 0 | 0 | 0 | 0 | 0 | 0 | 0 | 0 | 0 |
| BOX | 0 | 0 | 0 | 0 | 0 | 0 | 0 | 0 | 0 | 0 | 0 | 0 | 0 |
| BULM | 0.99999 | 0.99999 | 0.99998 | 0.99999 | 0.99999 | 0.99999 | 0.99999 | 0.99999 | 0 | 0 | 0 | 0 | 0 |
| ACKR | 0 | 0 | 0 | 0 | 0 | 0 | 0 | 0 | 0 | 0 | 0 | 0 | 0 |
| DACH | 0 | 0 | 0 | 0 | 0 | 0 | 0 | 0 | 0 | 0 | 0 | 0.00017 | 9.00E−05 |
| DALM | 0 | 0 | 0 | 0 | 0 | 0 | 0 | 0 | 0 | 0 | 0 | 0 | 0 |
| ESPR | 0 | 0 | 0 | 0 | 0 | 0 | 0 | 0 | 0 | 0 | 0 | 0 | 0 |
| FSP | 0 | 0 | 0 | 0 | 0 | 0 | 0 | 0 | 0 | 0 | 0 | 0 | 0 |
| FCR | 0 | 0 | 0 | 0 | 0 | 0 | 0 | 0 | 0.99999 | 0.99999 | 0 | 0.99982 | 0.99986 |
| EFOX | 0 | 0 | 0 | 0 | 0 | 0 | 0 | 0 | 0 | 0 | 0 | 0 | 0 |
| FBLD | 0 | 0 | 0 | 0 | 0 | 0 | 0 | 0 | 0 | 0 | 0 | 0 | 0 |
| GPIN | 0 | 0 | 0 | 0 | 0 | 0 | 0 | 0 | 0 | 0 | 0 | 0 | 0 |
| GSHP | 0 | 0 | 0 | 0 | 0 | 0 | 0 | 0 | 0 | 0 | 0 | 0 | 0 |
| GOLD | 0 | 0 | 1.00E−05 | 0 | 0 | 0 | 0 | 0 | 0 | 0 | 0.99997 | 0 | 0 |
| IBIZ | 0 | 0 | 0 | 0 | 0 | 0 | 0 | 0 | 0 | 0 | 0 | 0 | 0 |
| IRSE | 0 | 0 | 0 | 0 | 0 | 0 | 0 | 0 | 0 | 0 | 0 | 0 | 0 |
| IRWS | 0 | 0 | 0 | 0 | 0 | 0 | 0 | 0 | 0 | 0 | 0 | 0 | 0 |
| LAB | 0 | 0 | 0 | 0 | 0 | 0 | 0 | 0 | 0 | 0 | 0 | 0 | 0 |

TABLE 21D-continued

| | BULM Canid Identification Number (missing genotypes) | | | | | | | | FCR Canid Identification Number (missing genotypes) | | | | |
|---|---|---|---|---|---|---|---|---|---|---|---|---|---|
| Canid population* | 1098 (23) | 1105 (4) | 1106 (16) | 1108 (24) | 1109 (0) | 1110 (5) | 1111 (2) | 1112 (11) | 22417 (29) | 746 (39) | 752 (13) | 839 (33) | 791 (7) |
| MAST | 0 | 0 | 0 | 0 | 0 | 0 | 0 | 0 | 0 | 0 | 0 | 0 | 0 |
| PBGV | 0 | 0 | 0 | 0 | 0 | 0 | 0 | 0 | 0 | 0 | 0 | 0 | 0 |
| PAPI | 0 | 0 | 0 | 0 | 0 | 0 | 0 | 0 | 0 | 0 | 0 | 0 | 0 |
| PTWD | 0 | 0 | 0 | 0 | 0 | 0 | 0 | 0 | 0 | 0 | 0 | 0 | 0 |
| ROTT | 0 | 0 | 0 | 0 | 0 | 0 | 0 | 0 | 0 | 0 | 2.00E−05 | 0 | 4.00E−05 |
| STBD | 0 | 0 | 0 | 0 | 0 | 0 | 0 | 0 | 0 | 0 | 0 | 0 | 0 |
| SCDH | 0 | 0 | 0 | 0 | 0 | 0 | 0 | 0 | 0 | 0 | 0 | 0 | 0 |
| SPIN | 0 | 0 | 0 | 0 | 0 | 0 | 0 | 0 | 0 | 0 | 0 | 0 | 0 |
| SCOL | 0 | 0 | 0 | 0 | 0 | 0 | 0 | 0 | 0 | 0 | 0 | 0 | 0 |
| SSCH | 0 | 0 | 0 | 0 | 0 | 0 | 0 | 0 | 0 | 0 | 0 | 0 | 0 |
| WSSP | 0 | 0 | 0 | 0 | 0 | 0 | 0 | 0 | 0 | 0 | 0 | 0 | 0 |

TABLE 21E

| | DACH Canid Identification Number (missing genotypes) | | | | | | | | | |
|---|---|---|---|---|---|---|---|---|---|---|
| Canid population* | 20345 (8) | 20274 (14) | 1036 (19) | 1037 (9) | 1038 (26) | 1048 (15) | 1049 (10) | 1050 (8) | 1060 (13) | 1061 (28) |
| AHTR | 0 | 0 | 0 | 0 | 0 | 0 | 0 | 0 | 0 | 0 |
| AMWS | 0 | 0 | 0 | 0 | 0 | 0 | 0 | 0 | 0 | 0 |
| BASS | 0 | 0 | 0 | 5.00E−05 | 0 | 0 | 0 | 0 | 0 | 0 |
| BEAG | 0 | 0 | 0 | 0 | 2.00E−05 | 0 | 0 | 0 | 0 | 0 |
| BEAC | 0 | 0 | 0 | 0 | 0 | 0 | 0 | 0 | 0 | 0 |
| BMD | 0 | 0 | 0 | 0 | 0 | 0 | 0 | 0 | 0 | 0 |
| BICH | 0 | 0 | 0 | 0 | 0 | 0 | 0 | 0 | 0 | 0 |
| BORZ | 0.00012 | 0 | 0 | 0 | 0 | 0 | 0 | 0 | 0 | 0 |
| BOX | 0 | 0 | 0 | 0 | 0 | 0 | 0 | 0 | 0 | 0 |
| BULM | 0.0001 | 0 | 0 | 0 | 0 | 0 | 0 | 0 | 0 | 0 |
| ACKR | 0 | 0 | 0 | 0 | 0 | 0 | 0 | 0 | 0 | 0 |
| DACH | 0.99971 | 4.00E−05 | 0.99837 | 0.99993 | 0.99805 | 0.99999 | 0.99689 | 0.99999 | 0.99998 | 0.66498 |
| DALM | 0 | 0 | 0 | 0 | 0 | 0 | 0 | 0 | 0 | 0 |
| ESPR | 0 | 0 | 0 | 0 | 0 | 0 | 0 | 0 | 0 | 0 |
| FSP | 0 | 0 | 0 | 0 | 0 | 0 | 0 | 0 | 0 | 0 |
| FCR | 0 | 0 | 0 | 0 | 2.00E−05 | 0 | 0 | 0 | 0 | 0 |
| EFOX | 0 | 0 | 0 | 0 | 0 | 0 | 0 | 0 | 0 | 0 |
| FBLD | 0 | 0 | 0 | 0 | 0 | 0 | 0 | 0 | 0 | 0 |
| GPIN | 0 | 0 | 0 | 0 | 0 | 0 | 0 | 0 | 0 | 0 |
| GSHP | 0 | 0 | 0 | 0 | 0 | 0 | 0 | 0 | 0 | 0 |
| GOLD | 0 | 0 | 0.00162 | 0 | 0.00188 | 0 | 0.00308 | 0 | 1.00E−05 | 1.00E−05 |
| IBIZ | 0 | 0 | 0 | 0 | 0 | 0 | 0 | 0 | 0 | 0 |
| IRSE | 1.00E−05 | 0 | 0 | 0 | 0 | 0 | 0 | 0 | 0 | 0 |
| IRWS | 0 | 0 | 0 | 0 | 0 | 0 | 0 | 0 | 0 | 0 |
| LAB | 2.00E−05 | 0 | 0 | 0 | 0 | 0 | 0 | 0 | 0 | 0 |
| MAST | 0 | 0 | 0 | 0 | 0 | 0 | 0 | 0 | 0 | 0 |
| PBGV | 0 | 0 | 0 | 0 | 0 | 0 | 0 | 0 | 0 | 0 |
| PAPI | 0 | 0 | 0 | 0 | 0 | 0 | 0 | 0 | 0 | 0 |
| PTWD | 0 | 0 | 0 | 0 | 0 | 0 | 0 | 0 | 0 | 0 |
| ROTT | 0 | 0.99994 | 0 | 0 | 0 | 0 | 1.00E−05 | 0 | 0 | 0.33498 |
| STBD | 0 | 0 | 0 | 0 | 0 | 0 | 0 | 0 | 0 | 0 |
| SCDH | 0 | 0 | 0 | 0 | 0 | 0 | 0 | 0 | 0 | 0 |
| SPIN | 0 | 0 | 0 | 0 | 0 | 0 | 0 | 0 | 0 | 0 |
| SCOL | 0 | 0 | 0 | 0 | 0 | 0 | 0 | 0 | 0 | 0 |
| SSCH | 0 | 0 | 0 | 0 | 0 | 0 | 0 | 0 | 0 | 0 |
| WSSP | 0 | 0 | 0 | 0 | 0 | 0 | 0 | 0 | 0 | 0 |

TABLE 21F

| | GOLD Canid Identification Number (missing genotypes) | | | | | | | | | |
|---|---|---|---|---|---|---|---|---|---|---|
| Canid population* | 816 (0) | 807 (1) | 50 (10) | 614 (16) | 18477 (26) | 591 (7) | 592 (14) | 593 (22) | 603 (27) | 604 (4) |
| AHTR | 0 | 0 | 0 | 0 | 0 | 0 | 0 | 0 | 0 | 0 |
| AMWS | 0 | 0 | 0 | 0 | 0 | 0 | 0 | 0 | 0 | 0 |
| BASS | 0 | 0 | 0 | 0 | 0 | 0 | 0 | 0 | 0 | 0 |

TABLE 21F-continued

| | GOLD Canid Identification Number (missing genotypes) | | | | | | | | |
|---|---|---|---|---|---|---|---|---|---|
| Canid population* | 816 (0) | 807 (1) | 50 (10) | 614 (16) | 18477 (26) | 591 (7) | 592 (14) | 593 (22) | 603 (27) | 604 (4) |
| BEAG | 0 | 0 | 6.00E−05 | 0 | 0 | 0 | 0 | 0 | 0 | 0 |
| BEAC | 0 | 0 | 0 | 0 | 0 | 0 | 0 | 0 | 0 | 0 |
| BMD | 0 | 0 | 0 | 0.19213 | 0 | 0 | 0 | 0 | 0 | 0 |
| BICH | 0 | 0 | 0 | 0 | 0 | 0 | 0 | 0 | 0 | 0 |
| BORZ | 0 | 0 | 0 | 0 | 0 | 0 | 0 | 0 | 0 | 0 |
| BOX | 0 | 0 | 0 | 0 | 0 | 0 | 0 | 0 | 0 | 0 |
| BULM | 1.00E−05 | 0 | 0 | 0 | 0 | 0 | 0.00011 | 0 | 0 | 0 |
| ACKR | 0 | 0 | 0 | 0 | 0 | 0 | 0 | 0 | 0 | 0 |
| DACH | 0 | 0 | 0.7605 | 7.00E−05 | 0 | 0 | 0 | 0.00999 | 0.00015 | 0 |
| DALM | 0 | 0 | 0 | 0 | 0 | 0 | 0 | 0 | 0 | 0 |
| ESPR | 0 | 0 | 0 | 0 | 0 | 0 | 0 | 0 | 0 | 0 |
| FSP | 0 | 0 | 0 | 0 | 0 | 0 | 0 | 0 | 0 | 0 |
| FCR | 0 | 0 | 0 | 0 | 0 | 0 | 0 | 0 | 0 | 0 |
| EFOX | 0 | 0 | 0 | 0 | 0 | 0 | 0 | 0 | 0 | 0 |
| FBLD | 0 | 0 | 0 | 0 | 0 | 0 | 0 | 0 | 0 | 0 |
| GPIN | 0 | 0 | 0 | 0 | 0 | 0 | 0 | 0 | 0 | 0 |
| GSHP | 0 | 0 | 0 | 0 | 0 | 0 | 0 | 0 | 0 | 0 |
| GOLD | 0.99998 | 0.99999 | 0.23937 | 0.80778 | 0.99999 | 0.78123 | 0.99987 | 0.99 | 0.99984 | 0.99979 |
| IBIZ | 0 | 0 | 3.00E−05 | 0 | 0 | 0 | 0 | 0 | 0 | 0 |
| IRSE | 0 | 0 | 0 | 0 | 0 | 0 | 0 | 0 | 0 | |
| IRWS | 0 | 0 | 0 | 0 | 0 | 0 | 0 | 0 | 0 | 0 |
| LAB | 0 | 0 | 0 | 0 | 0 | 0 | 0 | 0 | 0 | 0 |
| MAST | 0 | 0 | 0 | 0 | 0 | 0 | 0 | 0 | 0 | 0 |
| PBGV | 0 | 0 | 0 | 0 | 0 | 0 | 0 | 0 | 0 | 0 |
| PAPI | 0 | 0 | 0 | 0 | 0 | 0 | 0 | 0 | 0 | 0 |
| PTWD | 0 | 0 | 0 | 0 | 0 | 0 | 0 | 0 | 0 | 0 |
| ROTT | 0 | 0 | 0 | 0 | 0 | 0.21876 | 0 | 0 | 0 | 0.0002 |
| STBD | 0 | 0 | 0 | 0 | 0 | 0 | 0 | 0 | 0 | 0 |
| SCDH | 0 | 0 | 0 | 0 | 0 | 0 | 0 | 0 | 0 | 0 |
| SPIN | 0 | 0 | 0 | 0 | 0 | 0 | 0 | 0 | 0 | 0 |
| SCOL | 0 | 0 | 0 | 0 | 0 | 0 | 0 | 0 | 0 | 0 |
| SSCH | 0 | 0 | 0 | 0 | 0 | 0 | 0 | 0 | 0 | 0 |
| WSSP | 0 | 0 | 0 | 0 | 0 | 0 | 0 | 0 | 0 | 0 |

TABLE 21G

| | ROTT Canid Identification Number (missing genotypes) | | | | | | | | |
|---|---|---|---|---|---|---|---|---|---|
| Canid population* | 817 (2) | 818 (2) | 886 (2) | 896 (0) | 22720 (15) | 1014 (14) | 1028 (0) | 1029 (26) | 1033 (79) | 1034 (0) |
| AHTR | 0 | 0 | 0 | 0 | 0 | 0 | 0 | 0 | 0 | 0 |
| AMWS | 0 | 0 | 0 | 0 | 0 | 0 | 0 | 0 | 0 | 0 |
| BASS | 0 | 0 | 0 | 0 | 0 | 0 | 0 | 0 | 0 | 0 |
| BEAG | 0 | 0 | 0 | 0 | 0 | 2.00E−05 | 0 | 0 | 0 | 0 |
| BEAC | 0 | 0 | 0 | 0 | 0 | 0 | 0 | 0 | 0 | 0 |
| BMD | 0 | 0 | 0 | 0 | 0 | 0 | 0 | 0 | 0 | 0 |
| BICH | 0 | 0 | 0 | 0 | 0 | 0 | 0 | 0 | 0 | 0 |
| BORZ | 0 | 0 | 0 | 0 | 0 | 0 | 0 | 0 | 0 | 0 |
| BOX | 0 | 0 | 0 | 0 | 0 | 0 | 0 | 0 | 0 | 0 |
| BULM | 0 | 0 | 0 | 0 | 0 | 0 | 0 | 0 | 0 | 0 |
| ACKR | 0 | 0 | 0 | 0 | 0 | 0 | 0 | 0 | 0 | 0 |
| DACH | 0 | 0 | 0 | 0 | 0 | 0.0017 | 0 | 0 | 0.00056 | 0 |
| DALM | 0 | 0 | 0 | 0 | 0 | 0 | 0 | 0 | 0 | 0 |
| ESPR | 0 | 0 | 0 | 0 | 0 | 0 | 0 | 0 | 0 | 0 |
| FSP | 0 | 0 | 0 | 0 | 0 | 0 | 0 | 0 | 0 | 0 |
| FCR | 0 | 0 | 0 | 0 | 0 | 0 | 0 | 0 | 0 | 0 |
| EFOX | 0 | 0 | 0 | 0 | 0 | 0 | 0 | 0 | 0 | 0 |
| FBLD | 0 | 0 | 0 | 0 | 0 | 0 | 0 | 0 | 0 | 0 |
| GPIN | 0 | 0 | 0 | 0 | 0 | 0 | 0 | 0 | 0 | 0 |
| GSHP | 0 | 0 | 0 | 0 | 0 | 0 | 0 | 0 | 0 | 0 |
| GOLD | 0.02636 | 0 | 0 | 0 | 0 | 5.00E−05 | 0 | 0 | 0 | 0 |
| IBIZ | 0 | 0 | 0 | 0 | 0 | 0 | 0 | 0 | 0 | 0 |
| IRSE | 0 | 0 | 0 | 0 | 0 | 0 | 0 | 0 | 0 | 0 |
| IRWS | 0 | 0 | 0 | 0 | 0 | 0 | 0 | 0 | 0 | 0 |
| LAB | 0 | 0 | 0 | 0 | 0 | 0 | 0 | 0 | 0 | 0 |
| MAST | 3.00E−05 | 0 | 0 | 0 | 0 | 0 | 0 | 0 | 0 | 0 |
| PBGV | 0 | 0 | 0 | 0 | 0 | 0 | 0 | 0 | 0 | 0 |
| PAPI | 0 | 0 | 0 | 0 | 0 | 0 | 0 | 0 | 0 | 0 |

TABLE 21G-continued

| | ROTT Canid Identification Number (missing genotypes) | | | | | | | | | |
|---|---|---|---|---|---|---|---|---|---|---|
| Canid population* | 817 (2) | 818 (2) | 886 (2) | 896 (0) | 22720 (15) | 1014 (14) | 1028 (0) | 1029 (26) | 1033 (79) | 1034 (0) |
| PTWD | 0 | 0 | 0 | 0 | 0 | 0 | 0 | 0 | 0 | 0 |
| ROTT | 0.97359 | 0.99999 | 0.99999 | 0.99999 | 0.99999 | 0.9982 | 0.99999 | 0.99998 | 0.99943 | 0.99999 |
| STBD | 0 | 0 | 0 | 0 | 0 | 0 | 0 | 0 | 0 | 0 |
| SCDH | 0 | 0 | 0 | 0 | 0 | 0 | 0 | 0 | 0 | 0 |
| SPIN | 0 | 0 | 0 | 0 | 0 | 0 | 0 | 0 | 0 | 0 |
| SCOL | 0 | 0 | 0 | 0 | 0 | 0 | 0 | 0 | 0 | 0 |
| SSCH | 0 | 0 | 0 | 0 | 0 | 0 | 0 | 0 | 0 | 0 |
| WSSP | 0 | 0 | 0 | 0 | 0 | 0 | 0 | 0 | 0 | 0 |

TABLE 21H

| | MAST Canid ID NO (missing genotypes) | | | | | | SCOL Canid ID NO (missing genotypes) | | |
|---|---|---|---|---|---|---|---|---|---|
| Canid population[a] | 23967 (14) | 991 (6) | 1015 (9) | 1016 (11) | 992 (1) | 1013 (80) | 15628 (24) | 375 (12) | 363 (12) |
| AHTR | 0 | 0 | 0 | 0 | 0 | 0 | 0 | 0 | 0 |
| AMWS | 0 | 0 | 0 | 0 | 0 | 0 | 0 | 0 | 0 |
| BASS | 0 | 0 | 0 | 0 | 0 | 0 | 0 | 0 | 0 |
| BEAG | 0 | 0 | 0 | 0 | 0 | 0 | 0 | 0 | 0 |
| BEAC | 0 | 0 | 0 | 0 | 0 | 0 | 0 | 0 | 0 |
| BMD | 0 | 0 | 0 | 0 | 0 | 0 | 0 | 0 | 0 |
| BICH | 0 | 0 | 0 | 0 | 0 | 0 | 0 | 0 | 0 |
| BORZ | 0 | 0 | 0 | 0 | 0 | 0 | 0 | 0 | 0 |
| BOX | 0 | 0 | 0 | 0 | 0 | 0 | 0 | 0 | 0 |
| BULM | 0 | 0 | 0 | 0 | 0 | 3.00E−05 | 0 | 4.00E−05 | 0 |
| ACKR | 0 | 0 | 0 | 0 | 0 | 0 | 0 | 0 | 0 |
| DACH | 0 | 0 | 0 | 0 | 0 | 0 | 0.00413 | 0 | 0.00057 |
| DALM | 0 | 0 | 0 | 0 | 0 | 0 | 0 | 0 | 0 |
| ESPR | 0 | 0 | 0 | 0 | 0 | 0 | 0 | 0 | 0 |
| FSP | 0 | 0 | 0 | 0 | 0 | 0 | 0 | 0.00503 | 0 |
| FCR | 0 | 0 | 0 | 0 | 0 | 0 | 0 | 0 | 0 |
| EFOX | 0 | 0 | 0 | 0 | 0 | 0 | 0 | 0 | 0 |
| FBLD | 0 | 0 | 0 | 0 | 0 | 0 | 9.00E−05 | 1.00E−05 | 0 |
| GPIN | 0 | 0 | 0 | 0 | 0 | 0 | 0 | 0 | 0 |
| GSHP | 0 | 0 | 0 | 0 | 0 | 0 | 0 | 0 | 0 |
| GOLD | 0.00012 | 0 | 0 | 0 | 0.00146 | 0 | 4.00E−05 | 0.00043 | 0.00105 |
| IBIZ | 0 | 0 | 0 | 0 | 0 | 0 | 0 | 0 | 0 |
| IRSE | 0 | 0 | 0 | 0 | 0 | 0 | 0 | 0 | 0 |
| IRWS | 0 | 0 | 0 | 0 | 0 | 0 | 0 | 0 | 0 |
| LAB | 0 | 0 | 0 | 0 | 0 | 0 | 0 | 0 | 0 |
| MAST | 0.99987 | 0.99999 | 0.99999 | 0.99999 | 0.99852 | 0.99995 | 0 | 0 | 0 |
| PBGV | 0 | 0 | 0 | 0 | 0 | 0 | 0 | 0 | 0 |
| PAPI | 0 | 0 | 0 | 0 | 0 | 0 | 0 | 0 | 0 |
| PTWD | 0 | 0 | 0 | 0 | 0 | 0 | 0 | 0 | 0 |
| ROTT | 0 | 0 | 0 | 0 | 0 | 0 | 0 | 0 | 0 |
| STBD | 0 | 0 | 0 | 0 | 0 | 0 | 0 | 0 | 0 |
| SCDH | 0 | 0 | 0 | 0 | 0 | 0 | 0 | 0 | 0 |
| SPIN | 0 | 0 | 0 | 0 | 0 | 0 | 0 | 0 | 0 |
| SCOL | 0 | 0 | 0 | 0 | 0 | 0 | 0.99572 | 0.99445 | 0.99837 |
| SSCH | 0 | 0 | 0 | 0 | 0 | 0 | 0 | 0 | 0 |
| WSSP | 0 | 0 | 0 | 0 | 0 | 0 | 0 | 0 | 0 |

[a]See Table 5 for abbreviations of canid populations.
KBB: pbe

The embodiments of the invention in which an exclusive property or privilege is claimed are defined as follows:

1. A method for determining the contributions of canid populations to a canid genome, comprising:
   (a) genotyping a sample obtained from a test canid to determine the identity of one or both alleles present in the test canid genome for each of a set of markers, wherein the set of markers is indicative of the contributions of canid populations to the genome of the test canid;
   (b) using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population; and
   (c) determining the contributions of canid populations to the test canid genome.

2. The method of claim 1, wherein the set of markers comprises at least about five markers.

3. The method of claim 1, wherein the set of markers comprises microsatellite markers.

4. The method of claim 3, wherein the micro satellite markers comprise at least 5 of the micro satellite markers set forth in Table 1.

5. The method of claim 1, wherein the set of markers comprises single nucleotide polymorphisms (SNPs).

6. The method of claim 5, wherein the SNP markers comprise at least 5 of the SNP markers set forth in Table 2.

7. The method of claim 1, wherein the set of markers comprises one or more population-specific markers.

8. The method of claim 7, wherein the one or more population-specific markers comprise one or more SNP markers.

9. The method of claim 8, wherein the one or more population specific SNP markers are selected from the group consisting of position 82 of SEQ ID NO: 202, position 57 of SEQ ID NO: 205, position 88 of SEQ ID NO: 211, position 76 of SEQ ID NO: 215, position 112 of SEQ ID NO: 218, position 50 of SEQ ID NO: 223, position 130 of SEQ ID NO: 223, position 246 of SEQ ID NO: 226, position 224 of SEQ ID NO: 227, position 181 of SEQ ID NO: 229, position 168 of SEQ ID NO: 231, position 196 of SEQ ID NO: 232, position 71 of SEQ ID NO: 233, and position 93 of SEQ ID NO: 239.

10. The method of claim 1, wherein the genotype information in each canid population profile comprises identities of one or both alleles of each of the set of markers.

11. The method of claim 1, wherein the genotype information in each canid population profile comprises allele frequencies for at least one allele of each of the set of markers.

12. The method of claim 1, wherein the database of canid population profiles comprises between about five and about 500 canid population profiles.

13. The method of claim 1, wherein the database of canid populations profiles comprise profiles for at least about five American Kennel Club registered breeds.

14. The method of claim 1, wherein the set of markers comprises fewer than about 1500 SNP markers and wherein the method determines the contributions of at least 87 canid populations to the test canid genome.

15. The method of claim 1, wherein the set of markers comprises fewer than about 200 SNP markers and wherein the method determines the contributions of at least 87 canid populations to the test canid genome.

16. The method of claim 1, wherein step (a) comprises amplifying genomic DNA of the test canid using primers specific for each of the set of markers and determining the size of the amplification product.

17. The method of claim 1, wherein the algorithm according to step (b) comprises a genotype clustering program.

18. The method of claim 1, wherein the algorithm according to step (b) comprises an assignment algorithm.

19. The method of claim 1, wherein applying the algorithm according to step (b) comprises determining the probability that a specific canid population contributed to the genome of the test canid by determining the conditional probability that the alleles in the test canid genome would occur in the specific canid population divided by the sum of conditional probabilities that the alleles in the test canid genome would occur in each canid population in the database.

20. The method of claim 1, wherein step (b) comprises discriminating between the contributions of two or more genetically related canid populations to the test canid genome by comparing the alleles in the test canid genome to a database comprising profiles of the two or more genetically related canid populations.

21. The method of claim 20, wherein the two or more genetically related canid populations comprise Belgian Sheep Dog and Belgian Tervuren.

22. The method of claim 20, wherein the two or more genetically related canid populations comprise Collie and Shetland Sheep Dog.

23. The method of claim 20, wherein the two or more genetically related canid populations comprise Whippet and Greyhound.

24. The method of claim 20, wherein the two or more genetically related canid populations comprise Siberian Husky and Alaskan Malamute.

25. The method of claim 20, wherein the two or more genetically related canid populations comprise Mastiff and Bullmastiff.

26. The method of claim 20, wherein the two or more genetically related canid populations comprise Greater Swiss Mountain Dog and Bernese Mountain Dog.

27. The method of claim 20, wherein the two or more genetically related canid populations comprise West Highland White Terrier and Cairn Terrier.

28. The method of claim 20, wherein the two or more genetically related canid populations comprise Lhasa Apso, Shih Tzu, and Pekinese.

29. The method of claim 1 further comprising the step of providing a document displaying the contributions of one or more canid populations to the genome of the test canid genome.

30. The method of claim 29, wherein the document provides additional information regarding the one or more canid populations that contributed to the genome of the test canid or the test canid.

31. The method of claim 30, wherein the additional information is health-related information.

32. The method of claim 30, wherein the additional information is insurance information.

33. The method of claim 29, wherein the document provides a certification of the contributions of one or more canid populations to the genome of the test canid genome.

34. The method of claim 29, wherein the document provides a representation of the one or more canid populations that contributed to the genome of the test canid.

35. A method for defining one or more canid populations, comprising:
   (a) performing a genotyping assay on a set of canid genomes, to determine the identity of one or both alleles for each of a set of markers, wherein the set of markers is indicative of the contributions of canid populations to the genomes of each member of the set of canids; and
   (b) applying a computer-implemented statistical model to define one or more distinct canid populations, wherein one or more distinct canid populations are characterized by a set of allele frequencies for each marker in the set of markers.

36. A computer readable medium comprising stored thereon:
   (a) a data structure stored thereon for use in distinguishing canid populations, the data structure comprising:
      (i) a marker field, which is capable of storing the name of a marker or of an allele of the marker; and
      (ii) a genotype information field, which is capable of storing genotype information for the marker in a canid population, wherein a record comprises an instantiation of the marker field and an instantiation of the genotype information field and a set of records represents a canid population profile; and
   (b) computer-executable instructions for implementing a method for determining the contributions of canid populations to a canid genome, comprising:
      (i) obtaining the identity of one or both alleles in a test canid genome for each of a set of markers; and
      (ii) determining the contributions of canid populations to the test canid genome by comparing the alleles in the test canid genome to a database comprising canid population profiles, wherein each canid population profile comprises genotype information for the set of markers in the canid population.

37. A computer-readable medium comprising a data structure stored thereon for use in distinguishing canid populations, the data structure comprising:
   (a) a marker field, which is capable of storing the name of a marker or of an allele of the marker; and
   (b) a genotype information field, which is capable of storing genotype information for the marker in a canid population, wherein a record comprises an instantiation of the marker field and an instantiation of the genotype information field and a set of records represents a canid population profile, wherein the marker field comprises a set of markers indicative of the contributions of canid populations to the genome of a test canid.

38. The computer readable medium of claim 36 wherein the marker field comprises a set of markers indicative of the contributions of canid populations to the genome of a test canid.

39. A method for determining the contributions of canid populations to a canid genome, comprising performing a genotyping assay on a sample obtained from a test canid to determine the identity of one or both alleles present in the test canid genome for each of a set of markers, wherein the set of markers is indicative of the contribution of canid populations to the genome of the test canid.

40. The method of claim 39, wherein the set of markers comprises at least five markers.

41. The method of claim 39, wherein the set of markers comprises microsatellite markers.

42. The method of claim 39, wherein the set of markers comprises single nucleotide polymorphisms (SNPs).

43. The method of claim 39, wherein the set of markers comprises one or more population-specific markers.

44. The method of claim 43, wherein the population-specific markers are SNP markers.

* * * * *

UNITED STATES PATENT AND TRADEMARK OFFICE
CERTIFICATE OF CORRECTION

PATENT NO. : 7,729,863 C1
APPLICATION NO. : 95/000621
DATED : September 25, 2012
INVENTOR(S) : Elaine Ostrander et al.

Page 1 of 1

It is certified that error appears in the above-identified patent and that said Letters Patent is hereby corrected as shown below:

Title page, item "(73) Assignees:" on the cover page of the Reexamination Certificate reading:

"The United States of America as represented by the National Institutes of Health (NIH), Washington, DC (US); The United States of America as represented by the Department of Health and Human Services (DHHS), Washington, DC (US)" should read --Fred Hutchinson Cancer Research Center, Seattle, Washington (US)--

Signed and Sealed this
First Day of January, 2013

David J. Kappos
*Director of the United States Patent and Trademark Office*

(12) INTER PARTES REEXAMINATION CERTIFICATE (0458th)
United States Patent
Ostrander et al.

(10) Number: US 7,729,863 C1
(45) Certificate Issued: Sep. 25, 2012

(54) METHODS AND MATERIALS FOR CANINE BREED IDENTIFICATION

(75) Inventors: Elaine Ostrander, Seattle, WA (US); Leonid Kruglyak, Seattle, WA (US); Heidi G Parker, Seattle, WA (US); Lisa V Kim, Sammamish, WA (US); Matthew Stephens, Seattle, WA (US); Tiffany B Malek, Seattle, WA (US); Nathan B Sutter, Seattle, WA (US); Scott Carlson, Seattle, WA (US)

(73) Assignees: The United States of America as represented by the National Institutes of Health (NIH), Washington, DC (US); The United States of America as represented by the Department of Health and Human Services (DHHS), Washington, DC (US)

Reexamination Request:
No. 95/000,621, Apr. 28, 2011

Reexamination Certificate for:
Patent No.: 7,729,863
Issued: Jun. 1, 2010
Appl. No.: 10/536,369
Filed: Feb. 1, 2006

(22) PCT Filed: Dec. 15, 2004
(86) PCT No.: PCT/US2004/042267
§ 371 (c)(1),
(2), (4) Date: Feb. 1, 2006
(87) PCT Pub. No.: WO2005/059110
PCT Pub. Date: Jun. 30, 2005

Related U.S. Application Data

(60) Provisional application No. 60/530,464, filed on Dec. 17, 2003.

(51) Int. Cl.
*G06F 7/00* (2006.01)

(52) U.S. Cl. .............................. 702/19; 435/6.1; 702/20; 702/13

(58) Field of Classification Search ........................ None
See application file for complete search history.

(56) References Cited

To view the complete listing of prior art documents cited during the proceeding for Reexamination Control Number 95/000,621, please refer to the USPTO's public Patent Application Information Retrieval (PAIR) system under the Display References tab.

*Primary Examiner*—Shri Ponnaluri

(57) ABSTRACT

In one aspect, the invention provides methods for determining the contributions of canid populations to a canid genome. The methods comprise the steps of: (a) obtaining the identity of one or both alleles in a test canid genome for each of a set of markers; and (b) determining the contributions of canid populations to the test canid genome by comparing the alleles in the test canid genome to a database comprising canid population profiles, wherein each canid population profile comprises genotype information for the set of markers in the canid populations.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5, 7, 8, 29 and 30 are cancelled.

Claims 2-4, 10-13, 16-28, 31 and 33-39 are determined to be patentable as amended.

Claims 40-44, dependent on an amended claim, are determined to be patentable.

New claims 45-49 are added and determined to be patentable.

Claims 6, 9, 14, 15 and 32 were not reexamined.

2. The method of claim [1] *13*, wherein the set of markers comprises at least about five markers.

3. The method of claim [1] *13*, wherein the set of markers comprises microsatellite markers.

4. [The method of claim 3, wherein the] *A method for determining the contributions of canid populations to a canid genome, comprising:*
  *(a) genotyping a sample obtained from a test canid to determine the identity of one or both alleles present in the test canid genome for each of a set of markers, wherein the set of markers is indicative of the contributions of canid populations to the genome of the test canid and wherein the set of markers comprises* microsatellite markers *that* comprise at least 5 of the microsatellite markers set forth in Table 1;
  *(b) using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population; and,*
  *(c) determining the contributions of canid populations to the test canid genome.*

10. The method of claim [1] *13*, wherein the genotype information in each canid population profile comprises identities of one or both alleles of each of the set of markers.

11. The method of claim [1] *13*, wherein the genotype information in each canid population profile comprises allele frequencies for at least one allele of each of the set of markers.

12. [The method of claim 1,] *A method for determining the contributions of canid populations to a canid genome, comprising:*
  *(a) genotyping a sample obtained from a test canid to determine the identity of one or both alleles present in the test canid genome for each of a set of markers, wherein the set of markers is indicative of the contributions of canid populations to the genome of the test canid;*
  *(b) using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein the database of canid population profiles comprises between about five and about 500 canid population profiles; and*
  *(c) determining the contributions of canid populations to the test canid genome.*

13. [The method of claim 1, wherein] *A method for determining the contributions of canid populations to a canid genome, comprising:*
  *(a) genotyping a sample obtained from a test canid to determine the identity of one or both alleles present in the test canid genome for each of a set of markers, wherein the set of markers is indicative of the contributions of canid populations to the genome of the test canid;*
  *(b) using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population and* the database of canid populations profiles [comprise] *comprises* profiles for at least about five American Kennel Club registered breeds; *and*
  *(c) determining the contributions of canid populations to the test canid genome.*

16. The method of claim [1] *13*, wherein step (a) comprises amplifying genomic DNA of the test canid using primers specific for each of the set of markers and determining the size of the amplification product.

17. The method of claim [1] *13*, wherein the algorithm according to step (b) comprises a genotype clustering program.

18. The method of claim [1] *13*, wherein the algorithm according to step (b) comprises an assignment algorithm.

19. The method of claim [1] *13*, wherein applying the algorithm according to step (b) comprises determining the probability that a specific canid population contributed to the genome of the test canid by determining the conditional probablility that the alleles in the test canid genome would occur in the specific canid population divided by the sum of conditional probabilities that the alleles in the test canid genome would occur in each canid population in the database.

20. The method of claim [1] *13*, wherein step (b) comprises discriminating between the contributions of two or more genetically related canid populations to the test canid genome by comparing the alleles in the test canid genome to a database comprising profiles of the two or more genetically related canid populations.

21. [The method of claim 20] *A method for determining the contributions of canid populations to a canid genome, comprising:*
  *(a) genotyping a sample obtained from a test canid to determine the identity of one or both alleles present in* the test canid genome for each of a set of markers, wherein the set of markers is indicative of the contributions of canid populations to the genome of the test canid;

(b) using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome by comparing the alleles in the test canid genome to a database comprising profiles of the two or more genetically related canid populations, and wherein the two or more genetically related canid populations comprise Belgian Sheep Dog and Belgian Tervuren; and (c) determining the contributions of canid populations to the test canid genome.

22. [The method of claim 20.] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome by comparing the alleles in the test canid genome to a database comprising profiles of the two or more genetically related canid populations, and wherein the two or more genetically related canid populations comprise* Collie and Shetland Sheep Dog; *and*

(c) *determining the contributions of canid populations to the test canid genome.*

23. [The method of claim 20.] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome* by comparing the alleles in the test canid genome to a database comprising profiles of the two or more genetically related canid populatons, and wherein the two or more genetically related canid populations comprise Whippet and Greyhound; *and*

(c) *determining the contributions of canid populations to the test canid genome.*

24. [The method of claim 20.] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome by comparing the alleles in the test canid genome to a database comprising profiles of the two or more genetically related canid populations, and wherein the two or more genetically related canid populations comprise* Siberian Husky and Alaskan Malamute; *and*

(c) *determining the contributions of canid populations to the test canid genome.*

25. [The method of claim 20.] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome by comparing the alleles in the test canid genome to a database comprising profiles of the two or more genetically related canid populations, and wherein the two or more genetically related canid populations comprise* Mastiff and Bullmastiff; *and*

(c) *determining the contributions of canid populations to the test canid genome.*

26. [The method of claim 20.] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome by comparing the alleles in the test canid genome to a database comprising profiles of the two or more genetically related canid populations, and wherein the two or more genetically related canid populations comprise Greater Swiss Mountain Dog and Bernese Mountain Dog; and (c) determining the contributions of canid populations to the test canid genome.

27. [The method of claim 20,] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more genetically related canid populations to the test canid genome by comparing the alleles in the test canid genome to a database comprising profiles of the two or more genetically related canid populations, and* wherein the two or more genetically related canid populations comprise West Highland White Terrier and Cairn Terrier; *and*

(c) *determining the contributions of canid populations to the test canid genome.*

28. [The method of claim 20,] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population, and wherein step (b) comprises discriminating between the contributions of two or more geneticfally related canid populations to the test canid genome by comparing the alleles in the test canid genome to a database comprising profiles of the two or more genetically related canid populations, and* wherein the two or more genetically related canid populations comprise Lhasa Apso, Shih Tzu, and Pekinese; *and*

(c) *determining the contributions of canid populations to the test canid genome.*

31. [The method of claim 1,] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population; and*

(c) *determining the contributions of canid populations to the test canid genome, and further providing a document displaying the contributions of one or more canid populations to the genome of the test canid genome, wherein the document provides additional information regarding the one or more canid populations that contributed to the genome of the test canid or the test canid and wherein the additional information is health-related information.*

33. [The method of claim 29,] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both alleles for each of the set of markers determined to be present in the test canid genome to a database comprising a plurality of canid population profiles, wherein each canid population profile comprises genotype information for the set of markers in the canid population; and*

(c) *determining the contributions of canid populations to the test canid genome, and further providing a document displaying the contributions of one or more canid populations to the genome of the test canid genome, wherein the document provides a certification of the contributions of one or more canid populations to the genome of the test canid genome.*

34. [The method of claim 29,] *A method for determining the contributions of canid populations to a canid genome, comprising:*

(a) *genotyping a sample obtained from a test canid to determine the identity of one or both alleles present in the test canid genome for each of a set of markers, wherein the set of markers is indicative of the contributions of canid populations to the genome of the test canid;*

(b) *using a specifically programmed computer comprising an algorithm to compare the identity of one or both*

*alleles for each of the set of markers determined to be present in the test canid genome to a database comprising a plurality of canid population profiles, wherein each canid population profile comprises genotype information for the set of markers in the canid population; and*

(c) *determining the contributions of canid populations to the test canid genome, and further providing a document displaying the contributions of one or more canid populations to the genome of the test canid genome, wherein the document provides a representation of the one or more canid populations that contributed to the genome of the test canid.*

35. A method for defining one or more canid populations, comprising:

(a) performing a genotyping assay on a set of canid genomes, to determine the identity of one or both alleles for each of a set of markers, wherein the set of markers is indicative of the contributions of canid populations to the genomes of each member of the set of canids; and (b) applying a computer-implemented statistical model to define one or more distinct canid populations, wherein one or more distinct canid populations are characterized by a set of allele frequencies for each marker in the set of markers *and the one or more distinct canid populations comprise at least about five American Kennel Club registered breeds*.

36. A computer readable medium comprising stored thereon:

(a) a datastructure thereon for use in distinguishing canid populations, the data structure comprising:
  (i) a marker field, which is capable of storing the name of a marker or of an allele of the marker; and
  (ii) a genotype information field, which is capable of storing genotype information for the marker in a canid population, wherein a record comprises an instantiation of the marker field and an instantiation of the genotype information field and a set of records represents a canid population profile; and (b) computer-executable instructions for implementing a method for determining the contributions of canid populations to a canid genome, comprising:
  (i) obtaining the identity of one or both alleles in a test canid genome for each of a set of markers; and
  (ii) determining the contributions of canid populations to the test canid genome by comparing the alleles in the test canid genome to a database comprising canid population profiles, wherein each canid population profile comprises genotype information for the set of markers in the canid population *and wherein the database of canid population profiles comprises at least about five American Kennel Club registered breeds*.

37. A computer-readable medium comprising a data structure stored thereon for use in distinguishing canid populations, the data structure comprising:

(a) a marker field, which is capable of storing the name of a marker or of an allele of the marker; and (b) a genotype information field, which is capable of storing genotype information for the marker in a canid population, wherein a record comprises an instantiation of the marker field and an instantiation of the genotype information field and a set of records represents a canid population profile, wherein the marker field comprises a set of markers indicative of the contributions of canid populations to the genome of a test canid *and wherein the canid populations comprise at least about five American Kennel Club registered breeds*.

39. A method for determining the contributions of canid populations to a canid genome, comprising performing a genotyping assay on a sample obtained from a test canid to determine the identity of one or both alleles present in the test canid genome for each of a set of markers, wherein the set of markers is indicative of the contribution of canid populations to the genome of the test canid *and wherein the canid populations comprise at least about five American Kennel Club registered breeds*.

45. The method of claim 13, wherein the set of markers comprises single nucleotide polymorphisms (SNPs).

46. The method of claim 13, wherein the set of markers comprises one or more population-specific markers.

47. The method of claim 46, wherein the one or more population-specific markers comprise one or more SNP markers.

48. The method of claim 13 further comprising the step of providing a document displaying the contributions of one or more canid populations to the genome of the test canid genome.

49. The method of claim 48, wherein the document provides additional information regarding the one or more canid populations that contributed to the genome of the test canid or the test canid.

\* \* \* \* \*

SEQUENCE LISTING

<160> NUMBER OF SEQ ID NOS: 327

<210> SEQ ID NO 1
<211> LENGTH: 20
<212> TYPE: DNA
<213> ORGANISM: Artificial Sequence
<220> FEATURE:

-continued

<223> OTHER INFORMATION: Oligonucleotide Primer

<400> SEQUENCE: 1
aacatggtga cgagaaggct                                                   20

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 2
ccaccactta cataaacatg gc                                                22

<210> SEQ ID NO 3
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 3
atagcccatg aaatcca                                                      17

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 4
cccttaggag gaggcaagac                                                   20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 5
ctatgtgcac gctgagagag                                                   20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 6
gtcagagccc cagagacaag                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 7
ccagattaac caggatgagg                                                   20

```
<210> SEQ ID NO 8
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 8
tctggattgt ggtcacaacc                                                  20

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 9
tcagcatcta gaaaattagg t                                                21

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 10
tctttgaaat gaaatgggcc                                                  20

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 11
tgcgatacac ttagaaaaca gg                                               22

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 12
gcaaatggca agatttcgtt                                                  20

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 13
tctttggtaa agtctccatg gg                                               22

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer
```

```
<400> SEQUENCE: 14
gaaagggtgt ggataaagag c                                        21

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 15
ggaacagatg agaagcatgg                                          20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 16
accgtgcaca agtcagtcag                                          20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 17
aggattttgt ggtgattggg                                          20

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 18
tactcgttct gtgccatttc t                                        21

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 19
cagctgtccg gggatataaa                                          20

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 20
gcccctattt tttttttcc c                                         21

<210> SEQ ID NO 21
<211> LENGTH: 20
```

```
<212> TYPE: DNA
<213> ORGANISM: Artificial Sequence
<220> FEATURE:
<223> OTHER INFORMATION: Oligonucleotide Primer

<400> SEQUENCE: 21
tttaggcatt tgaggaggag                                              20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 22
ctgctctctc ccccaactta                                              20

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 23
attcccttgt attgctca                                                18

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 24
tgaggctccg tgggtatgtg                                              20

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 25
cagtaatgtt ttgtggcctc tg                                           22

<210> SEQ ID NO 26
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 26
tgccctcaaa caatttgc                                                18

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 27
```
tcgggatgtt tctcttccac                                              20

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 28
tatttaaaaa atcccaggca ca                                           22

<210> SEQ ID NO 29
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 29
caacccaggg tggaagc                                                 17

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 30
atccaggtct ggaataccccc                                             20

<210> SEQ ID NO 31
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 31
ttaagcctta ttttgtgttg gg                                           22

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 32
cttttagggt gccttcaacc                                              20

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 33
acctccaaga tggctcttga                                              20

<210> SEQ ID NO 34
<211> LENGTH: 17
<212> TYPE: DNA
<213> ORGANISM: Artificial Sequence

```
<220> FEATURE:
<223> OTHER INFORMATION: Oligonucleotide Primer

<400> SEQUENCE: 34
attccccagc gatacca                                                    17

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 35
tggacgctaa gcctgacttt                                                 20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 36
tgggatgtgt gtcatgtgtg                                                 20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 37
aacttctggc tttcataccg                                                 20

<210> SEQ ID NO 38
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 38
ctggcagatt acaggtagc                                                  19

<210> SEQ ID NO 39
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 39
ttctctgtgt atgtgtacgc ttg                                             23

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 40
cattctgggc aggtttcatt                                                 20
```

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 41
tgcatcattt gtgggtgttt                                          20

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 42
ataccactgt ccctcctctt a                                        21

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 43
ggttattgta aagtctgagt gttg                                     24

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 44
gcacattcac aaagtggtgc                                          20

<210> SEQ ID NO 45
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 45
aagcatccag aatccctgg                                           19

<210> SEQ ID NO 46
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 46
tgtcataata gttggaatga c                                        21

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide Primer -continued

```
<400> SEQUENCE: 47
cctggattaa cagttgtctg g                                           21

<210> SEQ ID NO 48
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 48
ttttcaccag ctctgagata gc                                          22

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 49
tgcagggcag aggctggagg                                             20

<210> SEQ ID NO 50
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 50
tctcatgcaa atcttcgttc a                                           21

<210> SEQ ID NO 51
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 51
aaggcaggag gaggagcac                                              19

<210> SEQ ID NO 52
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 52
tcagctcagg gagtgatcc                                              19

<210> SEQ ID NO 53
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 53
aaatgggtaa ttcatccagt gc                                          22

<210> SEQ ID NO 54
```

```
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 54
atgtggggta aaataaagg                                                   19

<210> SEQ ID NO 55
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 55
gagggatggc tgtcaaga                                                    18

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 56
aggctctccg agggtaagac                                                  20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 57
ggctggactt ttgtcatttg                                                  20

<210> SEQ ID NO 58
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 58
cttcccatta tagccctgtc c                                                21

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 59
tccctcctga cactgcttta                                                  20

<210> SEQ ID NO 60
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 60
```
cccttttgca ctactgttga g							21

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 61
ttctcgtgac ccctaaagga							20

<210> SEQ ID NO 62
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 62
aaacaagaca gtaggaagag agg						23

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 63
tgggagcttc atacaaatgc							20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 64
aattactcgg cctctctggg							20

<210> SEQ ID NO 65
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 65
gtgatccact tgcttgtatc c							21

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 66
catgcctgac tcaactgatg							20

<210> SEQ ID NO 67
<211> LENGTH: 19
<212> TYPE: DNA

```
<213> ORGANISM: Artificial Sequence
<220> FEATURE:
<223> OTHER INFORMATION: Oligonucleotide Primer

<400> SEQUENCE: 67
ggggctctgt tattaggtg                                                   19

<210> SEQ ID NO 68
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 68
tgacttactc tagccacttt t                                                21

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 69
ttacatttag gggctccagt                                                  20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 70
gccttctttg gaaaaacacc                                                  20

<210> SEQ ID NO 71
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 71
acacatttgt gtgcttgtct tg                                               22

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 72
acaagccgac tctagcgaaa                                                  20

<210> SEQ ID NO 73
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 73
ggtcccatcc tcaaaatcct c                                                21
```

```
<210> SEQ ID NO 74
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 74
atttgccagg taccattcc                                                  19

<210> SEQ ID NO 75
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 75
gcagacgagc acaccgaa                                                   18

<210> SEQ ID NO 76
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 76
aatatgggag aggagaagag gg                                              22

<210> SEQ ID NO 77
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 77
tggctgtggc taaggctttg t                                               21

<210> SEQ ID NO 78
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 78
ccctctactt atgtctcggc c                                               21

<210> SEQ ID NO 79
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 79
ccaagaacag cctaagctgg                                                 20

<210> SEQ ID NO 80
<211> LENGTH: 18
<212> TYPE: DNA
<213> ORGANISM: Artificial Sequence
<220> FEATURE:
```

-continued

<223> OTHER INFORMATION: Oligonucleotide Primer

<400> SEQUENCE: 80
cagctggatt ggggactc                                                  18

<210> SEQ ID NO 81
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 81
ccgatgcctg tcctttga                                                  18

<210> SEQ ID NO 82
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 82
agtacttgag gcttggagtc ag                                             22

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 83
atggcaggtc aagagtatgg                                                20

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 84
ttcattggct ggtgactttg                                                20

<210> SEQ ID NO 85
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 85
agtaaagggt tctcaagtgt gc                                             22

<210> SEQ ID NO 86
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 86
cagttcatcc ttcccctct c                                               21

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 87
gattaaaagg gcaagcaacc                                              20

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 88
cagtgagcaa agcaaatgaa                                              20

<210> SEQ ID NO 89
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 89
aaggtagtcc cacgatcctc                                              20

<210> SEQ ID NO 90
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 90
tgatacccat taagtccatc c                                            21

<210> SEQ ID NO 91
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 91
ccaatattgt taagaagttc aagc                                         24

<210> SEQ ID NO 92
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 92
cctctagatc catccatatt gtca                                         24

<210> SEQ ID NO 93
<211> LENGTH: 23
<212> TYPE: DNA
<213> ORGANISM: Artificial Sequence
<220> FEATURE:
<223> OTHER INFORMATION: Oligonucleotide Primer -continued

```
<400> SEQUENCE: 93
aatggtggtg atattcacag aga                                           23

<210> SEQ ID NO 94
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 94
aggcagagct aaacctgagc                                               20

<210> SEQ ID NO 95
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 95
gaaattgttc catttctgtg acat                                          24

<210> SEQ ID NO 96
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 96
tacatctcca catctactga                                               20

<210> SEQ ID NO 97
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 97
atggcccacc gatacaca                                                 18

<210> SEQ ID NO 98
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 98
ttccccaagc cacacc                                                   16

<210> SEQ ID NO 99
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 99
cagcaattgg acaagaaaaa g                                             21

<210> SEQ ID NO 100
<211> LENGTH: 19
```

```
<212> TYPE: DNA
<213> ORGANISM: Artificial Sequence
<220> FEATURE:
<223> OTHER INFORMATION: Oligonucleotide Primer

<400> SEQUENCE: 100
cagcgaattt gggcactaa                                                 19

<210> SEQ ID NO 101
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 101
ccattcgcca caagtaggtt                                                20

<210> SEQ ID NO 102
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 102
ttccagactg ctgcctcc                                                  18

<210> SEQ ID NO 103
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 103
ccccaaatac atccctacat                                                20

<210> SEQ ID NO 104
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 104
cgtgctttgt tatggcttga                                                20

<210> SEQ ID NO 105
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 105
tacccataaa gttgggcttg                                                20

<210> SEQ ID NO 106
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 106
```

```
ctttcttccg ccactacctg                                              20
```

<210> SEQ ID NO 107
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 107

```
aatggcaagg atgctactcc                                              20
```

<210> SEQ ID NO 108
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 108

```
actggacact tcttttcaga cg                                           22
```

<210> SEQ ID NO 109
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 109

```
actcattttc tcttattctg cag                                          23
```

<210> SEQ ID NO 110
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 110

```
gctctcatcc ctgtgaaagc                                              20
```

<210> SEQ ID NO 111
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 111

```
aaaaacccac aacaaagtgc                                              20
```

<210> SEQ ID NO 112
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 112

```
caagggttag cacctgggta                                              20
```

<210> SEQ ID NO 113
<211> LENGTH: 20
<212> TYPE: DNA
<213> ORGANISM: Artificial Sequence

```
<220> FEATURE:
<223> OTHER INFORMATION: Oligonucleotide Primer

<400> SEQUENCE: 113
gggtgtgaaa acagccaact                                                 20

<210> SEQ ID NO 114
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 114
tggcatattc aacaaattgc                                                 20

<210> SEQ ID NO 115
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 115
ctgggtggtt cagtagttgg                                                 20

<210> SEQ ID NO 116
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 116
aagctgagcc attcttttcc                                                 20

<210> SEQ ID NO 117
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 117
ttgcagccta ttgtggactt t                                               21

<210> SEQ ID NO 118
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 118
cacaccagct cgtcctcata a                                               21

<210> SEQ ID NO 119
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 119
ggctgtggtt tgtccttgtt                                                 20
```

<210> SEQ ID NO 120
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 120
ttgggtttca cactcagcag                                              20

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 121
ggcacagaat ccaacttgag                                              20

<210> SEQ ID NO 122
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 122
cagggccatt ggtctagaaa                                              20

<210> SEQ ID NO 123
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 123
ccccaaaaaa tccaacca                                                18

<210> SEQ ID NO 124
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 124
aggccaaggg aatgatgctc                                              20

<210> SEQ ID NO 125
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 125
gggagtgggg gaaataaatg                                              20

<210> SEQ ID NO 126
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 126
atcatcctag cactcagaag g                                              21

<210> SEQ ID NO 127
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 127
ctgcttaaat tctcccagcg                                                20

<210> SEQ ID NO 128
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 128
agcatcaatt agatgtcagc g                                              21

<210> SEQ ID NO 129
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 129
tagcaagaaa atgtgccca                                                 19

<210> SEQ ID NO 130
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 130
tcctttgaat tagcacttgg c                                              21

<210> SEQ ID NO 131
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 131
tccaggaagt gtctgcagg                                                 19

<210> SEQ ID NO 132
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 132
tggattatta agggaattt agc                                             23

<210> SEQ ID NO 133

```
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 133
acgtcgagct cctggcat                                                   18

<210> SEQ ID NO 134
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 134
aacagcattt cagacagagg                                                 20

<210> SEQ ID NO 135
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 135
aaacggagtt ccatctctgg                                                 20

<210> SEQ ID NO 136
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 136
cctatgcagg gtaggcacat                                                 20

<210> SEQ ID NO 137
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 137
tcttcaaaga aaaccaacag g                                               21

<210> SEQ ID NO 138
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 138
gttctccaaa gcactcat                                                   18

<210> SEQ ID NO 139
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 139
```

```
acaccaaatg tgtgaaggca                                          20

<210> SEQ ID NO 140
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 140
ggggacaaat ttccactcct                                          20

<210> SEQ ID NO 141
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 141
atggagcatg ggtgagaaat                                          20

<210> SEQ ID NO 142
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 142
atcctggtat caaatctatc a                                        21

<210> SEQ ID NO 143
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 143
aatagactat gtaactgtct ctggc                                    25

<210> SEQ ID NO 144
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 144
gcaatggaaa gaggatggaa                                          20

<210> SEQ ID NO 145
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 145
gttgattggg agataatcca ca                                       22

<210> SEQ ID NO 146
<211> LENGTH: 23
<212> TYPE: DNA
```

```
<213> ORGANISM: Artificial Sequence
<220> FEATURE:
<223> OTHER INFORMATION: Oligonucleotide Primer

<400> SEQUENCE: 146
ttagagctta ctcatgatat ctg                                              23

<210> SEQ ID NO 147
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 147
cctggattat aagcatgaga gc                                               22

<210> SEQ ID NO 148
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 148
tttctgagcc acttttccat ag                                               22

<210> SEQ ID NO 149
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 149 ggggtgtcg gtggagttct                                                   20

<210> SEQ ID NO 150
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 150
gccacctcat tccaaaaaga                                                  20

<210> SEQ ID NO 151
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 151
tatggagatg gagggcacac                                                  20

<210> SEQ ID NO 152
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 152
atgaggaggt gcaactatcc                                                  20
```

-continued

```
<210> SEQ ID NO 153
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 153
caggctttgt tgaggtgtca                                                    20

<210> SEQ ID NO 154
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 154
aacactgaca tgcatccac                                                     19

<210> SEQ ID NO 155
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 155
tggtggataa atagataagg a                                                  21

<210> SEQ ID NO 156
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 156
attgcttgga taagaggggg                                                    20

<210> SEQ ID NO 157
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 157
tgtgagtagg gtagggcaag                                                    20

<210> SEQ ID NO 158
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 158
ggtgtcagga aaatgagacc a                                                  21

<210> SEQ ID NO 159
<211> LENGTH: 20
<212> TYPE: DNA
<213> ORGANISM: Artificial Sequence
<220> FEATURE:
```

-continued

<223> OTHER INFORMATION: Oligonucleotide Primer

<400> SEQUENCE: 159
aggcctgctg tttctcttct                                             20

<210> SEQ ID NO 160
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 160 tcccttttttg tggctgaa                                              18

<210> SEQ ID NO 161
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 161
ggcataaatt gtctttgccc                                             20

<210> SEQ ID NO 162
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 162
caagattcaa aacaagcaac c                                           21

<210> SEQ ID NO 163
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 163
ccatggagag tggttattgc                                             20

<210> SEQ ID NO 164
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 164
aatgacattg agcctgggaa                                             20

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 165
atagccttgg gaatttttgc                                             20

```
<210> SEQ ID NO 166
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 166
tatggacctt cgttcagagg                                                    20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 167
tcataaggca agaaaaacc                                                     19

<210> SEQ ID NO 168
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 168
ttgtcccttg tataactgat g                                                  21

<210> SEQ ID NO 169
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 169
ttagacaaaa taggcttcaa                                                    20

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 170
ttcagggaat tctttcttgg                                                    20

<210> SEQ ID NO 171
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 171
ttgtatggag gtggggagag                                                    20

<210> SEQ ID NO 172
<211> LENGTH: 20
<212> TYPE: DNA
<213> ORGANISM: Artificial Sequence
<220> FEATURE:
<223> OTHER INFORMATION: Oligonucleotide Primer
```

```
<400> SEQUENCE: 172
agatggggcc taaccaaagt                                                    20

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 173
cccttctggc ctcctacaca                                                    20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 174
caggttattc tgggctatgg                                                    20

<210> SEQ ID NO 175
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 175
tattccacat cattcacc                                                      18

<210> SEQ ID NO 176
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 176
atgcttcctg gtaagcaatc a                                                  21

<210> SEQ ID NO 177
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 177 cccctccag cttcggtgta g                                                   21

<210> SEQ ID NO 178
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 178
gagaggagaa acaaccaaca cc                                                 22

<210> SEQ ID NO 179
<211> LENGTH: 20
```

```
<212> TYPE: DNA
<213> ORGANISM: Artificial Sequence
<220> FEATURE:
<223> OTHER INFORMATION: Oligonucleotide Primer

<400> SEQUENCE: 179
acacatacac gcccaattca                                              20

<210> SEQ ID NO 180
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 180
catcttgctc tctcaac                                                 17

<210> SEQ ID NO 181
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 181
acctggcctc ttctgttgtc t                                            21

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 182
caagctgaga gccatgtagg                                              20

<210> SEQ ID NO 183
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 183
gatagatcca agccaacacc                                              20

<210> SEQ ID NO 184
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 184
ccccaggacc atttgttaga                                              20

<210> SEQ ID NO 185
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 185
```

-continued catttgtcat tgtggaaaac c                                              21

<210> SEQ ID NO 186
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 186
gtgctagtct ggctgtgctc a                                              21

<210> SEQ ID NO 187
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 187
tcatctccag cttttcatgg                                                20

<210> SEQ ID NO 188
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 188
atgtgaaccc cgcccaata                                                 19

<210> SEQ ID NO 189
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 189
gagccctgtt ctcaggttg                                                 19

<210> SEQ ID NO 190
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 190
caataccctg ataccaaaac c                                              21

<210> SEQ ID NO 191
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 191
aggccttctc tgtcctcttg                                                20

<210> SEQ ID NO 192
<211> LENGTH: 20
<212> TYPE: DNA
<213> ORGANISM: Artificial Sequence

```
<220> FEATURE:
<223> OTHER INFORMATION: Oligonucleotide Primer

<400> SEQUENCE: 192
tgtccaccca cagatgaatg                                              20

<210> SEQ ID NO 193
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 193
ggatgcttgg gaatcttgaa                                              20

<210> SEQ ID NO 194
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 194
tacaggcact ccttcctacg                                              20

<210> SEQ ID NO 195
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 195
aggtttgggc tcctcattct                                              20

<210> SEQ ID NO 196
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 196
gagacttaac acagtatttg                                              20

<210> SEQ ID NO 197
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 197
tcggggacat acttgaacc                                               19

<210> SEQ ID NO 198
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 198
aaccactatc caactttat                                               19
```

```
<210> SEQ ID NO 199
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 199
gaaagaggat gaagggtgtg                                                  20

<210> SEQ ID NO 200
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 200
caactaaggc agagaatacc a                                                21

<210> SEQ ID NO 201
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 201
cacgacgttg taaaacgac                                                   19

<210> SEQ ID NO 202
<211> LENGTH: 337
<212> TYPE: DNA
<213> ORGANISM: canine genomic DNA
<220> FEATURE:
<221> NAME/KEY: misc_feature
<222> LOCATION: (1)..(337)
<223> OTHER INFORMATION: Wherein N = A or C or G or T
<220> FEATURE:
<221> NAME/KEY: allele
<222> LOCATION: (82)..(82)
<223> OTHER INFORMATION: C to T
<220> FEATURE:
<221> NAME/KEY: allele
<222> LOCATION: (133)..(133)
<223> OTHER INFORMATION: T to C

<400> SEQUENCE: 202
gcttttggac aactttggat agactccttt ctctggaatg acttccagca tatggtgcag       60
cttcaaggcc agagaagaga ccagatgacc tttcaagtgt ccttccagtc caagnnnnn       120 nnnttccaat actgagggtt ttcaaactgg tgttggtatt tgcttttcaa agagagacag     180
actgagtttc tcatatcaaa tccctatagc ctcataaaag cacttttcag ttttattttc     240
catcagaaat tcctatgaaa agcatttgaa gtttcaaaag ctccctacac ccaagnngct     300
gattgagatt ttagcccaga gagtgacgta gatcaca                              337

<210> SEQ ID NO 203
<211> LENGTH: 341
<212> TYPE: DNA
<213> ORGANISM: canine genomic DNA
<220> FEATURE:
<221> NAME/KEY: misc_feature
<222> LOCATION: (1)..(341)
<223> OTHER INFORMATION: Wherein N = A or C or G or T
<220> FEATURE:
<221> NAME/KEY: allele
```

```
<222> LOCATION: (285)..(285)
<223> OTHER INFORMATION: G to A

<400> SEQUENCE: 203
gaattccaaa tgtcctgctt agggtccagc aggatagagg gatagnnnnn nnnnnnntga      60
ggtaggagga aacagtgact tttccagaaa cagtgcaaca tttctcctgc attttttaacc    120 tctatagatg atactcattt ctcattagcc agagttcctg cattccattg gcagtaagtt    180
gtccatcaga atccctgaaa nnacaacttt gggtgaactg gaagccattc acactttgcc    240
agttgggtaa tgccagttag tacataccct tctcataagg ttttgaatac ctgnnnnnnn    300
nnnnnnncca atgaataccc acacccttgg tagatgaaag a                        341

<210> SEQ ID NO 204
<211> LENGTH: 302
<212> TYPE: DNA
<213> ORGANISM: canine genomic DNA
<220> FEATURE:
<221> NAME/KEY: misc_feature
<222> LOCATION: (1)..(302)
<223> OTHER INFORMATION: Wherein N = A or C or G or T
<220> FEATURE:
<221> NAME/KEY: allele
<222> LOCATION: (50)..(50)
<223> OTHER INFORMATION: Deletion A
<220> FEATURE:
<221> NAME/KEY: allele
<222> LOCATION: (93)..(93)
<223> OTHER INFORMATION: C to G
<220> FEATURE:
<221> NAME/KEY: allele
<222> LOCATION: (128)..(128)
<223> OTHER INFORMATION: C to G
<220> FEATURE:
<221> NAME/KEY: allele
<222> LOCATION: (257)..(257)
<223> OTHER INFORMATION: C to T
<220> FEATURE:
<221> NAME/KEY: allele
<222> LOCATION: (271)..(271)
<223> OTHER INFORMATION: G to T

<400> SEQUENCE: 204
aagcatactt ccctgaaatg aggcttcact atctgatttg ctttggctaa taaatataaa     60
tagaagtgag atgggtcact tctaggctgt agctttaagg gcaggatgtg tgtcgctaaa   120
ttctcctctt ctcctgccat aatgactgac atcagnnntt ctccatcagc ttggggcctg   180
aagtgtaatg atgtagagaa gaaccaggct tatgtaagtg aggaataaac aaccttgtta   240
gaaactacag atatggcggt gtttattact gcagcataat ccaacacttt atggctgata   300
ca                                                                   302

<210> SEQ ID NO 205
<211> LENGTH: 408
<212> TYPE: DNA
<213> ORGANISM: canine genomic DNA
<220> FEATURE:
<221> NAME/KEY: misc_feature
<222> LOCATION: (1)..(408)
<223> OTHER INFORMATION: Wherein N = A or C or G or T
<220> FEATURE:
<221> NAME/KEY: allele
<222> LOCATION: (5)..(57)
<223> OTHER INFORMATION: T to C

<400> SEQUENCE: 205
agtcaaatcg ttcattggat tcccttgcac tcagagctta tgagaagagc tgacaatgta    60
```

```
ctcagcagcc gtgtccttct tcctaaatta ttggctttta tttcatcaga gtgaaagccc    120
ttnnnnnnnc agggtttgaa attgccatca cttcaaattt cctataagca cttcttgcat    180
gtgaatgttt actgaatgca gttaactgtt ttctaaattt aactagcttt aacgaatttg    240
attttcaaac tgaaaagaa ataattgatg tcaatttcat ttcaattcca caaagagaat    300 gggggtggg caatgcagaa atcatgtcct gaagcattta cttttatttt ttaattttt    360 aaagatttgt ttatttgaga gacagagaga gggagtacat tcaagcag              408

<210> SEQ ID NO 206
<211> LENGTH: 381
<212> TYPE: DNA
<213> ORGANISM: canine genomic DNA
<220> FEATURE:
<221> NAME/KEY: misc_feature
<222> LOCATION: (1)..(381)
<223> OTHER INFORMATION: Wherein N = A or C or G or T
<220> FEATURE:
<221> NAME/KEY: allele
<222> LOCATION: (156)..(156)
<223> OTHER INFORMATION: Insert T
<220> FEATURE:
<221> NAME/KEY: allele
<222> LOCATION: (258)..(258)
<223> OTHER INFORMATION: C to T
<220> FEATURE:
<221> NAME/KEY: allele
<222> LOCATION: (303)..(303)
<223> OTHER INFORMATION: C to T
<220> FEATURE:
<221> NAME/KEY: allele
<222> LOCATION: (312)..(312)
<223> OTHER INFORMATION: Insert A

<400> SEQUENCE: 206
aaaaggtggc acatatgaaa agttgttgtt ttttttttc ctaatgtcat ggcctgtcac    60
ttagacaaaa agcataatga gggaagtttc taagaattat annnnnnnnn nngctaatca   120
aattttaagg aatgtatatg gtggtgaggt gaaggatcaa gatggcagtt gtttgcaaag   180
gaaaggaagg tggaaataaa ggagtatcca agagggataa tataacaaaa aattattgag   240
tttcagagaa atcaggtgaa tggaagatgt aacagggctc taacatgaan ntggtccaag   300
nngattcaac ataaaaatta ccagtcatgg gtgcctgagt tgttcaaagt cagttaagcc   360
tcccttaagc ctctgactct t                                           381

<210> SEQ ID NO 207
<211> LENGTH: 344
<212> TYPE: DNA
<213> ORGANISM: canine genomic DNA
<220> FEATURE:
<221> NAME/KEY: misc_feature
<222> LOCATION: (1)..(344)
<223> OTHER INFORMATION: Wherein N = A or C or G or T
<220> FEATURE:
<221> NAME/KEY: allele
<222> LOCATION: (254)..(254)
<223> OTHER INFORMATION: G to A

<400> SEQUENCE: 207
ggggtttcta ttccattttc accacgtttg aaggacaaat tgaggctgcc ctcatacaaa    60
tgcccctggg cnnnnnnatt agggttgggg ttggggnn nnnnnnngg ccagaattcc   120 tctctcaccc aacaggggag gcagtaatgc cttattttgc cgtcttgggt ggtgacagta   180
gtgagagctt ggttctgggg ctaaacagag acagccttgc caacagatgt cagctcacca   240
gaagtggtca agcgttctc aaagtagcca cagtgctggg agcagccaag gctttcnnnn   300
```

```
nnnnannatn gaaactcaaa ctgtgtcaac agtatgcatt ccaa          344
```

<210> SEQ ID NO 208
<211> LENGTH: 370
<212> TYPE: DNA
<213> ORGANISM: canine genomic DNA
<220> FEATURE:
<221> NAME/KEY: misc_feature
<222> LOCATION: (1)..(370)
<223> OTHER INFORMATION: Wherein N = A or C or G or T
<220> FEATURE:
<221> NAME/KEY: allele
<222> LOCATION: (165)..(165)
<223> OTHER INFORMATION: G to C

<400> SEQUENCE: 208

```
acctcatgta tgtcttgttc cccaagaacc cttcgtccag ggatttttt  ttaaatgta    60
tttattcatg agagacagag agagagagag agaatggggc agagacacag gcagagggag  120
aagcaggctc cacacnnnnn nnnnnnngtg gggactcgat cccgggtctc caggatcagg  180
ccctggactg aaggtagtgc taaaccgctg agccacctgg gctgcccagc ctaatctttt  240
ttgttgttgt tgttttgttt tgtttttta  agattctatt tattttagag agagagggtt  300
aaaaaaactt tagcagactc catgctcagc acnngcccca tgagggctcg atctcaggac  360
cccaagatca                                                         370
```

<210> SEQ ID NO 209
<211> LENGTH: 337
<212> TYPE: DNA
<213> ORGANISM: canine genomic DNA
<220> FEATURE:
<221> NAME/KEY: misc_feature
<222> LOCATION: (1)..(337)
<223> OTHER INFORMATION: Wherein N = A or C or G or T
<220> FEATURE:
<221> NAME/KEY: allele
<222> LOCATION: (66)..(66)
<223> OTHER INFORMATION: T to A

<400> SEQUENCE: 209

```
ctctgctagg agaaaaggag agaaactact gcttttccta tggatttaa   cctccacctt    60
tcaatttttt cccctgggta agggacaggg taggattgga acagnggggca ggcagattgt  120
nnnnnnnnnn tatctgggat tgaatatggg ttgtaatagc tttagaaatt gtcatttctc  180
ttgccttgac cagccagttt tctgggaagt agaggatatg aaagcatttg tgctcttcca  240
gaataagatg tgtattcatg aaattagttg ttgctcttaa ataaaatgct tccttatgta  300
caaaattctc nagcaggctg aatggactga attgtgt                           337
```

<210> SEQ ID NO 210
<211> LENGTH: 480
<212> TYPE: DNA
<213> ORGANISM: canine genomic DNA
<220> FEATURE:
<221> NAME/KEY: misc_feature
<222> LOCATION: (1)..(480)
<223> OTHER INFORMATION: Wherein N = A or C or G or T
<220> FEATURE:
<221> NAME/KEY: allele
<222> LOCATION: (384)..(384)
<223> OTHER INFORMATION: A to G

<400> SEQUENCE: 210

```
caaatggttc aagaggagat tcttgtaata gttctgctat tggcaaggtg gtaggaggag    60
```

```
gctttcagga cacagcagca aggtgtttta nnnnnnnnnn nctcactgtg ttatggctct      120
cctgaggttc cagtccattg ggagtatatg ggtgaaacct taaatctcaa agggatcttc      180
cttaagactg acatgtacta tagtcagtca cttgatacat gaggcagatg acccagacaa      240
aagtggctac tactagggtg tccacatatg gctacacagt agaatcacct ggagagcttt      300
tacgatccca gtgcccaagt cataacctat tcaaattaaa ttacagtgtt ggggcnnnga      360
gtcagatagc aatatttttt aaagacccca gctgattcca gtgcattgca ccttttgcaa      420
ctaatgggct tatgatttat ctaacatcac acaagtgggg acaggaacct acaatggtta      480

<210> SEQ ID NO 211
<211> LENGTH: 313
<212> TYPE: DNA
<213> ORGANISM: canine genomic DNA
<220> FEATURE:
<221> NAME/KEY: misc_feature
<222> LOCATION: (1)..(313)
<223> OTHER INFORMATION: Wherein N = A or C or G or T
<220> FEATURE:
<221> NAME/KEY: allele
<222> LOCATION: (88)..(88)
<223> OTHER INFORMATION: T to C
<220> FEATURE:
<221> NAME/KEY: allele
<222> LOCATION: (138)..(138)
<223> OTHER INFORMATION: C to A
<220> FEATURE:
<221> NAME/KEY: allele
<222> LOCATION: (266)..(266)
<223> OTHER INFORMATION: T to G

<400> SEQUENCE: 211
aaagtaaaat caggtattct cctcctaact atgaaganan nntaatttttt agagtgaaat      60 ctgagttaac aactcctaca atcacaatct tgtttgccaa tccagcgtta tgagctgccc     120
atcccagaag aaaaaaactn nnnnnnnttg tggtgttatg aaatgagcct gcctatggac     180
tccaaaaaaa gctagatcca gggtgcaatg tccatctttg gtcatgccta tccctcatt     240 ccagtaattg accaacattt aggagttagt gttttccccc tatgcttact acttcagata     300
gatatgcatg cca                                                       313

<210> SEQ ID NO 212
<211> LENGTH: 353
<212> TYPE: DNA
<213> ORGANISM: canine genomic DNA
<220> FEATURE:
<221> NAME/KEY: misc_feature
<222> LOCATION: (1)..(353)
<223> OTHER INFORMATION: Wherein N = A or C or G or T
<220> FEATURE:
<221> NAME/KEY: allele
<222> LOCATION: (317)..(317)
<223> OTHER INFORMATION: T to A

<400> SEQUENCE: 212
caccctcaag aagttaaagc acaactcttc acccccttaag tatgggctac acagtgactt      60
ccttcgaaag aggacagttt gggaagggggg aaaaacagga nnnnnnnnnn ngagaagcct     120
aataaatact atcttagcca ggtgactaag gctggcaaca tcaagagcta tgtcaaataa     180
catatgccct tgatataata tgataagaat ggcactgtag acttcctccc tcaaatcctt     240
aaccactatc taatcatgag aaaaatatta gacaaccaaa attgaaggac atactacaaa     300
atatctaact actacttctc aaaaccgtca anncccagtct tctcaaaacc agg           353
```

```
<210> SEQ ID NO 213
<211> LENGTH: 336
<212> TYPE: DNA
<213> ORGANISM: canine genomic DNA
<220> FEATURE:
<221> NAME/KEY: misc_feature
<222> LOCATION: (1)..(336)
<223> OTHER INFORMATION: Wherein N = A or C or G or T
<220> FEATURE:
<221> NAME/KEY: allele
<222> LOCATION: (58)..(58)
<223> OTHER INFORMATION: G to C
<220> FEATURE:
<221> NAME/KEY: allele
<222> LOCATION: (108)..(108)
<223> OTHER INFORMATION: A to T

<400> SEQUENCE: 213 tagggacac agtttctaaa ggctgttcac agtttctaga ggcctccac agtttctgaa        60 ggacttttgc agctccctga tacatgaggt cctccaatgt ggccaataat ttaatccagn      120
nnnnnnnnnn ngcctctaga gttagtgtgc tagcaagatg gagtcttctg taacataacc     180
taagcacgag aatgacatcc tgtcacctt tccgtattt attgctttgc aacaaatcac        240
tggtcctgct caccctcaga gggaggcaga agatacaggg agataactcc taaacactaa     300
gagacaaaga aaatgagggc ttcttacatg tctgtc                                336

<210> SEQ ID NO 214
<211> LENGTH: 377
<212> TYPE: DNA
<213> ORGANISM: canine genomic DNA
<220> FEATURE:
<221> NAME/KEY: misc_feature
<222> LOCATION: (1)..(377)
<223> OTHER INFORMATION: Wherein N = A or C or G or T
<220> FEATURE:
<221> NAME/KEY: allele
<222> LOCATION: (129)..(129)
<223> OTHER INFORMATION: G to A
<220> FEATURE:
<221> NAME/KEY: allele
<222> LOCATION: (170)..(170)
<223> OTHER INFORMATION: Insert T

<400> SEQUENCE: 214
tctcaaactg ttgaagacca acagaatgat aaaatcttga aagcaacann nnnnnaaaac      60
attcatcata tacaaaggaa caatgagatt aacaattaac ttctcaaaag agataataga     120
ggccagaagt cagtggatga catattcaaa gtnnnnnnnn nnnnnnnnnn nnctcaacca     180
actgaacaaa acaaaaaatg aagatgaaan ngacacttag gtgactctgt cagnnnaaca    240
tgcttctctt gatcttgggg tcatgagttt gagtgcagag attatttaag gaaataaata    300
aaacctgtat atcttttaa atgaaaatga acatattccc agaaaagat tgaaagaatt      360 tgttcctagc agagacc                                                    377

<210> SEQ ID NO 215
<211> LENGTH: 312
<212> TYPE: DNA
<213> ORGANISM: canine genomic DNA
<220> FEATURE:
<221> NAME/KEY: misc_feature
<222> LOCATION: (1)..(312)
<223> OTHER INFORMATION: Wherein N = A or C or G or T
<220> FEATURE:
<221> NAME/KEY: allele
<222> LOCATION: (76)..(76)
<223> OTHER INFORMATION: C to T
<220> FEATURE:
```

```
<221> NAME/KEY: allele
<222> LOCATION: (108)..(108)
<223> OTHER INFORMATION: G to A
<220> FEATURE:
<221> NAME/KEY: allele
<222> LOCATION: (229)..(229)
<223> OTHER INFORMATION: G to A
<220> FEATURE:
<221> NAME/KEY: allele
<222> LOCATION: (238)..(238)
<223> OTHER INFORMATION: T to C
<220> FEATURE:
<221> NAME/KEY: allele
<222> LOCATION: (263)..(263)
<223> OTHER INFORMATION: A to G

<400> SEQUENCE: 215
catgtgaccc ttcctatgag actgtcacag aaccagccca cactcgggtt ggccggacct      60
gggtcaatcc tcagccgcca nnnnnnnnnn naggtgcagt gtgcccggag ggagcgatgg     120
cgtgagctaa gctggggca ctggtatcct ccagcagtga ggaggaggc accccaaaan      180 ntgctttaaa tgatcctaac agaaccccac agcgacagac attagccagg agggaagtga    240
ccaagtaaac ctgaaccgag acaggaggct ttattcaaga tcattctcat caaccaaatt    300
gcctctactt tc                                                        312

<210> SEQ ID NO 216
<211> LENGTH: 316
<212> TYPE: DNA
<213> ORGANISM: canine genomic DNA
<220> FEATURE:
<221> NAME/KEY: misc_feature
<222> LOCATION: (1)..(316)
<223> OTHER INFORMATION: Wherein N = A or C or G or T
<220> FEATURE:
<221> NAME/KEY: allele
<222> LOCATION: (212)..(212)
<223> OTHER INFORMATION: T to C

<400> SEQUENCE: 216
ggaagacccc aactctatta ttgcaggcat gccagtcctc gaggtctgga aatcaaagca      60
ggtaaagttt cagacttgtg tttcattcta acaatcaagt atctcttaaa acatgnnnnn    120
nnnattgtcc tggttcactt ggtgagaaat gctgatgcct cttaggagta ctaggagcta    180 gagcagggt agtgctctcg ctatccagct tttgtctatt tggtgatcat cagagaaccc    240
aagagaatgc cctgctcacc attagaacta gatgatatta tctgggtgga ttaacaaaat   300
ctgtaaccac agctga                                                   316

<210> SEQ ID NO 217
<211> LENGTH: 423
<212> TYPE: DNA
<213> ORGANISM: canine genomic DNA
<220> FEATURE:
<221> NAME/KEY: misc_feature
<222> LOCATION: (1)..(423)
<223> OTHER INFORMATION: Wherein N = A or C or G or T
<220> FEATURE:
<221> NAME/KEY: allele
<222> LOCATION: (274)..(274)
<223> OTHER INFORMATION: T to C

<400> SEQUENCE: 217
agtcttttgg tcctaaacat ggtagaaaac atctttgttg cattttttag aattaatcta      60
ttttaaattg acatattttg catgtaatat atttttcagg tatataaann nnnnnnnna    120 tattttata cactgcaaaa gatccccata tctggttaac atttgtcacc ttatatggta    180
```

```
aaaaaaattt tacaaaattt attcttgtga tgaaaactta agatttactc ttagcaactt    240
gcacatatac aatacagtag tagccaactt gctatctgtt atatcttcac tttgttgctg    300
tgtctaagaa gtgacagatg ccagtagagg tgtgggatcc tatatganna aatcccagta    360
tctgacattg cagagccttc tacctgccac ctctgagnca ccagtcagtg aggagtcaca    420
gtg                                                                  423
```

```
<210> SEQ ID NO 218
<211> LENGTH: 304
<212> TYPE: DNA
<213> ORGANISM: canine genomic DNA
<220> FEATURE:
<221> NAME/KEY: misc_feature
<222> LOCATION: (1)..(304)
<223> OTHER INFORMATION: Wherein N = A or C or G or T
<220> FEATURE:
<221> NAME/KEY: allele
<222> LOCATION: (112)..(112)
<223> OTHER INFORMATION: G to A

<400> SEQUENCE: 218
```

```
agacacatgc attttcccag ctgactttt gcacccagtg gctcataatc acaatcacat    60
gttatcaact tgcctcatag acccatttt tcagccnnnn nnnnnnngnc agtgtcacat    120
ctcaatacag tggccagaaa agtggttctt gcccctggtt tgcttaacct gagtatcatg    180
gggaacactg tcttctgaat tctagctgtg tgatctgtgt tcctatttat aaccatgttt    240
tatctttcag acctgacaca actagtctga tttggacatt ttgctcctgt tcacaatgaa    300
gatt                                                                304
```

```
<210> SEQ ID NO 219
<211> LENGTH: 316
<212> TYPE: DNA
<213> ORGANISM: canine genomic DNA
<220> FEATURE:
<221> NAME/KEY: misc_feature
<222> LOCATION: (1)..(316)
<223> OTHER INFORMATION: Wherein N = A or C or G or T
<220> FEATURE:
<221> NAME/KEY: allele
<222> LOCATION: (73)..(73)
<223> OTHER INFORMATION: G to A
<220> FEATURE:
<221> NAME/KEY: allele
<222> LOCATION: (136)..(136)
<223> OTHER INFORMATION: A to G

<400> SEQUENCE: 219
```

```
gtccaaagtt ggagatgata ggttctctca caataataat gtattgtttt cctcttacac    60
cctcactagg cagtccactg ctgacccaac tgnnnnnnnn tgcactatat caatttctga    120
ctttatggag ataaaatagc tgtgatgtac ccagcttata ataaccctcc ttctacttag    180
agccacttgt tctctcctca gttttatttt actcctgaaa aaaccctct tctcttttaa     240 actctattca taggtccttc acatcatttt aatcaaaaga tttcagggtc ttctataaca    300
acatttccca gtttca                                                    316
```

```
<210> SEQ ID NO 220
<211> LENGTH: 330
<212> TYPE: DNA
<213> ORGANISM: canine genomic DNA
<220> FEATURE:
<221> NAME/KEY: misc_feature
<222> LOCATION: (1)..(330)
```

```
<223> OTHER INFORMATION: Wherein N = A or C or G or T
<220> FEATURE:
<221> NAME/KEY: allele
<222> LOCATION: (89)..(89)
<223> OTHER INFORMATION: C to T

<400> SEQUENCE: 220
aaagcccagc tgttgtctgg agccctgnnn nnnngaaaca ctggactttc caggccctcc      60
cttgaccttg actttcaagg gctctgtccg gatgcccttg ccttctcctg cctgnnnnnn    120
nnngggagca aggaagctg gagctctggt tgttgcacaa cagaaagtcc tggctcctga     180
cactgagtga ttaaatgtga ttttctttt aagaaaaaag aagccttta tcatactcct      240 agggctgtca gaaaccattc cggtagattt tcctaagtct tgttttttca gatgcgaaag    300
tgggannccg tagctgtcct caccctatct                                      330

<210> SEQ ID NO 221
<211> LENGTH: 325
<212> TYPE: DNA
<213> ORGANISM: canine genomic DNA
<220> FEATURE:
<221> NAME/KEY: misc_feature
<222> LOCATION: (1)..(325)
<223> OTHER INFORMATION: Wherein N = A or C or G or T
<220> FEATURE:
<221> NAME/KEY: allele
<222> LOCATION: (93)..(93)
<223> OTHER INFORMATION: C to T

<400> SEQUENCE: 221
cctgtccttt agaatcctca tcttgtacat gagagaggga tgaagacagg gaaggcagga     60
gggacggagg gagaaggaag tagctggcta ttcttctgaa ttagaatatg atannnnnnn   120
nnttttaaat cgaaaaatag gaaaaattca aaatctgaca attagcagag ggcttttttgc  180 cctcagaata ttgcaaagaa tgaacaatca ttttataatt atgtccttt tgtattttgt    240 atttttgtat ggaagttaac acttccatag taacatacat cttctagant tatgacctcc   300
tttccctctg gtgcttgaat gtgta                                          325

<210> SEQ ID NO 222
<211> LENGTH: 325
<212> TYPE: DNA
<213> ORGANISM: canine genomic DNA
<220> FEATURE:
<221> NAME/KEY: misc_feature
<222> LOCATION: (1)..(325)
<223> OTHER INFORMATION: Wherein N = A or C or G or T
<220> FEATURE:
<221> NAME/KEY: allele
<222> LOCATION: (131)..(131)
<223> OTHER INFORMATION: Insert 2 "A"s
<220> FEATURE:
<221> NAME/KEY: allele
<222> LOCATION: (202)..(202)
<223> OTHER INFORMATION: C to T
<220> FEATURE:
<221> NAME/KEY: allele
<222> LOCATION: (242)..(242)
<223> OTHER INFORMATION: C to T

<400> SEQUENCE: 222
agtcatttat tgaagcaaag ggtgcaggga agggaaggag tagaaaataa aaatgaaaag     60
gaagattaag atcatattca aaaggccctt ataaaattca ttttggata aatctacaac    120 ggnnnnnnnn naccccaaat ttggatattt ggtctatttt cagtctctca tccatgtcaa   180
ttaacattag aagcaggaag ccctgtcctg ggactaatgg ctggctcaga gtcatgctac   240
```

```
ttgacccgat gccctgtaac tctacaatca tgggcagggt gccaagcaag aacaagcact    300
ccacactcaa tccaggtgta cagag                                          325
```

<210> SEQ ID NO 223
<211> LENGTH: 315
<212> TYPE: DNA
<213> ORGANISM: canine genomic DNA
<220> FEATURE:
<221> NAME/KEY: misc_feature
<222> LOCATION: (1)..(315)
<223> OTHER INFORMATION: Wherein N = A or C or G or T
<220> FEATURE:
<221> NAME/KEY: allele
<222> LOCATION: (50)..(50)
<223> OTHER INFORMATION: T to C
<220> FEATURE:
<221> NAME/KEY: allele
<222> LOCATION: (102)..(102)
<223> OTHER INFORMATION: Delete 8 Bases
<220> FEATURE:
<221> NAME/KEY: allele
<222> LOCATION: (130)..(130)
<223> OTHER INFORMATION: G to A

<400> SEQUENCE: 223

```
cgatatttag gaatgaagcc acattctttt catgacaaag catatgacct actctacaat     60
ctcctgaagc cagaatgctc ntacnctagt agtgaacaga gatctgaaga tctgaagaaa    120
ccaaacatag taaagaaaaa gacactgaga ggagagaagg ggcaagatgc agtgactctc    180
gcaatgcagt gacttaaggc accaaaccca tcagctagct atttaaatag ttggaaaata    240
agagtaaaag ccaagaaaca aaagataaga ttgttattaa agggcagana cnncgaagtg    300
cctatttgca tacca                                                     315
```

<210> SEQ ID NO 224
<211> LENGTH: 315
<212> TYPE: DNA
<213> ORGANISM: canine genomic DNA
<220> FEATURE:
<221> NAME/KEY: misc_feature
<222> LOCATION: (1)..(315)
<223> OTHER INFORMATION: Wherein N = A or C or G or T
<220> FEATURE:
<221> NAME/KEY: allele
<222> LOCATION: (116)..(116)
<223> OTHER INFORMATION: C to T
<220> FEATURE:
<221> NAME/KEY: allele
<222> LOCATION: (282)..(282)
<223> OTHER INFORMATION: A to G

<400> SEQUENCE: 224

```
aaatatctgt ttctgaaata tctccctaaa aaactgtata tgtctgtatg catacaattc     60
acgtagtata cagctaccgt gaacgtttct tgcatgatgt cagccagtag ggannnnnnn    120
nnnngaccaa actatagctt ttgacccatg agcatcaggc tgctaaatcc ccgcaagggc    180
cttttacaac tttatcctgg gcagaagaat tttccttggt gtgtttctct cactggtgtg    240
tctctttcag ctacttgttt tgtgttctga taagcagtta gagctcgtaa tgacactatt    300
acgggctaga tctgc                                                     315
```

<210> SEQ ID NO 225
<211> LENGTH: 324
<212> TYPE: DNA
<213> ORGANISM: canine genomic DNA
<220> FEATURE:

```
<221> NAME/KEY: misc_feature
<222> LOCATION: (1)..(324)
<223> OTHER INFORMATION: Wherein N = A or C or G or T
<220> FEATURE:
<221> NAME/KEY: allele
<222> LOCATION: (84)..(84)
<223> OTHER INFORMATION: Delete T
<220> FEATURE:
<221> NAME/KEY: allele
<222> LOCATION: (242)..(242)
<223> OTHER INFORMATION: G to A
<220> FEATURE:
<221> NAME/KEY: allele
<222> LOCATION: (243)..(243)
<223> OTHER INFORMATION: C to T

<400> SEQUENCE: 225
tttcctttgc ttctggtgct ggannnnnnc tttnnntggg aatttcatct cctgttttta      60
agaaaaagaa agatcagggt gtttttcttg tatttgctat ttttcaagtg cctctaactc     120
aaaataacac tcgtaccaca gtgatgtatt tggggnnnn nnnnnctgcc accctcagtg     180
tgtatatgta tttgtcaaaa gccagtgaat tatgcattta aaataggtac atttttattc     240
gatgtaagct aataccacaa tacaatttga tagaattttt aaaatagttt aaaaatagcc     300
cccaaaagcc agaagagtta gcaa                                            324

<210> SEQ ID NO 226
<211> LENGTH: 421
<212> TYPE: DNA
<213> ORGANISM: canine genomic DNA
<220> FEATURE:
<221> NAME/KEY: misc_feature
<222> LOCATION: (1)..(421)
<223> OTHER INFORMATION: Wherein N = A or C or G or T
<220> FEATURE:
<221> NAME/KEY: allele
<222> LOCATION: (224)..(224)
<223> OTHER INFORMATION: T to C
<220> FEATURE:
<221> NAME/KEY: allele
<222> LOCATION: (246)..(246)
<223> OTHER INFORMATION: G to A
<220> FEATURE:
<221> NAME/KEY: allele
<222> LOCATION: (249)..(249)
<223> OTHER INFORMATION: Insert A
<220> FEATURE:
<221> NAME/KEY: allele
<222> LOCATION: (251)..(251)
<223> OTHER INFORMATION: Delete A
<220> FEATURE:
<221> NAME/KEY: allele
<222> LOCATION: (378)..(378)
<223> OTHER INFORMATION: A to C

<400> SEQUENCE: 226
ttggtttgat cacctatgga aggctgaaca aatccgggta ggattagatc gnnnnnnggg      60
agagaacaat tctccttgcc ctctttgggt ctctggctga ttctgaggat taaactgact     120
taagacaggg taacaggaga aaagtgtaga cacattattg aattntnnnn nnacatggga     180
ggccttcact tcacaaggga gtgaagaccc agggacatga ccaaagcagg aagattttaa     240
accttctgac aaagaaacaa tgagtttgtg aagaattgac aaggcacagg gatttgggtt     300
aggggtagta aatgctgaaa aattaaggtt tgtttataca gccttctcag ccctaaagcc     360
cctcttggtg ataaggctgt gtcccctcct tcagtacaag gggaagttgt atctcacatg     420
t                                                                    421
```

```
<210> SEQ ID NO 227
<211> LENGTH: 395
<212> TYPE: DNA
<213> ORGANISM: canine genomic DNA
<220> FEATURE:
<221> NAME/KEY: misc_feature
<222> LOCATION: (1)..(395)
<223> OTHER INFORMATION: Wherein N = A or C or G or T
<220> FEATURE:
<221> NAME/KEY: allele
<222> LOCATION: (199)..(199)
<223> OTHER INFORMATION: A to C
<220> FEATURE:
<221> NAME/KEY: allele
<222> LOCATION: (224)..(224)
<223> OTHER INFORMATION: G to A

<400> SEQUENCE: 227
acacataact gaagcacacc agcaatatga cagtannnnn nnnnnnnnag ggaaaaaatg      60
tatgaacagg atgttgaggt tttactttta cttgttgcat tcccttaaaa aataataacc    120
attatggcaa aaatatggac ttcattttag tggtatctgt gtattcatat tattttgcac    180
ttttctaagg tttgcattat ctcacaattg aaaagaaaaa cacgagctaa gtaaatgtt    240 aacatatatt attgctacat ttaaaagnnn acaggaagtt taaaaacaaa tgcacccatt    300
attcattaat ttttcactgc tattaagttt aatcaactct tagttttctc tctcagncct    360
aagtagatta tttcaaggaa gtcatgctca atctt                                395

<210> SEQ ID NO 228
<211> LENGTH: 439
<212> TYPE: DNA
<213> ORGANISM: canine genomic DNA
<220> FEATURE:
<221> NAME/KEY: misc_feature
<222> LOCATION: (1)..(439)
<223> OTHER INFORMATION: Wherein N = A or C or G or T
<220> FEATURE:
<221> NAME/KEY: allele
<222> LOCATION: (249)..(249)
<223> OTHER INFORMATION: C to T
<220> FEATURE:
<221> NAME/KEY: allele
<222> LOCATION: (250)..(250)
<223> OTHER INFORMATION: C to T
<220> FEATURE:
<221> NAME/KEY: allele
<222> LOCATION: (254)..(254)
<223> OTHER INFORMATION: G to A
<220> FEATURE:
<221> NAME/KEY: allele
<222> LOCATION: (312)..(312)
<223> OTHER INFORMATION: A to G

<400> SEQUENCE: 228
taggtgcatc ccattctcag ggggccattg gggccacagc agccttcccn nnnngcctnn      60
nnnnnnnnnn gccgtggtgt ttcctctgcn nnnnnccagg ctggggcggc aggcaggggt    120
ggggcctccc ttggagaaan nnnagctgcc tctgtcctgg gctgggctga gctgggagag    180
gccacgccag gtccttctgc ccagatgcca cctcctcccc gctcctcttg gcctctccag    240
ccgcaggccc ggcgcctccc anngagtggg acctgctcct gtgagtcagn nnnngacnn    300 nnnnngtgca cagatnnact atannnngta tnnnactggt catgtgttta ttnnnnggag    360
tatcnnnnnn nnncnnacaa gcaattaatg cgcgnaaccc tngatnncat nnattnnann    420
gctcaaggcg aggcaaatt                                                 439

<210> SEQ ID NO 229
```

```
<211> LENGTH: 342
<212> TYPE: DNA
<213> ORGANISM: canine genomic DNA
<220> FEATURE:
<221> NAME/KEY: misc_feature
<222> LOCATION: (1)..(342)
<223> OTHER INFORMATION: Wherein N = A or C or G or T
<220> FEATURE:
<221> NAME/KEY: allele
<222> LOCATION: (181)..(181)
<223> OTHER INFORMATION: C to T
<220> FEATURE:
<221> NAME/KEY: allele
<222> LOCATION: (224)..(224)
<223> OTHER INFORMATION: Delete 2 Bases

<400> SEQUENCE: 229
ccaatgatct tgcacagtta tgttacnnnn nnnnncttta aaaaacatat aactgagtac      60
ggtggttccn nnnnnacatc ctttaattgc tccccagcat ctaaaggaca atgcccnnnc     120
tcctgaacac ggatacggat ccccacctca nngtcctgtc catttctctc gtatcacttg     180
ccatccacca actccagctc atttactgcc atggaaacaa agagagccat caaatttgag     240
atgttttatg ttacnnnnnn ntttagctga aacatctttt ttttgtctag ttatagtcct     300
aatcttcttt cannnnnntc cactccaata ccacctctac ca                       342

<210> SEQ ID NO 230
<211> LENGTH: 357
<212> TYPE: DNA
<213> ORGANISM: canine genomic DNA
<220> FEATURE:
<221> NAME/KEY: misc_feature
<222> LOCATION: (1)..(357)
<223> OTHER INFORMATION: Wherein N = A or C or G or T
<220> FEATURE:
<221> NAME/KEY: allele
<222> LOCATION: (261)..(261)
<223> OTHER INFORMATION: A to C
<220> FEATURE:
<221> NAME/KEY: allele
<222> LOCATION: (264)..(264)
<223> OTHER INFORMATION: T to C

<400> SEQUENCE: 230
caaatgttaa atggacatct gcnnnnnnnn nnnctgcacn nggctannnn nngnnggnnn      60
gaaannnnct ttgtcttcat gnnnttggnn nnnnntcann nnnngagcnn nnncgtgcca     120
nnnnnnnnnn nnngtgaata atttaatgtc tgaatcagac atgattctga acttctttgt    180
tttacagatg aggaaattga acttatctgt gtctgcttca accccaggat ttccttattc     240
tttgattcaa aacttgacct aaataatcct gtagaannat agagaaaagg gtcgtcgaaa     300
tgctcgtgat acgaaatgaa gagtctgatt gtcatgttct ttctcaggcc tctatca       357

<210> SEQ ID NO 231
<211> LENGTH: 317
<212> TYPE: DNA
<213> ORGANISM: canine genomic DNA
<220> FEATURE:
<221> NAME/KEY: misc_feature
<222> LOCATION: (1)..(317)
<223> OTHER INFORMATION: Wherein N = A or C or G or T
<220> FEATURE:
<221> NAME/KEY: allele
<222> LOCATION: (112)..(112)
<223> OTHER INFORMATION: A to G
<220> FEATURE:
<221> NAME/KEY: allele
<222> LOCATION: (168)..(168)
<223> OTHER INFORMATION: A to G
```

<400> SEQUENCE: 231
ggtaaaccag aagttcccca ggtgaaatgg ctttcctcc attaccctcc ccagtcacac    60
aaccagagga aagtgggctg aaactgagca ttcagngata gaggatgggg tgctgagtgn   120
nctnnnnnna cggaggtccc ataggtccaa gggctgaacc caggtacagg gggcgtgaga   180
aaggggcctg agaggtctac gggagactgg aaactctggg ggcgcagaag cgggggaaga   240
accctggcga tcacgcctgc gggctggcaa agggacggaa aacccaanng gggagaganc   300
ttgagccttc gcaacag                                                 317

<210> SEQ ID NO 232
<211> LENGTH: 325
<212> TYPE: DNA
<213> ORGANISM: canine genomic DNA
<220> FEATURE:
<221> NAME/KEY: misc_feature
<222> LOCATION: (1)..(325)
<223> OTHER INFORMATION: Wherein N = A or C or G or T
<220> FEATURE:
<221> NAME/KEY: allele
<222> LOCATION: (121)..(121)
<223> OTHER INFORMATION: T to C
<220> FEATURE:
<221> NAME/KEY: allele
<222> LOCATION: (196)..(196)
<223> OTHER INFORMATION: G to A

<400> SEQUENCE: 232
atttacatgg cagtgtgttc tggttatcta cttctgtata acaaatgacc ttaaaattta    60
gtggcttaaa acagtaattc atcattataa ttcacagttc ttngngttga ctgggccctc   120
ttgggtagtt cttgcttgca atctctcatg gagttgtagt caggtacagg ctgggagggg   180
ctgcaattct ctggaggttt tagtgagccc agcatccaaa atggtgccct catatggctg   240
gtgattgata gtggctgctg tctgggagct cagctggaac tatcaaatgg actgtcctca   300
tgtggctcat gttatgtggg ctttt                                         325

<210> SEQ ID NO 233
<211> LENGTH: 250
<212> TYPE: DNA
<213> ORGANISM: canine genomic DNA
<220> FEATURE:
<221> NAME/KEY: misc_feature
<222> LOCATION: (1)..(250)
<223> OTHER INFORMATION: Wherein N = A or C or G or T
<220> FEATURE:
<221> NAME/KEY: allele
<222> LOCATION: (67)..(67)
<223> OTHER INFORMATION: A to G
<220> FEATURE:
<221> NAME/KEY: allele
<222> LOCATION: (71)..(71)
<223> OTHER INFORMATION: A to C
<220> FEATURE:
<221> NAME/KEY: allele
<222> LOCATION: (165)..(165)
<223> OTHER INFORMATION: G to A
<220> FEATURE:
<221> NAME/KEY: allele
<222> LOCATION: (221)..(221)
<223> OTHER INFORMATION: C to A

<400> SEQUENCE: 233
attccatttt aggtctgcat aaaggcaaca atgttgtcaa aagtttagnn nnnnnnnnn    60 nntaaaacca atgaatcacg gaagtactaa ttagtaaaag ttgatcatgc acacagagtt  120
ctaaataagt aaattaatgg agagacataa tacacttatg gattgtagaa tttaagatgt    180
tagtcatctc caaattttc aaaagatata ataaaatttc catcaacttc ttggcaggca    240
ctctctaaaa    250

<210> SEQ ID NO 234
<211> LENGTH: 245
<212> TYPE: DNA
<213> ORGANISM: canine genomic DNA
<220> FEATURE:
<221> NAME/KEY: misc_feature
<222> LOCATION: (1)..(245)
<223> OTHER INFORMATION: Wherein N = A or C or G or T
<220> FEATURE:
<221> NAME/KEY: allele
<222> LOCATION: (97)..(97)
<223> OTHER INFORMATION: A to G
<220> FEATURE:
<221> NAME/KEY: allele
<222> LOCATION: (224)..(224)
<223> OTHER INFORMATION: Insert T

<400> SEQUENCE: 234
aaactctcct atttcacatt gaccattttt ctatgaatga aggaataata tttttataac    60
cctgttcccc tccctctgaa tgttttatga aaagaannnn nnnnnnnnn nnaaaattca    120 agaagtgaaa ggaaaattga attttccttc ctcagagaag aagtttaaat caatcatcct    180
tgagaaaaat ctaaatggtc caaattatct ggagccattt tttgtaagat tggatttgcc    240
agttc    245

<210> SEQ ID NO 235
<211> LENGTH: 297
<212> TYPE: DNA
<213> ORGANISM: canine genomic DNA
<220> FEATURE:
<221> NAME/KEY: misc_feature
<222> LOCATION: (1)..(297)
<223> OTHER INFORMATION: Wherein N = A or C or G or T
<220> FEATURE:
<221> NAME/KEY: allele
<222> LOCATION: (67)..(67)
<223> OTHER INFORMATION: A to G
<220> FEATURE:
<221> NAME/KEY: allele
<222> LOCATION: (73)..(73)
<223> OTHER INFORMATION: A to C
<220> FEATURE:
<221> NAME/KEY: allele
<222> LOCATION: (100)..(100)
<223> OTHER INFORMATION: T to C
<220> FEATURE:
<221> NAME/KEY: allele
<222> LOCATION: (108)..(108)
<223> OTHER INFORMATION: C to T
<220> FEATURE:
<221> NAME/KEY: allele
<222> LOCATION: (127)..(127)
<223> OTHER INFORMATION: T to A
<220> FEATURE:
<221> NAME/KEY: allele
<222> LOCATION: (147)..(147)
<223> OTHER INFORMATION: T to G
<220> FEATURE:
<221> NAME/KEY: allele
<222> LOCATION: (186)..(186)
<223> OTHER INFORMATION: A to G

<400> SEQUENCE: 235 acaaagaac cctcctgtct ctgtaaccan nnncaagaag gacagtaagg ctgggtcctt    60
atgtaaacga gcctgagtac atatctaagt gctctcatgc ttaagggcag aagttccctn    120

-continued

```
nnnnnnnnnn aaagtaaagg cagagataat ttcatctctg aggggaaagg gtaaaataat    180
gcttcagcaa tcactcaaat aggggcaggg agcatctgaa aaggattaat tcacccgtgc    240
aatagatatc tagctaaatc tctactatga gtattttctc tttctttcct ttaagat      297
```

<210> SEQ ID NO 236
<211> LENGTH: 338
<212> TYPE: DNA
<213> ORGANISM: canine genomic DNA
<220> FEATURE:
<221> NAME/KEY: misc_feature
<222> LOCATION: (1)..(338)
<223> OTHER INFORMATION: Wherein N = A or C or G or T
<220> FEATURE:
<221> NAME/KEY: allele
<222> LOCATION: (100)..(100)
<223> OTHER INFORMATION: C to A
<220> FEATURE:
<221> NAME/KEY: allele
<222> LOCATION: (273)..(273)
<223> OTHER INFORMATION: A to G

<400> SEQUENCE: 236

```
cttttggctt tctctgaatt tgcataaact ccagtaatct ttttttttccc cctgggttga    60 taatagtgtt tgtgttaaaa tcacaccttc ttttcatttc ttgcatgcat ataggctttt   120
ctcctgtttg tggacacaag tgcttttatc tcactctgca atcagtcaca accccgggtg   180
gaggcaggga acatttgcta caatatttcc tatataaaca gtttcactgt aaaaggaaca   240
atatggctct aattttgatg tatgatcagt ttagaaatat gcaaacacat ttgaatatac   300
atcctgtaca tgacaacagc aatgtgaaat tggataca                           338
```

<210> SEQ ID NO 237
<211> LENGTH: 304
<212> TYPE: DNA
<213> ORGANISM: canine genomic DNA
<220> FEATURE:
<221> NAME/KEY: misc_feature
<222> LOCATION: (1)..(304)
<223> OTHER INFORMATION: Wherein N = A or C or G or T
<220> FEATURE:
<221> NAME/KEY: allele
<222> LOCATION: (131)..(131)
<223> OTHER INFORMATION: T to C

<400> SEQUENCE: 237

```
taagttccac ctgtattgca tcagattgtt gttgaaaaac actgccaata attgcttttn    60
nnnttgccag gctagttggg agtggaaagg gggctggaac tatggaatca gacctaacta   120
tgatctactt cggtccctaa atccctgagt aacaacagca ggcagagcag tgaacctctc   180
tgatctacag tttctgcctc tgcaaaatgg gggtcattct tcccacctca tggaacaccc   240
tgtggtcttc agcctatttc tagcccgggg taggtgctca gagaagacaa gtgatgatgg   300
gttt                                                                304
```

<210> SEQ ID NO 238
<211> LENGTH: 412
<212> TYPE: DNA
<213> ORGANISM: canine genomic DNA
<220> FEATURE:
<221> NAME/KEY: misc_feature
<222> LOCATION: (1)..(412)
<223> OTHER INFORMATION: Wherein N = A or C or G or T
<220> FEATURE:
<221> NAME/KEY: allele
<222> LOCATION: (55)..(55)

```
<223> OTHER INFORMATION: Delete T
<220> FEATURE:
<221> NAME/KEY: allele
<222> LOCATION: (160)..(160)
<223> OTHER INFORMATION: A to T
<220> FEATURE:
<221> NAME/KEY: allele
<222> LOCATION: (197)..(197)
<223> OTHER INFORMATION: C to T
<220> FEATURE:
<221> NAME/KEY: allele
<222> LOCATION: (290)..(290)
<223> OTHER INFORMATION: T to C

<400> SEQUENCE: 238
gatcttttgt gctcagtgag agaantnnnn nttcaannnn nnnnnnnngn atccaacaaa    60
tacaaaaagc nnnnnaacat aaaatagaca tttataagtc acttgtatgt atattggctt   120
tttgtaaatt aaatcatgtt ttatataaca ttagaaccct gttgggtaag gccccctgaa   180
gtaaatggtt tgtaatagaa ataaattgcc ctaccacttg tgatgagcat agcataacaa   240
ccaaagttgt tgaatcactt tgttgtacac ctgaaactaa tgtaacattg tgtgtcaact   300
atactaaaaa ataataataa ataagttttt atttttaata actgctaaaa taaattaaaa   360
atgagtagtg atcctcgttt cagnaatacc tgaaacattt atctgcttat ga           412

<210> SEQ ID NO 239
<211> LENGTH: 300
<212> TYPE: DNA
<213> ORGANISM: canine genomic DNA
<220> FEATURE:
<221> NAME/KEY: misc_feature
<222> LOCATION: (1)..(300)
<223> OTHER INFORMATION: Wherein N = A or C or G or T
<220> FEATURE:
<221> NAME/KEY: allele
<222> LOCATION: (93)..(93)
<223> OTHER INFORMATION: A to G

<400> SEQUENCE: 239
ccttatccta ccacagcttc agccatgtct ccagggcctg tgggatccta gagcactcca    60
tcaaggaagc agngtgaggt gaggggggag ctacannnnn ggcggattga cttgtatctc   120
cacnnnnnnn ttcctgtcac attttgatga tctgtcctca ggtttatgac aaatgcttat   180
tacatggtgt atggagacca gtatacagaa acactcttgt ttcctgtaac tcattctttt   240
tatttttgaa ttcctacttg atactcctgt ctaaaatgag ccctaaatat cacaaactca   300

<210> SEQ ID NO 240
<211> LENGTH: 300
<212> TYPE: DNA
<213> ORGANISM: canine genomic DNA
<220> FEATURE:
<221> NAME/KEY: misc_feature
<222> LOCATION: (1)..(300)
<223> OTHER INFORMATION: Wherein N = A or C or G or T
<220> FEATURE:
<221> NAME/KEY: allele
<222> LOCATION: (136)..(136)
<223> OTHER INFORMATION: C to T
<220> FEATURE:
<221> NAME/KEY: allele
<222> LOCATION: (175)..(175)
<223> OTHER INFORMATION: C to T
<220> FEATURE:
<221> NAME/KEY: allele
<222> LOCATION: (191)..(191)
<223> OTHER INFORMATION: G to C

<400> SEQUENCE: 240
```

```
acccacagaa tccacaagca taattattgt ttaaagcctt tgtatttgga gccgattgtt      60
acaacagcaa ttatttttt aaaaattgta tttatttatt catgagagac acagaannnn      120
nnnnnnnnnn nnngacacag tgnnnnnnnn gaagcaggct ctctgtgggg agcccgatgt      180
gggactcgat gcctgggccc caatcacact ctgagccaaa ggcaaatact cacccactga      240
cccactcagg tgcccctata ccagcaatta gaacactagg cttgtcctta cacctatttt      300
```

```
<210> SEQ ID NO 241
<211> LENGTH: 304
<212> TYPE: DNA
<213> ORGANISM: canine genomic DNA
<220> FEATURE:
<221> NAME/KEY: misc_feature
<222> LOCATION: (1)..(304)
<223> OTHER INFORMATION: Wherein N = A or C or G or T
<220> FEATURE:
<221> NAME/KEY: allele
<222> LOCATION: (263)..(263)
<223> OTHER INFORMATION: C to T
<220> FEATURE:
<221> NAME/KEY: allele
<222> LOCATION: (266)..(266)
<223> OTHER INFORMATION: T to C

<400> SEQUENCE: 241
```

```
catctgctgg cacaacttcc tcttgctctg gggaggtcag ttttttctgt tttagtcaaa      60
ctcttcaact gattagatga ggtccacctg cattatgaag ggatatctgc tttannnnnn     120
nnnnnactga tttgaattcc aaaacacctt cacaaaaaac attccaaatg ttgtttgagc      180
aaatatctgg gcaccatggt ccagtcaggt tgacacaaaa ttaacagtca caccactatg      240
agtcctgtgt atccatatta tttctttaag ctacgtttat gaaagtgaaa tctaatagga      300
tgca                                                                   304
```

```
<210> SEQ ID NO 242
<211> LENGTH: 342
<212> TYPE: DNA
<213> ORGANISM: canine genomic DNA
<220> FEATURE:
<221> NAME/KEY: misc_feature
<222> LOCATION: (1)..(342)
<223> OTHER INFORMATION: Wherein N = A or C or G or T
<220> FEATURE:
<221> NAME/KEY: allele
<222> LOCATION: (47)..(47)
<223> OTHER INFORMATION: G to A
<220> FEATURE:
<221> NAME/KEY: allele
<222> LOCATION: (133)..(133)
<223> OTHER INFORMATION: C to T
<220> FEATURE:
<221> NAME/KEY: allele
<222> LOCATION: (173)..(173)
<223> OTHER INFORMATION: G to A
<220> FEATURE:
<221> NAME/KEY: allele
<222> LOCATION: (210)..(210)
<223> OTHER INFORMATION: G to A
<220> FEATURE:
<221> NAME/KEY: allele
<222> LOCATION: (302)..(302)
<223> OTHER INFORMATION: C to T
<220> FEATURE:
<221> NAME/KEY: allele
<222> LOCATION: (319)..(319)
<223> OTHER INFORMATION: C to A

<400> SEQUENCE: 242
```

```
tattgagccc aactgtatac ccgagcctgc gcttggtgct gagggggtag tggtggcaac      60
actgagcctt taccatccac tccaccgcac tcacagtgag atgaggatca gcacataaac     120
ccgggattcc agcgtgggac acgctgagac agaaggcaac ctgaggcaga cgggggtta     180 gggtgggtgg gacaggcagc catgannnnn nggacnnnnn tcannnnnna tgannannag     240
acacagatcn nnngttngan nagagagggt cattcnnnnn ggcaggagca gcgcgtgcaa     300
annngccatg atgcccagnn tgctgtgtca tgggaaccag at                       342
```

```
<210> SEQ ID NO 243
<211> LENGTH: 331
<212> TYPE: DNA
<213> ORGANISM: canine genomic DNA
<220> FEATURE:
<221> NAME/KEY: misc_feature
<222> LOCATION: (1)..(331)
<223> OTHER INFORMATION: Wherein N = A or C or G or T
<220> FEATURE:
<221> NAME/KEY: allele
<222> LOCATION: (54)..(54)
<223> OTHER INFORMATION: Insert A

<400> SEQUENCE: 243
```

```
tgacagtaag ttgtgcaggt tccttttctt tccccccaaa tgagtctttt actattttt      60 ttctaannnn agctaccttc agnnnnnnnn nnnnnncnaa gtcaannnnn acacatccct     120
tgacacagac acctaaatct ctgtaatttt tgagcaagaa cttgatttgc tatatgccat     180
aagctaaatg gatagtttgg ggcacacatt tgtctggaga caaagccttg ctctaaacaa     240
cagtttaaaa tgtttcagtg agcacctatt gaaagtgata tattatgcaa gcaatttctt     300
tgtagttatg cgtagaaaca gctcagctac t                                    331
```

```
<210> SEQ ID NO 244
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 244
gcttttggac aactttggat ag                                              22

<210> SEQ ID NO 245
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 245
gaattccaaa tgtcctgctt ag                                              22

<210> SEQ ID NO 246
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 246
aagcatactt ccctgaaatg ag                                              22

<210> SEQ ID NO 247
<211> LENGTH: 22
```

```
<212> TYPE: DNA
<213> ORGANISM: Artificial Sequence
<220> FEATURE:
<223> OTHER INFORMATION: Oligonucleotide Primer

<400> SEQUENCE: 247
agtcaaatcg ttcattggat tc                                              22

<210> SEQ ID NO 248
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 248
aaaaggtggc acatatgaaa ag                                              22

<210> SEQ ID NO 249
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 249
ggggtttcta ttccattttc ac                                              22

<210> SEQ ID NO 250
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 250
acctcatgta tgtcttgttc cc                                              22

<210> SEQ ID NO 251
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 251
ctctgctagg agaaaggag ag                                               22

<210> SEQ ID NO 252
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 252
caaatggttc aagaggagat tc                                              22

<210> SEQ ID NO 253
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 253
```

```
aaagtaaaat caggtattct cctcc                                              25
```

<210> SEQ ID NO 254
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 254

```
caccctcaag aagttaaagc ac                                                 22
```

<210> SEQ ID NO 255
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 255

```
tagggacac agtttctaaa gg                                                  22
```

<210> SEQ ID NO 256
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 256

```
tctcaaactg ttgaagacca ac                                                 22
```

<210> SEQ ID NO 257
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 257

```
catgtgaccc ttcctatgag ac                                                 22
```

<210> SEQ ID NO 258
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 258

```
ggaagacccc aactctatta ttg                                                23
```

<210> SEQ ID NO 259
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 259

```
agtcttttgg tcctaaacat gg                                                 22
```

<210> SEQ ID NO 260
<211> LENGTH: 20
<212> TYPE: DNA
<213> ORGANISM: Artificial Sequence

```
<220> FEATURE:
<223> OTHER INFORMATION: Oligonucleotide Primer

<400> SEQUENCE: 260
agacacatgc attttcccag                                              20

<210> SEQ ID NO 261
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 261
gtccaaagtt ggagatgata gg                                           22

<210> SEQ ID NO 262
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 262
aaagcccagc tgttgtctg                                               19

<210> SEQ ID NO 263
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 263
cctgtccttt agaatcctca tc                                           22

<210> SEQ ID NO 264
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 264
agtcatttat tgaagcaaag gg                                           22

<210> SEQ ID NO 265
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 265
cgatatttag gaatgaagcc ac                                           22

<210> SEQ ID NO 266
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 266
aaatatctgt ttctgaaata tctccc                                       26
```

<210> SEQ ID NO 267
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 267
tttcctttgc ttctggtgc                                                  19

<210> SEQ ID NO 268
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 268
ttggtttgat cacctatgga ag                                              22

<210> SEQ ID NO 269
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 269
acacataact gaagcacacc ag                                              22

<210> SEQ ID NO 270
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 270
taggtgcatc ccattctcag                                                 20

<210> SEQ ID NO 271
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 271
ccaatgatct tgcacagtta tg                                              22

<210> SEQ ID NO 272
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 272
caaatgttaa atggacatct gc                                              22

<210> SEQ ID NO 273
<211> LENGTH: 21
<212> TYPE: DNA
<213> ORGANISM: Artificial Sequence
<220> FEATURE:
<223> OTHER INFORMATION: Oligonucleotide Primer

```
<400> SEQUENCE: 273
ggtaaaccag aagttcccca g                                         21

<210> SEQ ID NO 274
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 274
atttacatgg cagtgtgttc tg                                        22

<210> SEQ ID NO 275
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 275
attccatttt aggtctgcat aaag                                      24

<210> SEQ ID NO 276
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 276
aaactctcct atttcacatt gacc                                      24

<210> SEQ ID NO 277
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 277
gaaccctcct gtctctgtaa cc                                        22

<210> SEQ ID NO 278
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 278
cttttggctt tctctgaatt tg                                        22

<210> SEQ ID NO 279
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 279
taagttccac ctgtattgca tc                                        22

<210> SEQ ID NO 280
```

```
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 280
gatcttttgt gctcagtgag ag                                              22

<210> SEQ ID NO 281
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 281
ccttatccta ccacagcttc ag                                              22

<210> SEQ ID NO 282
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 282
acccacagaa tccacaagc                                                  19

<210> SEQ ID NO 283
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 283
catctgctgg cacaacttc                                                  19

<210> SEQ ID NO 284
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 284
tattgagccc aactgtatac cc                                              22

<210> SEQ ID NO 285
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 285
tgacagtaag ttgtgcaggt tc                                              22

<210> SEQ ID NO 286
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 286
```

-continued tgtgatctac gtcactctct gg                                        22

<210> SEQ ID NO 287
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 287
tctttcatct accaagggtg tg                                        22

<210> SEQ ID NO 288
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 288
tgtatcagcc ataaagtgtt gg                                        22

<210> SEQ ID NO 289
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 289
ctgcttgaat gtactccctc tc                                        22

<210> SEQ ID NO 290
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 290
aagagtcaga ggcttaaggg ag                                        22

<210> SEQ ID NO 291
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 291
ttggaatgca tactgttgac ac                                        22

<210> SEQ ID NO 292
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 292
tgatcttggg gtcctgag                                             18

<210> SEQ ID NO 293
<211> LENGTH: 21
<212> TYPE: DNA

```
<213> ORGANISM: Artificial Sequence
<220> FEATURE:
<223> OTHER INFORMATION: Oligonucleotide Primer

<400> SEQUENCE: 293
acacaattca gtccattcag c                                              21

<210> SEQ ID NO 294
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 294
taaccattgt aggttcctgt cc                                             22

<210> SEQ ID NO 295
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 295
tggcatgcat atctatctga ag                                             22

<210> SEQ ID NO 296
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 296
cctggttttg agaagactgg                                                20

<210> SEQ ID NO 297
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 297
gacagacatg taagaagccc tc                                             22

<210> SEQ ID NO 298
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 298
ggtctctgct aggaacaaat tc                                             22

<210> SEQ ID NO 299
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 299
gaaagtagag gcaatttggt tg                                             22
```

```
<210> SEQ ID NO 300
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 300
tcagctgtgg ttacagattt tg                                              22

<210> SEQ ID NO 301
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 301
cactgtgact cctcactgac tg                                              22

<210> SEQ ID NO 302
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 302
aatcttcatt gtgaacagga gc                                              22

<210> SEQ ID NO 303
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 303
tgaaactggg aaatgttgtt atag                                            24

<210> SEQ ID NO 304
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 304
agatagggtg aggacagcta cg                                              22

<210> SEQ ID NO 305
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 305
tacacattca agcaccagag g                                               21

<210> SEQ ID NO 306
<211> LENGTH: 22
<212> TYPE: DNA
<213> ORGANISM: Artificial Sequence
<220> FEATURE:
```

<223> OTHER INFORMATION: Oligonucleotide Primer

<400> SEQUENCE: 306
ctctgtacac ctggattgag tg                                        22

<210> SEQ ID NO 307
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 307
tggtatgcaa ataggcactt c                                         21

<210> SEQ ID NO 308
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 308
gcagatctag cccgtaatag tg                                        22

<210> SEQ ID NO 309
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 309
ttgctaactc ttctggcttt tg                                        22

<210> SEQ ID NO 310
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 310
acatgtgaga tacaacttcc cc                                        22

<210> SEQ ID NO 311
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 311
aagattgagc atgacttcct tg                                        22

<210> SEQ ID NO 312
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 312
aatttgcctc gccttgag                                             18

```
<210> SEQ ID NO 313
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 313
tggtagaggt ggtattggag tg                                              22

<210> SEQ ID NO 314
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 314
tgatagaggc ctgagaaaga ac                                              22

<210> SEQ ID NO 315
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 315
ctgttgcgaa ggctcaag                                                   18

<210> SEQ ID NO 316
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 316
aaaagcccac ataacatgag c                                               21

<210> SEQ ID NO 317
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 317
ttttagagag tgcctgccaa g                                               21

<210> SEQ ID NO 318
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 318
gaactggcaa atccaatctt ac                                              22

<210> SEQ ID NO 319
<211> LENGTH: 24
<212> TYPE: DNA
<213> ORGANISM: Artificial Sequence
<220> FEATURE:
<223> OTHER INFORMATION: Oligonucleotide Primer
```

```
<400> SEQUENCE: 319
agcaacttga atcttaaagg aaag                                              24

<210> SEQ ID NO 320
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 320
tgtatccaat ttcacattgc tg                                                22

<210> SEQ ID NO 321
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 321
aaacccatca tcacttgtct tc                                                22

<210> SEQ ID NO 322
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 322
tcataagcag ataaatgttt cagg                                              24

<210> SEQ ID NO 323
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 323
tgagtttgtg atatttaggg ctc                                               23

<210> SEQ ID NO 324
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 324
aaaataggtg taaggacaag cc                                                22

<210> SEQ ID NO 325
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 325
tgcatcctat tagatttcac tttc                                              24

<210> SEQ ID NO 326
<211> LENGTH: 20
```

```
-continued

<212> TYPE: DNA
<213> ORGANISM: Artificial Sequence
<220> FEATURE:
<223> OTHER INFORMATION: Oligonucleotide Primer

<400> SEQUENCE: 326
atctggttcc catgacacag                                          20

<210> SEQ ID NO 327
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 327
agtagctgag ctgtttctac gc                                       22
```